US012655200B2

(12) United States Patent
Mackness et al.

(10) Patent No.: US 12,655,200 B2
(45) Date of Patent: Jun. 16, 2026

(54) METHODS OF TREATING ANTIBODY-MEDIATED DISORDERS WITH FcRn ANTAGONISTS

(71) Applicant: Genzyme Corporation, Cambridge, MA (US)

(72) Inventors: Brian Mackness, Lowell, MA (US); Huawei Qiu, Westborough, MA (US)

(73) Assignee: Genzyme Corporation, Cambridge, MA (US)

( * ) Notice: Subject to any disclaimer, the term of this patent is extended or adjusted under 35 U.S.C. 154(b) by 1369 days.

(21) Appl. No.: 16/938,727

(22) Filed: Jul. 24, 2020

(65) Prior Publication Data

US 2021/0024620 A1     Jan. 28, 2021

Related U.S. Application Data

(60) Provisional application No. 62/878,541, filed on Jul. 25, 2019.

(51) Int. Cl.
C07K 16/18 (2006.01)
A61K 39/00 (2006.01)
(Continued)

(52) U.S. Cl.
CPC ........ C07K 16/18 (2013.01); A61K 39/39533 (2013.01); A61K 51/10 (2013.01);
(Continued)

(58) Field of Classification Search
CPC combination set(s) only.
See application file for complete search history.

(56) References Cited

U.S. PATENT DOCUMENTS 6,030,613 A     2/2000  Blumberg et al.
6,737,056 B1    5/2004  Presta
(Continued)

FOREIGN PATENT DOCUMENTS

CA        2831770 C  *  3/2012  ............. C12N 15/09
WO    2000/042072 A2    7/2000
(Continued)

OTHER PUBLICATIONS

Killock D. Immunology: Abdegs: an alternative to IVIg? Nat Rev Rheumatol. Jul. 19, 2011;7(9):496. doi: 10.1038/nrrheum.2011.102. PMID: 21769129. (Year: 2011).*
(Continued)

*Primary Examiner* — Jeffrey Stucker
*Assistant Examiner* — Laura Ann Essex
(74) *Attorney, Agent, or Firm* — Steptoe LLP; Z. Ying Li; David Caianiello

(57)     ABSTRACT

The present disclosure provides methods of treating an antibody-mediated disorder (e.g., an autoimmune disease) using an FcRn antagonist, e.g., a binding polypeptide (e.g., an antibody and/or an immunoadhesin), comprising a modified Fc domain. The present disclosure also provides methods of enhancing diagnostic imaging using an FcRn antagonist disclosed herein. The present disclosure further provides methods of reducing exposure of normal tissue to a radiolabeled antibody during diagnostic imaging using an FcRn antagonist disclosed herein. Methods comprising administering to a subject a therapeutically effective amount of an FcRn antagonist disclosed herein are also provided.

26 Claims, 57 Drawing Sheets

Specification includes a Sequence Listing.

(51) Int. Cl.
　　*A61K 39/395*　　　(2006.01)
　　*A61K 51/10*　　　(2006.01)
(52) U.S. Cl.
　　CPC .... *A61K 2039/505* (2013.01); *C07K 2317/52*
　　　　(2013.01); *C07K 2317/76* (2013.01); *C07K*
　　　　*2317/92* (2013.01); *C07K 2317/94* (2013.01)

(56)　　　　　　References Cited

U.S. PATENT DOCUMENTS

| | | | |
|---|---|---|---|
| 6,821,505 | B2 | 11/2004 | Ward |
| 7,083,784 | B2 | 8/2006 | Dall'Acqua et al. |
| 7,371,826 | B2 | 5/2008 | Presta |
| 7,740,847 | B2 | 6/2010 | Allan et al. |
| 8,163,881 | B2 | 4/2012 | Ober |
| 8,318,907 | B2 | 11/2012 | Chamberlain et al. |
| 8,546,543 | B2 | 10/2013 | Lazar |
| 8,618,252 | B2 | 12/2013 | Farrington et al. |
| 8,834,871 | B2 | 9/2014 | Ober |
| 9,023,996 | B2 | 5/2015 | Grosse-Hovest et al. |
| 10,316,073 | B2 | 6/2019 | Ulrichts et al. |
| 10,344,085 | B2 | 7/2019 | Dengl et al. |
| 2006/0067930 | A1 | 3/2006 | Adams et al. |
| 2006/0276633 | A1 | 12/2006 | Jung et al. |
| 2008/0089892 | A1 | 4/2008 | Allan et al. |
| 2009/0163699 | A1 | 6/2009 | Chamberlain et al. |
| 2012/0328612 | A1 | 12/2012 | Grosse-Hovest et al. |
| 2013/0131319 | A1 | 5/2013 | Igawa et al. |
| 2014/0294810 | A1 | 10/2014 | Lowman et al. |
| 2015/0050269 | A1 | 2/2015 | Igawa et al. |
| 2015/0125444 | A1 | 5/2015 | Tsui et al. |
| 2017/0022270 | A1 | 1/2017 | Igawa et al. |
| 2017/0342168 | A1 | 11/2017 | Schlothauer |
| 2018/0037634 | A1 | 2/2018 | Viswanathan et al. |
| 2019/0263934 | A1 | 8/2019 | Qiu et al. |

FOREIGN PATENT DOCUMENTS

| | | | | |
|---|---|---|---|---|
| WO | 2002/060919 | A2 | 8/2002 | |
| WO | 2005/018572 | A2 | 3/2005 | |
| WO | 2005063815 | A2 | 7/2005 | |
| WO | 2006/031370 | A2 | 3/2006 | |
| WO | 2006/053301 | A2 | 5/2006 | |
| WO | 2006/130834 | A2 | 12/2006 | |
| WO | 2009/058492 | A2 | 5/2009 | |
| WO | 2011/089211 | A1 | 7/2011 | |
| WO | 2011/122011 | A2 | 10/2011 | |
| WO | 2013/011076 | A2 | 1/2013 | |
| WO | 2013/046704 | A2 | 4/2013 | |
| WO | 2013047748 | A1 | 4/2013 | |
| WO | 2014/177459 | A2 | 11/2014 | |
| WO | 2014/177460 | A1 | 11/2014 | |
| WO | WO 2015/100299 | A1 | 7/2015 | |
| WO | WO 2015/189249 | A1 | 12/2015 | |
| WO | 2016/071376 | A2 | 5/2016 | |
| WO | 2016/142782 | A1 | 9/2016 | |
| WO | WO 2016/183352 | A1 | 11/2016 | |
| WO | 2018/083122 | A1 | 5/2018 | |
| WO | WO-2018213097 | A1 * | 11/2018 | .............. A61P 31/16 |
| WO | 2019/110823 | A1 | 6/2019 | |
| WO | 2019/147973 | A1 | 8/2019 | |

OTHER PUBLICATIONS

Griffin LM, Snowden JR, Lawson AD, Wernery U, Kinne J, Baker TS. Analysis of heavy and light chain sequences of conventional camelid antibodies from *Camelus dromedarius* and *Camelus bactrianus* species. J Immunol Methods. Mar. 2014;405:35-46. doi: 10.1016/j.jim.2014.01.003. Epub Jan. 18, 2014. (Year: 2014).*

Patel DA, Puig-Canto A, Challa DK, Perez Montoyo H, Ober RJ, Ward ES. Neonatal Fc receptor blockade by Fc engineering ameliorates arthritis in a murine model. J Immunol. Jul. 15, 2011;187(2):1015-22. doi: 10.4049/jimmunol.1003780. Epub Jun. 20, 2011. PMID: 21690327; PMCID: PMC3157913. (Year: 2011).*

Shields RL, Namenuk AK, Hong K, Meng YG, Rae J, Briggs J, Xie D, Lai J, Stadlen A, Li B, Fox JA, Presta LG. J Biol Chem. Mar. 2, 2001;276(9):6591-604. doi: 10.1074/jbc.M009483200. Epub Nov. 28, 2000. PMID: 11096108. (Year: 2001).*

Dall'Acqua WF, Woods RM, Ward ES, Palaszynski SR, Patel NK, Brewah YA, Wu H, Kiener PA, Langermann S. Increasing the affinity of a human IgG1 for the neonatal Fc receptor: biological consequences. J Immunol. Nov. 1, 2002;169(9):5171-80. doi: 10.4049/jimmunol.169.9.5171. PMID: 12391234. (Year: 2002).*

Jazayeri JA, Carroll GJ. Fc-based cytokines : prospects for engineering superior therapeutics. BioDrugs. 2008;22(1):11-26. doi: 10.2165/00063030-200822010-00002. PMID: 18215087. (Year: 2008).*

Ulrichts P, Guglietta A, Dreier T, van Bragt T, Hanssens V, Hofman E, Vankerckhoven B, Verheesen P, Ongenae N, Lykhopiy V, Enriquez FJ, Cho J, Ober RJ, Ward ES, de Haard H, Leupin N. J Clin Invest. Oct. 1, 2018;128(10):4372-4386. doi: 10.1172/JCI97911. Epub Jul. 24, 2018. PMID: 30040076; PMCID: PMC6159959 (Year: 2018).*

Shamji MH, Valenta R, Jardetzky T, Verhasselt V, Durham SR, Würtzen PA, van Neerven RJJ. The role of allergen-specific IgE, IgG and IgA in allergic disease. Allergy. Dec. 2021;76(12):3627-3641. doi: 10.1111/all.14908. Epub Jun. 8, 2021. PMID: 33999439; PMCID: PMC8601105. (Year: 2021).*

Duarte-Rey C, Bogdanos DP, Leung PS, Anaya JM, Gershwin ME. IgM predominance in autoimmune disease: genetics and gender. Autoimmun Rev. May 2012;11(6-7):A404-12. doi: 10.1016/j.autrev.2011.12.001. Epub Dec. 8, 2011. PMID: 22178509. (Year: 2012).*

Abdiche et al., "The neonatal Fc receptor (FcRn) binds independently to both sites of the IgG homodimer with identical affinity," mAbs. (2015) 7(2):331-43.

Avery et al., "Utility of a human FcRn transgenic mouse model in drug discovery for early assessment and prediction of human pharmacokinetics of monoclonal antibodies," mAbs. (2016) 8(6):1064-78.

Biggar et al., "Real-time protein unfolding: a method for determining the kinetics of native protein denaturation using a quantitative real-time thermocycler," BioTechniques. (2012) 53(4):231-8.

Acqua et al., "Increasing the affinity of a human IgG1 for the neonatal Fc receptor: biological consequences," J Immunol. (2002) 169(9):5171-80.

Datta-Mannan et al., "Monoclonal Antibody Clearance: Impact of Modulating the Interaction of IgG with the Neonatal Fe Receptor," The Journal of Biological Chemistry. (2007) 282(3):1709-17.

Datta-Mannan et al., "Humanized IgG1 Variants with Differential Binding Properties to the Neonatal Fe Receptor: Relationship to Pharmacokinetics in Mice and Primates," Drug Metabolism and Disposition. (2007) 35(1):86-94.

Hinton et al., "An engineered human IgG1 antibody with longer serum half-life," J. Immunol. (2006) 176:346-56.

International Search Report and Written Opinion for International Application No. PCT/US2019/015204, dated Jun. 24, 2019 (29 pages).

Karlsson et al., "Comparison of surface plasmon resonance binding curves for characterization of protein interactions and analysis of screening data," Analytical Biochemistry. (2016) 502:53-63.

Kuo et al., "Neonatal Fe receptor and IgG-based therapeutics," mAbs. (2011) 3(5):422-30.

MackNess et al., "Antibody Fe engineered for enhanced neonatal FC receptor binding and prolonged circulation half-life," MABS. (2019) 1-13.

Medesan et al., "Delineation of the amino acid residues involved in transcytosis and catabolism of mouse IgG1," J Immunol. (1997) 158:2211-7.

Oganesyan et al., "Structural insights into neonatal Fe receptor-based recycling mechanisms," The Journal of Biological Chemistry. (2014) 289(11):7812-24.

Raghavan et al., "Analysis of the pH Dependence of the Neonatal Fe Receptor/Immunoglobulin G Interaction Using Antibody and Receptor Variants," Biochemistry. (1995) 34:14649-57.

Shields et al., "High Resolution Mapping of the Binding Site on Human IgG1 for FcγRI, FcγRII, FcγRIll, and FcRn and Design of IgG1 Variants with Improved Binding to the Fc gamma R," The Journal of Biological Chemistry. (2001) 72(9):6591-604.

(56)　　　　　References Cited

OTHER PUBLICATIONS

Schlothauer et al., "Analytical FcRn affinity chromatography for functional characterization of monoclonal antibodies," mAbs. (2013) 5(4):576-86.

Seijsing et al., "In vivo depletion of serum IgG by an affibody molecule binding the neonatal Fe receptor," Scientific Reports. (2018) 8:(5141).

Suzuki et al., "Importance of neonatal FcRn in regulating the serum half-life of therapeutic proteins containing the Fe domain of human IgG1: A comparative study of the affinity of monoclonal antibodies and Fe-Fusion proteins to human neonatal FcR," J. Immunol. (2010) 184:1968-76.

Swiercz et al., "Use of Fe-Engineered Antibodies as Clearing Agents to Increase Contrast During PET," The Journal of Nuclear Medicine. (2014) 55(7):1204-7.

Vaccaro et al., "Engineering the Fc region of immunoglobulin G to modulate in vivo antibody levels," Nature Biotechnology. (2005) 23(10):1283-8.

Xiao, "Pharmacokinetic Models for FcRn-Mediated IgG Disposition," J Biomed Biotechnol. (2012) 2012:282989.

Ying et al., "Engineered Soluble Monomeric IgG1 CH3 Domain," JBC (2013) 288:25154-164.

Yang et al., "Characterization of two engineered dimeric Zika virus envelope proteins as immunogens for neutralizing antibody selection and vaccine design" JBC (2019) 294:10638-48.

Zhou et al., "Development of a simple and rapid method for producing non-fucosylated oligomannose containing antibodies with increased effector function," Biotechnology and Bioengineering. (2008) 99(3):652-65.

Jazayeri et al., "Fc-based cytokines: prospects for engineering superior therapeutics" BioDrugs (2008). 22(1):11-26.

Patel et al., "FcRn blockade by Fc engineering ameliorates arthritis in a murine model," J Immunol (2011). 187(2):1015-22.

Ulrichts et al., "Neonatal Fc receptor antagonist efgartigimod safely and sustainably reduces IgGs in humans" J Clin Invest (2018). 128(10):4372-86.

Belousov et al., "Genetically encoded fluorescent indicator for intracellular hydrogen peroxide," Nat Methods. (2006) 3(4):281-6.

Caschera et al., "Contrast agents in diagnostic imaging: Present and future," Pharmacological Research. (2016) 110:65-75.

Griffin et al. "Analysis of heavy and light chain sequences of conventional camelid antibodies from *Camelus dromedarius* and *Camelus bactrianus* species," J Immunol Methods. (2014) 405:35-46.

Killock et al., "Immunology: Abdegs: an alternative to IVIg?" Nat Rev Rheumatol. (2011) 7(9):496.

Kobayashi et al., "New strategies for fluorescent probe design in medical diagnostic imaging," Chemical Reviews. (2010) 110(5):2620-40.

Monnet et al., "Selection of IgG variants with increased FcRn binding using random and directed mutagenesis: impact on effector functions," Frontiers in Immunology. (2015) 6(39):1-14.

Mould et al., "Pharmacokinetics and pharmacodynamics of monoclonal antibodies: concepts and lessons for drug development," BioDrugs. (2010) 24(1):23-39.

Oganov et al., Fundamentals of Evidence-Based Medicine—Textbook for the system of postgraduate and additional professional education of doctors./Under the general editorship of Academician of the Russian Academy of Medical Sciences (2010) p. 11.

Selezvena et al., "An integrated approach to the study of pharmacological substances in vitro, ex vivo, in vivo," International Scientific Research Journal (2015) 6(37):125-27.

Swiercz et al., "Use of Fc-Engineered Antibodies as Clearing Agents to Increase Contrast During PET," J Nuc Med. (2014) 55(7):1204-7.

Tyagi et al., "Chemical modification and chemical cross-linking for protein/enzyme stabilization," Biochemistry (Mosc). (1998) 63(3):334-44.

Suzuki, "Glycan Structures of Avian IgG: The Presence of Both Conserved and Species-Specific Glycans", TIGG (2018) 30(177):E221-29.

* cited by examiner

FIG. 1A                    FIG. 1B
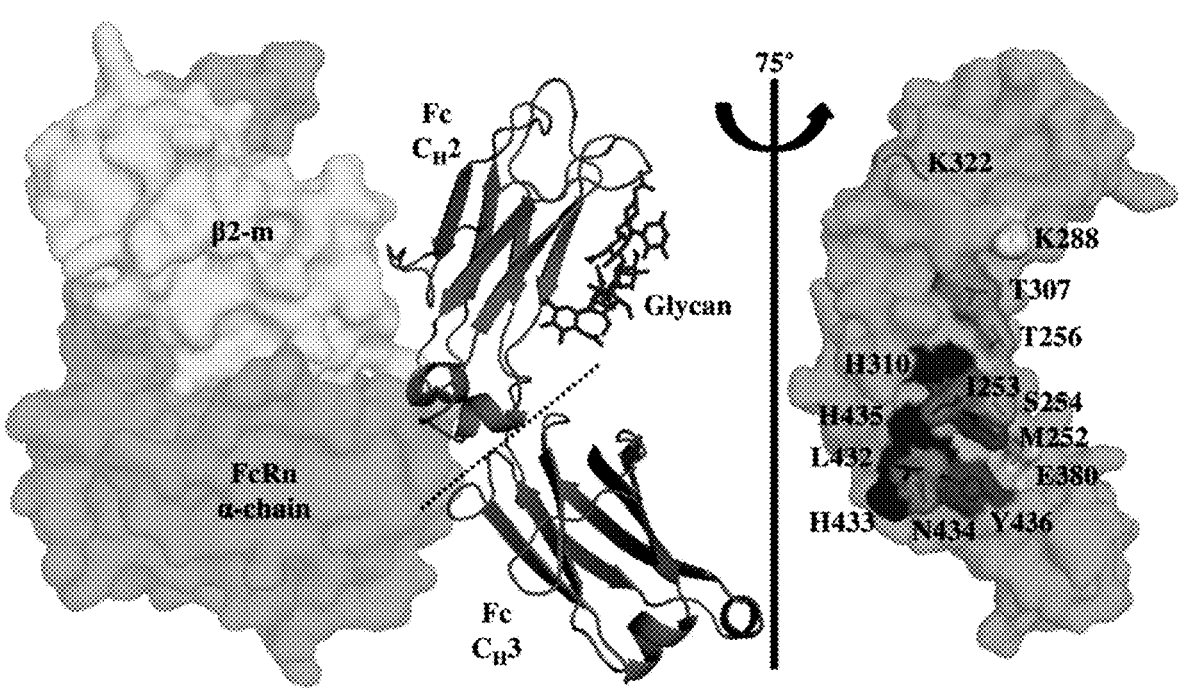

Human FcRn

Rat FcRn

FIG. 14

| Mutant | Position |
|---|---|

Fold Change in FcRn Off Rate

| Mutant | M252 | I253 | S254 | T256 | K288 | T307 | K322 | E380 | L432 | N434 | Y436 |
|---|---|---|---|---|---|---|---|---|---|---|---|
| A | | | | | | | | | | | |
| C | | | | | | | | | | | |
| D | | | | | | | | | | | |
| E | | | | | | | WT | | | | |
| F | | | | | | | | | | | |
| G | | | | | | | | | | | |
| H | | | | | | | | | | | |
| I | | WT | | | | | | | | | |
| K | | | | | WT | | WT | | | | |
| L | | | | | | | | | WT | | |
| M | WT | | | | | | | | | | |
| N | | | | | | | | | | WT | |
| P | | | | | | | | | | | |
| Q | | | | | | | | | | | |
| R | | | | | | | | | | | |
| S | | | WT | | | | | | | | |
| T | | | | WT | WT | | | | | | |
| V | | | | | | | | | | | |
| W | | | | | | | | | | | |
| Y | | | | | | | | | | | WT |

FIG. 15A
Antibody of Interest ▢
Biotinylated FcRn ▨
Streptavidin ▢
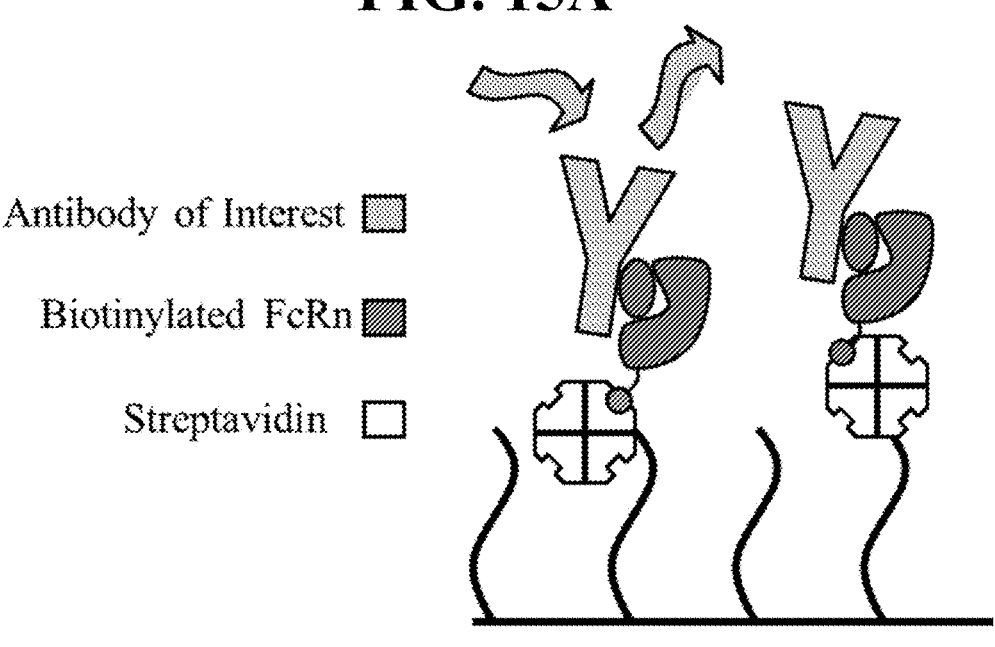
CM5 Sensor Chip
FIG. 15B
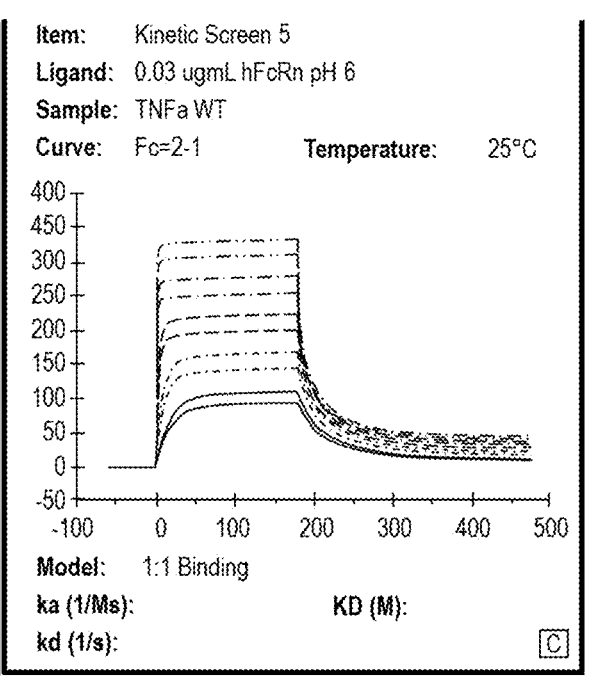
FIG. 15C

FIG. 16A
FIG. 16B
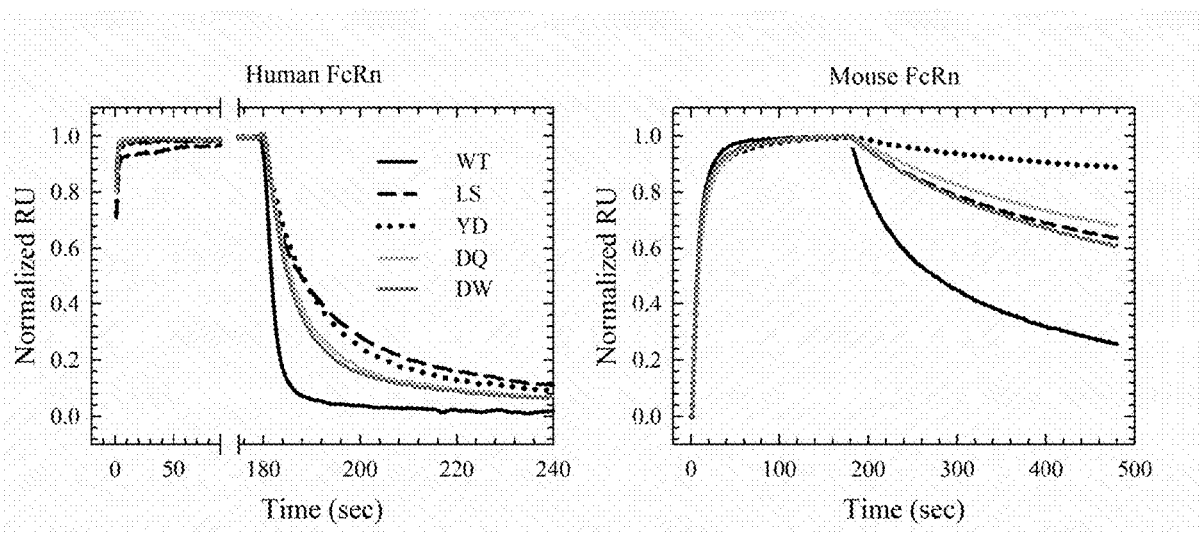
FIG. 17A
FIG. 17B
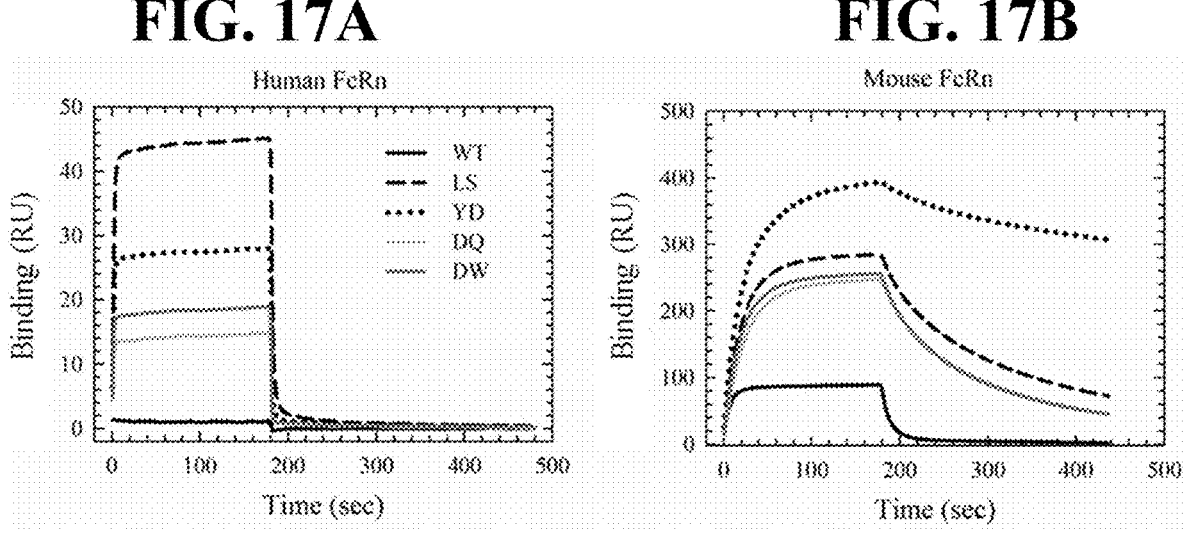

| Variant | mAb1 | mAb2 |
|---------|------|------|
| WT | 7.37 | 7.61 |
| LS | 8.29 | 8.32 |
| YD | 8.29 | 8.25 |
| DQ | 7.92 | 8.06 |
| DW | 7.92 | 8.11 |

| Variant | mAb1 | mAb2 |
|---------|------|------|
| WT | 69.0 | 69.3 |
| LS | 68.5 | 69.0 |
| YD | 59.6 | 60.5 |
| DQ | 67.9 | 69.3 |
| DW | 57.8 | 58.1 |

FIG. 27E
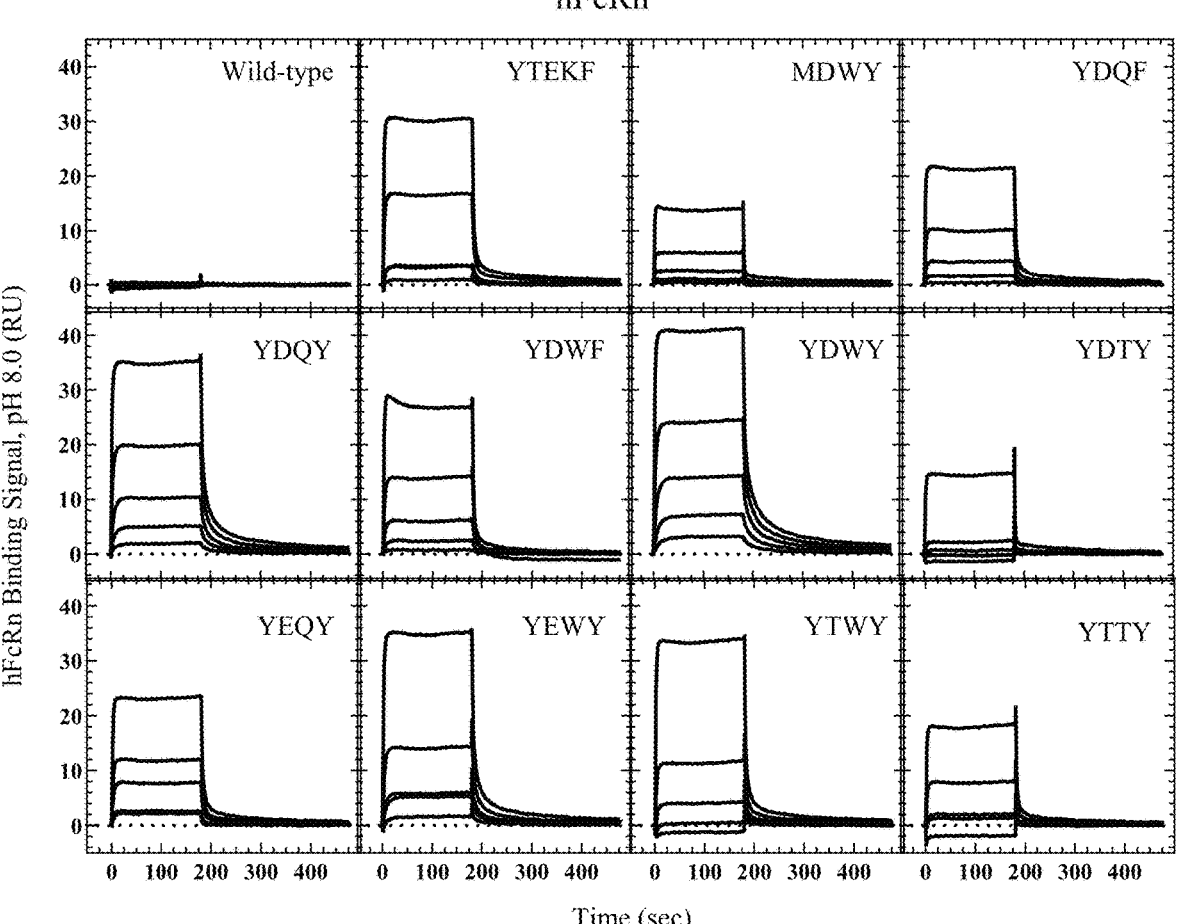

FIG. 32

Sequence alignment of the IgG subclasses using ClustalOmega

```
IgG1  APELLGGPSV  FLFPPKPKDT  LMISRTPEVT  CVVVDVSHED  PEVKFNWYVD  GVEVHNAKTK  290
IgG4  APEFLGGPSV  FLFPPKPKDT  LMISRTPEVT  CVVVDVSQED  PEVQFNWYVD  GVEVHNAKTK  290
IgG2  -APPVAGPSV  FLFPPKPKDT  LMISRTPEVT  CVVVDVSHED  PEVQFNWYVD  GVEVHNAKTK  290
IgG3  APELLGGPSV  FLFPPKPKDT  LMISRTPEVT  CVVVDVSHED  PEVQFKWYVD  GVEVHNAKTK  290
      :.****      *********   **********  *******:**  ***:*:****  **********

IgG1  PREEQYNSTY  RVVSVLTVLH  QDWLNGKEYK  CKVSNKALPA  PIEKTISKAK  GQPREPQVYT  350
IgG4  PREEQFNSTY  RVVSVLTVLH  QDWLNGKEYK  CKVSNKGLPS  SIEKTISKAK  GQPREPQVYT  350
IgG2  PREEQFNSTF  RVVSVLTVVH  QDWLNGKEYK  CKVSNKGLPA  PIEKTISKTK  GQPREPQVYT  350
IgG3  PREEQYNSTF  RVVSVLTVLH  QDWLNGKEYK  CKVSNKALPA  PIEKTISKTK  GQPREPQVYT  350
      *****:***:  *********:*  **********  ******.**:   *******:*  **********

IgG1  LPPSRDELTK  NQVSLTCLVK  GFYPSDIAVE  WESNGQPENN  YKTTPPVLDS  DGSFFLYSKL  410
IgG4  LPPSQEEMTK  NQVSLTCLVK  GFYPSDIAVE  WESNGQPENN  YKTTPPVLDS  DGSFFLYSRL  410
IgG2  LPPSREEMTK  NQVSLTCLVK  GFYPSDIAVE  WESNGQPENN  YKTTPPMLDS  DGSFFLYSKL  410
IgG3  LPPSREEMTK  NQVSLTCLVK  GFYPSDIAVE  WESSGQPENN  YNTTPPMLDS  DGSFFLYSKL  410
      ****::*:**  **********  **********  ***.******  *:****:***  ********:*

IgG1  TVDKSRWQQG  NVFSCSVMHE  ALHNHYTQKS  LSLSPGK  447  (SEQ  ID  NO:  1)
IgG4  TVDKSRWQEG  NVFSCSVMHE  ALHNHYTQKS  LSLSLGK  447  (SEQ  ID  NO:  2)
IgG2  TVDKSRWQQG  NVFSCSVMHE  ALHNHYTQKS  LSLSPGK  447  (SEQ  ID  NO:  3)
IgG3  TVDKSRWQQG  NIFSCSVMHE  ALHNRFTQKS  LSLSPGK  447  (SEQ  ID  NO:  4)
      *******:*  *:********  ****::****  ****  **

*  Identical
        :  Similar
```

Residues M252, T256, T307, and N434 are in boldface and underlined.

FIG. 33

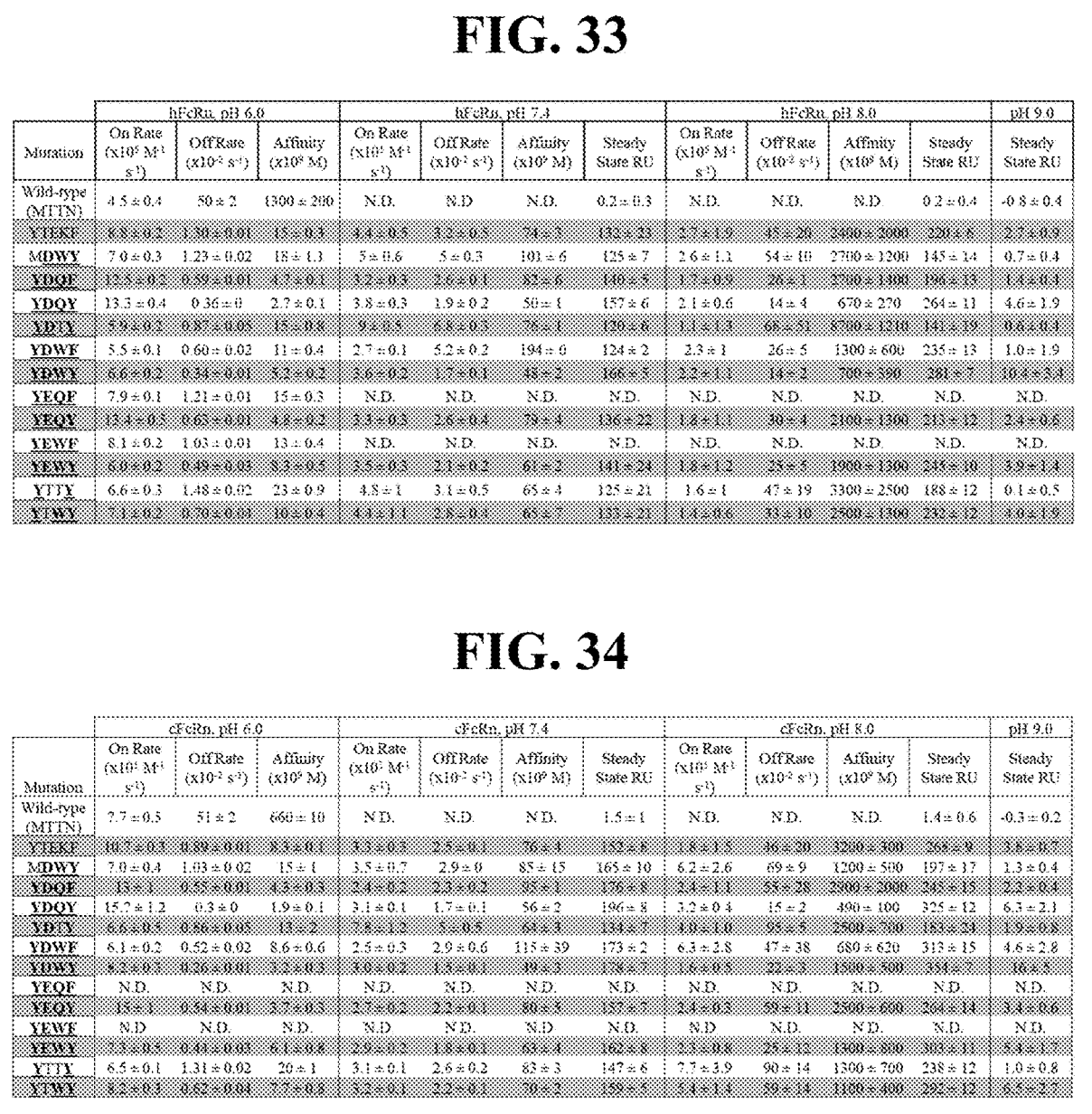

| Mutation | hFcRn, pH 6.0 | | | hFcRn, pH 7.4 | | | | hFcRn, pH 8.0 | | | | pH 9.0 |
| | On Rate (x10⁵ M⁻¹ s⁻¹) | OffRate (x10⁻² s⁻¹) | Affinity (x10⁸ M) | On Rate (x10⁵ M⁻¹ s⁻¹) | OffRate (x10⁻² s⁻¹) | Affinity (x10⁹ M) | Steady State RU | On Rate (x10⁵ M⁻¹ s⁻¹) | OffRate (x10⁻² s⁻¹) | Affinity (x10⁸ M) | Steady State RU | Steady State RU |
|---|---|---|---|---|---|---|---|---|---|---|---|---|
| Wild-type (MTTN) | 4.5 ± 0.4 | 50 ± 2 | 1300 ± 280 | N.D. | N.D. | N.D. | 0.2 ± 0.3 | N.D. | N.D. | N.D. | 0.2 ± 0.4 | -0.8 ± 0.4 |
| YDKF | | | | | | | | | | | | |
| MDWY | 7.0 ± 0.3 | 1.23 ± 0.02 | 18 ± 1.3 | 5 ± 0.6 | 5 ± 0.3 | 101 ± 6 | 125 ± 7 | 2.6 ± 1.1 | 54 ± 10 | 2700 ± 1200 | 145 ± 14 | 0.7 ± 0.4 |
| YDQF | | | | | | | | | | | | |
| YDQY | 13.3 ± 0.4 | 0.36 ± 0 | 2.7 ± 0.1 | 3.8 ± 0.3 | 1.9 ± 0.2 | 50 ± 1 | 157 ± 6 | 2.1 ± 0.6 | 14 ± 4 | 670 ± 270 | 264 ± 11 | 4.6 ± 1.9 |
| YDTY | | | | | | | | | | | | |
| YDWF | 5.5 ± 0.1 | 0.60 ± 0.03 | 11 ± 0.4 | 2.7 ± 0.1 | 5.2 ± 0.2 | 194 ± 6 | 124 ± 2 | 2.3 ± 1 | 26 ± 5 | 1300 ± 600 | 235 ± 13 | 1.0 ± 1.9 |
| YDWY | | | | | | | | | | | | |
| YEQF | 7.9 ± 0.1 | 1.21 ± 0.01 | 15 ± 0.3 | N.D. | N.D. | N.D. | N.D. | N.D. | N.D. | N.D. | N.D. | N.D. |
| YEQY | | | | | | | | | | | | |
| YEWF | 8.1 ± 0.2 | 1.03 ± 0.01 | 13 ± 0.4 | N.D. | N.D. | N.D. | N.D. | N.D. | N.D. | N.D. | N.D. | N.D. |
| YEWY | | | | | | | | | | | | |
| YTTY | 6.6 ± 0.3 | 1.48 ± 0.02 | 23 ± 0.9 | 4.8 ± 1 | 3.1 ± 0.5 | 65 ± 4 | 125 ± 21 | 1.6 ± 1 | 47 ± 19 | 3300 ± 2500 | 188 ± 12 | 0.1 ± 0.5 |
| YTWY | | | | | | | | | | | | |

FIG. 34

| Mutation | cFcRn, pH 6.0 | | | cFcRn, pH 7.4 | | | | cFcRn, pH 8.0 | | | | pH 9.0 |
| | On Rate (x10⁵ M⁻¹ s⁻¹) | OffRate (x10⁻² s⁻¹) | Affinity (x10⁸ M) | On Rate (x10⁵ M⁻¹ s⁻¹) | OffRate (x10⁻² s⁻¹) | Affinity (x10⁹ M) | Steady State RU | On Rate (x10⁵ M⁻¹ s⁻¹) | OffRate (x10⁻² s⁻¹) | Affinity (x10⁹ M) | Steady State RU | Steady State RU |
|---|---|---|---|---|---|---|---|---|---|---|---|---|
| Wild-type (MTTN) | 2.7 ± 0.5 | 51 ± 2 | 660 ± 10 | N.D. | N.D. | N.D. | 1.5 ± 1 | N.D. | N.D. | N.D. | 1.4 ± 0.6 | -0.3 ± 0.2 |
| YDKF | | | | | | | | | | | | |
| MDWY | 7.0 ± 0.4 | 1.03 ± 0.02 | 15 ± 1 | 3.5 ± 0.7 | 2.9 ± 0 | 85 ± 15 | 165 ± 10 | 6.2 ± 2.6 | 69 ± 9 | 1200 ± 500 | 197 ± 17 | 1.3 ± 0.4 |
| YDQF | | | | | | | | | | | | |
| YDQY | 15.2 ± 1.2 | 0.3 ± 0 | 1.9 ± 0.1 | 3.1 ± 0.1 | 1.7 ± 0.1 | 56 ± 2 | 196 ± 8 | 3.2 ± 0.4 | 15 ± 2 | 490 ± 100 | 325 ± 12 | 6.3 ± 2.1 |
| YDTY | | | | | | | | | | | | |
| YDWF | 6.1 ± 0.2 | 0.52 ± 0.02 | 8.6 ± 0.6 | 2.5 ± 0.3 | 2.9 ± 0.6 | 115 ± 39 | 173 ± 2 | 6.3 ± 2.8 | 47 ± 38 | 680 ± 620 | 313 ± 15 | 4.6 ± 2.8 |
| YDWY | | | | | | | | | | | | |
| YEQF | N.D. | N.D. | N.D. | N.D. | N.D. | N.D. | N.D. | N.D. | N.D. | N.D. | N.D. | N.D. |
| YEQY | | | | | | | | | | | | |
| YEWF | N.D. | N.D. | N.D. | N.D. | N.D. | N.D. | N.D. | N.D. | N.D. | N.D. | N.D. | N.D. |
| YEWY | | | | | | | | | | | | |
| YTTY | 6.5 ± 0.1 | 1.31 ± 0.02 | 20 ± 1 | 3.1 ± 0.1 | 2.6 ± 0.2 | 83 ± 3 | 147 ± 6 | 7.7 ± 3.9 | 90 ± 14 | 1300 ± 700 | 238 ± 12 | 1.0 ± 0.8 |
| YTWY | | | | | | | | | | | | |

SEQUENCE LISTING

<160> NUMBER OF SEQ ID NOS: 5

<210> SEQ ID NO 1
<211> LENGTH: 217
<212> TYPE: PRT
<213> ORGANISM: Homo sapiens

<400> SEQUENCE: 1

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
        210                 215
```

```
<210> SEQ ID NO 2
<211> LENGTH: 217
<212> TYPE: PRT
<213> ORGANISM: Homo sapiens

<400> SEQUENCE: 2
```

```
Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160
```

```
Tyr Lys Thr Thr Pro Pro Val Leu Asp Ser Asp Gly Ser Phe Phe Leu
                165             170             175

Tyr Ser Arg Leu Thr Val Asp Lys Ser Arg Trp Gln Glu Gly Asn Val
            180             185             190

Phe Ser Cys Ser Val Met His Glu Ala Leu His Asn His Tyr Thr Gln
        195             200             205

Lys Ser Leu Ser Leu Ser Leu Gly Lys
    210             215

<210> SEQ ID NO 3
<211> LENGTH: 216
<212> TYPE: PRT
<213> ORGANISM: Homo sapiens

<400> SEQUENCE: 3

Ala Pro Pro Val Ala Gly Pro Ser Val Phe Leu Phe Pro Pro Lys Pro
1               5               10              15

Lys Asp Thr Leu Met Ile Ser Arg Thr Pro Glu Val Thr Cys Val Val
            20              25              30

Val Asp Val Ser His Glu Asp Pro Glu Val Gln Phe Asn Trp Tyr Val
        35              40              45

Asp Gly Val Glu Val His Asn Ala Lys Thr Lys Pro Arg Glu Glu Gln
    50              55              60

Phe Asn Ser Thr Phe Arg Val Val Ser Val Leu Thr Val Val His Gln
65              70              75              80

Asp Trp Leu Asn Gly Lys Glu Tyr Lys Cys Lys Val Ser Asn Lys Gly
            85              90              95

Leu Pro Ala Pro Ile Glu Lys Thr Ile Ser Lys Thr Lys Gly Gln Pro
            100             105             110

Arg Glu Pro Gln Val Tyr Thr Leu Pro Pro Ser Arg Glu Glu Met Thr
            115             120             125

Lys Asn Gln Val Ser Leu Thr Cys Leu Val Lys Gly Phe Tyr Pro Ser
        130             135             140

Asp Ile Ala Val Glu Trp Glu Ser Asn Gly Gln Pro Glu Asn Asn Tyr
145             150             155             160

Lys Thr Thr Pro Pro Met Leu Asp Ser Asp Gly Ser Phe Phe Leu Tyr
                165             170             175

Ser Lys Leu Thr Val Asp Lys Ser Arg Trp Gln Gln Gly Asn Val Phe
            180             185             190

Ser Cys Ser Val Met His Glu Ala Leu His Asn His Tyr Thr Gln Lys
        195             200             205

Ser Leu Ser Leu Ser Pro Gly Lys
    210             215

<210> SEQ ID NO 4
<211> LENGTH: 217
<212> TYPE: PRT
<213> ORGANISM: Homo sapiens

<400> SEQUENCE: 4

Ala Pro Glu Leu Leu Gly Gly Pro Ser Val Phe Leu Phe Pro Pro Lys
1               5               10              15

Pro Lys Asp Thr Leu Met Ile Ser Arg Thr Pro Glu Val Thr Cys Val
            20              25              30

Val Val Asp Val Ser His Glu Asp Pro Glu Val Gln Phe Lys Trp Tyr
        35              40              45
```

-continued

```
Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
                100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
            195                 200                 205

Lys Ser Leu Ser Leu Ser Pro Gly Lys
    210                 215
```

```
<210> SEQ ID NO 5
<211> LENGTH: 8
<212> TYPE: PRT
<213> ORGANISM: Artificial Sequence
<220> FEATURE:
<223> OTHER INFORMATION: /note="Description of Artificial Sequence:
      Synthenic polypeptide, poly-histidine tag"

<400> SEQUENCE: 5

His His His His His His His His
1               5
```

METHODS OF TREATING ANTIBODY-MEDIATED DISORDERS WITH FcRn ANTAGONISTS

CROSS REFERENCE TO RELATED APPLICATION

This application claims priority from U.S. Patent Application 62/878,541, filed Jul. 25, 2019, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 23, 2020, is named 022548_US062_SL.txt and is 8,193 bytes in size.

BACKGROUND OF THE INVENTION

The interaction of antibodies with neonatal Fc receptor (FcRn) is a determinant in maintaining and prolonging the serum half-life of antibodies and Fc-derived therapeutics. FcRn is a heterodimer of an MHC class-I-like α-domain and a β2-microglobulin (β2-m) subunit which recognizes regions in the antibody Fc domain distinct from other Fcγ receptors (FcγRs). While FcRn is expressed in various tissues, it is thought to act mainly in the vascular endothelium and kidneys and at the blood brain barrier.

Antibody binding to FcRn is highly pH-dependent, and the interaction only occurs with high affinity (high nanomolar to low micromolar) at low pH (pH<6.5), but not at physiological pH (pH approximately 7.4). Upon acidification of the endosome to a pH less than 6.5, the interaction between IgG and FcRn becomes highly favorable, and is directly responsible for inhibiting degradation and promoting recycling of FcRn-bound antibodies to the cell surface. The increase in pH weakens the interaction and promotes release of antibodies into the bloodstream.

Fc engineering using high-throughput mutagenesis approaches has been extensively pursued to identify variants that enhance FcRn binding affinity, as enhanced binding would presumably lead to increased efficacy and reduced dosage frequency for therapeutic antibodies as a direct result of a prolonged serum half-life compared to wildtype IgG antibodies. However, variants that enhance FcRn binding affinity can have unpredicted results. For example, certain IgG variants that show large increases in FcRn affinity at pH 6.0, such as those with N434W or P257I/Q311I substitutions, among others, have wildtype or severely reduced serum half-lives in cynomolgus monkey and in mice transgenic for human FcRn (hFcRn) (see, e.g., Kuo et al., Mabs. (2011) 3(5):422-30; Datta-Mannan et al., *J Biol Chem.* (2007) 282:1709-17; and Datta-Mannan et al., *Metab Dispos.* (2007) 35:86-94). The T250Q/M428L (QL) variant has shown Fv-specific results in animal models (see, e.g., Datta-Mannan, 2007, supra; and Hinton et al., *J Immunol.* (2006) 176:346-56). The M252Y/S254T/T256E (YTE, Eu numbering) variant has shown a 10-fold enhancement in vitro, but displays decreased antibody-dependent cell-mediated cytotoxicity (ADCC) in vivo due to a 2-fold reduction in affinity for the FcγRIIIa receptor (see, e.g., Dall'Acqua et al., *J Immunol.* (2002) 169(9):5171-80).

Fc variants that bind FcRn with enhanced affinity and decreased pH dependence may find use in increasing the clearance of IgGs from the blood circulation. It has been found that FcRn-mediated IgG recycling is the dominant process for maintaining IgG plasma concentrations in humans (Xiao, *J Biomed Biotechnol.* (2012) 2012:282989). Increased clearance of IgGs from the circulation would be desirable, e.g., in autoimmune diseases such as systemic lupus erythematosus where circulating autoreactive antibodies cause pathology, and in situations where IgG-complexed toxins, drugs, or diagnostic agents need to be cleared rapidly from the body. Increased clearance of an undesired antibody can be achieved by using an FcRn antagonist, such as an antibody with an engineered Fc, that binds to FcRn with high affinity and does not dissociate rapidly at near neutral pH. Such engineered antibodies are called Abdegs, for antibodies that enhance IgG degradation (Swiercz et al., *J Nucl Med.* (2014) 55(7):1204-7). Such FcRn antagonists would not be released from cells, but would instead be predicted to remain bound to FcRn and block binding of other, lower affinity IgGs. As a result, FcRn function would be blocked and endogenous or undesired IgGs would be directed into the lysosomal pathway for degradation.

There is a need for methods of treating IgG-mediated diseases by using Fc variants that possess enhanced binding affinity for FcRn and exhibit loss of pH dependence in their binding to FcRn.

SUMMARY OF THE INVENTION

The present disclosure provides a method of treating an antibody-mediated (e.g., IgG-mediated) disorder in a subject in need thereof, comprising administering to the subject (e.g., a human) a therapeutically effective amount of an FcRn antagonist comprising a modified Fc domain. The therapeutically effective amount of the FcRn antagonist will increase the rate of serum IgG clearance in the treated subject.

In some embodiments, the modified Fc domain comprises a combination of at least four amino acid substitutions comprising: an aspartic acid (D) or a glutamic acid (E) at amino acid position 256, and a tryptophan (W) or a glutamine (Q) at amino acid position 307, wherein amino acid position 254 is not threonine (T), and further comprising: a phenylalanine (F) or a tyrosine (Y) at amino acid position 434; and a tyrosine (Y) at amino acid position 252. Unless otherwise indicated, all Fc residue positions described herein are according to the Eu numbering system.

In some embodiments, the modified Fc domain comprises a combination of amino acid residues selected from the group consisting of: a) a tyrosine (Y) at amino acid position 252, an aspartic acid (D) at amino acid position 256, a glutamine (Q) at amino acid position 307, and a tyrosine (Y) at amino acid position 434; b) a tyrosine (Y) at amino acid position 252, a glutamic acid (E) at amino acid position 256, a tryptophan (W) at amino acid position 307, and a tyrosine (Y) at amino acid position 434; c) a tyrosine (Y) at amino acid position 252, a glutamic acid (E) at amino acid position 256, a glutamine (Q) at amino acid position 307, and a tyrosine (Y) at amino acid position 434; d) a tyrosine (Y) at amino acid position 252, an aspartic acid (D) at amino acid position 256, a glutamine (Q) at amino acid position 307, and a phenylalanine (F) at amino acid position 434; e) a tyrosine (Y) at amino acid position 252, an aspartic acid (D) at amino acid position 256; a tryptophan (W) at amino acid position 307, and a tyrosine (Y) at amino acid position 434; f) a tyrosine (Y) at amino acid position 252, an aspartic acid (D) at amino acid position 256, a tryptophan (W) at amino acid position 307, and a phenylalanine (F) at amino acid position 434; g) a tyrosine (Y) at amino acid position 252 and a tyrosine (Y) at amino acid position 434; h) a tyrosine (Y) at amino acid position 252, a tryptophan (W) at amino acid position 307, and a tyrosine (Y) at amino acid position 434; i) a tyrosine (Y) at amino acid position 252, an aspartic acid (D) at amino acid position 256, and a tyrosine (Y) at amino acid position 434; or j) an aspartic acid (D) at amino acid position 256, a tryptophan (W) at amino acid position 307, and a tyrosine (Y) at amino acid position 434.

In certain embodiments, the modified Fc domain comprises a combination of amino acid substitutions selected from the group consisting of M252Y/T256D/T307Q/N434Y, M252Y/T256E/T307W/N434Y, M252Y/T256E/T307Q/N434Y, M252Y/T256D/T307Q/N434F, M252Y/T256D/T307W/N434Y, M252Y/T256D/T307W/N434F, M252Y/N434Y, M252Y/T307W/N434Y, M252Y/T256D/N434Y, and T256D/307W/N434Y.

In certain embodiments, the modified Fc domain is a modified human IgG Fc domain, such as a modified human IgG1, IgG2, IgG3, or IgG4 Fc domain, or a Fc domain derived from one or more of the human Fc domains.

In certain embodiments, the modified Fc domain has binding affinity for FcRn from one or more species, such as human, cynomolgus monkey, mouse, and rat. For example, the modified Fc domain has binding affinity for both human FcRn (hFcRn) and rat FcRn (rFcRn).

In certain embodiments, the modified Fc domain has enhanced FcRn binding affinity (e.g., enhanced binding affinity for hFcRn) compared to a wildtype Fc domain. In certain exemplary embodiments, the modified Fc domain has enhanced FcRn binding affinity at an acidic pH (e.g., about 6.0) compared to a wildtype Fc domain. In certain exemplary embodiments, the modified Fc domain has enhanced FcRn binding affinity at an acidic pH compared to an Fc domain having the quintuple mutations M252Y/S254T/T256E/H433K/N434F ("YTEKF").

In certain embodiments, the modified Fc domain has enhanced FcRn binding affinity at a non-acidic pH (e.g., about 7.4) compared to a wildtype Fc domain. In certain exemplary embodiments, the modified Fc domain has enhanced FcRn binding affinity at a non-acidic pH compared to an Fc domain having the YTEKF mutations.

In certain embodiments, the modified Fc domain has enhanced FcRn binding affinity at an acidic pH, and enhanced FcRn binding affinity at a non-acidic pH, compared to a wildtype Fc domain. In certain exemplary embodiments, the modified Fc domain has enhanced FcRn binding affinity at an acidic pH, and enhanced FcRn binding affinity at a non-acidic pH, compared to an Fc domain having the YTEKF mutations.

In certain embodiments, the modified Fc domain has reduced FcγRIIIa binding affinity compared to a wildtype Fc domain.

In certain embodiments, the FcRn antagonist is a binding polypeptide such as an antibody or comprises an antigen-binding fragment thereof (e.g., an Fv fragment, a single chain antibody (ScFv), an Fab, an Fab-H, an Fab', and an F(ab')2). The binding polypeptide may one or more targets that are not FcRn.

In some embodiments, the IgG-mediated disorder to be treated by the present methods is an autoimmune disease. In certain exemplary embodiments, the autoimmune disease is selected from the group consisting of graft versus host disease (GVHD), systemic lupus erythematosus (SLE), myasthenia gravis, systemic sclerosis (SSc)/scleroderma, rheumatoid arthritis, psoriatic arthritis, osteoarthritis, diabetes, multiple sclerosis, pemphigus vulgaris, atopic dermatitis, psoriasis, asthma, allergy, idiopathic pulmonary fibrosis (IPF), idiopathic thrombocytopenia purpura (ITP), and hidradenitis suppurativa.

In certain aspects, the present disclosure provides a method of enhancing diagnostic imaging comprising administering to a subject a therapeutically effective amount of an FcRn antagonist described herein. In certain embodiments, the method further comprises administering to the subject an effective amount of a radiolabeled antibody. In further embodiments, the FcRn antagonist is administered after the radiolabeled antibody and enhances contrast for the radiolabeled antibody.

In certain aspects, the present disclosure provides a method of reducing exposure of a non-target tissue to a radiolabeled antibody during diagnostic imaging, comprising administering to a subject a therapeutically effective amount of an FcRn antagonist described herein.

Also provided are use of the FcRn antagonists herein for the manufacture of a medicament for use in the present treatment and diagnostic methods, as well as FcRn antagonists for use in the present treatment and diagnostic methods.

The present disclosure also provides nucleic acids encoding the FcRn antagonist polypeptides, recombinant expression vectors and host cells for making the polypeptides, and pharmaceutical compositions comprising the FcRn antagonists disclosed herein. Methods of using the FcRn antagonists of the present disclosure to treat diseases are also provided.

The foregoing and other features and advantages of the present invention will be more fully understood from the following detailed description of illustrative embodiments taken in conjunction with the accompanying drawings.

BRIEF DESCRIPTION OF THE DRAWINGS

FIGS. 1A and 1B depict the structure of an FcRn interacting with an IgG1 Fc region. FIG. 1A depicts an interaction between hFcRn and an IgG1 Fc (pdb: 4n0u) showing one Fc monomer (dark gray ribbon), including the glycosylation shown as sticks labeled by "Glycan," in complex with the α-domain (gray) and β2-m (light gray) hFcRn subunits. A majority of the antibody residues involved in the interaction with FcRn are located in the loops directly adjacent to the $C_H2$-$C_H3$ interface (dotted line) and opposite the glycosylation site. FIG. 1B depicts a surface representation of the IgG1 Fc crystal structure (pdb: 5d4q) rotated 75° with respect to FIG. 1A. The FcRn binding interface is comprised of residues in the $C_H2$ and $C_H3$ domains. The saturation library was constructed at the eleven positions shown as sticks, as indicated: M252; I253; S254; T256; K288; T307; K322; E380; L432; N434 and Y436. All of these residues are in close proximity or direct contact with FcRn. The surfaces of the critical histidine residues responsible for the pH dependence (H310, H433, H435) cluster near the positions of interest and are as indicated.

FIG. 2A schematically presents an Octet screening assay. NiNTA biosensors capture the histidine-tagged antigen and, subsequently, the antibody variants for rat FcRn (rFcRn) binding kinetics. FIG. 2B depicts rFcRn binding kinetic profiles at pH 6.0 of the wildtype (solid), T307A/E380A/N434A (AAA) variant (short dashes), LS (short dashes interspersed by single dot), YTE (long dashes), H435A (long dashes interspersed by single dot) and H310A/H435Q (long dashes interspersed by two dots) antibodies, aligned to the start of the rFcRn association phase. The H435A and H310A/H435Q variants showed little to no FcRn binding.

The YTE variant has the slowest FcRn off-rate examined in Octet rFcRn binding assay. FIG. 2C graphically depicts normalization of FcRn binding kinetics at pH 6.0 by a subset of mutants obtained from the Octet screen. Most mutants retained significant binding to rFcRn, but several resembled the mock control (dotted line), indicating the loss of all rFcRn binding (long dashes, located below dotted line (mock)). Two variants (N434F and N434Y; solid lines) had slower rFcRn off-rates Two variants (solid lines) had slower rFcRn off-rates than the wildtype antibody (thick long dashes).

FIG. 2D depicts a scatterplot analysis of the rFcRn off-rates for all point mutations, with observable rFcRn binding kinetics separated by residue position. The saturation variants fell into one of the following four rFcRn off-rate regimes: no binding (not shown), faster binding (black), wildtype-like binding (white), slower binding (gray). Eighteen mutants (E380C, K288D, K288N, M252Y, T256D, T256E, N434F, N434P, N434Y, T307A, T307E, T307F, T307M, T307Q, T307W, Y436H, Y436N and Y436W) showed a significantly slower off-rate from rFcRn than the wildtype antibody (black dashed lines).

FIGS. 5A and 5B depict Biacore™ sensorgrams of various variants. FIG. 5A depicts the off-rates of human FcRn at pH 6.0 for the YTE variant (long dashes interspersed by single dot), LS variant (long dashes interspersed by two dots, wildtype (WT; dotted line), and lead saturation variants (leads E380C, K288D, K288N, M252Y, T256D, T256E, N434F, N434P, N434Y, T307A, T307E, T307F, T307M, T307Q, T307W, Y436H, Y436N, and Y436W); solid lines in various shades). In FIG. 5A, normalized sensorgrams are depicted showing improved hFcRn off-rates compared to the WT. FIG. 5B depicts the off-rates of rat FcRn at pH 6.0 for the AAA variant (dotted), LS variant (dashes interspersed by two dots), YTE variant (dashes interspersed by single dot), wildtype (solid line) and the 18 lead saturation variants (dashed lines in various frequencies and thicknesses). A representative injection of each of the eleven lead antibodies is shown for clarity. These lead single variants showed improved off-rate kinetics from both human and rat FcRn compared to the wildtype. FIG. 5C and FIG. 5D depict binding affinity plots for the 18 lead saturation (white circles) and wildtype (black circle) antibody variants for human (FIG. 5C) and rat (FIG. 5D) FcRn using the on and off-rates obtained from Biacore™ kinetic measurements. The benchmark variants are shown: AAA (diagonal lines facing bottom right), LS (dotted) and YTE (diagonal lines facing bottom left). Despite the improvement in the FcRn off-rate, a majority of the variants did not have a tighter affinity for human or rat FcRn, due to slower association kinetics. Eleven variants had slower off-rates from both species of FcRn.

FIG. 6A and FIG. 6B depict representative Biacore™ sensorgrams showing FcRn off-rates for human and rat FcRn, respectively. FIG. 6A depicts normalized sensorgrams for human FcRn of a representative variant of the single (T256E; dashed line), double (variant YETN (M252Y/T256E); solid light gray line), triple (variant MDQY (T256D/T307Q/N434Y); solid gray line) and quadruple (variant YEQY (M252Y/T256E/T307Q/N434Y); solid black line) combination variants in comparison to the wildtype (dotted line) and LS variant (long dashes interspersed by two dots). FIG. 6B depicts normalized sensorgrams for rat FcRn of a representative variant of the single (long dashes interspersed by two dots), double (variant METF; long dashes interspersed by single dot), triple (variant MEWY; long dashes), and quadruple (variant YDWF; short dashes) combination variants in comparison to the wildtype (dotted line) and YTE variant (solid line). Incorporation of multiple mutations decreased the off-rate and enhanced the binding affinity for FcRn to a greater extent than the benchmark variants. FIG. 6C and FIG. 6D depict plots of combination saturation variants showing on-rate as a function of off-rate for human (FIG. 6C) or rat (FIG. 6D) FcRn, which revealed that a majority of the variants possessed enhanced binding to FcRn at pH 6.0 as compared to the benchmark variants. The tightest binding variants to human and rat FcRn were the quadruple (variants YDWY, YDQY, YDWF, YEWY, and YEQY, for hFcRn) and double combinations (variants YTTY, YTTF, MDTY, YDTF, and MTWY, for rFcRn), respectively.

FIG. 7A and FIG. 7B depict representative sensorgrams of Biacore™ FcRn binding kinetics at pH 7.4 of the single (long dashes interspersed with two dots), double (long dashes interspersed with single dot), triple (long dashes) and quadruple (short dashes) combination variants in comparison to the wildtype (dotted), and the LS variant (FIG. 7A, solid line) and the YTE variant (FIG. 7B, solid line). Increasing the number of FcRn binding-enhancing mutations resulted in greater residual binding at physiological pH, with most double, triple and quadruple variants showing robust binding to both species of FcRn. FIG. 7C and FIG. 7D depict plots of the steady state resonance unit $$\left(RU; RU = \text{offset} + \frac{(R_{max} - \text{offset}) * [\text{Antibody}]}{[\text{Antibody}] + K_{D,app}}\right) \qquad \text{(Equation 2)}$$

of all saturation variants to human (FIG. 7C) or rat (FIG. 7D) FcRn at pH 7.4 as a function of the binding affinity at pH 6.0. In FIG. 7C, comparison of the residual FcRn binding at pH 7.4 with the FcRn binding affinity at pH 6.0 is shown. Lead combinations (MDQN, MDWN, YETN, YTWN, YDQN and YEQN) with improved FcRn binding properties occupy the lower left quadrant defined by the LS benchmark variant (diamond). In FIG. 7D, the LS (diamond) and YTE (triangle) variants serve as cutoffs for lead validation, respectively. These two variants had the tightest binding affinity at pH 6.0 and the largest residual binding at pH 7.4 for human and rat FcRn, respectively. In both FIGS. 7C and 7D, single (white circles), double (light gray circles), triple (dark gray circles), and quadruple (black circles) variants as well as the YTE variant (triangle) are shown.

FIG. 8A depicts the normalized elution profiles for the WT (solid black line), AAA (dotted line), LS (long dashes interspersed by two dots), YTE (long dashes interspersed by single dot), H435A (solid light gray line) and H310A/H435Q (AQ; solid dark gray line) variants. The pH is noted at the top of the graph. The FcRn binding null variants (H435A, H310A/H435Q) do not bind to the column and elute in the flow through (<10 mL). The AAA, LS and YTE variants elute at higher pH than the WT antibody. FIG. 8B depicts DSF profiles of the WT (black), LS (gray) and YTE (dark gray) variants. YTE was destabilized compared to WT and LS. FIG. 8C depicts FcRn affinity column elution profiles of the seven lead single variants used for the combination variants in comparison to the WT and LS variants (vertical dotted). Two variants (N434F/Y) elute at a higher pH than LS, signifying a reduced pH dependence on the interaction with FcRn for variants containing these mutations.

FIG. 9A depicts representative FcRn affinity chromatograms of single (long dashes interspersed by two dots), double (long dashes interspersed by single dot), triple (long dashes) and quadruple variants (short dashes). Increasing the number of FcRn binding-enhancing mutations shifted the elution towards higher pH values; LS variant (small dotted vertical line). FIG. 9B depicts a box plot of the elution pH for the lead saturation and combination variants, including the single (white circles), double (horizontal lines), triple (vertical lines) and quadruple (checkered) mutants, which indicated a trend toward higher pH values with an increasing number of FcRn enhancing mutants. FIG. 9C shows that the high correlation ($R^2$=0.94) between the elution pH from FcRn affinity chromatography and the hFcRn off-rate using Biacore™ revealed a loss in the pH dependence of the antibody-FcRn interaction with improved FcRn dissociation kinetics. The AAA (diagonal lines facing bottom right), LS (dotted) and YTE (diagonal lines facing bottom left) variants had similar hFcRn off-rates and elution pH values as the double variants. FIG. 9D depicts a box plot of the $T_m$ obtained from DSF of the combination saturation variants revealed that additional FcRn binding enhancing mutations destabilize the antibody compared to the WT, single or benchmark variants.

FIG. 10A depicts FcRn affinity chromatography of the M252Y (solid line), T256D (short dashes interspersed with single dot), T256E (long dashes), T307Q (long dashes interspersed with single dot), T307W (long dashes interspersed with two dots), N434F (dotted) and N434Y (short dashes) variants. Chromatograms revealed a shift in the elution pH compared to the wildtype and LS antibodies (vertical dotted lines). N434F and N434Y had a higher elution pH (pH approximately 8.3) than the LS variant (vertical dotted line). The pH at certain elution volumes are indicated above the chromatograms for reference. FIG. 10B depicts DSF profiles of seven lead variants, which showed that none of the seven lead single variants destabilized the antibodies to the same extent as the YTE variant (vertical dotted line). All variants, except T307Q (long dashes interspersed with single dot), were destabilized compared to WT (vertical dotted line).

FIG. 11A shows FcγRIIIa binding sensorgrams of the WT (black), LS (gray) and YTE (dark gray) variants revealed a reduced binding response by the YTE variant. FIG. 11B depicts a box plot of the FcγRIIIa binding responses of the benchmark, single and combination variants, as indicated. Variants with the M252Y mutations contain a reduced binding response to FcγRIIIa, including all of the quadruple variants. Combinations with N434F/Y typically show an increased response with FcγRIIIa. FIG. 11C depicts the FcγRIIIa binding responses of the seven lead single variants compared to the WT and YTE variants (horizontal dotted). The M252Y mutation shows a reduced FcγRIIIa binding compared to WT, while six show WT-like or increased binding to this receptor.

FIG. 12A depicts FcRn affinity chromatograms of seven lead combination variants in comparison to wildtype antibody and the LS variant (vertical dotted line and solid vertical line respectively). Each lead variant had an elution pH near the LS variant. FIG. 12B shows DSF profiles of the lead combination variants in comparison to the YTE and wildtype variants (vertical dotted lines as indicated). Six of the seven lead variants had a $T_m$ that was similar or more destabilized than the YTE variant: MDWN (long dashes interspersed by two dots); YTWN (long dashes); YDTN (solid line); YETN (long dashes interspersed by single dot); YDQN (dotted); YEQN (short dashes interspersed by single dot). The MDQN variant had a similar $T_m$ to the wildtype antibody (short dashes). FIG. 12C depicts Biacore™ sensorgrams of the FcγRIIIa binding kinetics of the seven lead variants in comparison to wildtype (larger dotted line) and the YTE variant (thick long dashes). The M252Y-containing variants, YDTN (solid line), YDQN (short dashes interspersed by single dot), YTWN (long dashes), YETN (long dashes interspersed by single dot) and YEQN (smaller dotted line), each possessed a reduced steady state RU in a similar manner as YTE. FIG. 12D shows steady state RU of the seven lead variants, wildtype and YTE variant. Only the MDWN and MDQN variants possessed a similar affinity for FcγRIIIa as the wildtype antibody.

FIG. 12E shows FcRn affinity chromatography elution profiles of the DQ (solid), DW (dotted) and YD (dashed) variants in comparison to WT and LS (vertical dotted lines). Each double variant showed an elution pH between WT and LS. FIG. 12F depicts DSF fluorescence profiles of the three variants in comparison to the YTE and WT variants (vertical dotted) revealed that YD (dashed) and DW (dotted) were slightly destabilized compared to YTE, but DQ (solid) was similar to the WT. FIG. 12G depicts FcγRIIIa binding sensorgrams in comparison to WT and YTE (horizontal dotted). YD (dashed) showed a similar binding response as YTE, while DQ (solid) and DW (dotted) showed a slight reduction compared to the WT. FIG. 12H depicts data showing that homogeneous bridging RF ELISA revealed the three lead variants and YTE showed significantly reduced or WT-like RF binding, unlike LS. \*\*p<0.001, \*p<0.01.

FIG. 13A and FIG. 13B show Biacore™ FcRn binding sensorgrams of lead combination variants for human FcRn (FIG. 13A) or rat FcRn (FIG. 13B) compared to wildtype (dotted line) and either LS (hFcRn, FIG. 13A, thick long dashes) or YTE (rFcRn, FIG. 13B, thick long dashes) at pH 6.0. Each combination variant had an overall tighter binding affinity to the respective FcRn despite altered on- and off-rates. FIG. 13C and FIG. 13D show Biacore™ FcRn sensorgrams at pH 7.4. Each hFcRn lead variant had a similar or reduced steady state FcRn binding response as compared to the LS variant. Only the M<u>DQ</u>N and M<u>DWN</u> variants showed less rFcRn binding at pH 7.4 than the YTE variant.

FIG. 14 is a table depicting Octet rFcRn Binding Off-rates of a Saturation Library according to certain embodiments with single mutations. Wildtype (WT) and wildtype-like (WT-like) species are indicated by white rectangles; WT species are as indicated. Variants with little to no rFcRn binding compared to wildtype are indicated by dark gray rectangles. Variants with faster rFcRn off-rate as compared to wildtype are indicated by light gray rectangles, and variants with slower rFcRn off-rate as compared to wildtype are indicated by black rectangles.

FIGS. 15A-C depict a new binding assay developed using a CM5 sensor chip. FIG. 15A is a schematic of the assay. FIG. 15B shows direct immobilization of FcRn. FIG. 15C shows streptavidin capture of biotinylated FcRn.

FIGS. 16A and 16B depict FcRn binding of mAb2 at pH 6.0. FIG. 16A depicts human FcRn. FIG. 16B depicts mouse FcRn.

FIGS. 17A and 17B depict FcRn binding of mAb2 at pH 7.4. FIG. 17A depicts human FcRn. FIG. 17B depicts mouse FcRn.

FIG. 23A depicts normalized cFcRn binding sensorgrams at pH 6.0 of WT (gray), LS (dark gray), DQ (solid black), DW (dotted) and YD (dashed) showing similar binding kinetics and affinities as hFcRn. FIG. 23B depicts that the cFcRn binding response for the three variants was dramatically reduced at physiological pH; LS (dark gray), but showed greater binding than WT (gray) in a similar manner as hFcRn. FIG. 23C depicts a comparison of the residual cFcRn binding response at pH 7.4 with the cFcRn binding affinity at pH 6.0 of WT (gray), LS (dark gray), DQ (solid black), DW (empty) and YD (empty square), revealing all three variants maintained the improved FcRn binding properties observed with hFcRn.

FIGS. 27A-G depict plots showing human and cyno FcRn binding kinetics at pH 6.0, pH 7.4, and pH 8.0 of the YTEKF (ABDEG™) benchmark and FcRn antagonists as indicated. FIG. 27A and FIG. 27B show the concentration dependent binding to human and cyno FcRn, respectively, at pH 6.0 of the WT, YTEKF, and FcRn antagonists. FIG. 27C and FIG. 27D show the concentration dependent binding to human and cyno FcRn, respectively, at pH 7.4 of the WT, YTEKF, and FcRn antagonists. FIG. 27E and FIG. 27F show the concentration dependent binding to human and cyno FcRn, respectively, at pH 8.0 of the WT, YTEKF, and FcRn antagonists. FIG. 27G show the concentration dependent binding to human and rat FcRn at pH 6.0 of the YEQF and YEWF variants.

FIG. 28A shows normalized sensorgrams of the FcRn antagonists (solid) with significant improvement in off rate from hFcRn at pH 6.0 compared to the WT (dashed) and YTEKF (dotted). FIG. 28B shows sensorgrams for hFcRn binding at pH 7.4, which demonstrate significant binding at elevated pH for the FcRn antagonists compared to YTEKF and WT (no binding). FIG. 28C shows normalization of the sensorgrams at pH 7.4, demonstrating significant off rates for the FcRn antagonists compared to YTEKF. FIG. 28D shows sensorgrams for hFcRn binding at pH 8.0, demonstrating significant binding at pH greater than physiological conditions for the FcRn antagonists compared to the YTEKF and WT (no binding). FIG. 28E shows normalization of the sensorgrams at pH 8.0, which demonstrate measurable off rates and affinities for the FcRn antagonists and YTEKF. FIG. 28F shows that pH 9.0 was sufficient to significantly impair hFcRn binding of the FcRn antagonist variants and resembled WT binding at this pH. FIG. 28G shows isoaffinity plots of the hFcRn binding affinities at pH 6.0 (black), 7.4 (gray) and 8.0 (light gray) of the FcRn antagonists, YTEKF (open squares) and WT (pH 6.0 only). Multiple variants possessed greater hFcRn binding affinities than YTEKF at all pH. FIG. 28H shows the binding affinity of FcRn antagonists as a function of pH and demonstrates an order of magnitude reduction in hFcRn binding affinity per pH unit.

FIG. 29A shows normalized sensorgrams of the FcRn antagonists (solid) showing significant improvement in off rate from cFcRn at pH 6.0 compared to the WT (dashed) and YTEKF (dotted). FIG. 29B shows sensorgrams for cFcRn binding at pH 7.4 showing significant binding at elevated pH for the FcRn antagonists compared to YTEKF and WT (no binding. FIG. 29C shows normalization of sensorgrams at pH 7.4, demonstrating significant off rates for the FcRn antagonists compared to YTEKF. FIG. 29D shows sensorgrams for hFcRn binding at pH 8.0 showing significant binding at pH greater than physiological conditions for the FcRn Antagonists compared to YTEKF and WT (no binding). FIG. 29E shows normalization of sensorgrams at pH 8.0 showing measurable off rates and affinities for the FcRn antagonists and YTEKF. FIG. 29F shows that a pH 9.0 was sufficient to significantly impair cFcRn binding of the FcRn antagonists and resembled WT binding at this pH. FIG. 29G shows isoaffinity plots of the cFcRn binding affinities at pH 6.0 (black), 7.4 (gray) and 8.0 (light gray) of the FcRn antagonists, YTEKF (open squares) and WT (pH 6.0 only). Multiple variants possessed greater cFcRn binding affinities than YTEKF at all pH. FIG. 29H shows binding affinity of FcRn antagonists as a function of pH and demonstrates an order of magnitude reduction in cFcRn binding affinity per pH unit.

FIG. 30A shows the clearance profiles for all groups. FIG. 30B shows the profiles for only Group 2 (control) and Group 6. FIG. 30C shows the profiles for Group 2 (control), Group 4 (YDQY hIgG1), and Group 7 (YTEKF hIgG1).

FIG. 32 shows a sequence alignment of the human IgG1, IgG2, IgG3, and IgG4 constant regions from residues 231-447 (Eu numbering). The FcRn mutagenesis positions described herein (M252, T256, T307, and N434) are conserved in all four subclasses.

FIG. 33 shows in vitro human FcRn binding characterization parameters of the FcRn-binding Fc variants under multiple pH conditions. For each variant, the substitution mutations relative to the WT sequence (M252/T256/T307/

Figure 2A:
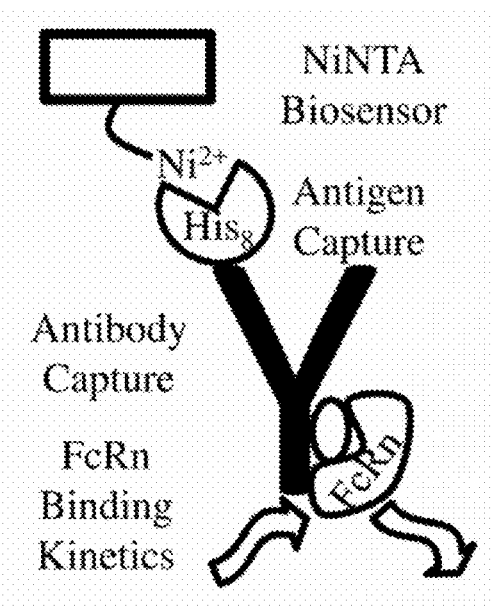
FIGS. 2A-D depict an Octet screening assay and results.

N434; MTTN) are bold and underlined (e.g., MDWY refers to a variant having T256D, T307W and N434Y mutations).

FIG. 34 shows in vitro cyno binding characterization parameters of the FcRn-binding Fc variants under multiple pH conditions.

DETAILED DESCRIPTION OF THE INVENTION

The present disclosure provides polypeptides (e.g., monoclonal antibodies or fragments thereof) having altered FcRn binding affinities. These polypeptides contain a modified IgG Fc domain that has enhanced FcRn binding affinity as compared to wildtype IgG (e.g., human IgG1, IgG2, IgG3, or IgG4) Fc domain under both acidic and non-acidic conditions. Thus, unlike a wildtype IgG Fc domain, the present polypeptides bind to FcRn in a manner that is less pH-dependent. These polypeptides remain bound to FcRn as the FcRn traffics between the cell surface and the cytoplasm, which have different pH conditions. As a result, other IgG molecules (e.g., serum IgG), which have wildtype (lower) FcRn binding affinities, are blocked from binding to the FcRn and are directed at increased rates into the lysosomal pathways for degradation, which leads to faster clearance of the IgG molecules from the body.

Due to their disruption of FcRn's normal function in mediating IgG recycling and maintaining serum IgG levels, the present polypeptides are termed "FcRn antagonists." An FcRn antagonist of the present disclosure may be an antibody, an immunoadhesin or another form of Fc fusion protein, or a Fc fragment or portion thereof. The FcRn antagonist may be, for example, a monomeric protein or a dimeric (hetero- or homo-dimeric) protein. Because the FcRn antagonists enhance serum IgG clearance from the body, they can be used in treating patients who suffer from IgG-mediated diseases or disorders (e.g., autoimmune diseases), or in removing from the body undesired IgG (e.g., therapeutic or diagnostic antibody that is no longer needed or beneficial).

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel et al., Eds., Current Protocols in Molecular Biology, John Wiley & Sons, Inc., NY, N.Y. (1987-2008), including all supplements; Green et al., Eds., Molecular Cloning: A Laboratory Manual (Fourth Edition); Antibodies: A Laboratory Manual, Chapter 14, Cold Spring Harbor Laboratory, Cold Spring Harbor (2013, 2$^{nd}$ edition).

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting. The words "have" and "comprise," or variations such as "has," "having," "comprises," or "comprising," will be understood to imply the inclusion of a stated integer or group of integers but not the exclusion of any other integer or group of integers.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients. All publications and other references mentioned herein are incorporated by reference in their entirety. So that the disclosure may be more readily understood, select terms are defined below.

The term "polypeptide" refers to any polymeric chain of amino acids and encompasses native or artificial proteins, polypeptide analogs or variants of a protein sequence, or fragments thereof, unless otherwise contradicted by context. A polypeptide may be monomeric or polymeric; that is, the term encompasses a protein having one or more covalently coupled, or noncovalently coupled, polypeptide chains. A polypeptide fragment comprises at least about 5 contiguous amino acids, at least about 10 contiguous amino acids, at least about 15 contiguous amino acids, or at least about 20 contiguous amino acids, for example.

The term "isolated protein" or "isolated polypeptide" refers to a protein or polypeptide that by virtue of its origin or source of derivation is not associated with naturally associated components that accompany it in its native state; is substantially free of other proteins from the same species; is expressed by a cell from a different species; or does not occur in nature. Thus, a protein or polypeptide that is chemically synthesized or synthesized in a cellular system different from the cell from which it naturally originates will be "isolated" from its naturally associated components. A protein or polypeptide may also be rendered substantially free of naturally associated components by isolation using protein purification techniques well known in the art.

As used herein, the term "binding protein" or "binding polypeptide" shall refer to a protein or polypeptide (e.g., an antibody or immunoadhesin) that contains at least one binding site which is responsible for selectively binding to a target antigen of interest (e.g., a human target antigen). Exemplary binding sites include an antibody variable domain, a ligand binding site of a receptor, or a receptor binding site of a ligand. In certain aspects, the binding proteins or binding polypeptides comprise multiple (e.g., two, three, four, or more) binding sites. In certain aspects, the binding protein or binding polypeptide is not a therapeutic enzyme.

The term "ligand" refers to any substance capable of binding, or of being bound, to another substance. Similarly, the term "antigen" refers to any substance to which an antibody may be generated. Although "antigen" is com-monly used in reference to an antibody binding substrate, and "ligand" is often used when referring to receptor binding substrates, these terms are not distinguishing, one from the other, and encompass a wide range of overlapping chemical entities. For the avoidance of doubt, antigen and ligand are used interchangeably throughout herein. Antigens/ligands may be a peptide, a polypeptide, a protein, an aptamer, a polysaccharide, a sugar molecule, a carbohydrate, a lipid, an oligonucleotide, a polynucleotide, a synthetic molecule, an inorganic molecule, an organic molecule, and any combination thereof.

The term "specifically binds" as used herein, refers to the ability of an antibody or an immunoadhesin to bind to an antigen with a dissociation constant (Kd) of at most about $1 \times 10^{-6}$ M, about $1 \times 10^{-7}$ M, about $1 \times 10^{-8}$ M, about $1 \times 10^{-9}$ M, about $1 \times 10^{-10}$ M, about $1 \times 10^{-11}$ M, about $1 \times 10^{-12}$ M or less, and/or to bind to an antigen with an affinity that is at least about two-fold greater than its affinity for a nonspecific antigen.

As used herein, the term "antibody" refers to such assemblies (e.g., intact antibody molecules, immunoadhesins, or variants thereof) which have significant known specific immunoreactive activity to an antigen of interest. Antibodies and immunoglobulins comprise light and heavy chains, with or without an interchain covalent linkage between them. Basic immunoglobulin structures in vertebrate systems are relatively well understood.

As will be discussed in more detail below, the generic term "antibody" comprises five distinct classes of antibody that can be distinguished biochemically. While all five classes of antibodies are clearly within the scope of the current disclosure, the discussion herein will generally be directed to the IgG class of immunoglobulin molecules. With regard to IgG, immunoglobulins comprise two identical light chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

Light chains of immunoglobulin are classified as either kappa (κ) or lambda (λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells, or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma (γ), mu (μ), alpha (α), delta (δ), or epsilon (ε), with some subclasses among them (e.g., γ1-γ4). It is the nature of this chain that determines the "class" or isotype of the antibody as IgG, IgM, IgA IgG, or IgE, respectively. The immunoglobulin isotype subclasses or subtypes (e.g., IgG1, IgG2, IgG3, IgG4, IgA1, etc.) are well-characterized and are known to confer functional specialization. Modified versions of each of these classes and isotypes are readily discernable to the skilled artisan in view of the instant disclosure and, accordingly, are within the scope of the current disclosure.

Both the light and heavy chains are divided into regions of structural and functional homology. The term "region" refers to a part or portion of an immunoglobulin or antibody chain and includes constant region or variable regions, as well as more discrete parts or portions of said regions. For example, light chain variable regions include "complementarity determining regions" or "CDRs" interspersed among "framework regions" or "FRs," as defined herein.

The regions of an immunoglobulin heavy or light chain may be defined as "constant" (C) region or "variable" (V) regions, based on a relative lack of sequence variation within the regions of various class members in the case of a "constant region," or based on a significant variation within the regions of various class members in the case of a "variable regions." The terms "constant region" and "variable region" may also be used functionally. In this regard, it will be appreciated that the variable regions of an immunoglobulin or antibody determine antigen recognition and specificity. Conversely, the constant regions of an immunoglobulin or antibody confer important effector functions such as secretion, trans-placental mobility, Fc receptor binding, complement binding, and the like. The subunit structures and three-dimensional configurations of the constant regions of the various immunoglobulin classes are well-known.

The constant and variable regions of immunoglobulin heavy and light chains are folded into domains. The term "domain" refers to a globular region of a heavy or light chain comprising peptide loops (e.g., comprising 3 to 4 peptide loops) stabilized, for example, by β-pleated sheet and/or an intra-chain disulfide bond. Constant region domains on the light chain of an immunoglobulin are referred to interchangeably as "light chain constant region domains," "CL regions" or "CL domains." Constant domains on the heavy chain (e.g., hinge, CH1, CH2 or CH3 domains) are referred to interchangeably as "heavy chain constant region domains," "CH" region domains or "CH domains." Variable domains on the light chain are referred to interchangeably as "light chain variable region domains," "light chain variable regions," "VL region domains" or "VL domains." Variable domains on the heavy chain are referred to interchangeably as "heavy chain variable region domains," "heavy chain variable regions," "VH region domains" or "VH domains."

By convention, the numbering of the amino acids of the variable constant region domains increases as they become more distal from the antigen-binding site or amino-terminus of the immunoglobulin or antibody. The N-terminus of each heavy and light immunoglobulin chain is a variable region and the C-terminus is a constant region. The CH3 and CL domains comprise the carboxy-terminus of the heavy and light chain, respectively. Accordingly, the domains of a light chain immunoglobulin are arranged in a VL-CL orientation, while the domains of the heavy chain are arranged in the VH-CH1-hinge-CH2-CH3 orientation.

The assignment of amino acids to each variable region domain is in accordance with the definitions of Kabat, Sequences of Proteins of Immunological Interest (National Institutes of Health, Bethesda, MD, 1987 and 1991). Kabat also provides a widely used numbering convention (Kabat numbering) in which corresponding residues between different heavy chain variable regions or between different light chain variable regions are assigned the same number. CDRs 1, 2 and 3 of a VL domain are also referred to herein, respectively, as CDR-L1, CDR-L2 and CDR-L3, or LCDR1, LCDR2, and LCDR3. CDRs 1, 2 and 3 of a VH domain are also referred to herein, respectively, as CDR-H1, CDR-H2 and CDR-H3, or HCDR1, HCDR2, and HCDR3. If so noted, the assignment of CDRs can be in accordance with IMGT® (Lefranc et al., *Dev Comp Immunol.* (2003) 27:55-77) in lieu of Kabat. Numbering of the heavy chain constant region is via the Eu index as set forth in Kabat (Kabat, Sequences of Proteins of Immunological Interest, National Institutes of Health, Bethesda, MD, 1987 and 1991).

As used herein, the term "VH domain" includes the amino terminal variable domain of an immunoglobulin heavy chain, and the term "VL domain" includes the amino terminal variable domain of an immunoglobulin light chain.

As used herein, the term "CH1 domain" includes the first (most amino terminal) constant region domain of an immunoglobulin heavy chain that extends, e.g., from about positions 114-223 in the Kabat numbering system (Eu positions 118-215). The CH1 domain is adjacent to the VH domain and amino terminal to the hinge region of an immunoglobulin heavy chain molecule, and does not form a part of the Fc region of an immunoglobulin heavy chain.

As used herein, the term "hinge region" includes the portion of a heavy chain molecule that joins the CH1 domain to the CH2 domain. The hinge region comprises approximately 25 residues and is flexible, thus allowing the two N-terminal antigen binding regions to move independently. Hinge regions can be subdivided into three distinct domains: upper, middle, and lower hinge domains (Roux et al., *J. Immunol.* (1998) 161:4083).

As used herein, the term "CH2 domain" includes the portion of a heavy chain immunoglobulin molecule that extends, e.g., from about positions 244-360 in the Kabat numbering system (Eu positions 231-340). The CH2 domain is unique in that it is not closely paired with another domain. Rather, two N-linked branched carbohydrate chains are interposed between the two CH2 domains of an intact native IgG molecule. In one embodiment, a binding polypeptide of the current disclosure comprises a CH2 domain derived from an IgG1 molecule (e.g., a human IgG1 molecule).

As used herein, the term "CH3 domain" includes the portion of a heavy chain immunoglobulin molecule that extends approximately 110 residues from N-terminus of the CH2 domain, e.g., from about positions 361-476 of the Kabat numbering system (Eu positions 341-447). The CH3 domain typically forms the C-terminal portion of the antibody. In some immunoglobulins, however, additional domains may extend from the CH3 domain to form the C-terminal portion of the molecule (e.g., the CH4 domain in the μ chain of IgM and the c chain of IgE). In one embodiment, a binding polypeptide of the current disclosure comprises a CH3 domain derived from an IgG1 molecule (e.g., a human IgG1 molecule).

As used herein, the term "CL domain" includes the constant region domain of an immunoglobulin light chain that extends, e.g., from about Kabat position 107A to about Kabat position 216. The CL domain is adjacent to the VL domain. In one embodiment, a binding polypeptide of the current disclosure comprises a CL domain derived from a kappa light chain (e.g., a human kappa light chain).

As used herein the term "FcRn antagonist" refers to any agent comprising an Fc region (e.g., a variant Fc region disclosed herein) that binds specifically to FcRn through the Fc region and inhibits the binding of immunoglobulin to FcRn.

As used herein, the term "Fc," "Fc domain," "Fc region," or "Fc fragment" is used interchangeably and is defined as the portion of a heavy chain constant region beginning in the hinge region just N-terminal of the papain cleavage site (i.e., residue 216 in IgG, taking the first residue of heavy chain constant region to be 114) and ending at the C-terminus of the heavy chain. Accordingly, a complete Fc, Fc domain, Fc region, or Fc fragment comprises at least a hinge region, a CH2 domain, and a CH3 domain. Sequence alignment of portions (CH2 and CH3 domains, residues 231 to 447, Eu numbering) of exemplary human IgG1, IgG2, IgG3, and IgG4 Fc domains is shown in FIG. 32. The term encompasses native/wildtype Fc and Fc variants as described herein and includes molecules in monomeric or multimeric (e.g., dimeric) form, whether digested from whole antibody or produced by other means such as recombinant technology. See, e.g., Ying et al., *JBC* (2013) 288:25154-164; and Yang et al., *JBC* (2019) 294:10638-48. In some embodiments, the modified Fc of the present disclosure comprises the entirety or an FcRn-binding portion of SEQ ID NO:1, 2, 3, or 4 shown in FIG. 32 (or a naturally occurring variant thereof), where the sequence has been modified to include the amino acid substitutions described herein.

The original immunoglobulin source of the native Fc is typically of human origin and can be any of the immunoglobulins, such as IgG1 and IgG2. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgA2). One example of a native Fc is a disulfide-bonded dimer resulting from papain digestion of an IgG. The term "native Fc," as used herein, is generic to the monomeric, dimeric, and multimeric forms.

The term "Fc variant," "modified Fc," or "modified Fc domain," as used herein, refers to a molecule or sequence that is modified from a native/wildtype Fc but still comprises a binding site for the FcRn. A Fc variant or a modified Fc domain also can be shorter or longer than a native Fc (e.g., shorter or longer than a sequence spanning residues 216 to 447 of human IgG, Eu numbering); for example, the Fc variant or modified Fc may lack certain N-terminal and/or C-terminal amino acid residues of the native Fc, or may contain additional amino acid residues at the N-terminus and/or C-terminus compared to a native Fc. A modified Fc domain itself does not include an antigen-binding domain of an antibody or an antibody variant, or a target-binding domain of an immunoadhesin, but the modified Fc domain can be linked to such a domain to form an FcRn antagonist that binds also to a non-FcRn target. The term encompasses a molecule or sequence that is humanized from a non-human native Fc. Furthermore, a native Fc comprises regions that can be removed because they provide structural features or biological activities that are not required for the FcRn antagonists (e.g., antibody-like binding polypeptides) described herein. Thus, the term encompasses a molecule or sequence that lacks one or more native Fc sites or residues, or in which one or more Fc sites or residues have been modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor (an FcγR), or (7) antibody-dependent cellular cytotoxicity (ADCC) or complement-dependent cytotoxicity (CDC).

As indicated above, the variable regions of an antibody allow it to selectively recognize and specifically bind epitopes on antigens. That is, the VL domain and VH domain of an antibody combine to form the variable region (Fv) that defines a three-dimensional antigen-binding site. This quaternary antibody structure forms the antigen-binding site present at the end of each arm of the Y. More specifically, the antigen-binding site is defined by three complementarity-determining regions (CDRs) on each of the heavy and light chain variable regions. As used herein, the term "antigen-binding site" includes a site that specifically binds (immunoreacts with) an antigen (e.g., a cell surface or soluble antigen). The antigen-binding site includes an immunoglobulin heavy chain and light chain variable regions and the binding site formed by these variable regions determines the specificity of the antibody. An antigen-binding site is formed by variable regions that vary from one antibody to another. The FcRn-antagonizing binding polypeptides such as antibodies of the current disclosure comprise at least one antigen-binding site.

In certain embodiments, binding polypeptides of the current disclosure comprise at least two antigen-binding domains that provide for the association of the binding polypeptide with the selected antigen. The antigen-binding domains need not be derived from the same immunoglobulin molecule. In this regard, the variable region may or be derived from any type of animal that can be induced to mount a humoral response and generate immunoglobulins against the desired antigen. As such, the variable region of a binding polypeptide may be, for example, of mammalian origin e.g., may be human, murine, rat, goat, sheep, non-human primate (such as cynomolgus monkeys, rhesus monkeys, macaques, etc.), lupine, or camelid (e.g., from camels, llamas and related species).

In naturally occurring antibodies, the six CDRs present on each antibody are short, non-contiguous sequences of amino acids that are specifically positioned to form the antigen-binding site as the antibody assumes its three-dimensional configuration in an aqueous environment. The remainder of the heavy and light variable domains show less intermolecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to the immunoreactive antigen epitope.

Exemplary binding polypeptides include antibody variants. As used herein, the term "antibody variant" includes synthetic and engineered forms of antibodies which are altered such that they are not naturally occurring, e.g., antibodies that comprise at least two heavy chain portions but not two complete heavy chains (such as, domain deleted antibodies or minibodies); multi-specific forms of antibodies (e.g., bi-specific, tri-specific, etc.) altered to bind to two or more different antigens or to different epitopes on a single antigen); heavy chain molecules joined to scFv molecules and the like. In addition, the term "antibody variant" includes multivalent forms of antibodies (e.g., trivalent, tetravalent, etc., antibodies that bind to three, four or more copies of the same antigen.

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen). The subject binding polypeptides typically has at least one binding site specific for a human antigen molecule.

The term "specificity" refers to the ability to specifically bind (e.g., immunoreact with) a given target antigen (e.g., a human target antigen). A binding polypeptide may be mono-specific and contain one or more binding sites which specifically bind a target or a polypeptide may be multi-specific and contain two or more binding sites which specifically bind the same or different targets. In certain embodiments, a binding polypeptide is specific for two different (e.g., non-overlapping) portions of the same target. In certain embodiments, a binding polypeptide is specific for more than one target. Exemplary binding polypeptides (e.g., anti-bodies) which comprise antigen-binding sites that bind to antigens are known in the art and one or more CDRs from such antibodies can be included in an antibody as described herein.

The term "antigen" or "target antigen," as used herein, refers to a molecule or a portion of a molecule that is capable of being bound by the binding site of a binding polypeptide. A target antigen may have one or more epitopes.

The term "about" or "approximately" means within about 20%, such as within about 10%, within about 5%, or within about 1% or less of a given value or range.

As used herein, "administer" or "administration" refers to the act of injecting or otherwise physically delivering a substance as it exists outside the body (e.g., an FcRn antagonist provided herein) into a patient, such as by, but not limited to, pulmonary (e.g., inhalation), mucosal (e.g., intra-nasal), intradermal, intravenous, intramuscular, subcutane-ous delivery and/or any other method of physical delivery described herein or known in the art. When a disease, or a symptom thereof, is being managed or treated, administra-tion of the substance typically occurs after the onset of the disease or symptoms thereof. When a disease, or symptom thereof, is being prevented, administration of the substance typically occurs before the onset of the disease or symptoms thereof and may be continued chronically to defer or reduce the appearance or magnitude of disease-associated symp-toms.

As used herein, the term "composition" is intended to encompass a product containing the specified ingredients (e.g., an FcRn antagonist provided herein) in, optionally, the specified amounts, as well as any product which results, directly or indirectly, from combination of the specified ingredients in, optionally, the specified amounts.

"Effective amount" means the amount of active pharma-ceutical agent (e.g., an FcRn antagonist of the present disclosure) sufficient to effectuate a desired physiological outcome in an individual in need of the agent. The effective amount may vary among individuals depending on the health and physical condition of the individual to be treated, the formulation of the composition, assessment of the indi-vidual's medical condition, and other relevant factors.

As used herein, the terms "subject" and "patient" are used interchangeably. As used herein, a subject is a mammal such as a non-primate (e.g., mice, rats, cows, pigs, horses, cats, dogs, etc.) or a primate (e.g., monkeys and humans). In preferred embodiments, the subject is a human.

As used herein, the term "therapy" refers to any protocol, method and/or agent that can be used in the prevention, management, treatment and/or amelioration of a disease or a symptom related thereto. In some embodiments, the term "therapy" refers to any protocol, method and/or agent that can be used in the modulation of an IgG-mediated disease (e.g., an autoimmune response) or condition in a subject or a symptom related thereto. In some embodiments, the terms "therapies" and "therapy" refer to a biological therapy, supportive therapy, and/or other therapies useful in the prevention, management, treatment and/or amelioration of a disease or a symptom related thereto, known to one of skill in the art such as medical personnel. In other embodiments, the terms "therapies" and "therapy" refer to a biological therapy, supportive therapy, and/or other therapies useful in the modulation of an immune response in a subject or a symptom related thereto known to one of skill in the art such as medical personnel.

As used herein, the terms "treat," "treatment" and "treat-ing" refer to the reduction or amelioration of the progres-sion, severity, and/or duration of a disease or a symptom related thereto, resulting from the administration of one or more therapies (including, but not limited to, the adminis-tration of one or more prophylactic or therapeutic agents, such as an FcRn antagonist provided herein). The term "treating," as used herein, can also refer to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

FcRn Antagonists

The present FcRn antagonists comprise (including con-sisting of or consisting essentially of) a modified Fc domain, and may be, for example, antibodies, antibody variants or fragments such as Fc fragments, immunoadhesins, and Fc fusion proteins. The FcRn antagonists may comprise a monomeric or dimeric Fc fragment.

Fc domains from any IgG subtype can be used to generate an FcRn of the present disclosure. In some embodiments, the modified Fc is derived from a human IgG1, IgG2, IgG3, or IgG4 Fc domain and comprise the substitutions described herein relative to the wildtype origin. In certain other embodiments, the modified Fc is an artificial Fc derived from more than one IgG subtype. In other embodiments, the Fc domains comprise a chimeric hinge (i.e., a hinge com-prising hinge portions derived from hinge domains of dif-ferent antibody isotypes, e.g., an upper hinge domain from an IgG4 molecule and an IgG1 middle hinge domain).

In certain embodiments, the modified Fc domain is derived from a human IgG1 Fc domain. In other embodi-ments, the modified Fc domain is derived from a human IgG4 Fc domain. In the case of Fc domains of other subtypes, the skilled artisan will appreciate that any of the amino acid substitutions described herein can be adapted accordingly (see FIG. 32). Unless otherwise indicated, Fc residue positions referred to herein are in accordance with the Eu Ig numbering system. As seen in FIG. 32, the human IgG CH2 and CH3 domains are highly conserved among the four different subtypes. The Eu numbering system applies to all subtypes.

In some embodiments, the modified Fc domain may comprise an amino acid substitution selected from M252, I253, S254, T256, K288, T307, K322, E380, L432, N434, or Y436, and any combinations thereof. In some embodiments, the modified Fc domain may comprise a double amino acid substitution at any two amino acid positions selected from M252, I253, S254, T256, K288, T307, K322, E380, L432, N434, and Y436. In some embodiments, the modified Fc domain may comprise a triple amino acid substitution at any three amino acid positions selected from M252, I253, S254, T256, K288, T307, K322, E380, L432, N434, and Y436. In some embodiments, the modified Fc domain may comprise a quadruple amino acid substitution at any four amino acid positions selected from M252, I253, S254, T256, K288, T307, K322, E380, L432, N434, and Y436. In some embodiments, it may be desirable for a modified Fc domain to comprise an amino acid substitution at any of the amino acid positions selected from M252, I253, S254, T256, K288, T307, K322, E380, L432, or Y436, and any combinations thereof, wherein amino acid position N434 is not substituted (i.e., amino acid position N434 is wildtype).

In some embodiments, the modified Fc domain may comprise an amino acid substitution selected from M252Y (i.e., a tyrosine at amino acid position 252), T256D, T256E, K288D, K288N, T307A, T307E, T307F, T307M, T307Q, T307W, E380C, N434F, N434P, N434Y, Y436H, Y436N, or Y436W, and any combinations thereof. In some embodiments, the modified Fc domain may comprise a double amino acid substitution selected from M252, wherein the substitution is M252Y; T256, wherein the substitution is T256D, or T256E; K288, wherein the substitution is K288D, or K288N; T307, wherein the substitution is T307A, T307E, T307F, T307M, T307Q, or T307W; E380, wherein the substitution is E380C; N434, wherein the substitution is N434F, N434P, or N434Y; Y436, wherein the substitution is Y436H, Y436N, or Y436W. In some embodiments, the modified Fc domain may comprise a triple amino acid substitution selected from M252, wherein the substitution is M252Y; T256, wherein the substitution is T256D, or T256E; K288, wherein the substitution is K288D, or K288N; T307, wherein the substitution is T307A, T307E, T307F, T307M, T307Q, or T307W; E380, wherein the substitution is E380C; N434, wherein the substitution is N434F, N434P, or N434Y; Y436, wherein the substitution is Y436H, Y436N, or Y436W. In some embodiments, the modified Fc domain may comprise a quadruple amino acid substitution selected from M252, wherein the substitution is M252Y; T256, wherein the substitution is T256D, or T256E; K288, wherein the substitution is K288D, or K288N; T307, wherein the substitution is T307A, T307E, T307F, T307M, T307Q, or T307W; E380, wherein the substitution is E380C; N434, wherein the substitution is N434F, N434P, or N434Y; Y436, wherein the substitution is Y436H, Y436N, or Y436W. In some embodiments, it may be desirable for a modified Fc domain to comprise an amino acid substitution at any of the amino acid positions selected from M252Y, T256D, T256E, K288D, K288N, T307A, T307E, T307F, T307M, T307Q, T307W, E380C, Y436H, Y436N, or Y436W, and any combinations thereof, wherein amino acid position N434 is not substituted with a phenylalanine (F) or a tyrosine (Y). In some embodiments, it may be desirable for a modified Fc domain to comprise an amino acid substitution at any of the amino acid positions selected from M252Y, T256D, T256E, K288D, K288N, T307A, T307E, T307F, T307M, T307Q, T307W, E380C, Y436H, Y436N, or Y436W, and any combinations thereof, wherein amino acid position N434 is not substituted with a tyrosine (Y). In some embodiments, it may be desirable for a modified Fc domain to comprise an amino acid substitution at any of the amino acid positions selected from M252Y, T256D, T256E, K288D, K288N, T307A, T307E, T307F, T307M, T307Q, T307W, E380C, Y436H, Y436N, or Y436W, and any combinations thereof, wherein amino acid position N434 is not substituted (i.e., amino acid position N434 is wildtype).

In certain embodiments, the modified Fc domain may comprise an amino acid substitution selected from M252, T256, T307, or N434, and any combinations thereof. In certain embodiments, the modified Fc domain may comprise a double amino acid substitution at any two amino acid positions selected from M252, T256, T307, and N434. In certain embodiments, the modified Fc domain may comprise a triple amino acid substitution at any three amino acid positions selected from M252, T256, T307, and N434. In certain embodiments, the modified Fc domain may comprise a quadruple amino acid substitution at amino acid positions M252, T256, T307, and N434. In some embodiments, it may be desirable for a modified Fc domain to comprise an amino acid substitution selected from M252, T256, or T307, and any combinations thereof, wherein amino acid position N434 is not substituted (i.e., amino acid position N434 is wildtype).

In exemplary embodiments, the modified Fc domain may comprise an amino acid substitution selected from M252, wherein the substitution is M252Y; T256, wherein the substitution is T256D, or T256E; T307, wherein the substitution is T307Q, or T307W; or N434, wherein the substitution is N434F, or N434Y, and any combinations thereof. In certain embodiments, the modified Fc domain may comprise a double amino acid substitution at any two amino acid positions selected from M252, wherein the substitution is M252Y; T256, wherein the substitution is T256D, or T256E; T307, wherein the substitution is T307Q, or T307W; or N434, wherein the substitution is N434F, or N434Y. In certain embodiments, the modified Fc domain may comprise a triple amino acid substitution at any three amino acid positions selected from M252, wherein the substitution is M252Y; T256, wherein the substitution is T256D, or T256E; T307, wherein the substitution is T307Q, or T307W; or N434, wherein the substitution is N434F, or N434Y. In certain embodiments, the modified Fc domain may comprise a quadruple amino acid substitution at amino acid positions selected from M252, wherein the substitution is M252Y; T256, wherein the substitution is T256D, or T256E; T307, wherein the substitution is T307Q, or T307W; or N434, wherein the substitution is N434F, or N434Y. In some embodiments, it may be desirable for a modified Fc domain to comprise an amino acid substitution selected from M252Y, T256D, T256E, T307Q, or T307W, and any combinations thereof, wherein amino acid position N434 is not substituted with a phenylalanine (F) or a tyrosine (Y). In some embodiments, it may be desirable for a modified Fc domain to comprise an amino acid substitution selected from M252Y, T256D, T256E, T307Q, or T307W, and any combinations thereof, wherein amino acid position N434 is not substituted with a tyrosine (Y). In some embodiments, it may be desirable for a modified Fc domain to comprise an amino acid substitution selected from M252Y, T256D, T256E, T307Q, or T307W, and any combinations thereof, wherein amino acid position N434 is not substituted (i.e., amino acid position N434 is wildtype).

In certain embodiments, the modified Fc domain may comprise an amino acid substitution selected from T256D, or T256E, and/or T307W, or T307Q, and further comprises an amino acid substitution selected from N434F, or N434Y, or M252Y. In some embodiments, it may be desirable for a modified Fc domain to comprise an amino acid substitution selected from T256D, or T256E, and/or T307W, or T307Q, and further comprise the amino acid substitution M252Y, wherein amino acid position N434 is not substituted with a phenylalanine (F) or a tyrosine (Y). In some embodiments, it may be desirable for a modified Fc domain to comprise an amino acid substitution selected from T256D, or T256E, and/or T307W, or T307Q, and further comprise the amino acid substitution M252Y, wherein amino acid position N434 is not substituted with a tyrosine (Y). In some embodiments, it may be desirable for a modified Fc domain to comprise an amino acid substitution selected from T256D, or T256E, and/or T307W, or T307Q, and further comprise the amino acid substitution M252Y, wherein amino acid position N434 is not substituted (i.e., amino acid position N434 is wild-type).

In some embodiments, the modified Fc domain may comprise the amino acid substitutions shown in FIG. 33. For example, the modified Fc domain may comprise double amino acid substitutions M252Y/N434Y (YY); or triple amino acid substitutions selected from M252Y/T307W/N434Y (YWY), M252Y/T256D/N434Y (YDY), and T256D/307W/N434Y (DWY).

In some embodiments, the modified Fc domain may comprise a quadruple amino acid substitution selected from M252Y/T256D/T307Q/N434F (YDQF), M252Y/T256D/T307W/N434F (YDWF), M252Y/T256D/T307Q/N434Y (YDQY), M252Y/T256E/T307Q/N434Y (YEQY), M252Y/T256D/T307W/N434Y (YDWY), and M252Y/T256E/T307W/N434Y (YEWY).

In some embodiments, the modified Fc domain having one or more, e.g., two or more, three of more, or four or more, amino acid substitutions as disclosed herein.

The modified Fc has enhanced FcRn binding affinities at both an acidic pH (e.g., less than about 7.0, no more than about 6.5, or no more than about 6.0) and a non-acidic pH (e.g., no less than about 7.0, or no less than about 7.4), as compared to its wildtype counterpart.

As used herein, the term "enhanced" refers to a 10% increase in a given parameter, and can encompass at least a 20% increase, 30% increase, 40% increase, 50% increase, 60% increase, 70% increase, 80% increase, 90% increase, 95% increase, 97% increase, 99% or even a 100% increase over the control, baseline, or prior-in-time value. The term "enhanced" can refer to at least a 1-fold, 1.5-fold, 2-fold, 2.5-fold, 3-fold, 3.5-fold, 4-fold, 4.5-fold, 5-fold, 6-fold, 7-fold, 8-fold, 9-fold, 10-fold, 20-fold, 50-fold, 100-fold, 1000-fold increase of a given parameter over the control, baseline, or prior-in-time value. In certain embodiments, the term "enhanced" refers to an increase relative to a wildtype standard, e.g., a wildtype Fc domain. In other embodiments, the term "enhanced" refers to an increase relative to an FcRn antagonist, e.g., an FcRn antagonist comprising M252Y/S254T/T256E/H433K/N434F ("YTEKF hIgG1"; see, e.g., Swiercz et al., supra).

In some embodiments, the FcRn antagonist may exhibit a species-specific FcRn binding affinity. In some embodiments, the FcRn antagonist may exhibit human as well as cyno FcRn binding affinity. In one embodiment, a binding polypeptide may exhibit rat and/or mouse FcRn binding affinity. In some embodiments, a binding polypeptide may exhibit cross-species FcRn binding affinity. Such binding polypeptides are said to be cross-reactive across one or more different species. In one embodiment, a binding polypeptide may exhibit both human and rat FcRn binding affinity.

The neonatal Fc receptor (FcRn) interacts with the Fc region of antibodies to promote recycling through rescue from normal lysosomal degradation. This process is a pH-dependent process that occurs in the endosomes at acidic pH (e.g., a pH less than 6.5) but not under the physiological pH conditions of the bloodstream (e.g., a non-acidic pH). The FcRn antagonist of the present disclosure has enhanced FcRn binding affinity or slower FcRn off-rate under both acidic and non-acidic conditions compared to a polypeptide comprising a wildtype Fc domain. An acidic pH is a pH less than about 7.0, e.g., about pH 6.5, at about pH 6.0, at about pH 5.5, at about pH 5.0. An elevated, non-acidic pH is a pH of about 7 or greater, such as about pH 7.4, about pH 7.6, about pH 7.8, about pH 8.0, about pH 8.5, or about pH 9.0. In certain embodiments, the polypeptide comprising a modified Fc domain described herein exhibits loss of pH-dependence in FcRn binding; that is, unlike wildtype Fc, the polypeptide does not have drastically lower binding affinity to FcRn under non-acidic conditions compared to acidic conditions. Such polypeptides are therefore useful as FcRn antagonists to promote clearance of IgGs with wildtype FcRn binding properties from the circulation because the FcRn antagonists, by binding to FcRn tightly in a pH-independent, or less pH-dependent, manner, disrupt the FcRn-mediated recycling of IgGs that have wildtype (i.e., lower) FcRn binding affinity.

Fc domains of immunoglobulins are involved in non-antigen binding functions and have several effector functions mediated by binding to Fc receptors, e.g., binding of the FcRn. As illustrated in FIG. 1A, Fc domains are comprised of a CH2 domain and a CH3 domain. A majority of the Fc residues involved in the interaction with FcRn are located in the loops directly adjacent to the CH2-CH3 interface (FIG. 1A, dotted line) and opposite the glycosylation site. FIG. 1B illustrates the surface representation of the IgG1 Fc crystal structure (pdb: 5d4q) and shows residues in the CH2 and CH3 domains that comprise the FcRn binding interface.

In certain embodiments, the present FcRn antagonist may comprise a modified Fc domain comprising one or more amino acid mutations (e.g., substitutions) which alter the effector functions (e.g., ADCC or CDC function) of the Fc domain, as compared to a corresponding wildtype molecule, e.g., a molecule having the same structure as the FcRn antagonist except that it has a wildtype Fc domain. For an antibody FcRn antagonist, its corresponding wildtype molecule may be a whole, unaltered antibody, including an antibody of approximately the same immunogenicity. For example, an FcRn antagonist having reduced ADCC and/or CDC effector function (e.g., those containing the LALA mutations) may be less likely to cause undesired side effects when administered to patients.

In certain embodiments, the present FcRn antagonist may comprise a modified Fc domain comprising one or more amino acid mutations (e.g., substitutions) which alter (e.g., increase or decrease) the circulating half-life (e.g., serum half-life) of the FcRn antagonist, as compared to the corresponding wildtype molecule. For example, a decrease in serum half-life may be advantageous when the FcRn antagonist is not desired to be present in the patient's body for a prolong period of time.

In certain embodiments, the present FcRn antagonist may comprise a modified Fc domain comprising one or more mutations (e.g., substitutions) which provide one or more desired biochemical characteristics such as the ability to remain monomeric, the ability to noncovalently dimerize, an increased ability to localize at a target site, and glycosylation patterns, as compared to the corresponding wildtype molecule. For example, the modified Fc domain may have reduced glycosylation (e.g., N- or O-linked glycosylation). Exemplary amino acid substitutions which confer reduced or altered glycosylation are disclosed in International PCT Publication No. WO 2005/018572. In some embodiments, the Fc domain is modified to eliminate glycosylation (e.g., "agly" antibodies). An "agly" FcRn antagonist may have an improved safety and stability profile in vivo. Numerous art-recognized methods are available for making "agly" antibodies or antibodies with altered glycans. For example, genetically engineered host cells (e.g., modified yeast, e.g., Picchia, or CHO cells) with modified glycosylation pathways (e.g., glycosyl-transferase deletions) can be used to produce such antibodies.

In certain embodiments, the Fc domain may be mutated to decrease effector function using techniques known in the art. In some embodiments, the modified Fc herein also has altered binding affinity to an Fc-gamma receptors (FcγR). The FcγRs belong to a family that includes several members, e.g., FcγRI, FcγRIIa, FcγRIIb, FcγRIIIa, and FcγRIIIb. In some embodiments, the modified Fc herein, while having enhanced FcRn binding affinities, has reduced FcγRIIIa binding affinity, compared to a wildtype Fc domain.

In some embodiments, the FcRn antagonists are antibodies. Suitable antibodies include without limitation, human antibodies, humanized antibodies, or chimeric antibodies, and may be full-length antibodies or single chain antibodies. The antibodies may target soluble targets (e.g., cytokines and secreted circulating proteins) associated with a disease state.

Proteins, including antibodies, with low thermodynamic stability have an increased propensity for misfolding and aggregation and would limit or hinder the activity, efficacy, and potential of the protein as a useful therapeutic. In certain embodiments, the FcRn antagonist has approximately the same or comparable thermal stability as a polypeptide comprising a wildtype Fc domain or a modified Fc domain having the triple amino acid substitutions M252Y/S254T/T256E (YTE).

The resulting physiological profile, bioavailability and other biochemical effects of the modifications, such as localization, biodistribution and serum half-life, may easily be measured and quantified using well-known immunological techniques without undue experimentation.

In certain embodiments, the FcRn antagonist of the current disclosure is an isolated binding polypeptide and comprises an antigen-binding fragment derived from an antibody, fused to the modified Fc domain. The term "antigen-binding fragment" refers to a polypeptide fragment of an immunoglobulin or antibody which binds antigen or competes with intact antibody (i.e., with the intact antibody from which they were derived) for antigen binding (i.e., specific binding).

In some embodiments, the binding polypeptide comprises a single chain variable region sequence (ScFv) fused to a modified Fc herein. Single chain variable region sequences comprise a single polypeptide having one or more antigen-binding sites, e.g., a VL domain linked by a flexible linker to a VH domain. ScFv molecules can be constructed in a VH-linker-VL orientation or VL-linker-VH orientation. The flexible hinge that links the VL and VH domains that make up the antigen-binding site includes from about 10 to about 50 amino acid residues. Connecting peptides are known in the art.

In some embodiments, a binding polypeptide of the current disclosure is a multivalent (e.g., tetravalent) antibody which is produced by fusing a DNA sequence encoding an antibody with a ScFv molecule (e.g., an altered ScFv molecule). For example, in one embodiment, these sequences are combined such that the ScFv molecule (e.g., an altered ScFv molecule) is linked at its N-terminus or C-terminus to an Fc fragment of an antibody via a flexible linker (e.g., a gly/ser linker). In another embodiment a tetravalent antibody of the current disclosure can be made by fusing an ScFv molecule to a connecting peptide, which is fused to a modified Fc domain to construct an ScFv-Fab tetravalent molecule.

In another embodiment, a binding polypeptide of the current disclosure is an altered minibody. An altered minibody of the current disclosure is a dimeric molecule made up of two polypeptide chains each comprising an ScFv molecule which is fused to a modified Fc domain via a connecting peptide. Minibodies can be made by constructing an ScFv component and connecting peptide components using methods described in the art (see, e.g., U.S. Pat. No. 5,837,821 or WO 94/09817). In another embodiment, a tetravalent minibody can be constructed. Tetravalent minibodies can be constructed in the same manner as minibodies, except that two ScFv molecules are linked using a flexible linker. The linked scFv-scFv construct is then joined to a modified Fc domain.

In another embodiment, a binding polypeptide of the current disclosure comprises a diabody. Diabodies are dimeric, tetravalent molecules each having a polypeptide similar to scFv molecules, but usually having a short (less than 10, e.g., about 1 to about 5) amino acid residue linker connecting both variable domains, such that the VL and VH domains on the same polypeptide chain cannot interact. Instead, the VL and VH domain of one polypeptide chain interact with the VH and VL domain (respectively) on a second polypeptide chain (see, for example, WO 02/02781). Diabodies of the current disclosure comprise an scFv-like molecule fused to a modified Fc domain.

In other embodiments, the binding polypeptides comprise multi-specific or multivalent antibodies comprising one or more variable domain in series on the same polypeptide chain, e.g., tandem variable domain (TVD) polypeptides. Exemplary TVD polypeptides include the "double head" or "Dual-Fv" configuration described in U.S. Pat. No. 5,989,830. In the Dual-Fv configuration, the variable domains of two different antibodies are expressed in a tandem orientation on two separate chains (one heavy chain and one light chain), wherein one polypeptide chain has two VH domains in series separated by a peptide linker (VH1-linker-VH2) and the other polypeptide chain consists of complementary VL domains connected in series by a peptide linker (VL1-linker-VL2). In the cross-over double head configuration, the variable domains of two different antibodies are expressed in a tandem orientation on two separate polypeptide chains (one heavy chain and one light chain), wherein one polypeptide chain has two VH domains in series separated by a peptide linker (VH1-linker-VH2) and the other polypeptide chain consists of complementary VL domains connected in series by a peptide linker in the opposite orientation (VL2-linker-VL1). Additional antibody variants based on the "Dual-Fv" format include the Dual-Variable-Domain IgG (DVD-IgG) bispecific antibody (see U.S. Pat. No. 7,612,181 and the TBTI format (see US 2010/0226923 A1). In some embodiments, binding polypeptides comprise multi-specific or multivalent antibodies comprising one or more variable domain in series on the same polypeptide chain fused to a modified Fc domain.

In another exemplary embodiment, the binding polypeptide comprises a cross-over dual variable domain IgG (CODV-IgG) bispecific antibody based on a "double head" configuration (see US20120251541 A1).

In another exemplary embodiment, the binding polypeptide is an immunoadhesin. As used herein, an "immunoadhesin" refers to a binding polypeptide comprising one or more binding domains (e.g., from a receptor, ligand, or cell-adhesion molecule) linked to an immunoglobulin constant domain (i.e., an Fc region) (see, e.g., Ashkenazi et al., *Methods* (1995) 8(2):104-15, and Isaacs, *Brit J Rheum.* (1997) 36:305-7, which are incorporated by reference herein in their entireties). An example of immunoadhesins is a chimeric molecule between a ligand-binding domain of a receptor and an IgG Fc domain. In some embodiments, the FcRn antagonists are immunoadhesins that bind to and sequester cytokines involved in inflammation.

Immunoadhesins are identified by the suffix "-cept" in their international nonproprietary names (INN). Like antibodies, immunoadhesins have long circulating half-lives, are readily purified by affinity-based methods, and have avidity advantages conferred by bivalency. Examples commercially available therapeutic immunoadhesins include etanercept (ENBREL®), abatacept (ORENCIA®), rilonacept (ARCALYST®), aflibercept (ZALTRAP®/EYLEA®), and belatacept (NULOJIX®).

In certain embodiments, the isolated binding polypeptides are antibody mimics such as affibodies, affilins, affimers, affitins, alphabodies, anticalins, avimers, DARPins, Fynomers, Kunitz domain peptides, monobodies, and nanoC-LAMPs, fused to the modified Fc domains described herein.

In certain embodiments, the binding polypeptide comprises immunoglobulin-like domains. Suitable immunoglobulin-like domains include, without limitation, fibronectin domains (see, e.g., Koide et al., *Methods Mol Biol.* (2007) 352:95-109, which is incorporated by reference herein in its entirety), DARPin (see, e.g., Stumpp et al., *Drug Discov Today* (2008) 13 (15-16):695-701, which is incorporated by reference herein in its entirety), Z domains of protein A (see, Nygren et al., *FEBS J.* (2008) 275 (11):2668-76, which is incorporated by reference herein in its entirety), Lipocalins (see, e.g., Skerra et al. (2008) *FEBS J.* 275 (11):2677-83, which is incorporated by reference herein in its entirety), Affilins (see, e.g., Ebersbach et al., *J Mol Biol.* (2007) 372 (1):172-85, which is incorporated by reference herein in its entirety), Affitins (see, e.g., Krehenbrink et al., (2008) *J Mol Biol.* 383 (5):1058-68, which is incorporated by reference herein in its entirety), Avimers (see, e.g., Silverman et al., (2005) *Nat Biotechnol.* 23 (12):1556-61, which is incorporated by reference herein in its entirety), Fynomers, (see, e.g, Grabulovski et al., *J Biol Chem.* (2007) 282 (5):3196-3204, which is incorporated by reference herein in its entirety), and Kunitz domain peptides (see, e.g, Nixon et al., (2006) *Curr Opin Drug Discov Devel* 9 (2):261-8, which is incorporated by reference herein in its entirety).

A binding polypeptide of the present disclosure, comprising a modified Fc domain described herein, can include the CDR sequences or the variable domain sequences of a known "parent" antibody. In some embodiments, the parent antibody and the antibody of the disclosure can share similar or identical sequences except for modifications to the Fc domain as disclosed herein.

Nucleic Acids and Expression Vectors

Polynucleotides encoding the polypeptides disclosed herein are typically inserted in an expression vector for introduction into host cells that may be used to produce the desired quantity of the described polypeptides such as antibodies, fragments thereof, or immunoadhesins. Accordingly, in certain aspects, the invention provides expression vectors comprising polynucleotides disclosed herein and host cells comprising these vectors and polynucleotides.

The term "vector" or "expression vector" is used herein, for the purposes of the specification and claims, to mean vectors used for introducing into and expressing a desired gene in a cell. Such vectors may easily be selected from the group consisting of plasmids, phages, and viruses (e.g., baculoviruses, vaccinia viruses, lentiviruses, adenoviruses, adeno-associated viruses, and retroviruses). In general, a vector will comprise a selection marker and appropriate restriction sites to facilitate cloning of the desired gene and the ability of the vector to enter and/or replicate in eukaryotic or prokaryotic cells.

Numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals. In some embodiments the cloned variable region genes are inserted into an expression vector along with the heavy and light chain constant region genes (such as human genes) synthesized as discussed above.

In other embodiments, a binding polypeptide as described herein may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980.

More generally, once a vector or DNA sequence encoding an FcRn antagonist of the present disclosure has been prepared, the expression vector may be introduced into an appropriate host cell. Introduction of the plasmid into the host cell can be accomplished by various techniques such as transfection (including electrophoresis and electroporation), protoplast fusion, calcium phosphate precipitation, cell fusion with enveloped DNA, microinjection, and infection with intact virus. The transformed cells are grown under conditions appropriate to the production of the present binding polypeptides, and assayed for their synthesis. Exemplary assay techniques include enzyme-linked immunosorbent assay (ELISA), radioimmunoassay (RIA), or fluorescence-activated cell sorter analysis (FACS), immunohistochemistry and the like.

Host cells used for expression of the present polypeptide can be of eukaryotic (e.g., mammalian, insect, yeast or plant) or prokaryotic origin. In some embodiments, the host cell line used for expression of the polypeptide is of mammalian origin; those skilled in the art can determine particular host cell lines which are best suited for the desired gene product to be expressed therein. Exemplary host cell lines include, but are not limited to, Chinese hamster ovary (CHO) cells (e.g., DG44 and DUXB11, CHO lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), BFA-1c1BPT (bovine endothelial cells), RAJI (human lymphocyte), and 293 (human kidney). In one embodiment, the cell line provides for altered glycosylation, e.g., afucosylation, of the binding polypeptides (e.g., antibodies) expressed therefrom (e.g., PER.C6® (Crucell) or FUT8-knock-out CHO cell lines (POTELLIGENT™ cells) (Biowa, Princeton, NJ)). In one embodiment, NS0 cells may be used. Host cell lines are typically available from commercial services, the American Tissue Culture Collection, or from published literature. Techniques for mammalian cell cultivation under tissue culture conditions are known in the art and include homogeneous suspension culture, e.g., in an airlift reactor or in a continuous stirrer reactor, or immobilized or entrapped cell culture, e.g., in hollow fibers, microcapsules, on agarose microbeads or ceramic cartridges. If necessary and/or desired, the solutions of polypeptides can be purified by the customary chromatography methods, for example, gel filtration, ion-exchange chromatography, chromatography over DEAE-cellulose and/or (immuno-) affinity chromatography.

Methods of Treatment

In one aspect, the present disclosure provides methods of treating a subject (e.g., a human patient) in need thereof comprising administering an effective amount of an FcRn antagonist disclosed herein. In certain embodiments, the present disclosure provides articles of manufacture (e.g., kits) for use in such treatment methods. The patient has an IgG-mediated disease or disorder and will benefit from faster clearance of serum IgG by being treated with the FcRn antagonist of the present disclosure. As used herein, the terms "antibody-related," "antibody-mediated," and "antibody-responsive" disorder, condition, or disease refer to a disorder, condition, or disease that may be ameliorated by removal undesired antibody (e.g., certain autoreactive IgG, or exogenously provided therapeutic or diagnostic IgG that is no longer needed or beneficial to the patient).

In certain embodiments, the IgG-mediated disorder may be, an autoimmune disease such as graft versus host disease (GVHD), systemic lupus erythematosus (SLE), myasthenia gravis, systemic sclerosis (SSc)/scleroderma, rheumatoid arthritis, psoriatic arthritis, osteoarthritis, diabetes, multiple sclerosis, pemphigus vulgaris, atopic dermatitis, psoriasis, asthma, allergy, idiopathic pulmonary fibrosis (IPF), idiopathic thrombocytopenia purpura (ITP), and hidradenitis suppurativa.

In certain embodiments, the IgG-mediated disorder may be an allergy. The allergy may be, for example, a food allergy (e.g., egg allergy, fish allergy, shellfish allergy, fruit allergy, garlic allergy, hot pepper allergy, oat allergy, meat allergy, milk allergy, peanut allergy, rice allergy, sesame allergy, soy allergy, sulfite allergy, tartrazine allergy, tree nut allergy, wheat allergy and the like), a drug allergy (e.g., tetracycline allergy, Dilantin allergy, Tegretol allergy, penicillin allergy, cephalosporin allergy, sulfonamide allergy, non-steroidal anti-inflammatory allergy, intravenous contrast dye allergy and the like), an environmental allergy (e.g., grass allergy, pollen allergy, cat allergy, dog allergy, insect allergy, mold allergy, perfume allergy, cosmetic allergy, semen allergy, latex allergy, water allergy, house dust mite allergy, nickel allergy, gold allergy, chromium allergy, cobalt chloride allergy, photographic developer allergy, fungicide allergy and the like) and a contact allergy (e.g., latex allergy, paraphenylenediamine allergy, glyceryl monothioglycolate allergy, toluenesulfanomide formaldehyde allergy and the like).

In certain embodiments, the FcRn antagonists disclosed herein can be used in combination with one or more additional therapeutic agents. In certain embodiments, a combination therapy comprising an FcRn antagonist disclosed herein can target the innate immune system and/or the adaptive immune system, for example, by binding to and removing from circulation pro-inflammatory cytokines. In some embodiments, the FcRn antagonists themselves can bind to and remove pro-inflammatory cytokines, achieving the combined effects of removing autoreactive serum IgG as well as pro-inflammatory cytokines. In certain embodiments, a combination therapy comprising an FcRn antagonist disclosed herein can include can include a TLR-inhibitor, e.g., an IRAK-4 inhibitor.

In certain embodiments, the FcRn antagonists can be used to reduce serum levels of an Fc-containing agent (e.g., a therapeutic or diagnostic agent) in a subject. Clearance of an Fc-containing agent may be desired in cases where the Fc-containing agent is detrimental (e.g., toxic) to a subject, or wherein the Fc-containing reagent is only desired to be present in a subject for a certain period of time, for example, when the Fc-containing agent is immunogenic or when the Fc-containing agent is an antibody-drug conjugate, respectively. In certain embodiments, clearance of an Fc-containing agent reduces the amount of exposure of the subject to the Fc-containing agent. The level of any Fc-containing agent in the serum may be reduced by employing an FcRn antagonist described herein. Accordingly, in certain embodiments, an FcRn antagonist disclosed herein is used to reduce the serum levels of an Fc-containing agent in a subject that has been administered the Fc-containing agent.

In another aspect, a method of enhancing diagnostic imaging is provided comprising administering to a subject a therapeutically effective amount of an FcRn antagonist disclosed herein. FcRn antagonists disclosed herein may be used to reduce both background levels and systemic exposure to radiolabeled antibody during diagnostic imaging. In certain embodiments, diagnostic imaging includes, without limitation, positron emission tomography (PET), single photon emission computed tomography (SPECT), a combination of PET and computerized tomography (CT), and the like.

In certain embodiments, a subject is administered an effective amount of a radiolabeled antibody, and optionally, an FcRn antagonist is administered after administration of the radiolabeled antibody. In certain embodiments, contrast of the radiolabeled antibody is enhanced in a subject using the FcRn antagonists described herein e.g., by clearing unbound radiolabeled antibodies from the circulation, allowing for increased contrast (e.g., reduced background signals) and reduction in the harmful effects of exposure to radiolabeled antibodies. Accordingly, in certain embodiments, a method of reducing exposure of normal tissue to a radiolabeled antibody during diagnostic imaging comprising administering to a subject a therapeutically effective amount of an FcRn antagonist disclosed herein is provided.

In certain embodiments, the FcRn antagonists disclosed herein can be used to clear a therapeutic agent from a subject. For example, a subject administered a therapeutic agent may develop antibodies, e.g., anti-drug antibodies, that reduce the availability and/or efficacy of the administered therapeutic agent. The presence of anti-drug antibodies in a subject may result in unwanted side effects. Accordingly, the FcRn antagonists disclosed herein remove the anti-drug antibodies that develop in a subject.

By routine experimentation, the skilled artisan would be able to determine an effective amount of an FcRn antagonist as described herein (e.g., a quadruple variant with enhanced FcRn binding at pH 6.0 and pH 7.4). In certain embodiments, an effective amount of an FcRn antagonist is nontoxic. A therapeutically effective amount of an FcRn antagonist may vary according to various factors. For example, without limitation, the age, sex, disease stage, and medical history of a subject to be administered an FcRn antagonist can affect the proper determination of a therapeutically effective amount of the FcRn antagonist. A suitable dosage regimen may be determined in order to provide an effective therapeutic response in a subject. Dosages may be divided and administered over a certain period of time, e.g., administered daily for one week.

In certain embodiments, the present disclosure provides kits and methods for the diagnosis and/or treatment of disorders, e.g., an IgG-mediated disorder in a mammalian subject in need of such treatment. In exemplary embodiments, the subject is a human.

Pharmaceutical Compositions and Administration Thereof

Methods of preparing and administering the present FcRn antagonists to a subject are well known to or can be readily determined by those skilled in the art. The route of administration may be oral, parenteral, topical, or inhalation. The term "parenteral" as used herein includes intravenous, intraarterial, intraperitoneal, intramuscular, subcutaneous, rectal or vaginal administration. While all these forms of administration are clearly contemplated as being within the scope of the current disclosure, a form for administration would be a solution for injection, in particular for intravenous or intraarterial injection or drip. Usually, a suitable pharmaceutical composition for injection may comprise a buffer (e.g., acetate, histidine, phosphate or citrate buffer), a surfactant (e.g., polysorbate), optionally a stabilizer agent (e.g., human albumin), a preservative, etc. In some embodiments, the FcRn antagonist can be delivered directly to the site of the adverse cellular population, thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the compositions and methods of the current disclosure, pharmaceutically acceptable carriers include, but are not limited to, 0.01-0.1 M, e.g., 0.05 M phosphate buffer, or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringeability exists. It should be stable under the conditions of manufacture and storage and will typically be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, isotonic agents will be included, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a modified binding polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, exemplary methods of preparation include vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will typically have labels or package inserts indicating that the associated compositions are useful for treating a subject suffering from, or predisposed to IgG-mediated disorders.

Effective doses of the present pharmaceutical compositions vary depending upon many different factors, including means of administration, target site, the patient's health status, medical history, age, sex, and weight. Treatment dosages may be titrated using routine methods known to those of skill in the art to optimize safety and efficacy.

The present FcRn antagonists can be administered on multiple occasions. Intervals between single dosages can be weekly, monthly or yearly. Intervals can also be irregular as indicated by measuring blood levels of IgG in the patient. In some methods, dosage is adjusted to achieve a plasma FcRn antagonist concentration of about 1-1000 μg/ml and in some methods about 25-300 μg/ml. Alternatively, the FcRn antagonist can be administered as a sustained release formulation, in which case less frequent administration is required. For antibodies, dosage and frequency vary depending on the half-life of the antibody in the patient.

A pharmaceutical composition herein can comprise one or more species of the present FcRn antagonists and a pharmaceutically acceptable, non-toxic, sterile carrier such as physiological saline, nontoxic buffers, and the like. The dosage and frequency of administration can vary depending on whether the treatment is prophylactic or therapeutic. In prophylactic applications, pharmaceutical compositions containing an FcRn antagonist or a cocktail thereof are administered to a patient not already in the disease state to enhance the patient's resistance to development of a disease (e.g., a genetically susceptible patient). Such an amount is defined to be a "prophylactic effective dose." In this use, the precise amounts again depend upon the patient's state of health and general immunity, but generally range from about 0.1 to about 25 mg per dose, especially about 0.5 to about 2.5 mg per dose. A relatively low dosage is administered at relatively infrequent intervals over a long period of time. Some patients continue to receive treatment for the rest of their lives. In therapeutic applications, a relatively high dosage (e.g., from about 1 to 400 mg/kg of antibody per dose, such as dosages of from about 5 to 25 mg) at relatively short intervals is sometimes required until progression of the disease is reduced or terminated, or until the patient shows partial or complete amelioration of disease symptoms. Thereafter, the patient can be administered a prophylactic regime.

EXEMPLARY EMBODIMENTS

Exemplary, non-limiting embodiments of the present disclosure are provided below.

1. A method of treating an antibody-mediated disorder in a subject in need thereof, comprising administering to the subject a therapeutically effective amount of an FcRn antagonist comprising a modified Fc domain, wherein the modified Fc domain comprises a combination of at least four amino acid substitutions comprising:
an aspartic acid (D) or a glutamic acid (E) at amino acid position 256, and a tryptophan (W) or a glutamine (Q) at amino acid position 307, wherein amino acid position 254 is not threonine (T), and further comprising:
a phenylalanine (F) or a tyrosine (Y) at amino acid position 434; and
a tyrosine (Y) at amino acid position 252,
wherein amino acid positions are according to EU numbering.

2. A method of treating an antibody-mediated disorder in a subject in need thereof, comprising administering to the subject a therapeutically effective amount of an FcRn antagonist comprising a modified Fc domain having a combination of amino acid substitutions at positions selected from the group consisting of:
a) a tyrosine (Y) at amino acid position 252, an aspartic acid (D) at amino acid position 256, a glutamine (Q) at amino acid position 307, and a tyrosine (Y) at amino acid position 434;
b) a tyrosine (Y) at amino acid position 252, a glutamic acid (E) at amino acid position 256, a tryptophan (W) at amino acid position 307, and a tyrosine (Y) at amino acid position 434;
c) a tyrosine (Y) at amino acid position 252, a glutamic acid (E) at amino acid position 256, a glutamine (Q) at amino acid position 307, and a tyrosine (Y) at amino acid position 434;
d) a tyrosine (Y) at amino acid position 252, an aspartic acid (D) at amino acid position 256, a glutamine (Q) at amino acid position 307, and a phenylalanine (F) at amino acid position 434; or
e) a tyrosine (Y) at amino acid position 252, an aspartic acid (D) at amino acid position 256, a tryptophan (W) at amino acid position 307, and a tyrosine (Y) at amino acid position 434, wherein the amino acid substitutions are according to EU numbering.

3. A method of treating an antibody-mediated disorder in a subject in need thereof, comprising administering to the subject a therapeutically effective amount of an FcRn antagonist comprising a modified Fc domain comprising: a quadruple amino acid substitution selected from the group consisting of M252Y/T256D/T307Q/N434Y, M252Y/T256E/T307W/N434Y, M252Y/T256E/T307Q/N434Y, M252Y/T256D/T307Q/N434F, and M252Y/T256D/T307W/N434Y, wherein the amino acid substitutions are according to EU numbering.

4. A method of treating an antibody-mediated disorder in a subject in need thereof, comprising administering to the subject a therapeutically effective amount of an FcRn antagonist comprising a modified Fc domain comprising a tyrosine (Y) at amino acid position 252, an aspartic acid (D) at amino acid position 256, a glutamine (Q) at amino acid position 307, and a tyrosine (Y) at amino acid position 434, according to EU numbering.

5. A method of treating an antibody-mediated disorder in a subject in need thereof, comprising administering to the subject a therapeutically effective amount of an FcRn antagonist comprising a modified Fc domain comprising a tyrosine (Y) at amino acid position 252, a glutamic acid (E) at amino acid position 256, a tryptophan (W) at amino acid position 307, and a tyrosine (Y) at amino acid position 434, according to EU numbering.

6. A method of treating an antibody-mediated disorder in a subject in need thereof, comprising administering to the subject a therapeutically effective amount of an FcRn antagonist comprising a modified Fc domain comprising a tyrosine (Y) at amino acid position 252, a glutamic acid (E) at amino acid position 256, a glutamine (Q) at amino acid position 307, and a tyrosine (Y) at amino acid position 434, according to EU numbering.

7. A method of treating an antibody-mediated disorder in a subject in need thereof, comprising administering to the subject a therapeutically effective amount of an FcRn antagonist comprising a modified Fc domain comprising a tyrosine (Y) at amino acid position 252, an aspartic acid (D) at amino acid position 256, a glutamine (Q) at amino acid position 307, and a phenylalanine (F) at amino acid position 434, according to EU numbering.

8. A method of treating an antibody-mediated disorder in a subject in need thereof, comprising administering to the subject a therapeutically effective amount of an FcRn antagonist comprising a modified Fc domain comprising a tyrosine (Y) at amino acid position 252, an aspartic acid (D) at amino acid position 256, a tryptophan (W) at amino acid position 307, and a tyrosine (Y) at amino acid position 434, according to EU numbering.

9. The method of any preceding embodiment, wherein the modified Fc domain is a modified human Fc domain.

10. The method of any preceding embodiment, wherein the modified Fc domain is a modified IgG1 Fc domain.

11. The method of any preceding embodiment, wherein the FcRn antagonist has human FcRn binding affinity.

12. The method of any preceding embodiment, wherein the FcRn antagonist has human and rat FcRn binding affinity.

13. The method of any preceding embodiment, wherein the FcRn antagonist has enhanced FcRn binding affinity compared to an FcRn antagonist comprising a wild-type Fc domain.

14. The method of any preceding embodiment, wherein the FcRn antagonist has enhanced FcRn binding affinity at an acidic pH compared to an FcRn antagonist comprising a wild-type Fc domain.

15. The method of any preceding embodiment, wherein the FcRn antagonist has enhanced FcRn binding affinity at an acidic pH compared to an FcRn antagonist comprising M252Y/S254T/T256E/H433K/N434F, according to EU numbering.

16. The method of any preceding embodiment, wherein the FcRn antagonist has enhanced FcRn binding affinity at a non-acidic pH compared to an FcRn antagonist comprising a wild-type Fc domain.

17. The method of any preceding embodiment, wherein the FcRn antagonist has enhanced FcRn binding affinity at a non-acidic pH compared to an FcRn antagonist comprising M252Y/S254T/T256E/H433K/N434F, according to EU numbering.

18. The method of any preceding embodiment, wherein the FcRn antagonist has enhanced FcRn binding affinity at an acidic pH, and enhanced FcRn binding affinity at a non-acidic pH, compared to an FcRn antagonist comprising a wild-type Fc domain.

19. The method of any preceding embodiment, wherein the FcRn antagonist has enhanced FcRn binding affinity at an acidic pH, and enhanced FcRn binding affinity at a non-acidic pH, compared to an FcRn antagonist comprising M252Y/S254T/T256E/H433K/N434F, according to EU numbering.

20. The method of any preceding embodiment, wherein the acidic pH is about 6.0.

21. The method of any preceding embodiment, wherein the non-acidic pH is about 7.4.

22. The method of any preceding embodiment, wherein the FcRn antagonist has a reduced serum half-life compared to an FcRn antagonist comprising a wild-type Fc domain.

23. The method of any preceding embodiment, wherein the FcRn antagonist has a reduced serum half-life compared to an FcRn antagonist comprising M252Y/S254T/T256E/H433K/N434F, according to EU numbering.

24. The method of any preceding embodiment, wherein the FcRn antagonist has reduced FcγRIIIa binding affinity compared to an FcRn antagonist comprising a wild-type Fc domain.

25. The method of any preceding embodiment, wherein the FcRn antagonist has reduced thermal stability compared to an FcRn antagonist comprising a wild-type Fc domain.

26. The method of any preceding embodiment, wherein the FcRn antagonist is a binding polypeptide.

27. The method of any preceding embodiment, wherein the FcRn antagonist is an antibody or fragment thereof selected from the group consisting of an Fv fragment, a single chain antibody (ScFv), an Fab, an Fab-H, an Fab', an F(ab')2, an Fd, a dAb, and a multimeric version thereof, a single domain antibody, a maxibody, a minibody, a diabody, a triabody, a tetrabody, a vNAR, and a bis-scFv.

28. The method of any preceding embodiment, wherein the antibody is a monoclonal antibody.

29. The method of any preceding embodiment, wherein the antibody is a chimeric, humanized, or human antibody.

30. The method of any preceding embodiment, wherein the antibody is a full-length antibody.

31. The method of any one of embodiments 1-25, wherein the FcRn antagonist is an antibody mimic selected from the group consisting of an affibody, an affilin, an affimer, an affitin, an alphabody, an anticalin, an avimer, a DARPin, a Fynomer, a Kunitz domain peptide, a monobody, and a nanoCLAMP.

32. The method of embodiment 31, wherein the FcRn antagonist is an affibody.

33. The method of any preceding embodiment, wherein the FcRn antagonist further comprises an albumin binding domain.

34. The method of any preceding embodiment, wherein the FcRn antagonist specifically binds one or more targets.

35. The method of any preceding embodiment, wherein the antibody-mediated disorder is an autoimmune disease.

36. The method of embodiment 35, wherein the autoimmune disease is selected from the group consisting of graft versus host disease (GVHD), systemic lupus erythematosus (SLE), myasthenia gravis, systemic sclerosis (SSc)/scleroderma, rheumatoid arthritis, psoriatic arthritis, osteoarthritis, diabetes, multiple sclerosis, pemphigus vulgaris, atopic dermatitis, psoriasis, asthma, allergy, idiopathic pulmonary fibrosis (IPF), idiopathic thrombocytopenia purpura (ITP), and hidradenitis suppurativa.

37. A method of enhancing diagnostic imaging comprising administering to a subject a therapeutically effective amount of an FcRn antagonist comprising a modified Fc domain comprising a quadruple amino acid substitution selected from the group consisting of M252Y/T256D/T307Q/N434Y, M252Y/T256E/T307W/N434Y, M252Y/T256E/T307Q/N434Y, M252Y/T256D/T307Q/N434F, and M252Y/T256D/T307W/N434Y, wherein the amino acid substitutions are according to EU numbering.

38. The method of embodiment 37, further comprising administering to the subject an effective amount of a radiolabeled antibody.

39. The method of embodiment 38, wherein the FcRn antagonist is administered after the radiolabeled antibody.

40. The method of embodiment 37 or 38, wherein the method enhances contrast for the radiolabeled antibody.

41. A method of reducing exposure of a non-target tissue to a radiolabeled antibody during diagnostic imaging comprising administering to a subject a therapeutically effective amount of an FcRn antagonist comprising a modified Fc domain comprising: a quadruple amino acid substitution selected from the group consisting of M252Y/T256D/T307Q/N434Y, M252Y/T256E/T307W/N434Y, M252Y/T256E/T307Q/N434Y, M252Y/T256D/T307Q/N434F, and M252Y/T256D/T307W/N434Y, wherein the amino acid substitutions are according to EU numbering.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

Examples

The present invention is further illustrated by the following examples. They should not be construed as further limiting.

Example 1: Materials and Methods

Protein Reagents

The following proteins were expressed and isolated: antigen with a C-terminal 8×Histidine tag (SEQ ID NO:5); rat FcRn (rFcRn, UniProt: P1359, p51 subunit: residues 23-298; UniProt: P07151, β2-m: residues 21-119); biotinylated cynomolgus FcRn (cynoFcRn, UniProt: Q8SPV9, p51 subunit: residues 24-297 with a C-terminal Avi-tag; UniProt: Q8SPW0, β2-m: residues 21-119); biotinylated human FcRn (hFcRn, UniProt: P55899, p51 subunit: residues 24-297 with a C-terminal Avi-tag; UniProt: P61769, β2-m: residues 21-119); Human CD16a (UniProt: P08637, FcγRIIIa: residues 17-208 with C-terminal HPC4 tag and valine at position 158 (V158)). The H435A and H310A/H435Q heavy chain variants were obtained from HEK293 conditioned media. mAb2 (IgG1) variants were cloned by Evitria and purified from suspension CHO K1 conditioned media using mAbSelect™ SuRe™ affinity columns (GE Healthcare) and buffer exchanged into phosphate-buffered saline (PBS) pH 7.4 for subsequent experiments.

Saturation Library Construction

The WT IgG1 mAb1 (IgG1) antibody heavy and light chains with leader DNA sequences were incorporated into the pBH6414 and pBH6368 mammalian expression plasmids, respectively, using the NcoI and HindIII restriction enzyme sites. The saturation library was created with the Lightning Site Directed Mutagenesis Kit (Agilent) and NNK (N=A/C/G/T, K=G/T) and WWC=A/T) primers (IDT Technologies) to introduce all possible amino acids at the following positions: M252, I253, S254, T256, K288, T307, K322, E380, L432, N434 and Y436 (Eu numbering). The heavy chain DNA sequences of the three control variants in the mAb1 backbone, AAA (T307A/E380A/N434A), LS (M428L/N434S) and YTE (M252Y/S254T/T256E), were constructed into the pBH6414 vector by LakePharma.

The combination saturation library was obtained through site-directed mutagenesis of the mAb1 heavy chain with the Q5 Mutagenesis Kit (NEBiolabs) and T256D, T256E, T307Q, T307W, N434F and N434Y primers with the WT and M252Y templates in the PCR reaction. Mutation incorporation into the mAb3 backbone was performed using the Q5® Mutagenesis kit (NEBiolabs) with M252Y, T256D, T307Q and T307W primers. The creation of all of the Fc variants was confirmed through Sanger Sequencing (Genewiz, Inc.).

Recombinant Antibody Expression and Purification

For conditioned media screening, DNA containing the mutant heavy chain and the wildtype light chain of mAb1 were transfected into 1 mL of Expi293 mammalian cells (Invitrogen™) for expression according to the manufacturer's instructions. The cells were incubated at 37° C., 5% carbon dioxide and 80% humidity with shaking at 900 rotations per minute (RPM) in a 2 mL 96 well plate (Greiner Bio-One) and sealed with an aerated membrane. The conditioned media was collected five days post-transfection and stored at −80° C. until use. The lead variants in the backbones mAb1 and mAb3 were expressed on a 30 mL scale in 125 mL flasks with 0.2 μm vented caps (Corning). The 125 mL culture flasks were shaken at 125 RPM during the entire expression duration. The conditioned media was collected five days post-transfection and filtered through 0.22 μm, 50 mL conical filters (Corning) and stored at 4° C. until purification.

Isolation of mAb1 and mAb3 was performed using 1 mL mAbSelect™ SuRe™ HiTrap® columns (GE Healthcare). Following a wash step of PBS pH 7.4 for ten column volumes, the antibodies were eluted with five column volumes of 0.1 M citric acid pH 3.0 (Sigma) and neutralized with 0.5 mL of 1 M tris base pH 9.0 (Sigma). The eluted antibodies were buffer exchanged against PBS pH 7.4 and concentrated to >1 mg mL$^{-1}$ using 30 kDa MWCO Amicon® Concentrators (Millipore®) for subsequent studies. The concentration of the purified antibodies was determined from their UV absorbance at 280 nm (UV$_{280}$) with an appropriate extinction coefficient.

Octet Conditioned Media Screening and Analysis

Screening of conditioned media containing the mAb1 variants was performed on an Octet QK 384 with Ni-NTA biosensors (PALL Life Sciences). His-tagged antigen was captured at 15 μg mL$^{-1}$ for 300 sec in PBS, 0.1% Bovine Serum Albumin (BSA, Sigma) and 0.01% Tween-20 (Sigma) pH 7.4 (PBST-BSA 7.4) followed by a 20 second wash with PBST-BSA pH 7.4. The antibodies were captured for 200 sec in conditioned media diluted 1:1 with PBST-BSA pH 7.4. Following buffer wash steps in pH 6.0 buffer, FcRn binding kinetics were obtained using 200 nM rFcRn for association and dissociation times of 150 and 200 sec, respectively, at pH 6.0. At all steps during the Octet screening, the temperature was 30° C. with a shake speed of 1000 RPM. The rFcRn binding kinetic profiles were corrected to the initiation of the FcRn association phase and modeled to a 1:1 binding model using the Octet 7.1 Analysis Software.

FcRn Binding Kinetics

FcRn binding kinetics under multiple pH conditions (pH 6.0, 7.4, 8.0 and 9.0) were measured using a Biacore™ T200 instrument (GE Healthcare) using the biotin CAPture kit (GE Healthcare) (see, e.g., Abdiche et al., MAbs (2015) 7:331-43; Karlsson et al., Anal. Biochem. (2016) 502:53-63). The CAPture reagent was captured to the CAP chip to a surface density of >1500 RU, followed by FcRn for a variable capture time at 30 μL min$^{-1}$ to account for the reduced binding affinities with higher pH. The FcRn concentrations and capture times for each pH were as follows: pH 6.0:0.1 μg mL$^{-1}$ FcRn for 24 sec, pH 7.4 and 8.0:1 μg mL$^{-1}$ for 60 sec and pH 9.0:10 μg mL$^{-1}$ for 60 sec. The running buffers for all pH conditions was 20 mM Bis-Tris Propane; 150 mM NaCl, 0.05% Tween-20 with the pH adjusted accordingly to pH 6.0, 7.4, 8.0 and 9.0. A concentration series of each antibody variants starting from 1000 nM in a three-fold dilution was established to cover a wide range in binding affinities. Kinetic measurements were performed for 180 sec and 360 sec association and dissociation times, respectively, with subsequent regeneration of the CAP surface with guanidine hydrochloride and sodium hydroxide each cycle. Steady state RU measurements at pH 7.4, 8.0 and 9.0 were obtained at 1000 nM in triplicate.

Sensorgrams at each pH were fit to a 1:1 or bivalent binding model using the Biacore T200™ Evaluation Software. The bivalent model accounts for the avidity effects observed at high FcRn capture levels and the two FcRn binding sites per IgG. See, e.g., Suzuki et al., *J Immunol.* (2010) 184:1968-76. Each concentration series was fit independently to obtain the average on and off rates and binding affinities. The residual binding was determined from the steady state binding response prior to the start of the dissociation phase and averaged.

FcRn Affinity Chromatography

In one experiment, the FcRn affinity column was created from protocols adapted from Schlothauer et al., mAbs (2013) 5:576-86. A 1 mL Streptavidin HP HiTrap® column (GE Healthcare) was equilibrated with binding buffer (20 mM sodium phosphate (Sigma) pH 7.4, 150 mM sodium chloride (NaCl; Sigma)) at 1 mL min⁻¹ for five column volumes followed by an injection of 4 milligram of biotinylated cynoFcRn. The column was washed with binding buffer and stored at 4° C. until use.

The FcRn affinity column was equilibrated with low pH buffer (20 mM 2-(N-morpholino)ethanesulfonic acid (MES; Sigma) pH 5.5; 150 mM NaCl) for five column volumes prior to injection with 300 µg of each antibody. The pHs of the antibody solutions were adjusted to pH 5.5 with low pH buffer. Following a ten column volume wash with low pH buffer, the antibodies were eluted by a linear pH gradient with high pH buffer (20 mM 1,3-bis(tris(hydroxymethyl) methylamino)propane (bis tris propane; Sigma) pH 9.5; 150 mM NaCl) over 30 column volumes at 1 mL min⁻¹ in 1 mL fractions and monitoring the UV₂₈₀. The FcRn affinity column was re-equilibrated with ten column volumes of low pH buffer for subsequent runs or binding buffer for storage. All variants were performed in triplicate.

The FcRn affinity column elution profile for each variant was modeled to a single Gaussian distribution using Equation 1 in Sigmaplot 11 (Systat Software, Inc.) to determine the elution volume at the UV₂₈₀ maximum:

$$UV_{280} = y_0 + a * \exp^{\frac{-(x-x_0)^2}{2b}} \qquad \text{(Equation 1)}$$

where $x_0$ is the elution volume at the UV₂₈₀ peak maximum, $y_0$ is the baseline UV₂₈₀ absorbance and $a$ and $b$ are related to the full width at half max of the distribution. The pH of each fraction was measured by a Corning Pinnacle 540 pH meter and correlated to the elution volume using a linear regression.

In another experiment, The FcRn affinity column was adapted from Schlothauer et al., supra with biotinylated hFcRn on a 1 mL Streptavidin HP HiTrap® column (GE Healthcare). The column was injected with 300 µg of each antibody in low pH buffer (20 mM 2-(N-morpholino)ethanesulfonic acid (MES; Sigma) pH 5.5; 150 mM NaCl) on an AKTA Pure System (AKTA). The antibodies were eluted by a linear pH gradient created with low and high pH buffer (20 mM 1,3-bis(tris(hydroxymethyl)methylamino)propane (bis tris propane; Sigma) pH 9.5; 150 mM NaCl) over 30 column volumes at 0.5 mL min⁻¹ and monitoring the absorbance and pH. The column was re-equilibrated with low pH buffer for subsequent runs. All variants were performed in triplicate. The FcRn affinity column elution profiles were fit to a single Gaussian distribution in Sigmaplot 11 (Systat Software, Inc.) to determine the elution volume and pH from at the UV₂₈₀ maximum.

Differential Scanning Fluorimetry

The Differential Scanning Fluorimetry (DSF) experiments were performed on a BioRad CFX96™ real time system thermal cycler (BioRad) on 20 µL reactions. The antibody samples and 5000× stock of Sypro™ Orange dye (Invitrogen™) were diluted to 0.4 mg mL⁻¹ and 10×, respectively, in PBS pH 7.4. The antibodies and Sypro™ Orange were mixed in a 1:1 ratio in 96-well PCR plates and sealed with adhesive Microseal® (BioRad) to final concentrations of 0.2 mg mL⁻¹ of each antibody and 5× Sypro™ Orange dye. All antibody variants were performed in triplicate. The thermal cycler program consisted of a 2 minute equilibration step at 20° C. followed by constant temperature ramping rate of 0.5° C./5 sec to a final temperature of 100° C. Fluorescence measurements of each well were acquired using the FAM excitation wavelength (485 nm) and ROX emission (625 nm) detectors suitable for Sypro™ orange fluorescence (see, e.g., Biggar et al., *Biotechniques* (2012) 53:231-38). The DSF fluorescence intensity profile and first derivative were exported from the BioRad CFX™ Manager and analyzed in Sigmaplot 11. The $T_m$ was defined as the midpoint of the first transition in the fluorescence intensity profile.

FcγRIIIa Binding Kinetics

Binding kinetics and affinity were measured using a Biacore™ T200 instrument (GE Healthcare) (Zhou et al., *Biotechnol Bioeng.* (2008) 99:652-65). Anti-HPC4 antibody (Roche), at 50 µg mL⁻¹ in Acetate pH 4.5, was coupled to the surface of CM5 sensor chip for 600 sec at 10 µl min⁻¹ with amine chemistry to a final density of >20,000 RU. The running buffer for the FcγRIIIa binding kinetics experiments was HEPES Buffered Saline with 0.05% Surfactant P-20 (HBS-P+, GE Healthcare) and 2 mM Calcium Chloride (CaCl₂, Fluka) at pH 7.4. Each kinetic trace was initialized with the capture of 1.25 µg mL⁻¹ HPC4-tagged FcγRIIIa-V158 for 30 sec at 5 µl min⁻¹. Association and dissociation kinetics at 300 nM of each variant were measured for each variant for 120-180 sec for each step at 5 µl min-1. Upon completion of the kinetic measurements, the CM5 chip was regenerated with HBS-P+ buffer supplemented with 10 mM EDTA (Ambion®). Prior to the next kinetic measurements, the CM5 chip was washed for 120 sec with HBS-P+ with CaCl₂.

In one experiment, the FcγRIIIa kinetic experiments were analyzed in a similar manner as described for the FcRn binding at pH 7.4. For the WT, benchmark, lead single and combination variants, kinetics at a series of a 3-fold serial dilution from 1000 nM were obtained to determine the binding affinity to FcγRIIIa. The steady state RU at each concentration and replicate were determined, plotted as a function of antibody concentration and fit to a steady state model as shown in Equation 2:

$$RU = \text{offset} + \frac{(R_{max} - \text{offset}) * [\text{Antibody}]}{[\text{Antibody}] + K_{D,app}} \qquad \text{(Equation 2)}$$

where offset is the baseline RU at 0 nM antibody, $R_{max}$ is the plateau RU at high antibody concentrations, [Antibody] is the concentration of antibody and $K_{D,app}$ is the apparent binding affinity of the interaction between the variants and FcγRIIIa.

In another experiment, the FcγRIIIa kinetic experiments were analyzed in a similar manner as described for the FcRn binding at pH 7.4 using the average steady state binding response. For all variants, the steady state RU of 300 nM antibody was determined in triplicate and averaged. The fold change in response change relative to WT (Response Fold Change) was determined for comparison between the variants in each backbone.

Isoelectric Focusing

The isoelectric point (pI) of the lead variants was determined using capillary electrophoresis on a Maurice C (Protein Simple). Each 200 µL sample contained 0.35% methyl cellulose (Protein Simple), 4% pharmalyte 3-10 (GE Healthcare), 10 mM arginine (Protein Simple), 0.2 mg mL$^{-1}$ antibody and the 4.05 and 9.99 pI markers (Protein Simple). The sample was loaded into the capillary for 1 min at 1500 V, followed by a separation phase for 6 min at 3000 V and monitored using tryptophan fluorescence. The pI for each variant was determined using the Maurice C software and defined as the pH at the fluorescence maximum for the major species.

Homogeneous Bridging Rheumatoid Factor (RF) ELISA

Antibodies were biotinylated and digoxigen-labeled using the EZ-Link Sulfo-NHS-LC-Biotin and Mix-n-Stain™ Digoxigenin Antibody Labeling Kits (Biotium) according to the manufacturer's instructions. A stock solution containing 4 µg mL$^{-1}$ of the biotinylated and digoxigenin-labeled antibodies was prepared for each variant and mixed in a 1:1 ratio with 300 U/mL RF (Abcam). Following incubation at room temperature for 20 hours, 100 µL of each antibody-RF mixture was added to Streptawell™ plates (Sigma-Aldrich) and incubated at room temperature for 2 hours. The plate was washed three times with PBS pH 7.4 with 0.05% Tween-20 and 100 µL of a 1:2000 dilution of HRP-conjugated anti-digoxigenin secondary antibody (Abcam) was added to each well. After a 2-hour incubation at room temperature, the wells were washed and treated with 100 µL of the TMB substrate (Abcam) for 15 minutes at room temperature. The reaction was stopped with 100 µL of the stop solution (Abcam) and the absorbance was measured at 450 nm on a SpectraMax® plate reader. A well containing no antibody-RF mixture provided the blank subtraction and the experiment was repeated three times. P-values were determined using the student's t-test.

Example 2: Octet Screening of Saturation Point Mutations in Conditioned Media

FcRn is a heterodimer of an MHC class-I-like α-domain and a β2-microglobulin (β2-m) subunit (FIG. 1A), common to a majority of the Fc receptors. FcRn recognizes regions on the antibody Fc heavy chain distinct from the other FcγRs (see, e.g., Oganesyan et al., *J Biol Chem.* (2014) 289:7812-24; and Shields et al., *J Biol Chem.* (2001) 276:6591-604).

Figure 2B:
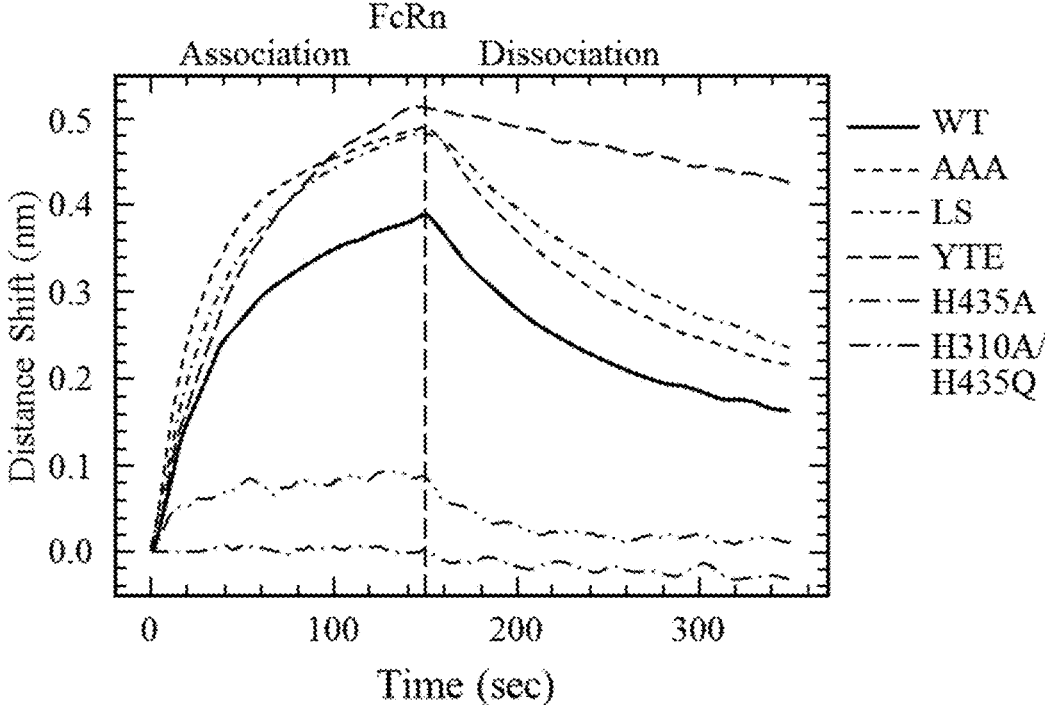

In order to identify variants with slower FcRn off-rates than the WT antibody, a biolayer interferometry (BLI)-based assay was designed to screen the antibody variants in conditioned media in a high throughput manner (FIG. 2A). This assay was developed using several benchmark variants which enhance (AAA, LS and YTE) or reduce (H435A, H310A/H435Q) the affinity for FcRn at pH 6.0, in comparison to the WT antibody. NiNTA biosensors captured the his-tagged antigen and, subsequently, each antibody variant at pH 7.4 to mimic conditioned media (FIG. 2A). Binding kinetics to rat FcRn (rFcRn) at pH 6.0, which has a ~25-fold slower off-rate from human IgG1 and is more amenable for Octet studies than human FcRn (hFcRn), were measured for each of the variants (FIG. 2B). The H435A (FIG. 2B, long dashes interspersed with single dot) and H310A/H435Q (FIG. 2B, long dashes interspersed with two dots) variants show little to no FcRn binding kinetics (also see, e.g., Shields et al., supra; Medesan et al., *J Immunol.* (1997)

158:2211-7; and Raghavan et al., *Biochemistry* (1995) 34(45):14649-57). The AAA (FIG. 2B, short dashes), LS (FIG. 2B, short dashes interspersed with single dot) and YTE (FIG. 2B, long dashes) variants all display slower dissociation kinetics compared to the WT (FIG. 2B, solid line) with between a 2-7.3-fold reduction in the FcRn off-rate. This demonstrated that Octet screening is suitable to distinguish between variants with perturbed rFcRn dissociation kinetics.

Figure 2C:
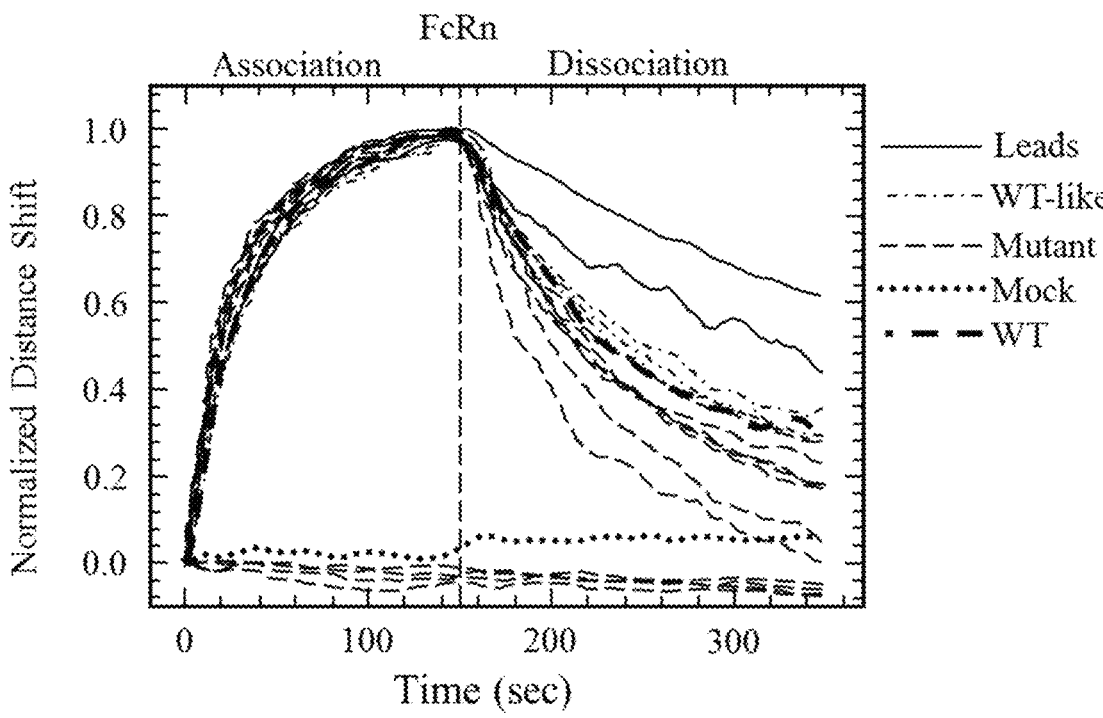

An IgG1 antibody, mAb1, served as a model system to create a saturation mutagenesis library to screen for mutants with a reduced FcRn off-rate. Eleven positions in the Fc region of mAb1 were selected based on their proximity or direct contribution to the FcRn interface (FIGS. 1A and 1B) (see, e.g., Oganesyan et al., supra; and Shields et al., supra). All point mutations at these positions were constructed using site directed mutagenesis and transfected in Expi293 cells for expression. Conditioned media screening was performed for the saturation library mutants as described above. The normalized FcRn binding Octet sensorgrams for a subset of the variants are shown in FIG. 2C (long dashes) with the wildtype (FIG. 2C, thick long dashes) and mock-negative control (FIG. 2C, dotted line). The mock showed a lack of observable FcRn binding. Several mutants clearly disrupted the binding of rFcRn as little to no signal change was observed in the kinetic profiles (FIG. 2C, long dashes, located below the dotted line (mock)). The cutoff for variants with improved FcRn off-rate was defined as three standard deviations lower than the mean of the WT antibody. In the subset of mutations shown in FIG. 2C, two (FIG. 2C, solid lines) had significantly reduced off-rates compared to the wildtype antibody (FIG. 2C, thick long dashes), while the remaining variants had similar (FIG. 2C, short dashes interspersed by single dot) or faster (FIG. 2C, long dashes above dotted line (mock)) rFcRn off-rates.

Figure 2D:
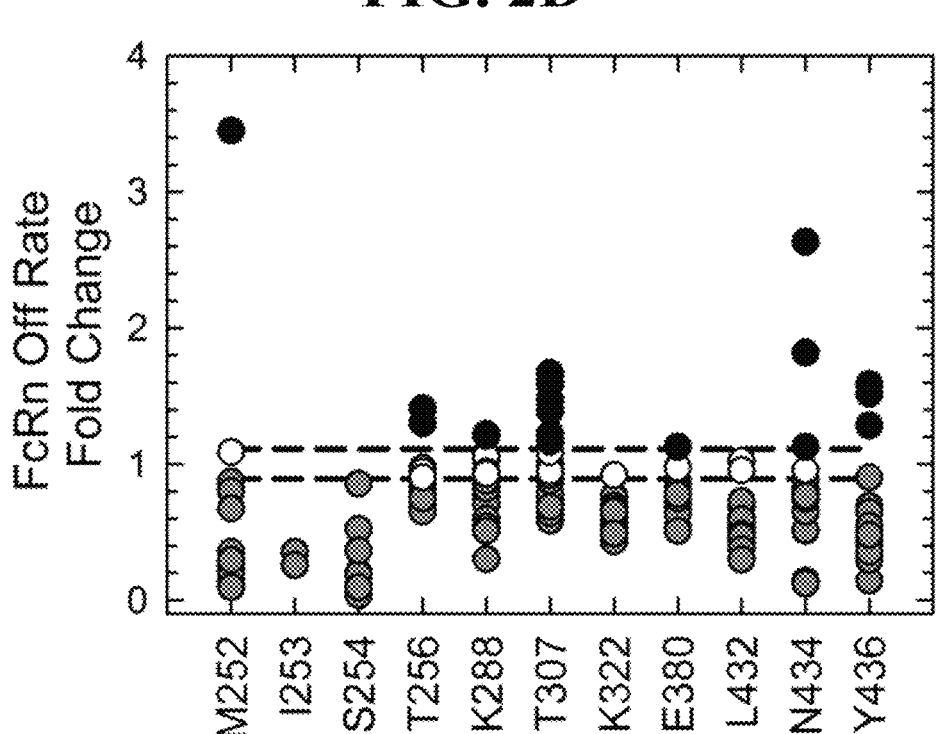

The rFcRn off-rates for all of the single point mutations are shown in FIG. 2D and FIG. 14 by position and mutation. In FIG. 14, the data is sorted into one of four categories depending on the fold change of rFcRn off-rate compared to wildtype, and wildtype species are indicated by black squares.

In FIG. 14, the fold-change in the rFcRn off-rate for all possible substitutions at the eleven positions of the saturation library were normalized to the average of the WT antibody and color coded. All mutants fell into one of four categories: little to no binding (dark gray), faster rFcRn off-rate (gray), WT-like rFcRn off-rate (horizontal lines) and slower rFcRn off-rate (grids). Multiple variants possessed slower rFcRn off-rates than the WT antibody (grids).

Mutants colored in dark gray in FIG. 14 showed little to no binding to rFcRn in a similar manner as the mock (FIG. 2C, dotted line), and localized to the M252, I253 and S254 loop. The only mutations at I253 were methionine and valine, and both significantly increased the rFcRn off-rate, further supporting the importance of I253 to the FcRn interaction. Another 120 variants (FIG. 2D and FIG. 14, light gray rectangles) destabilized the interaction with rFcRn with approximately 50% located in each the $C_H2$ and $C_H3$ domains. Twenty-five mutants have a WT-like off-rate (FIG. 2D and FIG. 14, white rectangles) with eight of the 11 position possessing at least one WT-like mutation (FIG. 14, white rectangles). The following mutations had a significantly reduced rFcRn off-rate compared to wildtype (FIG. 2D and FIG. 14, black rectangles): M252Y, T256D/E, K288D/N, T307A/E/F/M/Q/W, E380C, N434F/P/Y and Y436H/N/W. The M252Y, N434F and N434Y mutations possessed off-rates greater than two-fold slower than the WT antibody (FIG. 2D). These mutations were expressed and purified with protein A chromatography for further in vitro FcRn kinetic characterization.

Example 3: Biacore™ FcRn Binding Kinetics at pH 6.0

Figure 3:
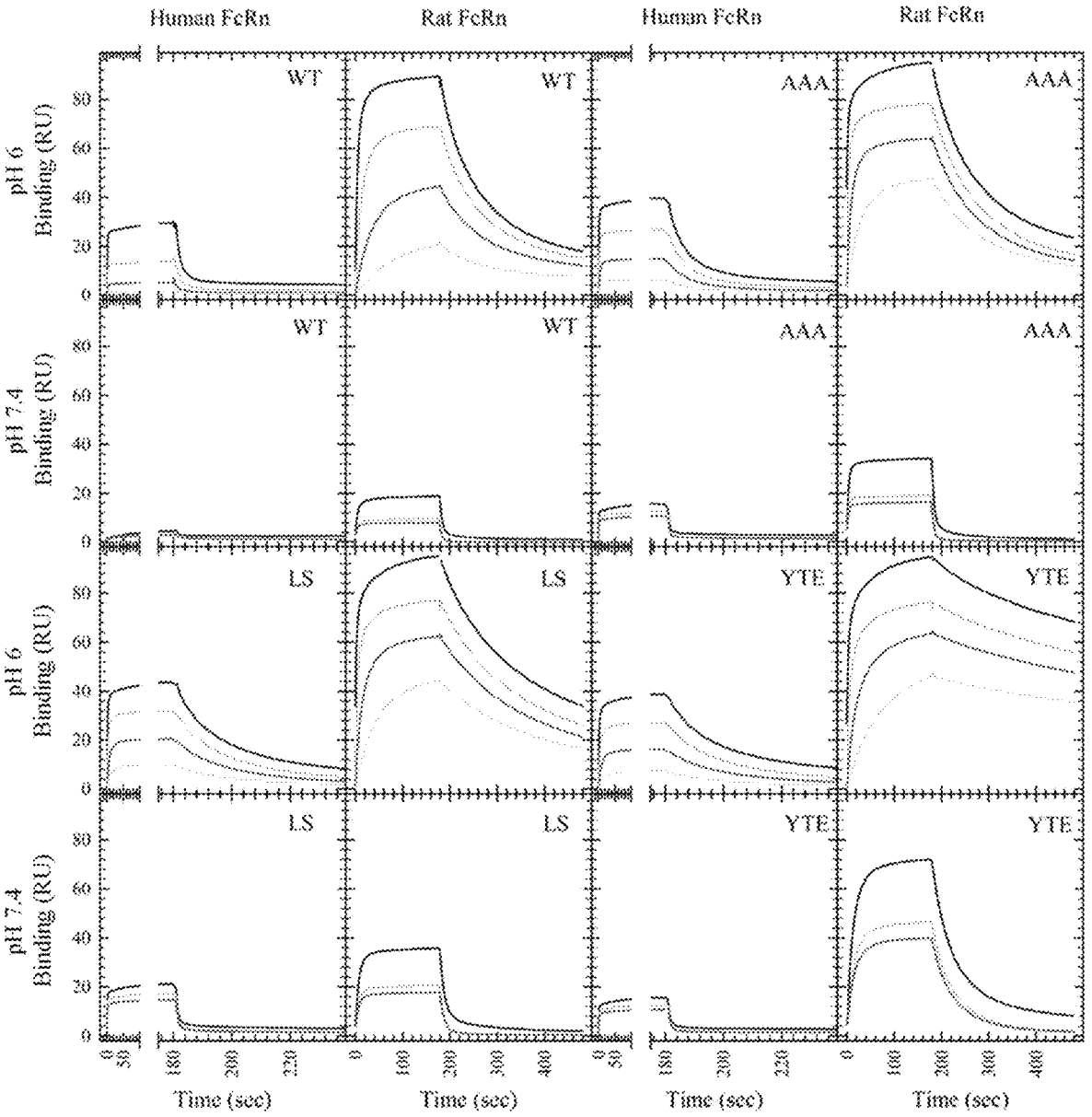
FIG. 3 graphically depicts Biacore™ kinetics of benchmark and wildtype variants with human and rat FcRns at pH 6.0 and pH 7.4. All FcRn binding curves for the concentration series of the wildtype (upper left), AAA variant (upper right), M428/N434S (LS) variant (lower left) and M252Y/S254T/T256E (YTE) variant (lower right) are shown for each human (first and third columns) and rat (second and fourth column) FcRn at pH 6.0 (first and third rows) and pH 7.4 (second and fourth rows). The AAA, LS and YTE variants showed slower off-rates from FcRn than the wildtype antibody. In general, the antibodies bind rFcRn with an approximately 10-fold increased affinity compared to wildtype. The LS variant had the tightest affinity at pH 7.4 and the greatest residual binding at pH 7.4 to hFcRn, while rFcRn bound the YTE variant most tightly.
Figure 4A:
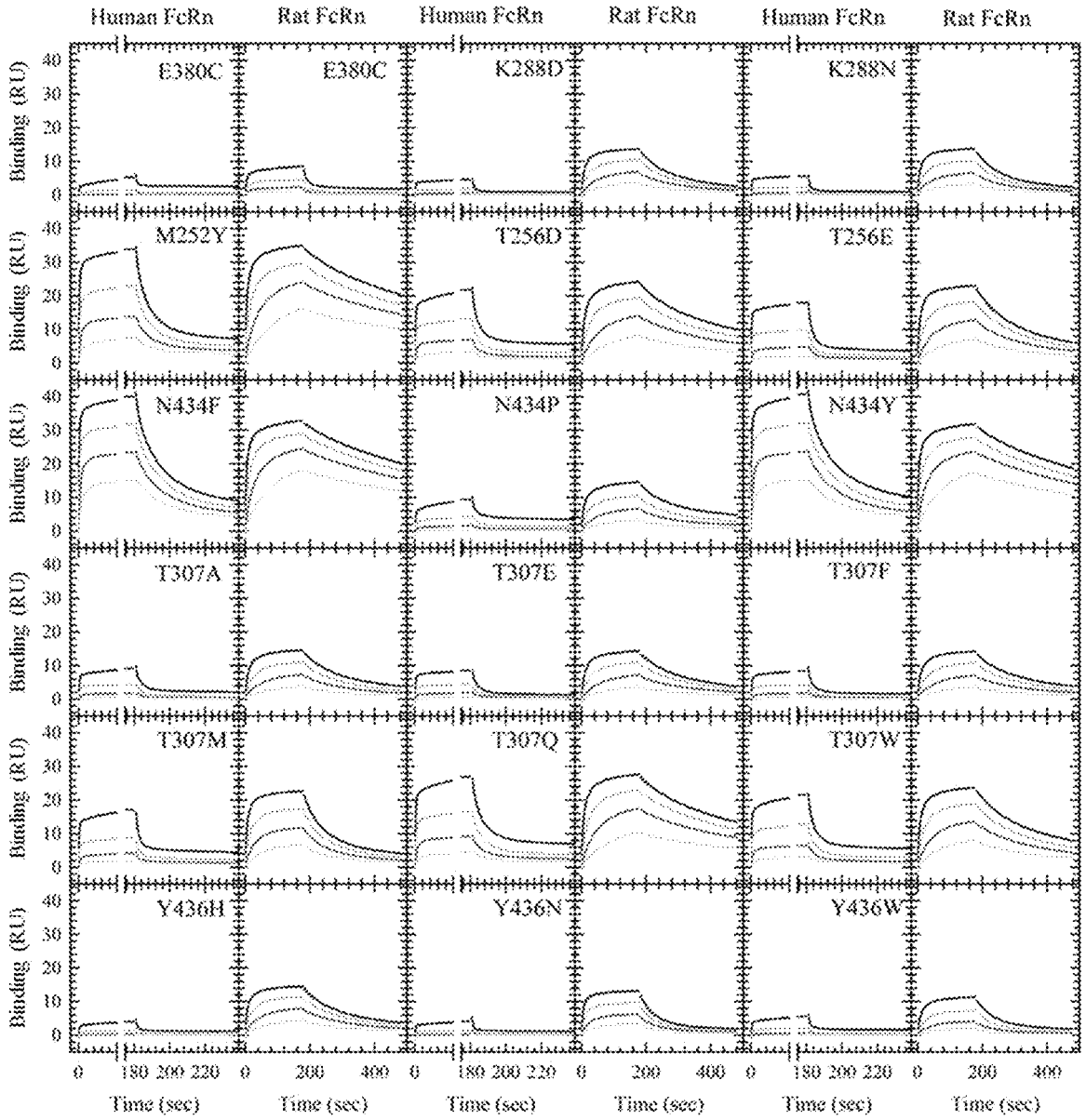
FIG. 4A graphically depicts Biacore™ kinetics of the lead saturation variants with human and rat FcRn at pH 6.0. FcRn binding kinetic traces of the concentration series for the 18 lead saturation variants are shown. M252Y, T256D, T256E, N434F, N434P, N434Y, T307A, T307E, T307F, T307Q and T307W had slower off-rates from both human and rat FcRn. The remaining variants were specific for rat FcRn only.
Figure 4B:
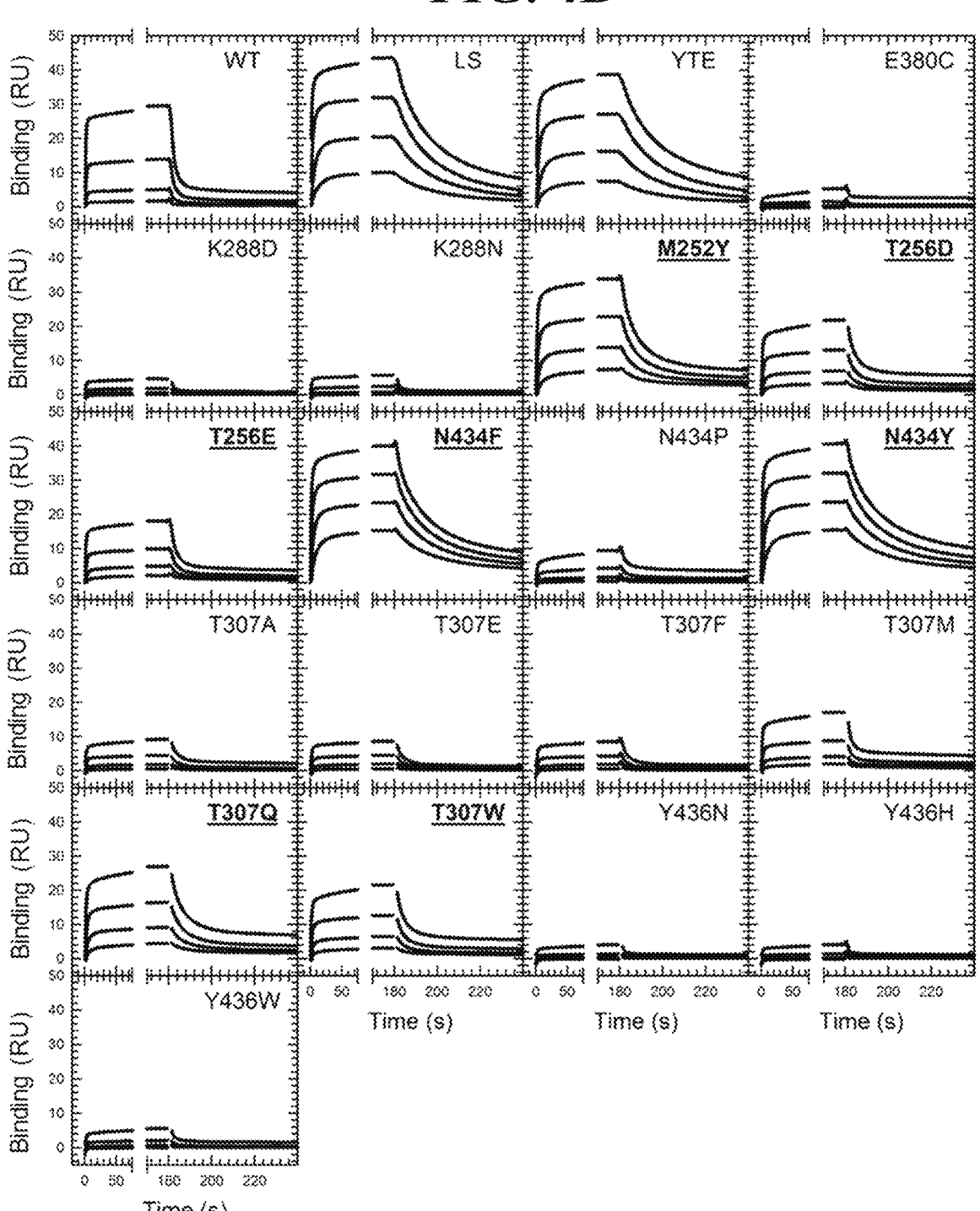
FIG. 4B graphically depicts FcRn binding kinetics of the WT, benchmark and lead single saturation variants with human FcRn at pH 6.0. FcRn binding sensorgrams with a concentration series of the WT, LS, YTE and the 18 saturation variants with human FcRn at pH 6.0. Single saturation variants used for the combination library are underlined and bold.
Figures 5A, 5B:
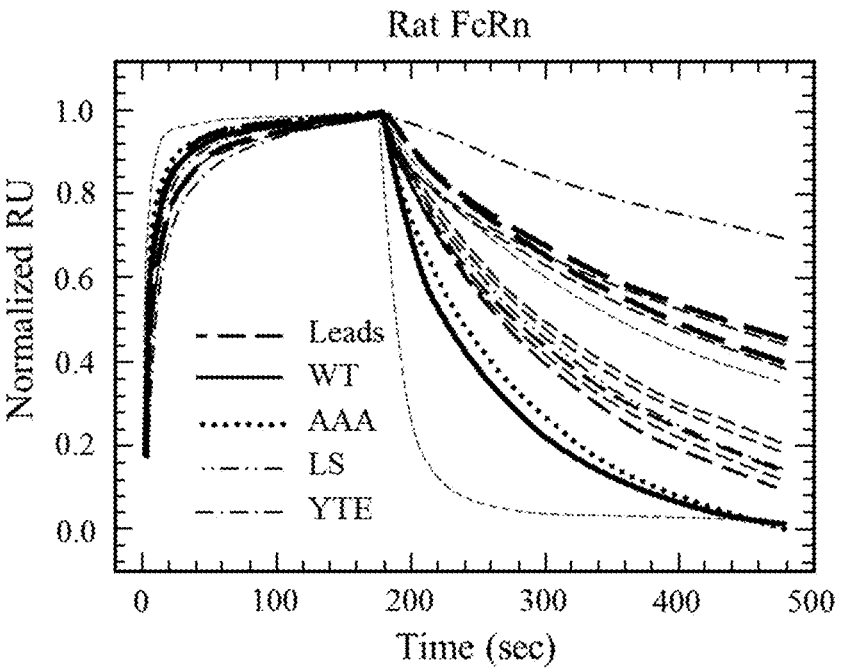
FIGS. 5A-D depict data showing that multiple variants having slower off-rates from both human and rat FcRn at pH 6.0.

The AAA, LS and YTE variants served as positive controls in the FcRn binding kinetics measurements using Biacore™ to both human and rat FcRn at pH 6.0. Concentration-dependent binding to FcRn was observed for all variants, including the wildtype, benchmark (FIG. 3) and leads (FIGS. 4A and 4B), and the binding profile of a single injection with human and rat FcRn are shown in FIGS. 5A and 5B, respectively. The wildtype antibody had binding affinity for human and rat FcRn of 2380±470 nM and 207±43 nM affinities, respectively (Table 1).

TABLE 1

| In vitro Characterization Parameters of Purified Lead Antibodies for mAb1 | | | | | | |
|---|---|---|---|---|---|---|
| | Octet pH 6.0 rFcRn | FcRn Affinity Column Elution | DSF $T_m$ | Biacore™ pH 6.0 hFcRn | | |
| Mutant | Off-rate | pH | (° C.) | On-rate | Off-rate | $K_{D, app}$ |
| E380C | 2.08 ± 0.18 | 7.18 ± 0.11 | 64.7 ± 0.5 | 1.73 ± 0.39 | 4.57 ± 1.50 | >10,000 |
| K288D | 3.79 ± 0.06 | 7.33 ± 0.10 | 65.8 ± 0.1 | 3.31 ± 1.10 | 5.13 ± 0.75 | >10,000 |
| K288N | 4.11 ± 0.08 | 7.39 ± 0.02 | 66.7 ± 0.3 | 4.12 ± 1.42 | 4.54 ± 0.34 | >10,000 |
| M252Y | 0.95 ± 0.03 | 7.88 ± 0.03 | 64.4 ± 0.2 | 5.50 ± 1.83 | 1.43 ± 0.23 | 3100 ± 1500 |
| N434F | 1.18 ± 0.05 | 8.30 ± 0.05 | 67.8 ± 0.2 | 35.4 ± 15.3 | 0.50 ± 0.08 | 165 ± 73 |
| N434P | 3.80 ± 0.08 | 7.56 ± 0.02 | 63.6 ± 0.5 | 2.42 ± 0.54 | 3.35 ± 1.10 | >10,000 |
| N434Y | 1.33 ± 0.04 | 8.46 ± 0.02 | 67.3 ± 0.5 | 35.9 ± 9.6 | 0.52 ± 0.10 | 137 ± 33 |
| T256D | 2.24 ± 0.03 | 7.82 ± 0.07 | 64.7 ± 0.2 | 4.41 ± 1.72 | 2.51 ± 0.65 | 6700 ± 3540 |
| T256E | 3.26 ± 0.04 | 7.63 ± 0.06 | 66.3 ± 0.6 | 3.90 ± 2.37 | 3.38 ± 0.28 | >10,000 |
| T307A | 2.98 ± 0.06 | 7.61 ± 0.03 | 68.0 ± 0.4 | 2.85 ± 0.72 | 2.91 ± 0.46 | >10,000 |
| T307E | 3.29 ± 0.08 | 7.58 ± 0.03 | 70.2 ± 0.5 | 4.37 ± 1.63 | 2.98 ± 0.37 | 8130 ± 5070 |
| T307F | 2.80 ± 0.07 | 7.61 ± 0.03 | 70.2 ± 0.3 | 2.70 ± 0.83 | 2.92 ± 0.13 | >10,000 |
| T307M | 3.47 ± 0.13 | 7.40 ± 0.08 | 70.0 ± 0.4 | 4.08 ± 0.83 | 3.87 ± 0.28 | >10,000 |
| T307Q | 1.84 ± 0.05 | 7.86 ± 0.06 | 70.3 ± 0.6 | 3.96 ± 1.10 | 2.15 ± 0.22 | 5720 ± 1530 |
| T307W | 2.42 ± 0.08 | 7.75 ± 0.07 | 63.0 ± 0.5 | 3.33 ± 0.83 | 2.77 ± 0.29 | 8740 ± 2440 |
| Y436H | 3.22 ± 0.08 | 7.33 ± 0.05 | 68.7 ± 0.3 | 2.59 ± 0.78 | 6.06 ± 1.00 | >10,000 |
| Y436N | 5.25 ± 0.22 | 7.22 ± 0.05 | 65.8 ± 0.5 | 4.60 ± 2.36 | 7.37 ± 3.34 | >10,000 |
| Y436W | 5.18 ± 0.18 | 7.39 ± 0.03 | 68.6 ± 0.7 | 2.84 ± 1.90 | 4.62 ± 0.92 | >10,000 |
| WT | 5.01 ± 0.45 | 7.37 ± 0.05 | 69.0 ± 0.2 | 16.2 ± 2.9 | 3.86 ± 0.38 | 2380 ± 470 |
| AAA | 3.77 ± 1.03 | 7.94 ± 0.06 | 61.3 ± 0.6 | 8.37 ± 1.82 | 1.44 ± 0.04 | 1780 ± 380 |
| LS | 3.38 ± 0.23 | 8.29 ± 0.03 | 68.5 ± 0.3 | 19.3 ± 3.5 | 0.52 ± 0.03 | 272 ± 40 |
| YTE | 0.66 ± 0.17 | 8.14 ± 0.03 | 61.2 ± 0.3 | 14.3 ± 4.4 | 0.45 ± 0.07 | 342 ± 117 |

| | Biacore™ pH 6.0 rFcRn | | | Biacore™ pH 7.4 | |
|---|---|---|---|---|---|
| | | | | hFcRn Steady | rFcRn Steady |
| Mutant | On-rate | Off-rate | $K_{D, app}$ | State RU | State RU |
| E380C | 1.71 ± 0.25 | 106 ± 1 | 6310 ± 880 | 5.7 ± 0.1 | 27.7 ± 4.0 |
| K288D | 6.61 ± 3.01 | 8.43 ± 0.60 | 149 ± 63 | 3.8 ± 0.2 | 21.9 ± 3.1 |
| K288N | 6.42 ± 2.80 | 10.7 ± 0.9 | 190 ± 73 | 3.9 ± 0.2 | 20.4 ± 2.7 |
| M252Y | 10.6 ± 3.1 | 2.64 ± 0.62 | 25 ± 3 | 8.6 ± 0.9 | 57.7 ± 10.7 |
| N434F | 12.6 ± 1.4 | 3.36 ± 1.79 | 26 ± 13 | 20.1 ± 3.4 | 54.9 ± 9.1 |
| N434P | 3.44 ± 0.07 | 6.67 ± 0.18 | 194 ± 9 | 3.5 ± 0.4 | 4.3 ± 0.6 |
| N434Y | 14.5 ± 1.82 | 3.46 ± 1.86 | 23 ± 12 | 22.6 ± 4.2 | 47.0 ± 6.3 |
| T256D | 6.09 ± 1.84 | 4.84 ± 0.08 | 86 ± 27 | 5.8 ± 0.6 | 30.4 ± 3.4 |
| T256E | 6.29 ± 1.59 | 6.94 ± 0.97 | 113 ± 15 | 4.8 ± 0.5 | 23.0 ± 2.7 |
| T307A | 6.09 ± 2.72 | 7.08 ± 0.67 | 132 ± 48 | 5.2 ± 0.6 | 23.1 ± 2.8 |
| T307E | 5.55 ± 2.82 | 6.03 ± 0.20 | 141 ± 65 | 5.7 ± 0.7 | 21.5 ± 2.6 |
| T307F | 5.69 ± 2.83 | 6.15 ± 0.14 | 131 ± 63 | 4.9 ± 0.7 | 21.9 ± 2.7 |
| T307M | 6.81 ± 2.34 | 17.1 ± 4.0 | 279 ± 140 | 4.4 ± 0.7 | 15.3 ± 1.9 |
| T307Q | 7.35 ± 2.15 | 4.04 ± 0.28 | 58 ± 16 | 6.4 ± 0.8 | 24.3 ± 3.0 |
| T307W | 7.11 ± 2.29 | 7.37 ± 0.41 | 111 ± 32 | 5.8 ± 0.7 | 19.2 ± 3.3 |
| Y436H | 5.06 ± 0.13 | 7.30 ± 0.88 | 131 ± 9 | 3.6 ± 0.5 | 16.3 ± 1.8 |
| Y436N | 10.1 ± 4.9 | 20.3 ± 3.1 | 233 ± 86 | 3.6 ± 0.4 | 17.4 ± 2.0 |
| Y436W | 3.44 ± 2.18 | 23.7 ± 7.7 | 1140 ± 950 | 3.7 ± 0.4 | 10.3 ± 1.2 |
| WT | 7.26 ± 1.01 | 15.2 ± 0.23 | 207 ± 43 | 4.3 ± 1.0 | 12.2 ± 0.5 |
| AAA | 15.7 ± 3.3 | 11.7 ± 1.1 | 77 ± 18 | 13.9 ± 3.1 | 23.6 ± 4.9 |
| LS | 9.08 ± 1.58 | 6.58 ± 0.39 | 74 ± 9 | 18.3 ± 4.6 | 24.8 ± 4.8 |
| YTE | 6.52 ± 0.46 | 1.21 ± 0.21 | 18 ± 2 | 13.2 ± 3.5 | 53.9 ± 1.2 |

45

46

All data shown in Table 1 was obtained using the experimental techniques shown at the top of each column.

The rFcRn off-rate by Octet using purified proteins was measured as a comparison to the kinetic constants obtained from the screening in conditioned media. The elution pH was determined by FcRn affinity chromatography in triplicate (n=3) and DSF probed the thermal stability in triplicate (n=3). FcRn binding kinetics to human and rat FcRn were obtained from Biacore™ with a series of antibody concentrations in duplicate (n=2) and fit independently. The steady state binding response (RU) of each variant with human and rat FcRn at pH 7.4 was measured with 1000 nM antibody in triplicate (n=3) using Biacore™. Units for each measurement are as follows: Octet pH 6.0 rFcRn Off-rate ($\times 10^{-3}$ $s^{-1}$); Elution pH (unit-less); DSF $T_m$ (° C.); Biacore™ pH 6.0 hFcRn On-rate ($\times 10^4$ $M^{-1}$ $s^1$), Off-rate ($\times 10^{-1}$ $s^1$) and $K_{D,app}$ ($\times 10^9$ M); Biacore™ pH 6.0 rFcRn On-rate ($\times 10^4$ $M^{-1}$ $s^{-1}$), Off-rate ($\times 10^{-3}$ $s^{-1}$) and $K_{D,app}$ ($\times 10^9$ M); and Biacore™ pH 7.4 Steady State Binding Response (RU).

In FIG. 5B, the AAA (dotted), LS (dashes interspersed by two dots) and YTE (dashes interspersed by single dot) variants had between a 1.6 and 10.4-fold enhanced binding affinity compared to WT. The identity of the benchmark variant with the tightest FcRn affinity was species specific as LS had the tightest affinity to hFcRn, while rFcRn had a tighter affinity for YTE (Table 2A).

TABLE 2A

| | FcRn Affinity Column Elution | DSF | Biacore™ pH 6.0 | | | | | | Biacore™ pH 7.4 | |
| | | | hFcRn | | | rFcRn | | | hFcRn | rFcRn |
| Variant | pH | $T_m$ (° C.) | On-rate | Off-rate | $K_{D,app}$ | On-rate | Off-rate | $K_{D,app}$ | Steady State RU | Steady State RU |
|---|---|---|---|---|---|---|---|---|---|---|
| MDQN | 7.92 ± 0.06 | 67.9 ± 0.4 | 3.76 ± 0.38 | 8.72 ± 0.10 | 232 ± 24 | 1.33 ± 0.22 | 1.27 ± 0.07 | 9.54 ± 1.66 | 10.7 ± 1.0 | 39.1 ± 4.5 |
| MDTF | 8.41 ± 0.07 | 62.3 ± 0.2 | 9.68 ± 0.64 | 2.90 ± 0.04 | 29.9 ± 2.0 | 2.18 ± 0.20 | 0.39 ± 0.01 | 1.78 ± 0.17 | 29.2 ± 4.0 | 63.0 ± 6.0 |
| MDTY | 8.45 ± 0.04 | 61.5 ± 0.2 | 18.3 ± 0.6 | 2.85 ± 0.01 | 15.6 ± 0.5 | 4.13 ± 0.15 | 0.25 ± 0.35 | 0.60 ± 0.85 | 37.1 ± 5.0 | 71.6 ± 6.6 |
| MDWN | 7.92 ± 0.04 | 57.8 ± 0.4 | 5.29 ± 0.14 | 8.92 ± 0.32 | 169 ± 8 | 1.57 ± 0.12 | 1.29 ± 0.01 | 8.24 ± 0.85 | 12.2 ± 1.3 | 42.1 ± 4.7 |
| MEQN | 7.84 ± 0.06 | 68.0 ± 0.5 | 2.87 ± 0.01 | 14.3 ± 0.2 | 499 ± 6 | 1.46 ± 0.25 | 1.56 ± 0.94 | 10.7 ± 6.7 | 5.8 ± 0.6 | 23.4 ± 3.1 |
| METF | 8.23 ± 0.03 | 64.1 ± 0.7 | 5.36 ± 1.41 | 4.19 ± 0.03 | 78.2 ± 20.5 | 1.08 ± 0.11 | 0.81 ± 0.07 | 7.53 ± 1.03 | 23.3 ± 3.2 | 59.0 ± 5.6 |
| METY | 8.38 ± 0.04 | 63.5 ± 0.6 | 6.28 ± 1.62 | 3.93 ± 0.02 | 62.6 ± 16.2 | 1.27 ± 0.11 | 0.98 ± 0.07 | 7.71 ± 0.84 | 26.8 ± 3.7 | 62.2 ± 6.3 |
| MEWN | 7.78 ± 0.04 | 58.2 ± 0.4 | 4.32 ± 0.36 | 14.0 ± 0.1 | 323 ± 27 | 1.81 ± 0.01 | 1.92 ± 0.05 | 10.6 ± 0.26 | 7.7 ± 0.9 | 33.0 ± 4.2 |
| MTQF | 8.56 ± 0.14 | 69.3 ± 0.2 | 5.74 ± 1.05 | 2.46 ± 0.05 | 42.9 ± 7.9 | 1.04 ± 0.07 | 0.40 ± 0.01 | 3.89 ± 0.26 | 34.2 ± 4.6 | 62.5 ± 7.6 |
| MTQY | 8.68 ± 0.15 | 69.2 ± 0.2 | 6.22 ± 1.38 | 2.02 ± 0.06 | 32.4 ± 7.3 | 1.16 ± 0.06 | 0.48 ± 0.01 | 4.11 ± 0.23 | 38.4 ± 5.2 | 63.0 ± 7.7 |
| MTWF | 8.61 ± 0.06 | 60.9 ± 0.2 | 7.87 ± 0.31 | 3.01 ± 0.08 | 38.2 ± 1.8 | 2.11 ± 0.06 | 0.57 ± 0.01 | 2.70 ± 0.08 | 30.5 ± 4.2 | 65.1 ± 6.4 |
| MTWY | 8.62 ± 0.14 | 62.1 ± 0.5 | 14.8 ± 0.8 | 3.17 ± 0.03 | 21.5 ± 1.2 | 4.80 ± 0.07 | 0.30 ± 0.04 | 0.62 ± 0.08 | 37.2 ± 4.9 | 69.6 ± 7.0 |
| YDTN | 8.29 ± 0.06 | 59.6 ± 0.9 | 6.33 ± 1.23 | 5.93 ± 0.20 | 93.6 ± 18.4 | 2.85 ± 0.11 | 1.67 ± 0.16 | 5.86 ± 0.61 | 9.7 ± 1.8 | 56.0 ± 5.6 |
| YETN | 7.83 ± 0.06 | 60.7 ± 0.7 | 5.92 ± 0.05 | 7.57 ± 0.30 | 128 ± 5 | 3.24 ± 0.07 | 2.73 ± 0.02 | 8.43 ± 0.20 | 9.8 ± 1.2 | 55.1 ± 6.1 |
| YTQN | 7.87 ± 0.06 | 63.1 ± 0.1 | 3.45 ± 0.29 | 9.60 ± 0.01 | 278 ± 23 | 2.55 ± 0.24 | 1.05 ± 0.63 | 4.11 ± 2.51 | 10.6 ± 1.2 | 49.2 ± 5.6 |
| YTTF | 8.56 ± 0.09 | 62.2 ± 0.1 | 12.7 ± 0.7 | 2.30 ± 0.01 | 18.0 ± 1.0 | 4.03 ± 0.06 | 0.12 ± 0.02 | 0.29 ± 0.04 | 43.8 ± 5.8 | 79.3 ± 9.9 |
| YTTY | 8.95 ± 0.02 | 62.0 ± 0.1 | 20.6 ± 0.6 | 1.71 ± 0.02 | 8.32 ± 0.2 | 5.40 ± 0.07 | 0.14 ± 0.04 | 0.26 ± 0.08 | 54.1 ± 7.1 | 67.9 ± 7.9 |
| YTWN | 8.14 ± 0.02 | 59.3 ± 0.2 | 4.83 ± 0.20 | 5.70 ± 0.03 | 118 ± 5 | 2.08 ± 0.07 | 1.09 ± 0.03 | 5.21 ± 0.22 | 15.9 ± 1.7 | 66.1 ± 7.1 |

(Title row) In vitro Characterization Parameters of Purified Double Combination Antibodies for mAb1

Figure 5C:
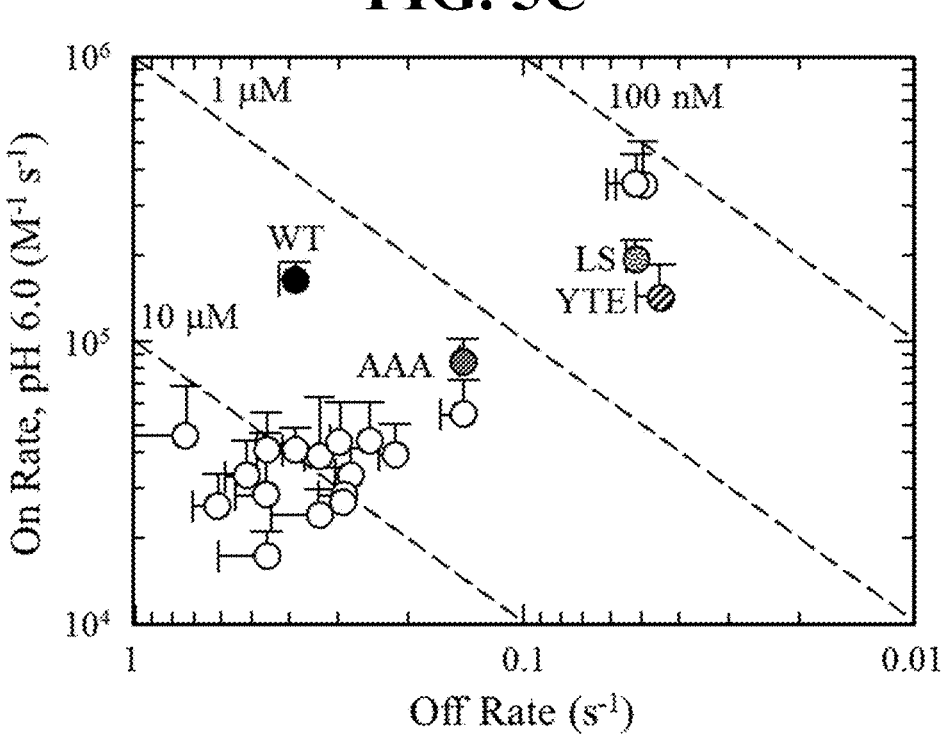
Figure 5D:
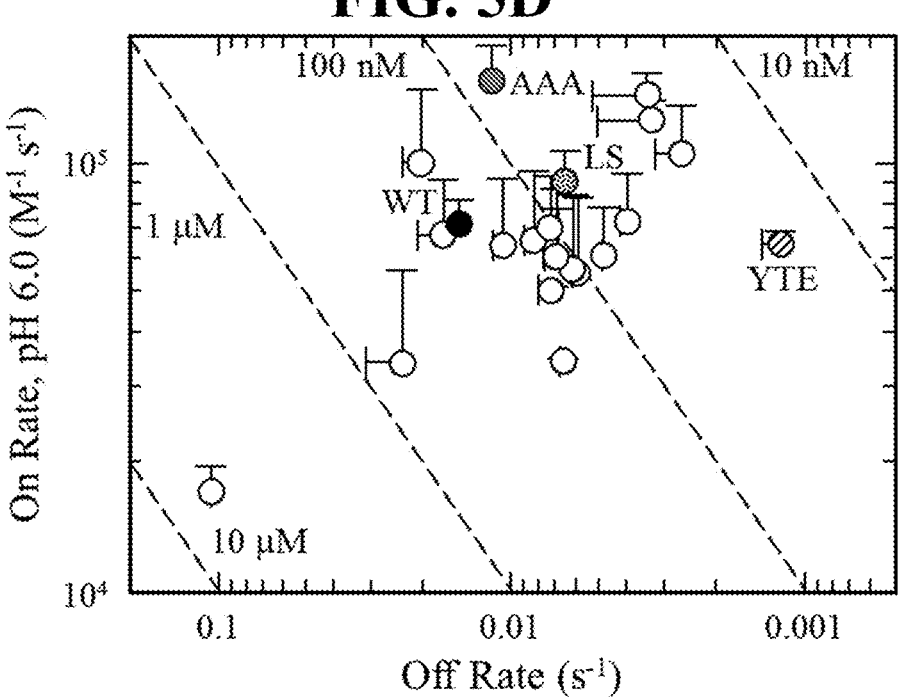

A vast majority of the lead variants for both human and rat FcRn (FIGS. 5A and 5B, solid lines in various shades) had significantly slower on-rates than the WT or the benchmark variants (>2-fold) (Table 1). The N434F and N434Y mutations were the only variants which displayed an enhanced on-rate for both species of FcRn. Without being bound to any theory, as a result of the slower association kinetics with hFcRn, the apparent binding affinities of the lead variants were generally weaker than WT, unlike rFcRn (FIGS. 5C and 5D, Table 1). The affinities for rFcRn were weaker than YTE (FIG. 5D, diagonal lines facing bottom left, Table 2A).

Without being bound to any theory, these results indicated that a single mutation was not sufficient to enhance the affinity to surpass the LS and YTE variants. Ranking the FcRn off-rates (due to the weak binding affinities of the variants to hFcRn) revealed a subset with reduced off-rates to both human and rat FcRn: M252Y, N434F/P/Y, T256D/E and T307A/E/F/Q/W (Table 2A). These variants are of further interest in combination to further improve the FcRn binding capabilities of the Fc region to surpass the benchmark variants.

In vitro characterization parameters for the lead variants are shown in Table 2B.

TABLE 2B

| | | | | | | | | | | |
|---|---|---|---|---|---|---|---|---|---|---|
| In vitro Characterization Parameters of Lead Variants | | | | | | | | | | |
| | FcRn | | Biacore ™ FcγRIIIa | | | | | | Biacore ™ pH 7.4 | |
| | Affinity | DSF | V158 | | Biacore ™ pH 6.0 | | | | hFcRn | rFcRn |
| mAb1 | Column | $T_m$ | Affinity | | | hFcRn | | rFcRn | Steady | Steady |
| Variant | pH | (° C.) | Fold Change | On Rate | Off-rate | $K_{D, app}$ | $K_{D, app}$ | State RU | State RU |
| WT | 7.37 | 69.0 ± 0.2 | 1.00 | 16.2 ± 2.9 | 3.9 ± 0.4 | 2380 ± 470 | 207 ± 43 | 4.2 ± 0.9 | 13.0 ± 3.2 |
| LS | 8.29 | 68.5 ± 0.3 | 1.04 ± 0.04 | 1.9 ± 0.4 | 5.0 ± 0.1 | 272 ± 40 | 74 ± 9 | 18.3 ± 4.6 | 24.8 ± 4.8 |
| YTE | 8.14 | 61.2 ± 0.3 | 0.52 ± 0.03 | 1.4 ± 0.4 | 4.7 ± 0.1 | 342 ± 117 | 18 ± 2 | 13.2 ± 3.5 | 53.9 ± 1.2 |
| M252Y | 7.88 | 64.4 ± 0.2 | 0.46 ± 0.03 | 5.5 ± 1.8 | 1.4 ± 0.2 | >3000 | 25 ± 3 | 8.6 ± 1.0 | 50.5 ± 5.6 |
| N434F | 8.30 | 67.8 ± 0.2 | 1.16 ± 0.08 | 35 ± 15 | 0.5 ± 0.1 | 165 ± 73 | 26 ± 13 | 22.2 ± 2.6 | 61.5 ± 6.5 |
| N434Y | 8.46 | 67.3 ± 0.5 | 1.41 ± 0.06 | 36 ± 10 | 0.5 ± 0.1 | 137 ± 33 | 23 ± 12 | 25.5 ± 2.9 | 66.0 ± 7.1 |
| T256D | 7.82 | 64.7 ± 0.2 | 0.92 ± 0.04 | 4.4 ± 1.7 | 2.5 ± 0.7 | >3000 | 86 ± 27 | 5.8 ± 0.5 | 23.2 ± 2.8 |
| T256E | 7.63 | 66.3 ± 0.6 | 0.89 ± 0.04 | 3.9 ± 2.4 | 3.4 ± 0.2 | >3000 | 113 ± 15 | 4.5 ± 0.4 | 17.0 ± 2.1 |
| T307Q | 7.86 | 70.3 ± 0.6 | 1.00 ± 0.04 | 4.0 ± 1.1 | 2.2 ± 0.2 | >3000 | 58 ± 16 | 6.6 ± 0.7 | 31.3 ± 3.7 |
| T307W | 7.75 | 63.0 ± 0.5 | 0.97 ± 0.04 | 3.3 ± 0.8 | 2.8 ± 0.3 | >3000 | 111 ± 32 | 5.6 ± 0.7 | 21.9 ± 2.8 |
| DQ | 7.92 | 67.9 ± 0.4 | 0.73 ± 0.03 | 3.8 ± 0.4 | 8.7 ± 0.1 | 232 ± 24 | 9.5 ± 1.7 | 10.7 ± 1.0 | 39.1 ± 4.5 |
| DW | 7.92 | 57.8 ± 0.4 | 0.89 ± 0.04 | 5.3 ± 0.1 | 8.9 ± 0.3 | 169 ± 8 | 8.2 ± 0.9 | 12.2 ± 1.3 | 42.1 ± 4.7 |
| YD | 8.29 | 59.6 ± 0.9 | 0.48 ± 0.02 | 6.3 ± 1.2 | 5.9 ± 0.20 | 94 ± 18 | 5.9 ± 0.6 | 9.7 ± 1.8 | 56.0 ± 5.6 |

In Table 2B, all data was obtained using the experimental techniques at the top of each column. FcRn affinity chromatography, DSF and FcγRIIIa binding were performed in triplicate (n=3). FcRn binding kinetics to human and rat FcRn were obtained in quadruplicate and fit independently. Units: DSF $T_m$ (° C.); FcγRIIIa Binding (Fold change relative to WT), Biacore™ pH 6.0 hFcRn On Rate ($\times 10^4$ $M^{-1}$ $s^{-1}$), Off-rate ($\times 10^{-1}$ $s^{-1}$) and $K_{D,app}$ ($\times 10^9$ M); Biacore™ pH 6.0 rFcRn $K_{D,app}$ ($\times 10^9$ M); Biacore™ pH 7.4 hFcRn and rFcRn Steady State RU (RU).

Example 4: The Combination Variants Further Decrease FcRn Binding Off-Rate

Multiple lead mutations were located at a single position (FIG. 14, black rectangles), such as T307 and N434, where six and three mutations, respectively, were identified that showed slower FcRn dissociation kinetics. Only mutations with the slowest FcRn off-rates to hFcRn at these positions were used for the creation of combination variants. In this case, T307Q, T307W, N434F and N434Y were mixed with M252Y, T256D and T256E to obtain double, triple and quadruple variants using mixed primer PCR and site directed mutagenesis. In total, the combination library consisted of 54 variants including the seven lead single, 18 double, 20 triple, 8 quadruple variants and the WT antibody. The nomenclature of these variants is as follows: the wild-type background contains M252, T256, T307 and N434 and is relabeled as MTTN. As such, the triple variant, <u>Y</u>T<u>QY</u>, contains the M252<u>Y</u>, T307<u>Q</u> and N434<u>Y</u> mutations, while maintaining the WT threonine at position 256.

Figure 6A:
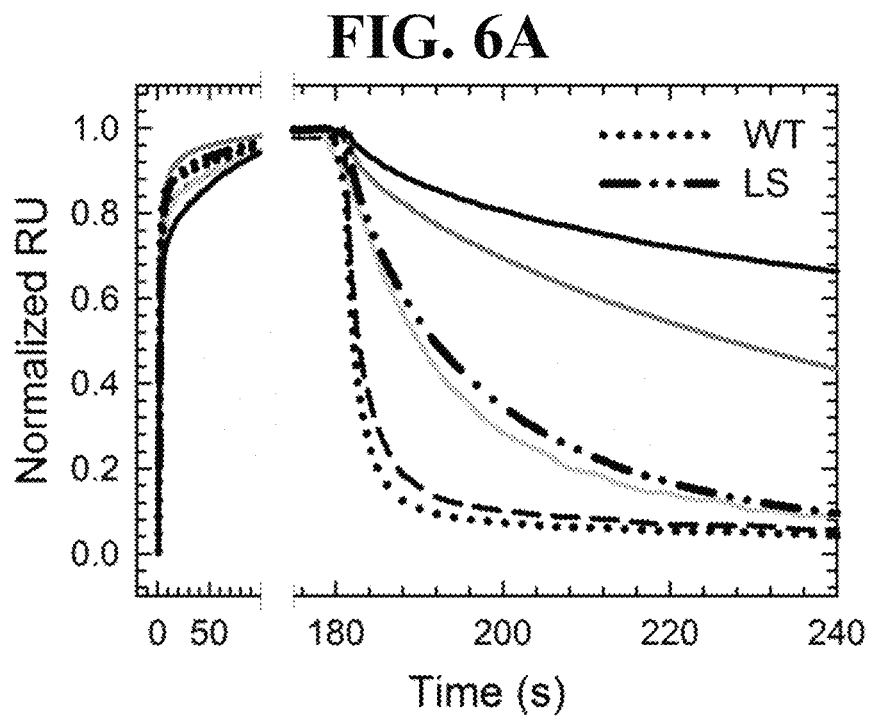
FIGS. 6A-D depict data showing that combinations of the lead saturation mutations further improved the FcRn off-rates and binding affinities.
Figure 6B:
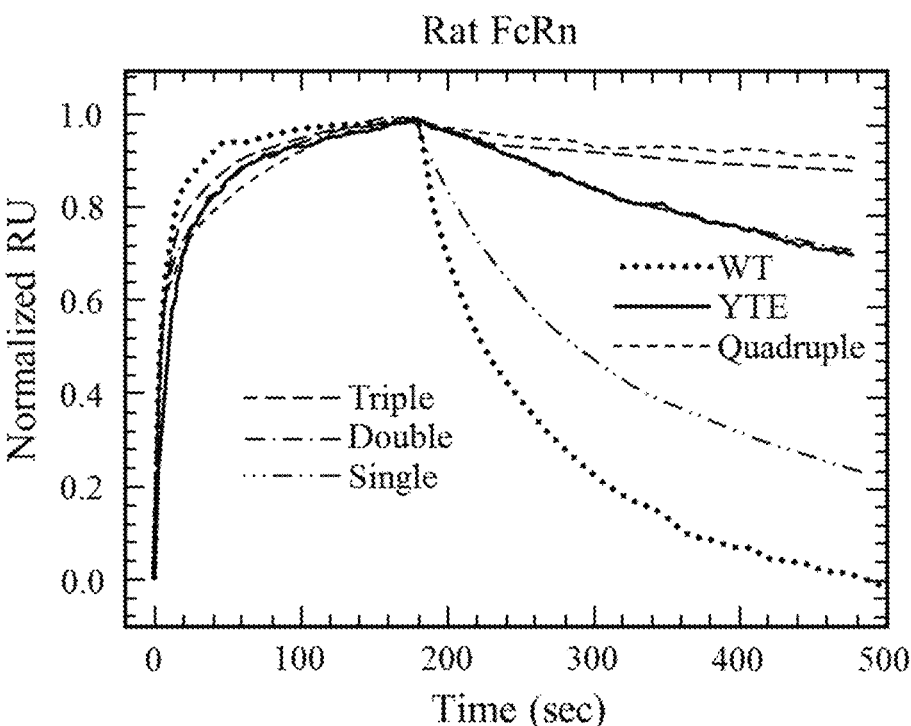
Figure 6C:
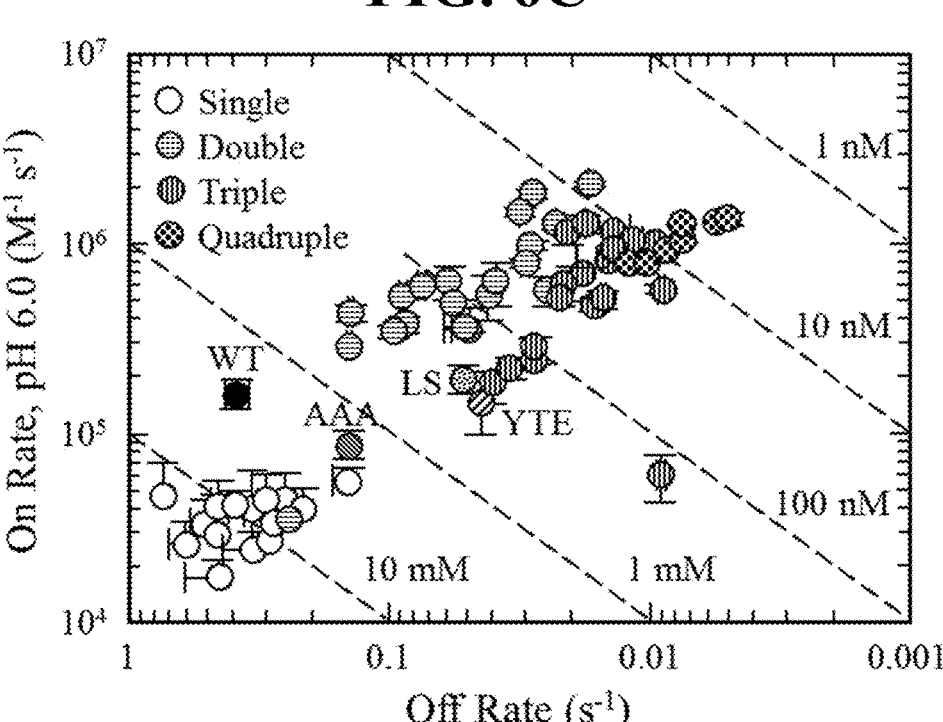
Figure 6D:
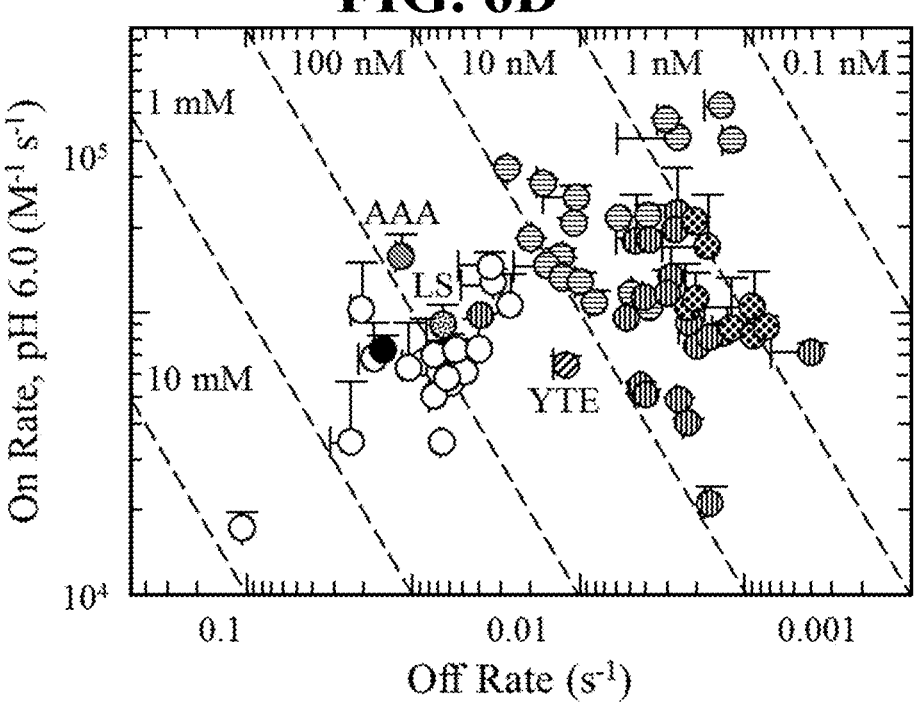

As with the single mutations, FcRn binding kinetics at pH 6.0 using Biacore™ was used to determine which combination variants have improved affinity. A representative FcRn binding kinetic trace of each the single (long dashes interspersed with two dots), double (long dashes interspersed with single dot), triple (long dashes) and quadruple (short dashes) are shown in FIGS. 6A and 6B, in comparison to the WT (dotted line) and the benchmark variant with the tightest affinity for their respective species of FcRn (hFcRn:

LS (long dashes interspersed by two dots); rFcRn: YTE (solid line)). The hFcRn on and off-rates (FIG. 6C) revealed that two single, 15 double, 18 triple and eight quadruple variants had an enhanced binding affinity than the LS variant (FIG. 6C, dotted). Similarly, all combinations, except one triple variant, had a tighter affinity to rFcRn than the YTE (FIG. 6D, diagonal lines facing bottom left). In the case of hFcRn, additional FcRn-enhancing mutations further increased the binding affinity (FIG. 6C). The five combinations with the tightest affinity to hFcRn were all quadruple variants (FIG. 6C, checkered) with binding affinities approximately 500-fold greater than wildtype. A similar phenomenon did not occur with rFcRn (FIG. 6D), as the variants with the highest affinity were double variants (FIG. 6D, horizontal lines). The triple (FIG. 6D, vertical lines) and quadruple (FIG. 6D, checkered) variants typically showed only slight decreases in the off-rate (less than 2-fold), but also displayed decreased association-rates (FIG. 6D). Without being bound to any theory, these results suggest that a lower limit possibly exists regarding the FcRn apparent binding affinity (approximately 0.5 nM) that has been reached with rFcRn, but not hFcRn (FIG. 6B). In total, more than 40 combination variants had a tighter affinity than the benchmark variants and further characterization is required to select combinations with favorable properties for in vivo studies.

Figure 8A:
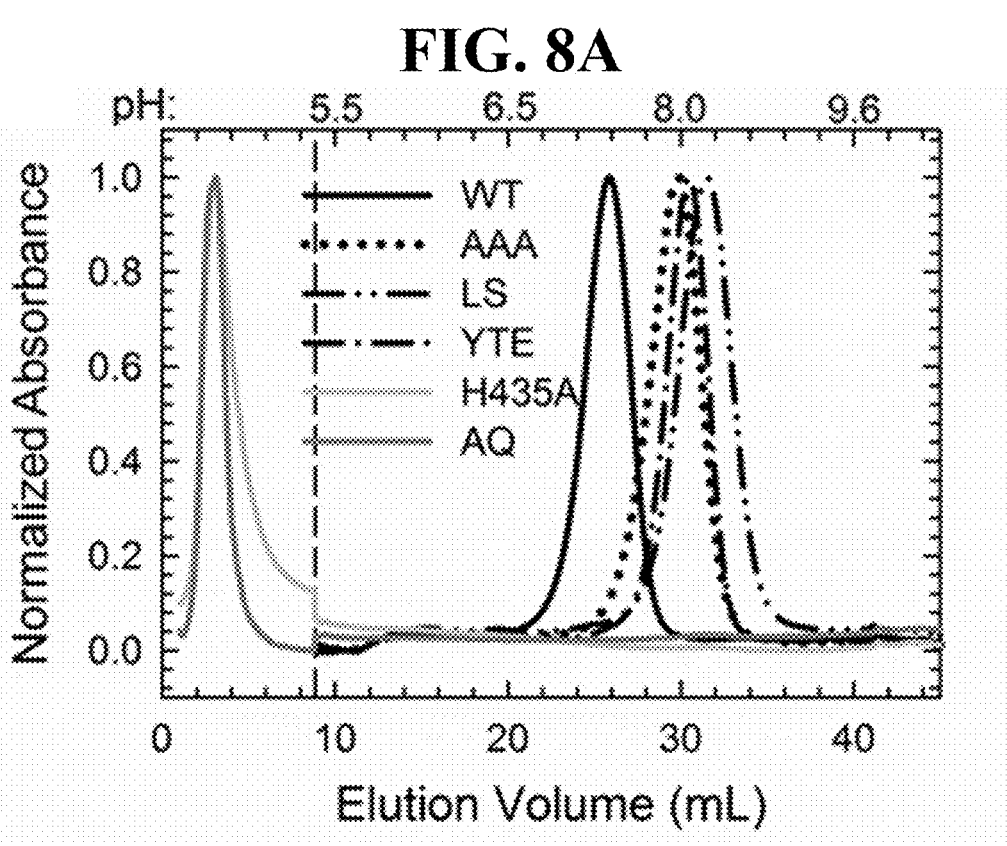
FIGS. 8A-C depict data obtained from FcRn affinity chromatography and differential scanning fluorimetry (DSF) of the benchmark variants.
Figure 8B:
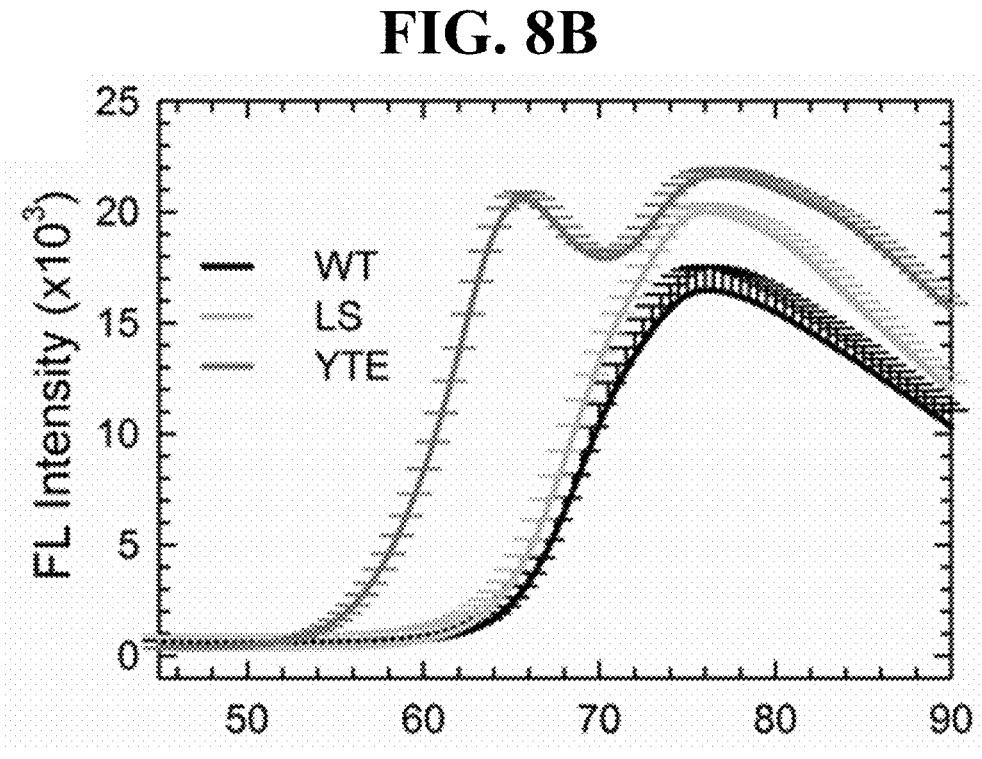
Figure 8C:
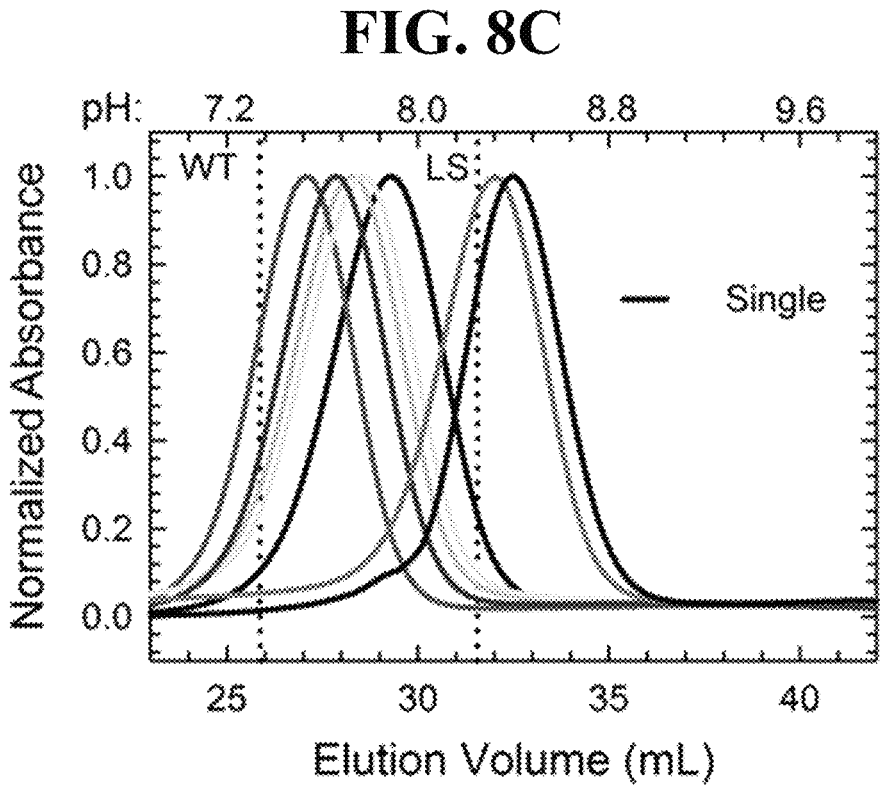
Figure 9A:
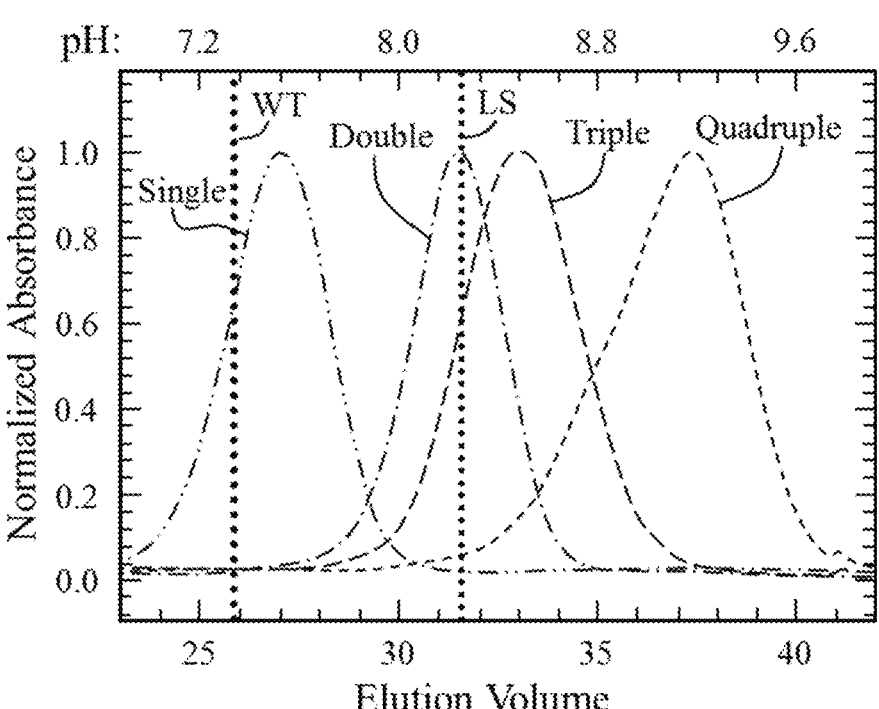
FIGS. 9A-D depict data showing that combination variants significantly perturbed pH dependence and thermal stability.
Figure 9B:
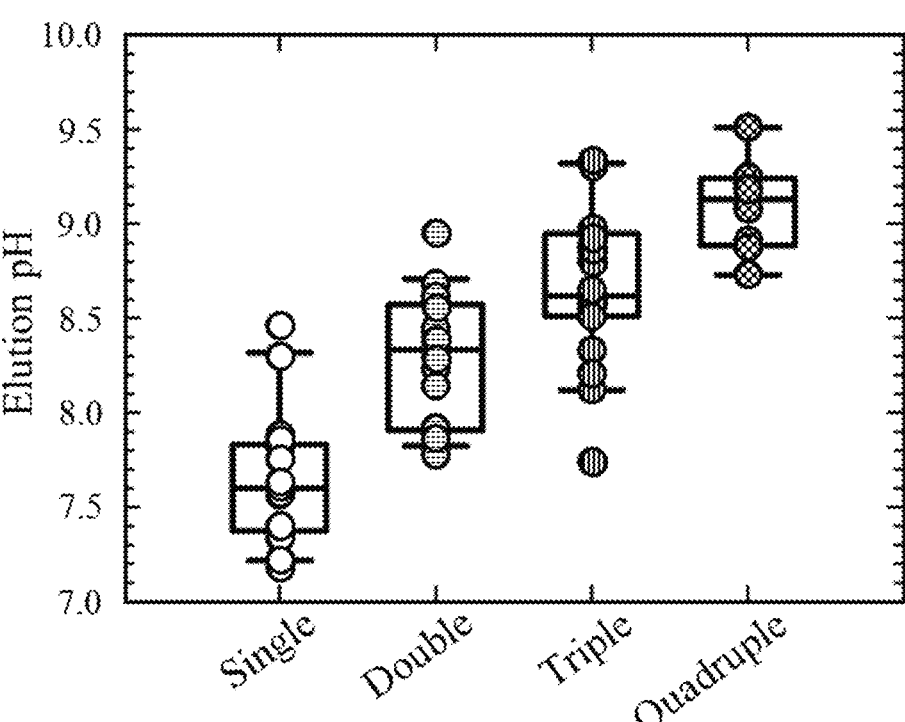
Figure 9C:
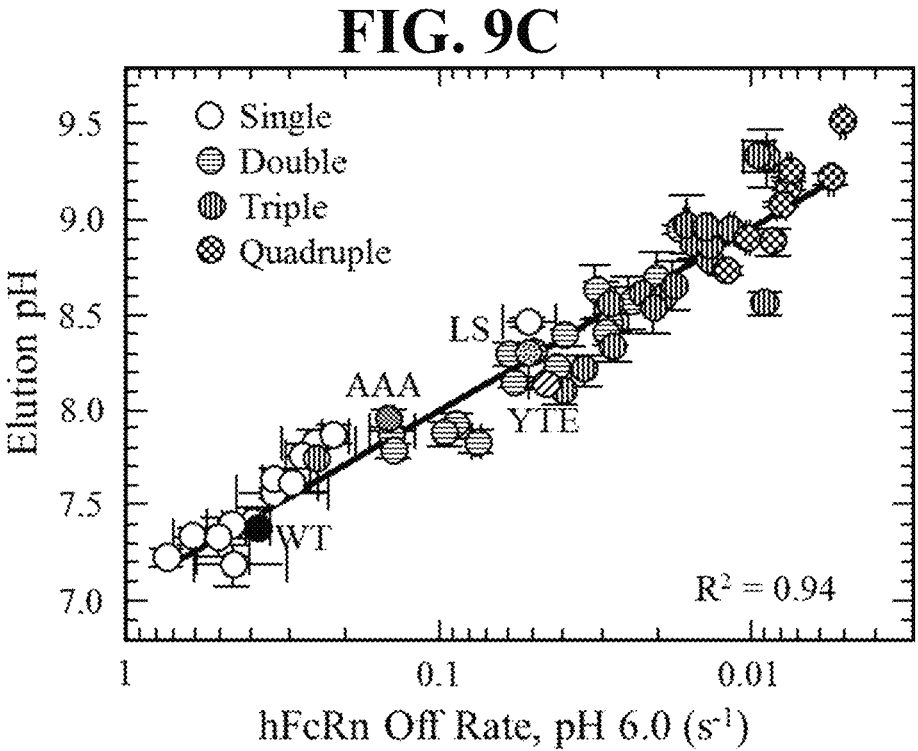

Example 5: Combination Variants Retain Significant Binding at Physiological pH As a result of the significantly improved FcRn affinity at pH 6.0, the effect on the pH dependence was investigated using FcRn affinity chromatography and Biacore™ steady state measurements at pH 7.4. FcRn affinity chromatography employs a linear pH gradient to directly measure the perturbation of the pH dependence by the mutations. H435A and H310A/H435Q, variants with weak FcRn binding, did not bind to the column regardless of pH (FIG. 8A). WT eluted near physiological pH (pH 7.37±0.05), while AAA, LS and YTE required a higher pH (Table 2B). All combination variants and the seven lead single variants required a higher pH to elute from the affinity column than WT (FIGS. 8A and 8C). The N434F/Y variants eluted at a greater pH than LS (Table 2B) which, without intending to be bound by scientific theory, indicates that these variants, both alone and in combination, disrupted the pH dependence. Representative chromatograms showed a clear shift to higher elution pH with the number of mutations (FIGS. 9A and 9B). A strong correlation (R2=0.94) between the elution pH and the hFcRn off-rates (FIG. 9C) indicates that the slower FcRn off-rate at pH 6.0 directly contributed to the increased elution pH for the FcRn variants.

Figure 7A:
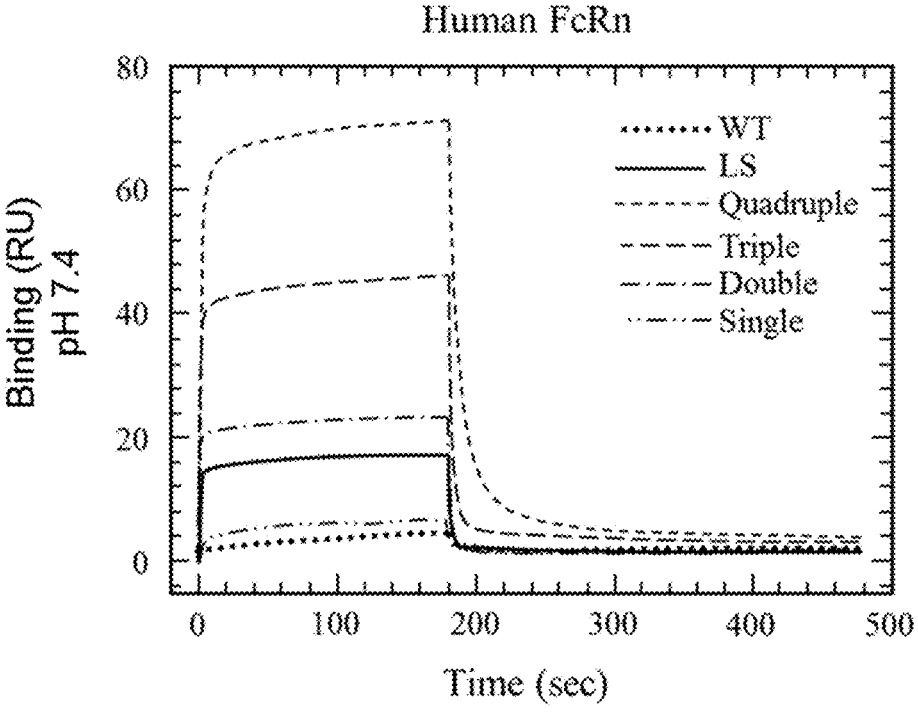
FIGS. 7A-D depict data showing that enhanced FcRn binding at pH 6.0 disrupted the pH dependence of the interaction.
Figure 7B:
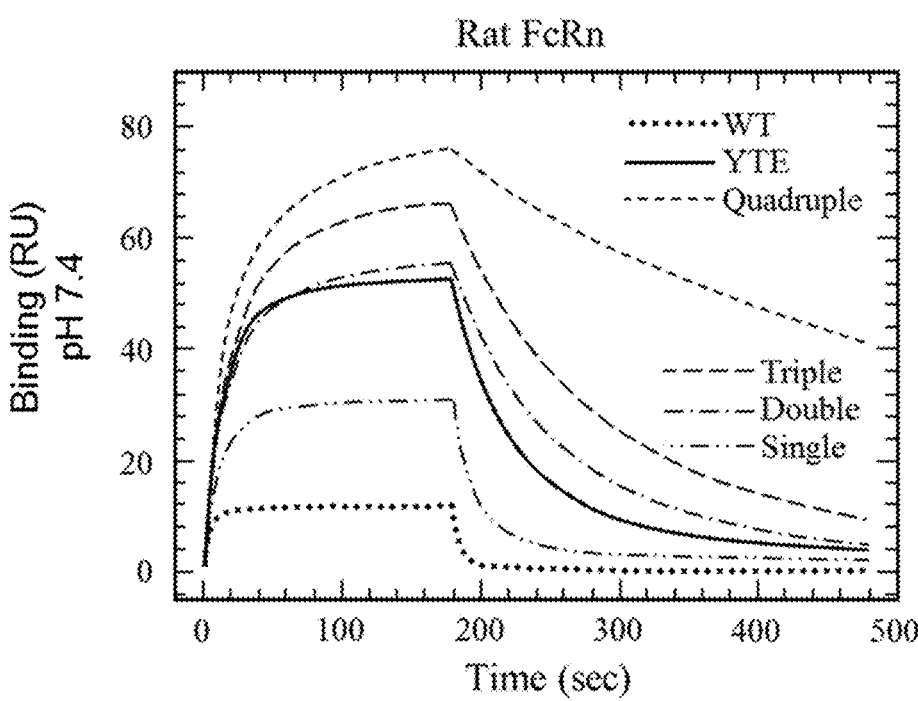

FcRn binding kinetic experiments were performed at pH 7.4 using Biacore™ to measure the residual binding activity under physiological conditions. The steady state RU was used as a measure of residual FcRn binding affinity, as some variants showed unreliable kinetics and little to no binding at this pH. Representative kinetic traces of the single (long dashes interspersed with two dots), double (long dashes interspersed with single dot), triple (long dashes) and quadruple (short dashes) variants are shown in FIGS. 7A and 7B, in comparison to LS (FIG. 7A, solid) and YTE (FIG. 7B, solid). These two variants displayed the greatest residual binding to human and rat FcRn at pH 7.4, respectively. A majority of the lead single variants had slightly elevated FcRn binding in comparison to WT (4.3±1.0 RU), but less than AAA (13.1±1.7 RU), LS (18.5±2.6 RU) and YTE (13.1±1.6 RU), except for the N434F/Y mutations (Tables 2A and 2B). The combination variants also possessed significant residual binding to both species of FcRn at pH 7.4 (FIGS. 7A and 7B) to an even greater extent than N434F/Y. Without being bound to any theory, an ideal candidate for in vivo studies are variants with increased FcRn binding at low pH (such as the AAA, LS and YTE variants), but maintain a low level of binding at elevated pH, in a similar manner as the WT. In a plot shown in FIGS. 7C and 7D, these combinations would occupy the lower left quadrant designated by the affinities of the LS and YTE variants at each pH to human and rat FcRn, respectively.

Example 6: FcRn Affinity Chromatography

Figure 7C:
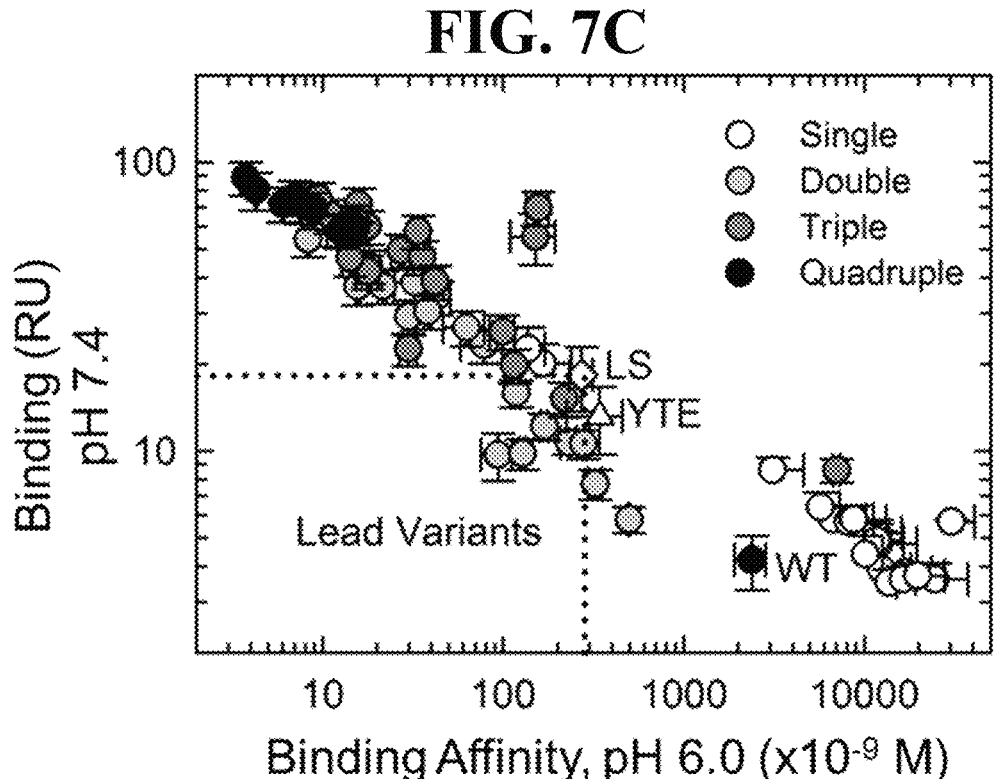
Figure 7D:
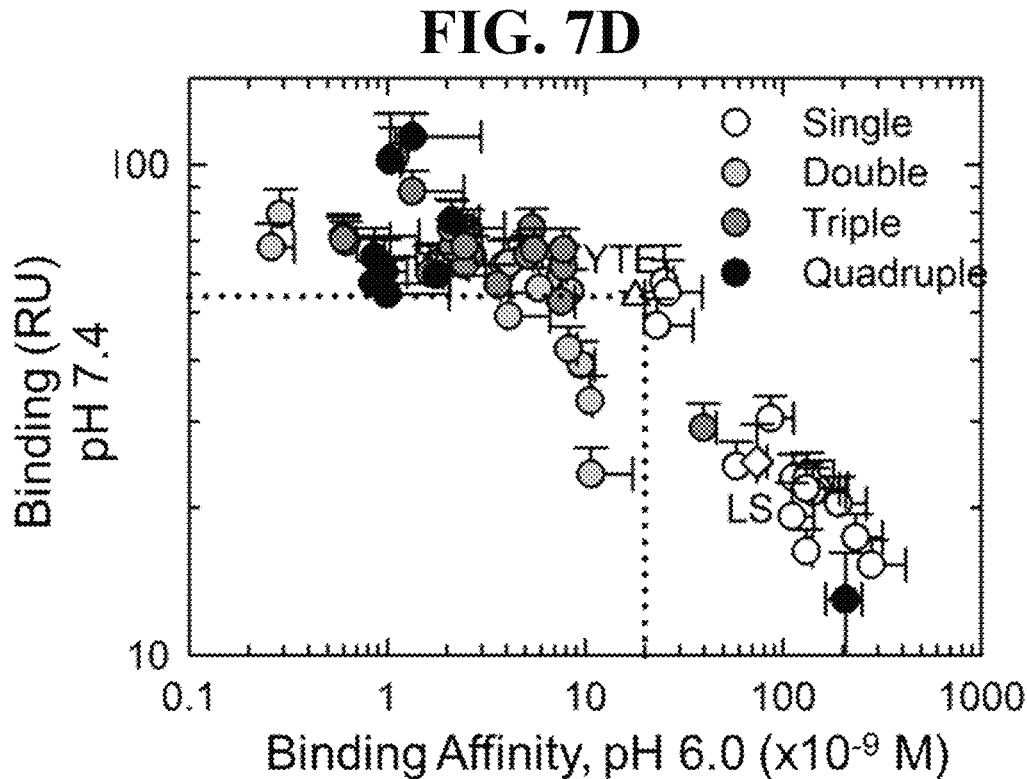

The combination variants displayed a moderate positive correlation (hFcRn: $R^2=0.69$, rFcRn: $R^2=0.71$) between the apparent binding affinity at pH 6.0 and the steady state RU at pH 7.4 (FIGS. 7C and 7D). Without being bound by any theory, these results indicate that a significantly higher affinity at pH 6.0 typically translates to a greater residual FcRn binding at pH 7.4. These variants could remain bound to FcRn in the bloodstream and have short serum half-lives and/or promote their clearance, similar to the high FcRn affinity Abdeg mutations (YTEKF; see, e.g., Swiercz et al., *J Nucl Med*. (2014) 55:1204-7; and Vaccaro et al., *Nat Biotechnol*. (2005) 23:1283-8). As the IgG-FcRn interaction is pH-dependent and occurs only at low pH (<pH 6.5), the saturation mutations may strengthen the interaction through hydrophobic or charge-derived contributions, that may disrupt the deprotonation of the critical histidine residues (FIG. 1B, as indicated) and weakening of this interaction at physiological pH. As a result, the FcRn-binding interaction consequently becomes less sensitive on the environmental pH.

Figure 10A:
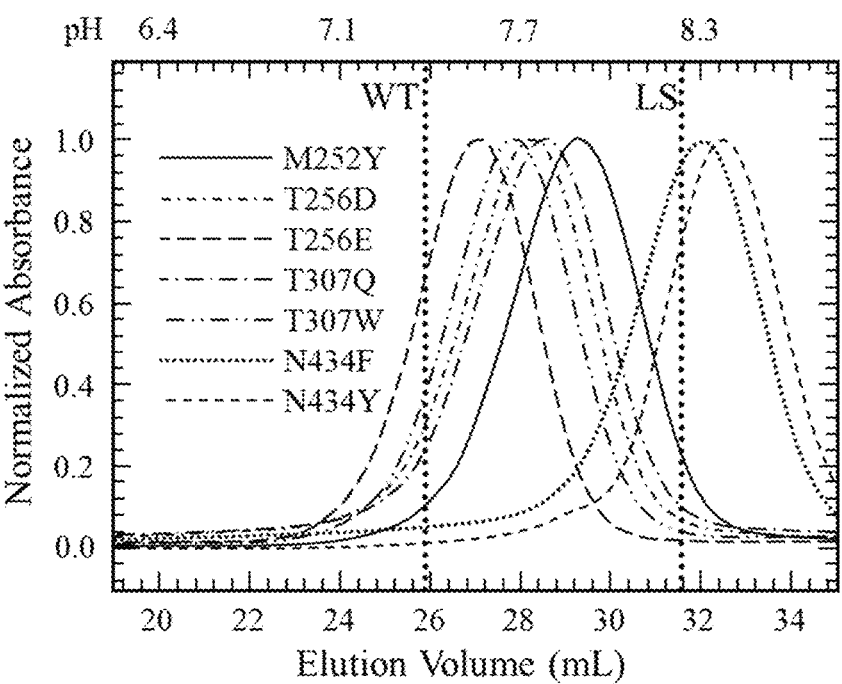
FIGS. 10A and 10B depict data obtained from FcRn affinity chromatography and DSF of seven lead variants.

FcRn affinity chromatography employs a linear pH gradient to directly measure the perturbation of the FcRn interactions pH dependence (see, e.g., Schlothauer et al., supra). FcRn affinity chromatography with the AAA, LS, YTE, H435A and H310A/H435Q variants revealed that H435A (FIG. 8A, solid light gray line) and H310A/H435Q (FIG. 8A, AQ, solid dark gray line) do not bind to FcRn even at pH 5.5 and elute in the flow-through. The wildtype antibody eluted near physiological pH (pH 7.37±0.05), while AAA, LS and YTE, which have slower off-rates and tighter FcRn binding affinities than the wildtype by Octet (FIGS. 2B-D) and Biacore™ (FIG. 3), required a considerably higher pH to dissociate from the column (AAA: 7.94±0.06; LS: 8.29±0.03; YTE: 8.14±0.03). Elution profiles revealed that all of the variants in the combination library required a higher pH to elute from the affinity column than wildtype. Representative chromatograms at the average elution pH for the single (long dashes interspersed with two dots), double (long dashes interspersed by single dot), triple (long dashes) and quadruple (short dashes) variants are shown in FIG. 9A. The seven lead single variants (M252Y, T256D, T256E, T307Q, T307W, N434F and N434Y) required a higher pH to dissociate from the column compared to WT (FIG. 10A, Table 3), while those with wildtype-like kinetics to hFcRn (K288D/N, Y436H/H/W) all eluted at a similar pH to the wildtype.

TABLE 3

In vitro Characterization Parameters of Lead Antibody Variants

| Variant | FcRn Affinity Column pH | DSF $T_m$ (° C.) | hFcRn On-rate ($\times 10^4$ $M^{-1}$ $s^{-1}$) | hFcRn Off-rate ($\times 10^{-1}$ $s^{-1}$) | hFcRn $K_{D,app}$ ($\times 10^9$ M) | rFcRn On-rate ($\times 10^4$ $M^{-1}$ $s^{-1}$) | rFcRn Off-rate ($\times 10^{-3}$ $s^{-1}$) | rFcRn $K_{D,app}$ ($\times 10^9$ M) |
|---|---|---|---|---|---|---|---|---|
| WT | 7.37 | 69.0 ± 0.2 | 16.2 ± 2.9 | 3.9 ± 0.4 | 2380 ± 470 | 7.3 ± 1.0 | 15.2 ± 0.2 | 207 ± 43 |
| E380C | 7.18 | 64.7 ± 0.5 | 1.7 ± 0.4 | 4.6 ± 1.5 | >10,000 | 1.7 ± 0.25 | 106 ± 1 | 6310 ± 880 |
| K288D | 7.33 | 65.8 ± 0.1 | 3.3 ± 1.1 | 5.1 ± 0.8 | >10,000 | 6.6 ± 3.0 | 8.4 ± 0.6 | 149 ± 63 |
| K288N | 7.39 | 66.7 ± 0.3 | 4.1 ± 1.4 | 4.5 ± 0.3 | >10,000 | 6.4 ± 2.8 | 10.7 ± 0.9 | 190 ± 73 |
| M252Y | 7.88 | 64.4 ± 0.2 | 5.5 ± 1.8 | 1.4 ± 0.2 | 3100 ± 1500 | 10.6 ± 3.1 | 2.6 ± 0.6 | 25 ± 3 |
| N434F | 8.30 | 67.8 ± 0.2 | 35 ± 15 | 0.5 ± 0.1 | 165 ± 73 | 12.6 ± 1.4 | 3.4 ± 1.8 | 26 ± 13 |
| N434P | 7.56 | 63.6 ± 0.5 | 2.4 ± 0.5 | 3.4 ± 1.1 | >10,000 | 3.4 ± 0.1 | 6.7 ± 0.2 | 194 ± 9 |
| N434Y | 8.46 | 67.3 ± 0.5 | 36 ± 10 | 0.5 ± 0.1 | 137 ± 33 | 14.5 ± 1.8 | 3.5 ± 1.9 | 23 ± 12 |
| T256D | 7.82 | 64.7 ± 0.2 | 4.4 ± 1.7 | 2.5 ± 0.7 | 6700 ± 3540 | 6.1 ± 1.8 | 4.8 ± 0.1 | 86 ± 27 |
| T256E | 7.63 | 66.3 ± 0.6 | 3.9 ± 2.4 | 3.4 ± 0.2 | >10,000 | 6.3 ± 1.6 | 6.9 ± 1.0 | 113 ± 15 |
| T307A | 7.61 | 68.0 ± 0.4 | 2.9 ± 0.7 | 2.9 ± 0.5 | >10,000 | 6.1 ± 2.7 | 7.1 ± 0.7 | 132 ± 48 |
| T307E | 7.58 | 70.2 ± 0.5 | 4.4 ± 1.6 | 3.0 ± 0.4 | 8130 ± 5070 | 5.6 ± 2.8 | 6.0 ± 0.2 | 141 ± 65 |
| T307F | 7.61 | 70.2 ± 0.3 | 2.7 ± 0.8 | 2.9 ± 0.1 | >10,000 | 5.7 ± 2.8 | 6.2 ± 0.1 | 131 ± 63 |
| T307M | 7.40 | 70.0 ± 0.4 | 4.1 ± 0.8 | 3.9 ± 0.3 | >10,000 | 6.8 ± 2.3 | 17.1 ± 4.0 | 279 ± 140 |
| T307Q | 7.86 | 70.3 ± 0.6 | 4.0 ± 1.1 | 2.2 ± 0.2 | 5720 ± 1530 | 7.4 ± 2.2 | 4.0 ± 0.3 | 58 ± 16 |
| T307W | 7.75 | 63.0 ± 0.5 | 3.3 ± 0.8 | 2.8 ± 0.3 | 8740 ± 2440 | 7.1 ± 2.3 | 7.4 ± 0.4 | 111 ± 32 |
| Y436H | 7.33 | 68.7 ± 0.3 | 2.6 ± 0.8 | 6.1 ± 1.0 | >10,000 | 5.1 ± 0.1 | 7.3 ± 0.9 | 131 ± 9 |
| Y436N | 7.22 | 65.8 ± 0.5 | 4.6 ± 2.4 | 7.4 ± 3.3 | >10,000 | 10.1 ± 4.9 | 20.3 ± 3.1 | 233 ± 86 |
| Y436W | 7.39 | 68.6 ± 0.7 | 2.8 ± 1.9 | 4.6 ± 0.9 | >10,000 | 3.4 ± 2.2 | 23.7 ± 7.7 | 1140 ± 950 |

All data were obtained using the experimental techniques at the top of each column. The elution pH was determined by FcRn affinity chromatography in triplicate (n=3) and DSF probed the thermal stability in triplicate (n=3). FcRn binding kinetics to human and rat FcRn were obtained from Biacore™ with a series of antibody concentrations (n=4) and fit independently. Units for each measurement are as follows: Elution pH (unit-less); DSF $T_m$ (° C.); Biacore™ pH 6.0 hFcRn On-rate ($\times 10^4$ $M^{-1}$ $s^{-1}$), Off-rate ($\times 10^{-1}$ $s^{-1}$) and $K_{D,app}$ ($\times 10^9$ M); Biacore™ pH 6.0 rFcRn On-rate ($\times 10^4$ $M^{-1}$ $s^{-1}$), Off-rate ($\times 10^{-3}$ $s^{-1}$) and $K_{D,app}$ ($\times 10^9$ M).

The N434F/Y variants both eluted at a greater pH than the LS variant (N434F: 8.30±0.05; N434Y: 8.46±0.02) and showed considerable FcRn binding at pH 7.4 (Table 4). These results indicate that these variants alone can disrupt the pH dependence. In general, the average elution pH increased with an increasing the number of FcRn binding enhancing mutations (FIG. 9B). A strong correlation ($R^2$=0.94) appeared with the elution pH in comparison to the hFcRn off-rates (FIG. 9C); without being bound to any theory, indicating that the disruption of the pH dependence of the interaction directly contributes to the slower FcRn off-rates observed for the combination library at pH 6.0.

Example 7: Thermal Stability

Figure 10B:
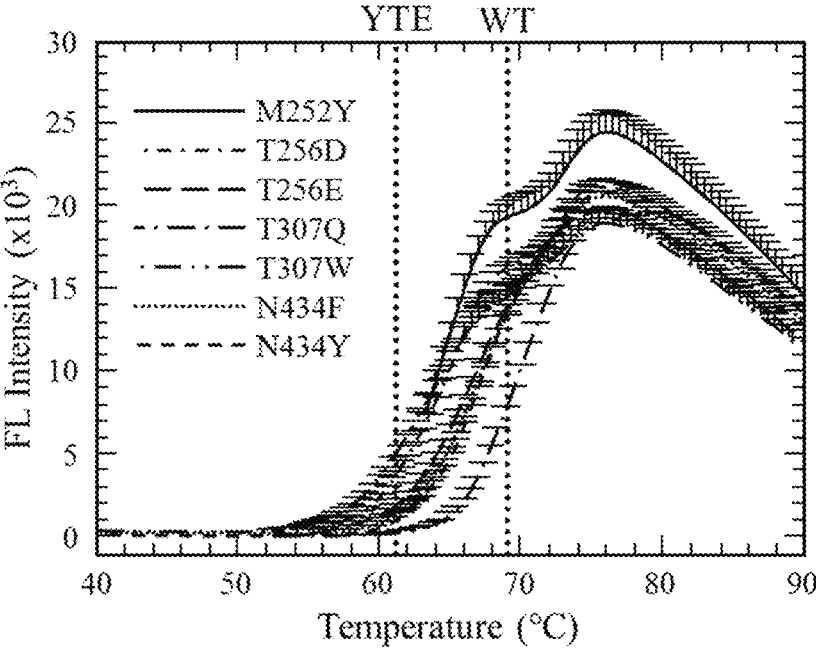

Most proteins, including antibodies, with low thermodynamic stability have an increased propensity for misfolding and aggregation and would limit or hinder their activity, efficacy and potential as novel therapeutics. The thermal stability of each variant was determined using DSF and the reported melting temperature ($T_m$) was defined as the midpoint of the first transition in the Sypro™ Orange fluorescence intensity profile. In comparison to the WT with a $T_m$ of 69.0±0.2° C., the LS variant is WT-like (68.5±0.3° C.) and AAA and YTE are thermally destabilized by ~8° C. (AAA: 61.3±0.6° C.; YTE: 61.2±0.3° C.) (FIGS. 8B, 9B, and 10B; and Tables 2B, 3 and 4). In comparison to WT and LS with a $T_m$ of 69.0±0.2° C., the AAA and YTE variants had lower thermal stabilities by ~8° C. by DSF.

TABLE 4

In vitro Characterization Parameters of the Benchmark and Lead Combinations

| Variant | FcRn Affinity Column pH | DSF $T_m$ (° C.) | hFcRn On-rate ($\times 10^4$ $M^{-1}$ $s^{-1}$) | hFcRn Off-rate ($\times 10^{-1}$ $s^{-1}$) | hFcRn $K_{D,app}$ ($\times 10^9$ M) | rFcRn On-rate ($\times 10^4$ $M^{-1}$ $s^{-1}$) |
|---|---|---|---|---|---|---|
| WT | 7.37 | 69.0 ± 0.2 | 16.2 ± 2.9 | 3.9 ± 0.4 | 2380 ± 470 | 7.3 ± 1.0 |
| AAA | 7.94 | 61.3 ± 0.6 | 8.4 ± 1.8 | 1.4 ± 0.1 | 1780 ± 380 | 15.7 ± 3.3 |
| LS | 8.29 | 68.5 ± 0.3 | 19.3 ± 3.5 | 0.5 ± 0.1 | 272 ± 40 | 9.1 ± 1.6 |
| YTE | 8.14 | 61.2 ± 0.3 | 14.3 ± 4.4 | 0.5 ± 0.1 | 342 ± 117 | 6.5 ± 0.5 |
| MDQN | 7.92 | 67.9 ± 0.4 | 3.8 ± 0.4 | 8.7 ± 0.1 | 232 ± 24 | 1.3 ± 0.2 |
| MDWN | 7.92 | 57.8 ± 0.4 | 5.3 ± 0.1 | 8.9 ± 0.3 | 169 ± 8 | 1.6 ± 0.1 |
| YDTN | 8.29 | 59.6 ± 0.9 | 6.3 ± 1.2 | 5.9 ± 0.20 | 94 ± 18 | 2.9 ± 0.1 |
| YETN | 7.83 | 60.7 ± 0.7 | 5.9 ± 0.1 | 7.6 ± 0.3 | 128 ± 5 | 3.2 ± 0.1 |
| YTWN | 8.14 | 59.3 ± 0.2 | 4.8 ± 0.2 | 5.7 ± 0.1 | 118 ± 5 | 2.1 ± 0.1 |
| YDQN | 8.51 | 60.5 ± 0.1 | 2.5 ± 0.2 | 2.8 ± 0.1 | 115 ± 7 | 0.5 ± 0.1 |
| YEQN | 8.12 | 61.9 ± 0.8 | 1.9 ± 0.1 | 4.1 ± 0.1 | 218 ± 6 | 0.5 ± 0.1 |

TABLE 4-continued

In vitro Characterization Parameters of the Benchmark and Lead Combinations

| | Biacore ™ pH 6.0 rFcRn | | Biacore ™ pH 7.4 | | |
| | | | hFcRn | rFcRn | FcγRIIIa V158 |
| Variant | Off-rate ($\times 10^{-3}$ s$^{-1}$) | $K_{D,app}$ ($\times 10^{9}$ M) | Steady State RU | Steady State RU | $K_{D,app}$ ($\times 10^{9}$ M) |
|---|---|---|---|---|---|
| WT | 15.2 ± 0.2 | 207 ± 43 | 4.2 ± 0.9 | 13.0 ± 3.2 | 467 ± 99 |
| AAA | 11.7 ± 1.1 | 77 ± 18 | 13.9 ± 3.1 | 23.6 ± 4.9 | 450 ± 19 |
| LS | 6.6 ± 0.4 | 74 ± 9 | 18.3 ± 4.6 | 24.8 ± 4.8 | 369 ± 19 |
| YTE | 1.2 ± 0.2 | 18 ± 2 | 13.2 ± 3.5 | 53.9 ± 1.2 | 1040 ± 160 |
| MDQN | 1.3 ± 0.1 | 9.5 ± 1.7 | 10.7 ± 1.0 | 39.1 ± 4.5 | 600 ± 4 |
| MDWN | 1.3 ± 0.1 | 8.2 ± 0.9 | 12.2 ± 1.3 | 42.1 ± 4.7 | 512 ± 30 |
| YDTN | 1.7 ± 0.2 | 5.9 ± 0.6 | 9.7 ± 1.8 | 56.0 ± 5.6 | 1060 ± 60 |
| YETN | 2.7 ± 0.1 | 8.4 ± 0.2 | 9.8 ± 1.2 | 55.1 ± 6.1 | 878 ± 101 |
| YTWN | 1.1 ± 0.1 | 5.2 ± 0.2 | 15.9 ± 1.7 | 66.1 ± 7.1 | 896 ± 53 |
| YDQN | 0.3 ± 0.1 | 5.1 ± 0.3 | 19.8 ± 2.7 | 65.2 ± 6.6 | 1060 ± 50 |
| YEQN | 0.4 ± 0.1 | 7.8 ± 0.4 | 15.2 ± 2.1 | 61.8 ± 6.4 | 1620 ± 210 |

The mutations introduced into the wildtype backbone are underlined. All data was obtained using the experimental techniques shown at the top of each column. The elution pH and $T_m$ was determined in triplicate (n=3). FcRn binding kinetics to human and rat FcRn at pH 6.0 were obtained from Biacore™ (n=4) and fit independently. Steady state FcRn binding response at pH 7.4 was measured using Biacore™ at a single antibody concentration in triplicate. The FcγRIIIa binding affinity was determined from a series of antibody concentrations in duplicate using Biacore™. Units for each measurement are as follows: Elution pH (unit-less); DSF $T_m$ (° C.); Biacore™ pH 6.0 hFcRn On-rate ($\times 10^{5}$ M$^{-1}$ s$^{-1}$), Off-rate ($\times 10^{-2}$ s$^{-1}$) and $K_{D,app}$ ($\times 10^{9}$ M); Biacore™ pH 6.0 rFcRn On-rate ($\times 10^{5}$ M$^{-1}$ s$^{1}$), Off-rate ($\times 10^{-3}$ s$^{1}$) and $K_{D,app}$ ($\times 10^{9}$ M); Biacore™ pH 7.4 Steady State Binding Response (RU) and FcγRIIIa $K_{D,app}$ ($\times 10^{9}$ M).

Figure 9D:
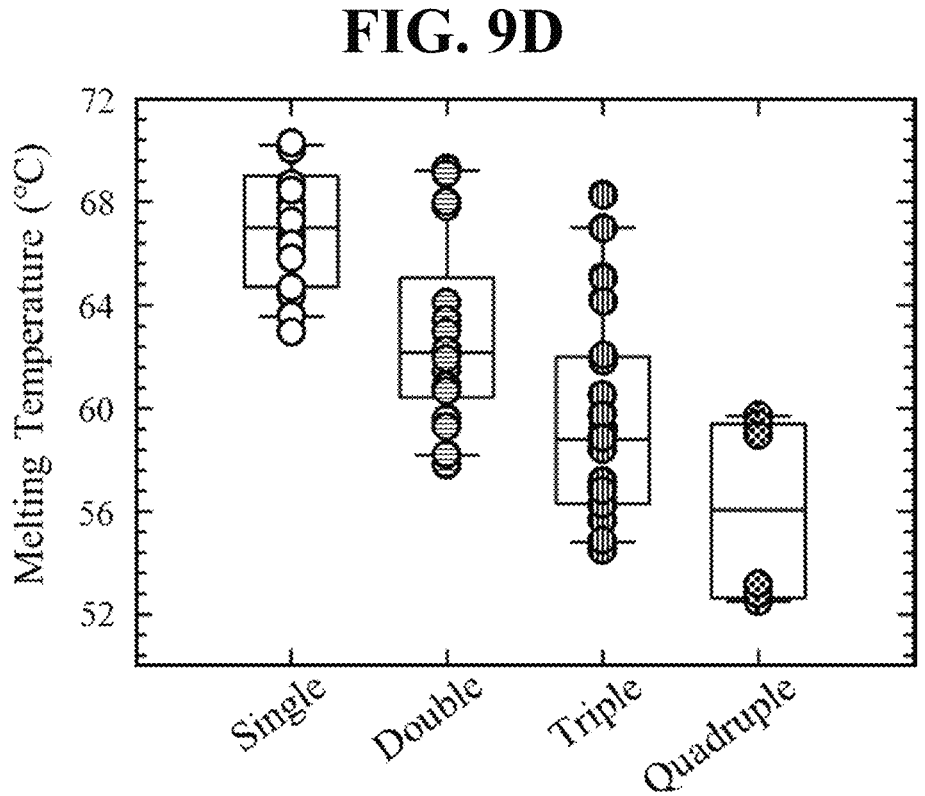

Twelve of 18 lead saturation variants (variants E380C, M252Y, T256D, T256E, K288N, K288D, N434P, T307A, T307W, Y436H, Y436N, Y436W) had a reduced $T_m$ compared to wildtype, and several of the T307 mutants (T307E/F/M/Q) showed a slight stabilization (Table 4). None of the seven single variants used for combinations (FIG. 10B and Table 4) were significantly destabilized relative to YTE (FIG. 8B and Table 5). The addition of double (FIG. 9D, horizontal lines), triple (FIG. 9D, vertical lines) and quadruple (FIG. 9D, checkered) mutations to the Fc domain led to a further decrease in overall thermal stability compared to the single mutations (FIG. 9D, white circles). Multiple variants exhibited a $T_m$ lower than AAA or YTE (61.2±0.3° C.) with >60% of these variants containing T307W. The quadruple variants (FIG. 9D, checkered) showed a distinct bimodal distribution of melting temperatures with combinations containing T307Q having approximately 6° C. more thermal stability than those possessing T307W (FIG. 9D).

Example 8: The Fc Variants Alter the Binding Interaction with FcγRIIIa

Figures 11A, 11B:
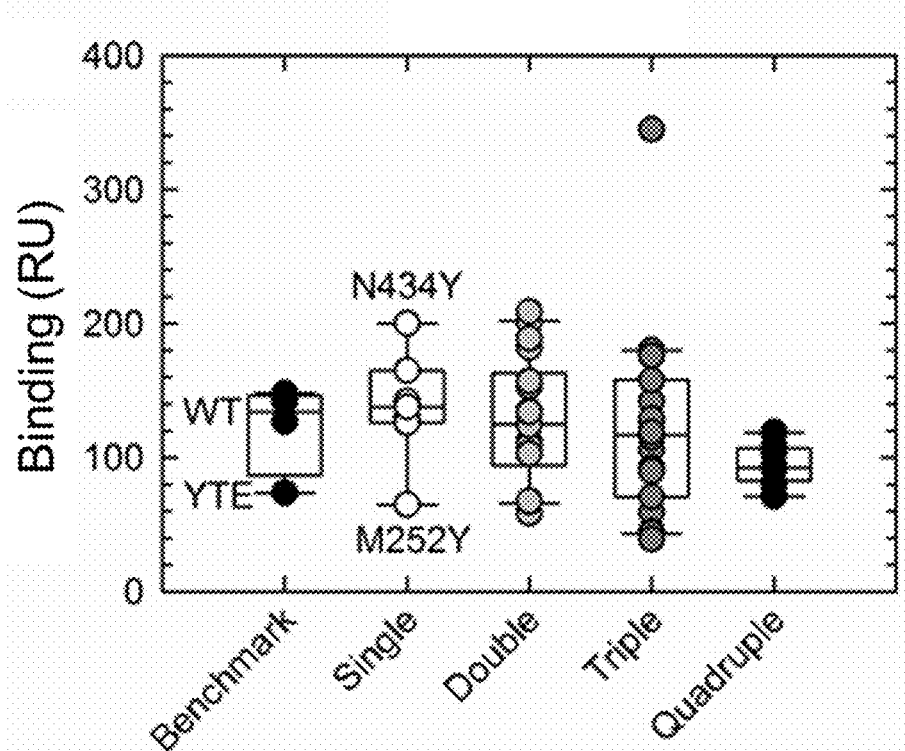
FIGS. 11A-C depict data showing that FcγRIIIa binding was reduced in M252Y-containing combination variants.

Besides the interaction with FcRn, the Fc regions hinge and $C_H2$ domains are responsible for the interaction with other Fc receptors, including FcγRIIIa. As five of the seven single variants used for the construction of the combination saturation library are located within the $C_H2$ domain, the ability to interact with these receptors may be compromised relative to wildtype, despite their location far from the interaction interface. Using Biacore™ to measure the FcγRIIIa binding in a similar manner as the FcRn binding at pH 7.4 revealed that the YTE (FIG. 11A, dark gray) variant showed an approximately 50% reduction in binding response compared to the wildtype (FIG. 11A, black). Without being bound to any theory, the reduced FcγRIIIa binding for YTE is a result of the M252Y mutation (FIG. 11B, lowest white circle) as this variant alone has significantly decreased affinity for this receptor. The other single mutations did not share this reduced affinity (FIG. 11B, white circles) and N434F/Y variants alone enhanced the binding by 16-40%. These effects were transferred to most, but not all, of their corresponding combinations. For example, M252Y-containing combinations had between a 17 and 72% reduction in FcγRIIIa binding (Table 5).

TABLE 5

Concentrations of the Saturation Library Variants in Conditioned Media

| | Position | | | | | | | | | | |
| Mutant | M252 | I253 | S254 | T256 | K288 | T307 | K322 | E380 | L432 | N434 | Y436 |
| | | | | | | -1 Concentration (µg mL$^{-1}$) | | | | | |
|---|---|---|---|---|---|---|---|---|---|---|---|
| A | 89.4 | 3.4 | 99.5 | 4.5 | 106 | <0.1 | 110 | 206 | 173 | 108 | 22.0 |
| C | <0.1 | 0.2 | 108 | <0.1 | <0.1 | <0.1 | 323 | <0.1 | 138 | 31.8 | <0.1 |
| D | 22.7 | <0.1 | <0.1 | <0.1 | <0.1 | <0.1 | 169 | 127 | 133 | <0.1 | 2.2 |
| E | <0.1 | 136 | 93.0 | 163 | <0.1 | 23.5 | 167 | WT | 2.7 | 65.9 | 8.9 |
| F | <0.1 | <0.1 | <0.1 | <0.1 | <0.1 | <0.1 | 154 | 127 | 118 | <0.1 | <0.1 |
| G | 46.7 | <0.1 | 172 | 106 | <0.1 | 4.9 | 124 | 146 | 107 | <0.1 | <0.1 |
| H | <0.1 | <0.1 | <0.1 | 207 | <0.1 | 7.0 | 229 | 103 | 124 | <0.1 | 173 |
| I | <0.1 | WT | <0.1 | 193 | 53.9 | <0.1 | 63.0 | 60.2 | 182 | 16.3 | <0.1 |

TABLE 5-continued

Concentrations of the Saturation Library Variants in Conditioned Media

| | Position | | | | | | | | | | |
|---|---|---|---|---|---|---|---|---|---|---|---|
| Mutant | M252 | I253 | S254 | T256 | K288 | T307 | K322 | E380 | L432 | N434 | Y436 |
| | | | | | −1 Concentration (μg mL$^{-1}$) | | | | | | |
| K | 1.2 | 4.1 | <0.1 | 3.2 | WT | 88.8 | WT | 69.2 | 25.0 | <0.1 | 67.0 |
| L | <0.1 | <0.1 | 103 | 124 | <0.1 | <0.1 | 181 | 169 | WT | 77.7 | <0.1 |
| M | WT | 80.0 | 1.5 | 122 | <0.1 | <0.1 | 112 | 76.8 | 97.3 | 30.5 | 90.1 |
| N | <0.1 | <0.1 | 89.6 | 46.8 | <0.1 | 126 | 231 | 190 | 235 | WT | 18.9 |
| P | 0.7 | <0.1 | 18.5 | 2.7 | 92.6 | <0.1 | 1.3 | 175 | <0.1 | 120 | <0.1 |
| Q | 176 | 35.7 | 20.9 | 123 | 1.0 | 14.0 | 216 | 197 | 188 | 55.4 | 96.9 |
| R | 0.8 | <0.1 | <0.1 | 189 | <0.1 | 1.5 | 209 | 9.1 | 142 | 102 | 25.0 |
| S | <0.1 | 71.1 | WT | 141 | <0.1 | 88.8 | 99.3 | 153 | 106 | <0.1 | 3.0 |
| T | 19.7 | 12.5 | <0.1 | WT | 83.8 | WT | 218 | 176 | 114 | 75.2 | 34.1 |
| V | 63.6 | 89.9 | 67.1 | 150 | <0.1 | <0.1 | 88.9 | 239 | 114 | 68.0 | 18.0 |
| W | 2.8 | <0.1 | <0.1 | 2.9 | 4.9 | <0.1 | 66.8 | 171 | <0.1 | 21.6 | 128 |
| Y | 0.7 | <0.1 | 150 | 117 | <0.1 | 1.1 | 143 | 11.3 | 26.1 | <0.1 | WT |

One variant, MDQF (FIG. 11B, highest in triple variant category), showed a dramatic 140% increase in FcγRIIIa binding. Thus, the combination saturation library offered variants with a wide range of Fc receptor functionalities that could be leveraged to tailor therapeutic antibodies with particular effector functions.

Figure 11C:
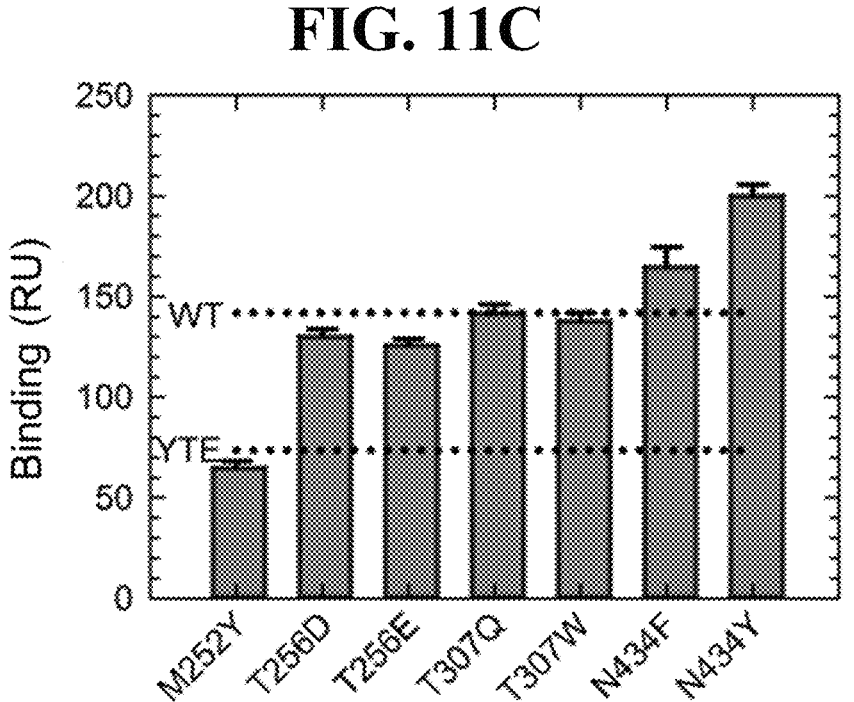

FIG. 11C shows a box plot of the FcγRIIIa binding responses of the seven lead single variants compared to the WT and YTE variants.

Figure 12A:
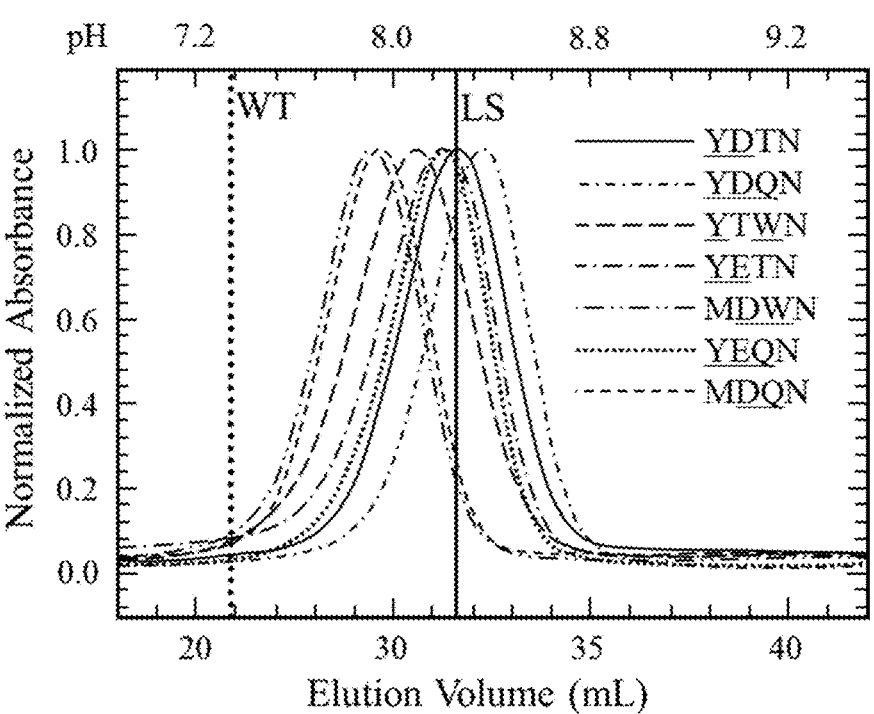
FIGS. 12A-D depict data obtained from FcRn affinity chromatography, DSF, and FcγRIIIa binding of seven lead combination variants.
Figure 12B:
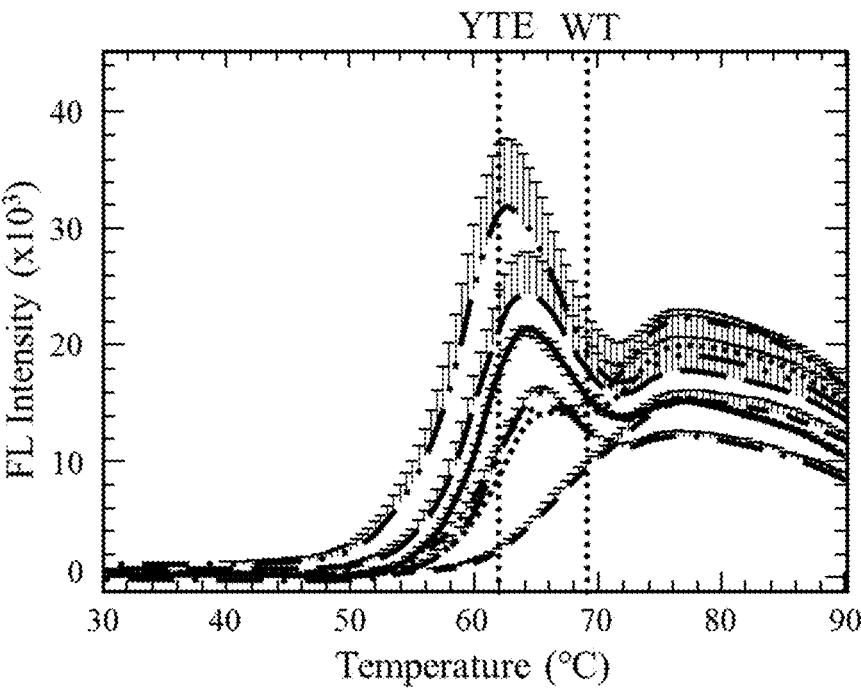

Example 9: Seven Lead Combinations Balance the pH-Dependence of the FcRn Interaction Without being bound to any theory, candidate variants for further study in vivo occupied the lower left quadrant of the plots shown in FIGS. 7C and 7D. Seven variants satisfied these criteria for hFcRn and comprised five double and two triple combinations (MDQN, MDWN, YDTN, YETN, YTWN, YDQN and YEQN), and did not contain a mutation at the N434 position (Table 3). Each of these combinations eluted from the FcRn affinity column between AAA (pH 7.94±0.06) and LS (pH 8.29±0.03) with YDQN eluting at the highest pH of 8.51±0.14 (FIG. 12A, Table 5), indicating only a slight perturbation in the pH dependence and greater residual binding at pH 7.4 (Table 2A). One of the variants (MDQN) possessed a wildtype-like thermal stability, and six had a similar or reduced $T_m$ compared to the YTE variant (FIG. 12B, Table 4). In an FcγRIIIa binding assay, five combination variants showed a similar reduction as YTE (Table 4). Further investigation with the single mutations revealed that M252Y significantly affected FcγRIIIa binding and, without being bound by any theory, translates this effect towards combinations with this mutation. The remaining six single mutations were WT-like or possessed slightly improved binding to this receptor.

Figure 12C:
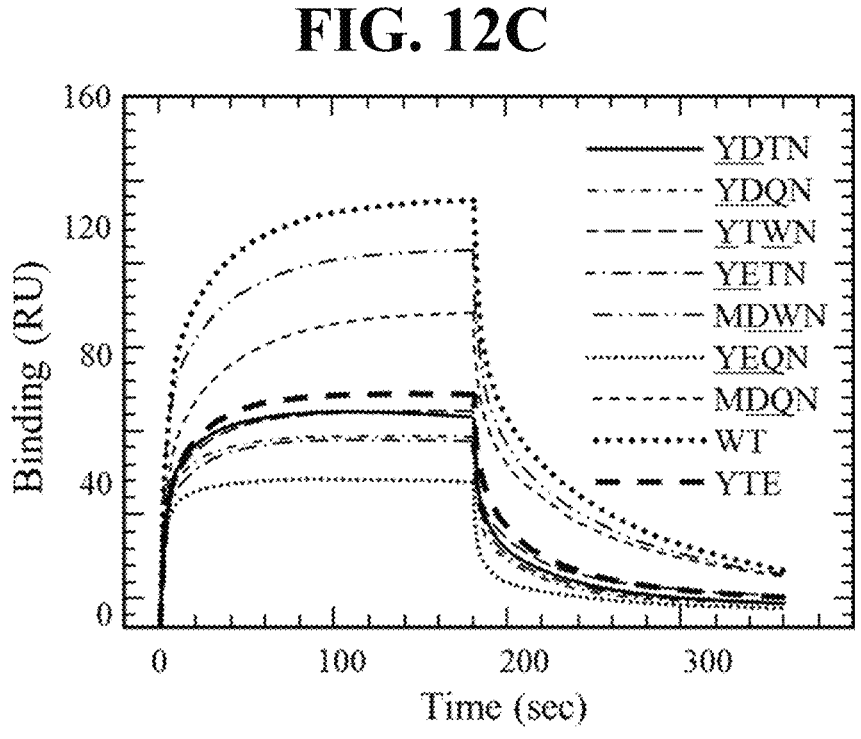
Figure 12D:
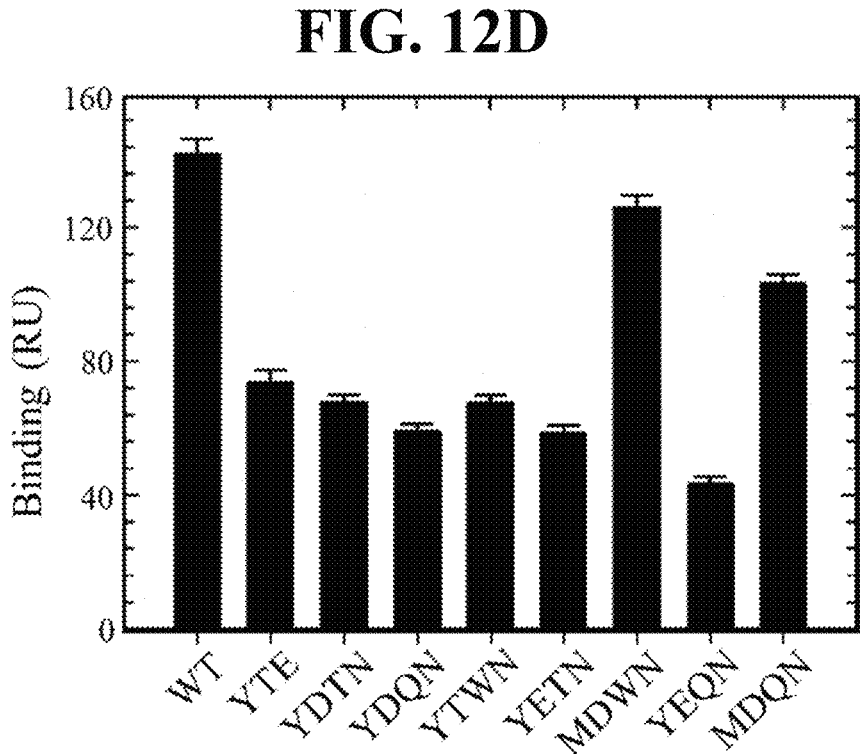
Figure 12E:
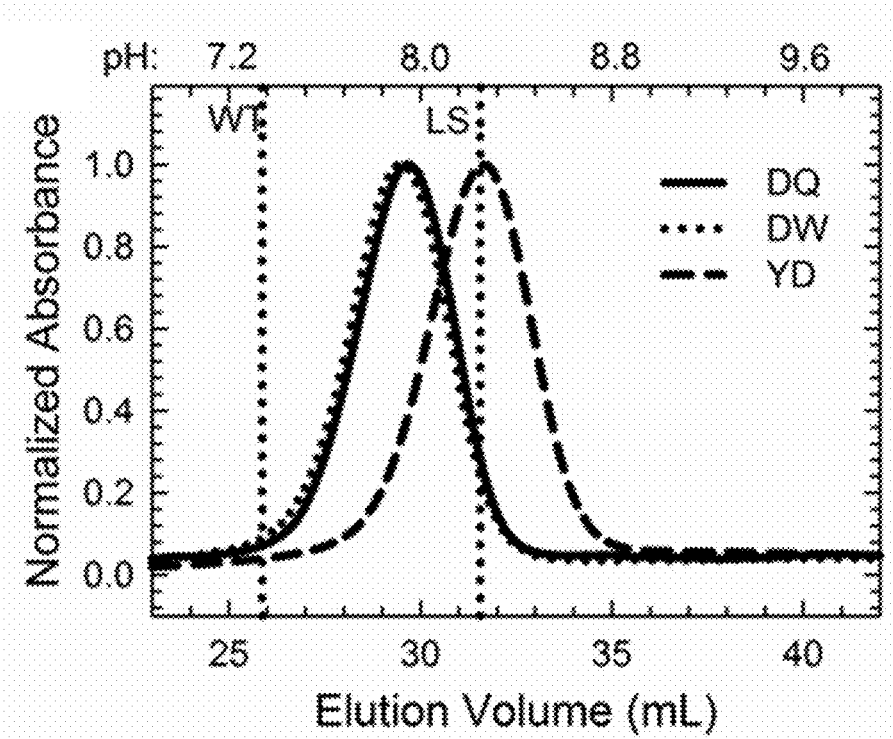
FIGS. 12E-H depict data showing that three lead variants displayed a range of key antibody attributes.
Figure 12F:
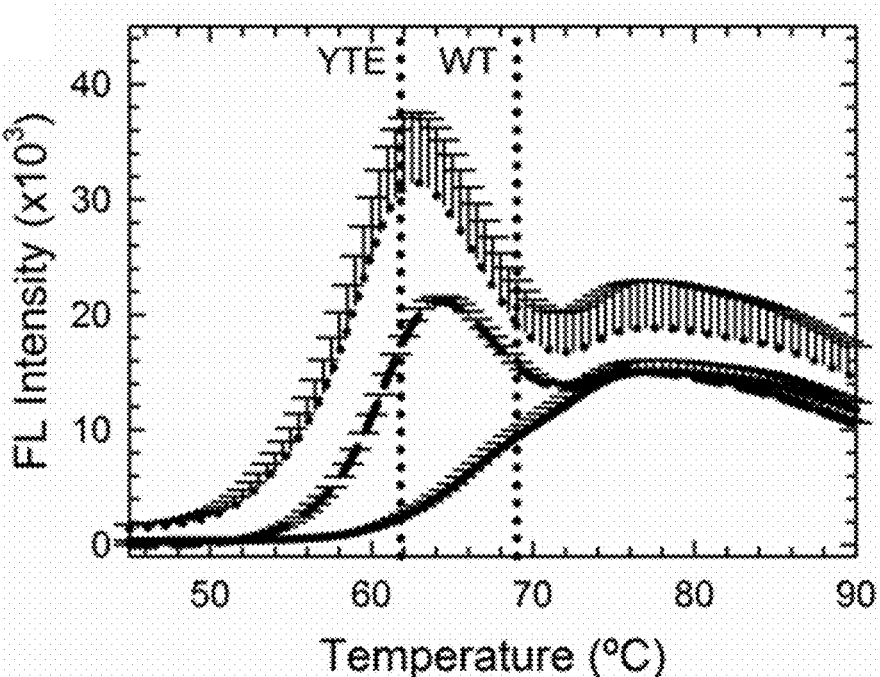
Figure 12G:
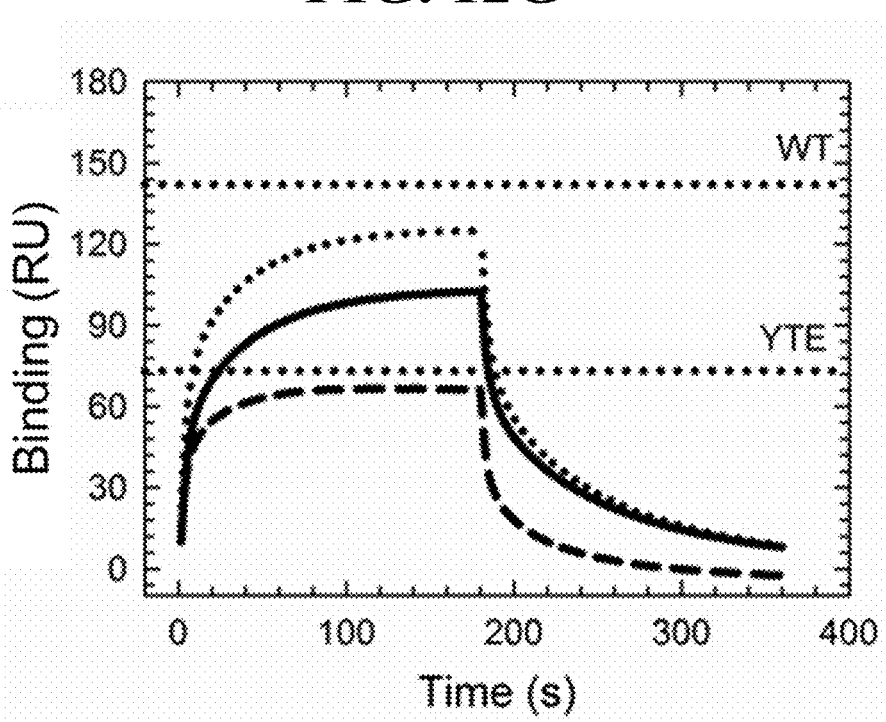
Figure 12H:
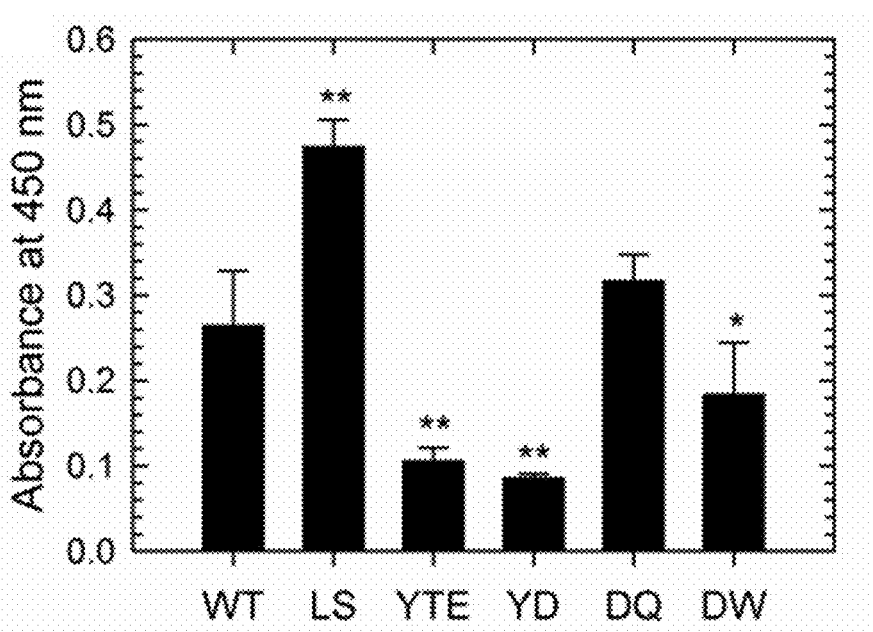

Three combination variants were selected for further studies based on their FcRn binding properties, thermal stabilities and FcγRIIIa binding. DQ (T256D/T307Q), DW (T256D/T307W) and YD (M252Y/T256D) each provided optimal FcRn binding properties (Table 2B) as the LS variant (FIG. 12E). Each variant offers a diverse range of thermal stability and FcγRIIIa binding properties (FIGS. 12F and 12G, Table 2B) that provided a range of functionality. FIG. 12H is a plot of homogeneous bridging RF.

Figure 13A:
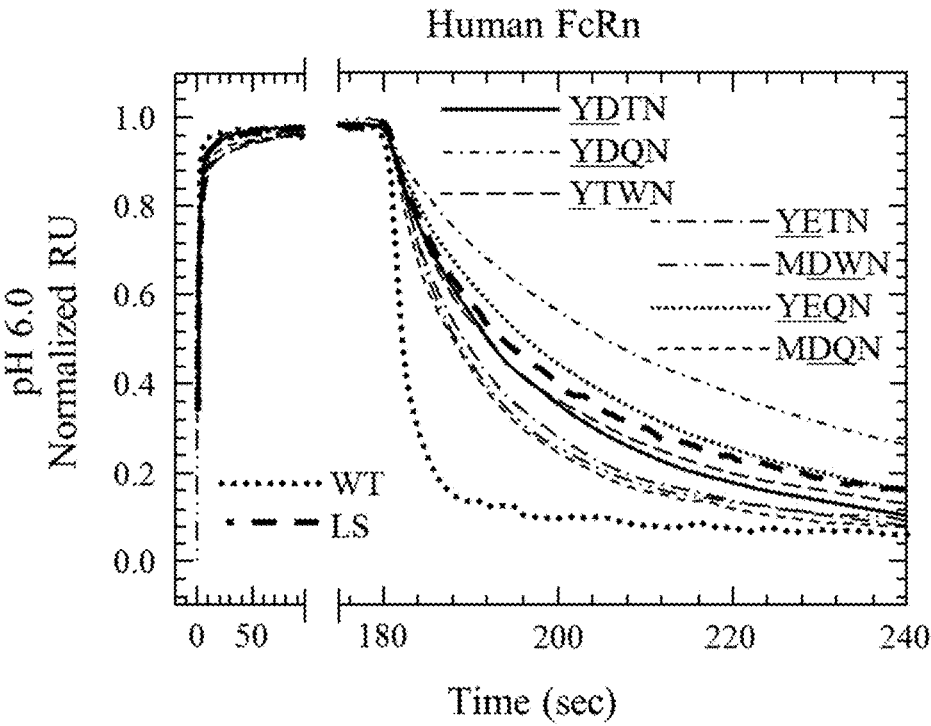
FIGS. 13A-D depict data showing a comparison of FcRn binding kinetics of the lead combination variants at pH 6.0 and pH 7.4.
Figure 13B:
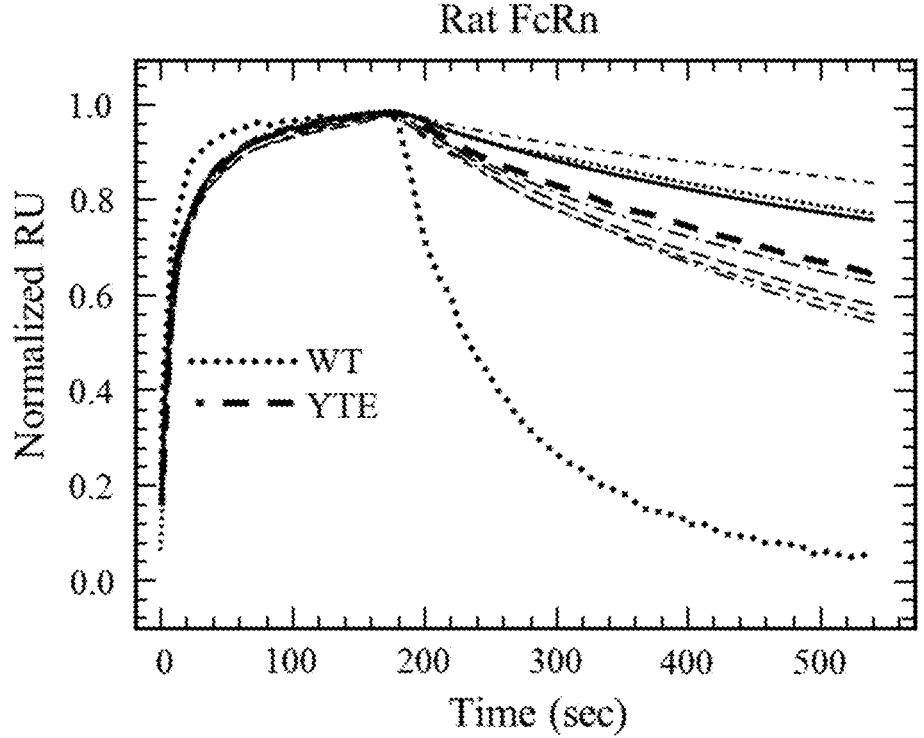
Figures 13C, 13D:
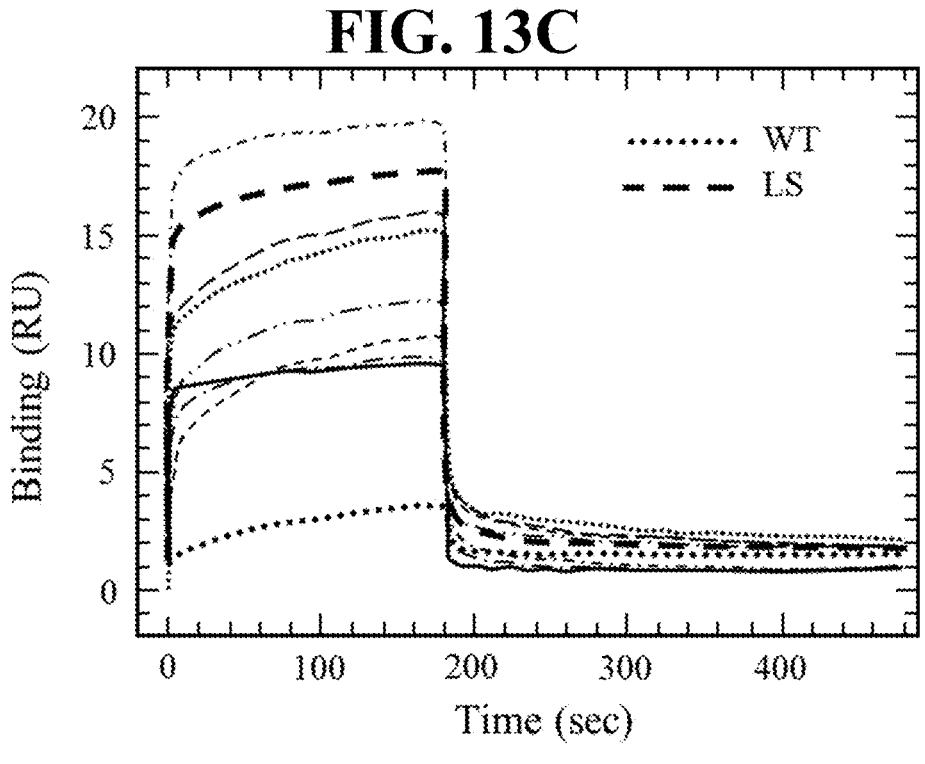

The enhancement in apparent binding affinity for both human and rat FcRn at pH 6.0 compared to the LS (FIG. 13A, thick long dashes) and YTE variants (FIG. 13B, thick long dashes), respectively, was a compromise between the on- and off-rates (FIGS. 13A and 13B, Table 4). Typically, combinations with faster off-rates also possessed faster on-rates and vice versa. This observation was maintained between human and rat FcRn (Table 4). Furthermore, all of these variants had a lower steady state response than the LS variant (FIG. 13C, thick long dashes) to hFcRn at pH 7.4. These results were not consistent with rFcRn, as the five M252Y-containing variants, YDTN, YETN, YTWN, YDQN and YEQN, had elevated FcRn binding at pH 7.4 (Table 5) compared to YTE. The MDQN and MDWN variants were the only combinations that were cross-reactive between human and rat FcRn. Furthermore, these two variants did not perturb the interaction with FcγRIIIa to a similar extent as the M252Y-containing variants (FIGS. 12C and 12D and Table 5; MDQN: 600±4 nM; MDWN: 512±30 nM; WT: 467±99 nM). Thus, saturation and combination mutagenesis at key FcRn interaction positions has led to the identification of lead variants that balanced the pH dependence of the interaction, maintained functionality with an Fc receptor, could enhance FcRn functionality in vivo, and could extend the serum half-life of therapeutic antibodies.

Example 10: Rheumatoid Factor Binding Characteristics of Lead Combination Variants The isoelectric point and RF binding of the lead variants was investigated, as these mutations may alter antibody surface charge and immunogenicity. More acidic antibodies have been thought to prolong antibody pharmacokinetics. Compared to the WT and LS controls, all three leads resulted in a ~0.2 pH unit reduction in the pI, as a result of the T256D substitution. FcRn-enhancing mutations may simultaneously alter binding to host antibodies, such as rheumatoid factor (RF), due to overlapping interaction interfaces. A homogeneous bridging ELISA was adapted to measure the change in RF binding for the lead variants. Interestingly, LS and YTE showed completely opposite shifts in RF binding compared to WT (FIG. 12H). LS significantly increased the RF binding, while YTE showed a significant decrease (p<0.001). YD (p<0.001) and DW (p<0.01) also significantly reduced RF binding, while DQ produced a similar response as WT. Without being bound to any theory, these results indicate that DQ, DW and YD can provide an immunogenic advantage compared to LS. The YD, DW and DQ variants represent a range of key antibody characteristics that can be leveraged in conjunction with the improved FcRn binding properties over the benchmark YTE and LS variants.

Example 11: Lead Combination Variants are Transferable to Other Antibodies

A new binding assay was developed using a CM5 sensor chip, as depicted in FIG. 15A. The binding assay includes a step to immobilize streptavidin on a CM5 sensor chip to capture biotinylated FcRn to about 30 RU, replenished as necessary. Antibody binding kinetics were measured at pH 6.0 and 7.4, and pH 8.5 for regeneration. FIGS. 15B and 15C show the direct immobilization of FcRn and streptavidin capture of biotinylated FcRn respectively, using the new binding assay.

FcRn binding of MAb2 at pH 6.0: With mouse FcRn, lead mAb2 variants demonstrate slower off-rates than the LS variant (dashes) and wildtype (black) (FIG. 16A). For human FcRn, the lead variants all have faster on-rates but similar off-rates as LS (dashes) (FIG. 16B).

FcRn binding of MAb2 at pH 7.4: All lead variants showed a reduced human FcRn binding at pH 7.4 compared to LS (dashes) (FIG. 17A). As with the mAb1mAb1' background, the DW (MDWN) and DQ (MDQN) variants also showed lower residual binding to mouse (rat) FcRn at pH 7.4 (FIG. 17B).

Figure 18:
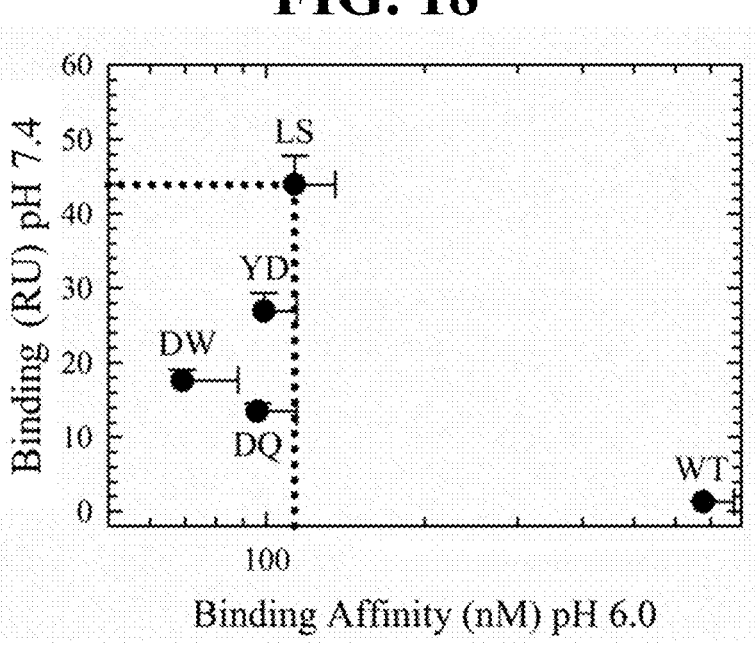
FIG. 18 graphically depicts the pH dependence of various mAb2 variants. Lead variants maintained a higher binding affinity at pH 6 and a lower residual binding at pH 7.4 than LS.
Figure 19:
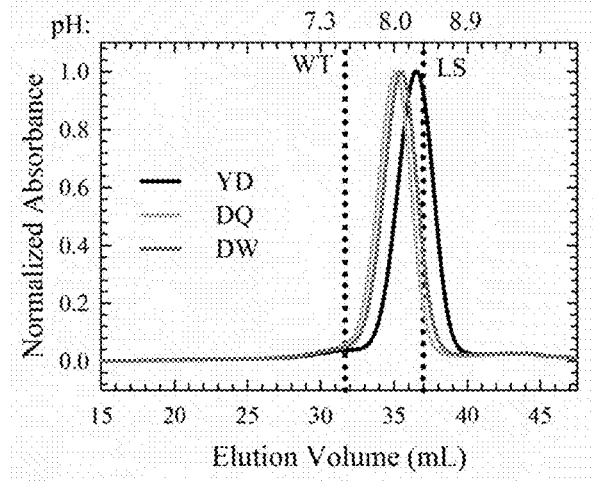
FIG. 19 depicts a comparison of FcRn binding pH dependence using the backbones of mAb1 and mAb2. mAb1 and mAb2 are human IgG1 antibodies targeting two unrelated antigens.

Lead variants maintained a higher binding affinity at pH 6.0 and a lower residual binding at pH 7.4 compared to LS (FIG. 18). Importantly, variants were found to be transfer- able between different IgG1 backgrounds with little effect on FcRn binding. As shown in FIG. 19, LS had a similar elution pH regardless of the background. WT, DQ and DW in the mAb2 background showed a higher elution pH than in the mAb1 background, possibly as a result of tighter binding at pH 6.0 in the mAb2 background.

Figure 20:
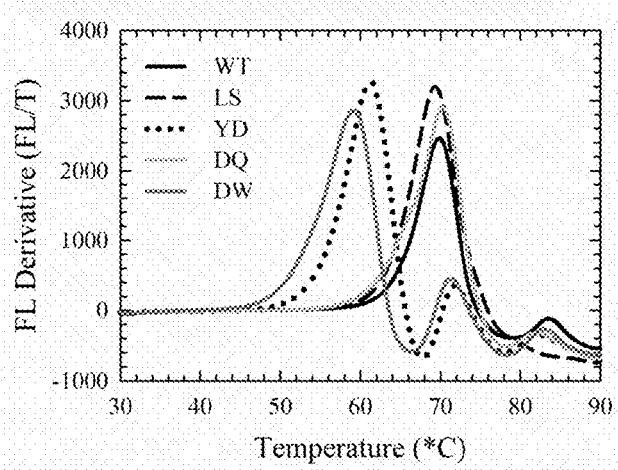
FIG. 20 depicts a comparison of thermal stability using the backbones of mAb1 and mAb2.

MAb2 background variants all showed a slightly increased thermal stability as shown in FIG. 20.

Figure 21:
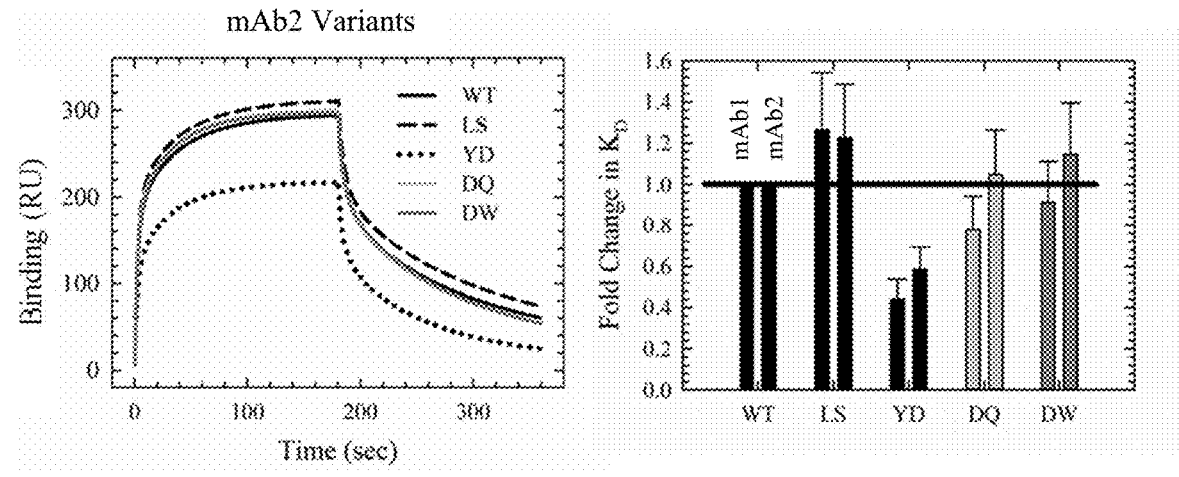
FIG. 21 depicts a comparison of FcγRIIIa binding using the backbones of mAb1 and mAb2.

As shown in FIG. 21, similar to the MAb1 background, YD (YDTN) showed a reduction in FcγRIIIa binding response (left) and affinity (right). DQ (light gray) and DW (dark gray) showed FcγRIIIa binding properties similar to WT (black) in the MAb2 background. The effect on FcγRIIIa binding for LS is consistent between MAb1 and mAb2.

Thus, the lead variants in the mAb2 background do not significantly affect the FcRn binding, pH dependence, ther- mal stability, or FcγRIIIa binding as compared to the same lead variants in the MAb1 background.

Figure 22:
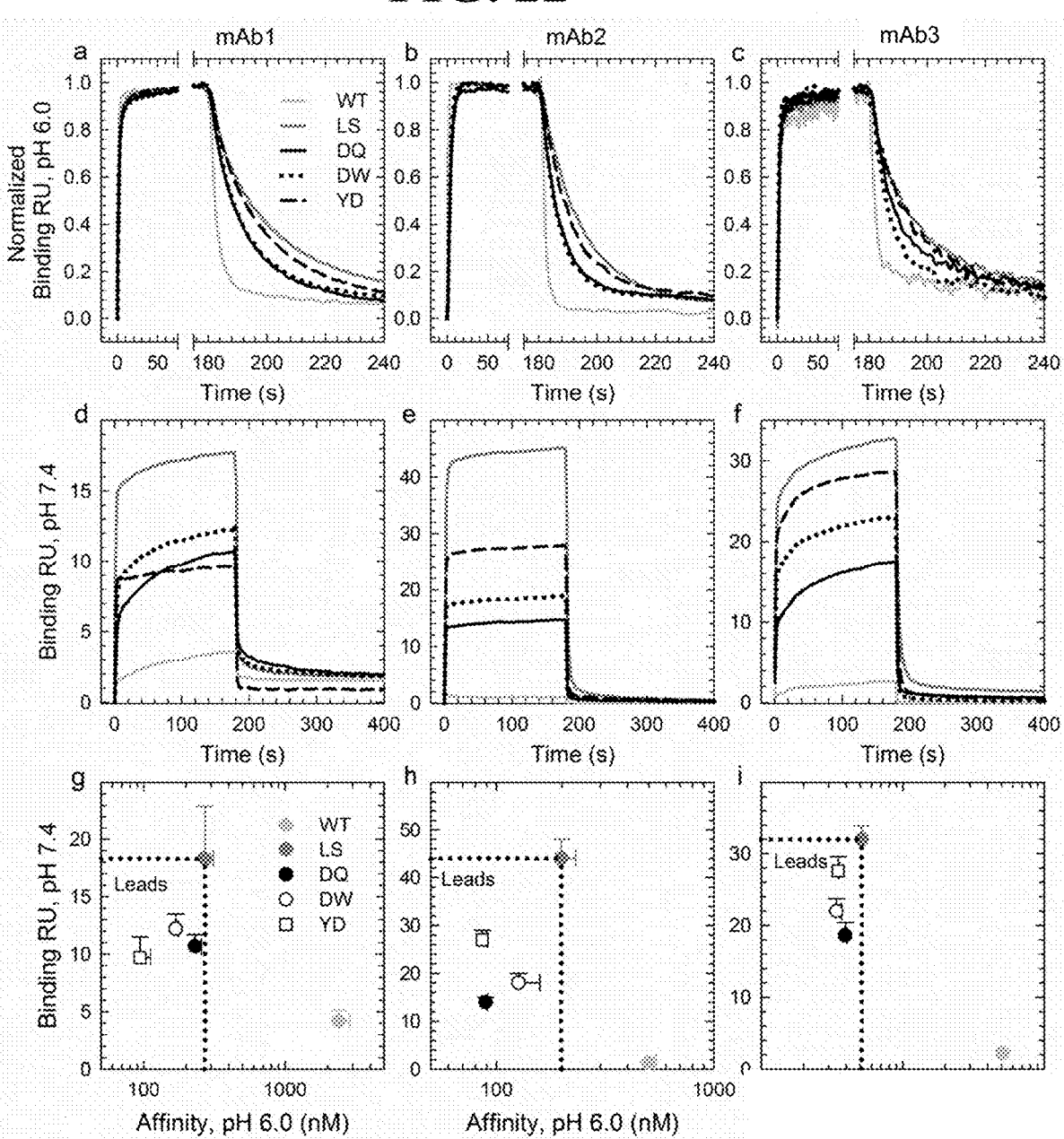
FIG. 22 is a panel of plots showing that the DQ, DW and YD variants were transferable among IgG1 backbones. Panels a-c depict normalized FcRn binding sensorgrams at pH 6.0 in three IgG1 backbones with the WT (light gray), LS (dark gray), DQ (solid black), DW (dotted) and YD (dashed) variants showing similar kinetics at low pH. These three variants, DQ, DW and YD, possessed slightly faster on and off-rates than the LS variant but maintained a tighter FcRn binding affinity. Panels d-f depict FcRn binding sensorgrams at pH 7.4; LS benchmark variant (solid black). Panels g-i depict the FcRn binding response at pH 7.4 compared to the binding affinity at pH 6.0 for each antibody backbone with the WT (gray), LS (dark gray), DQ (solid black), DW (empty) and YD (empty square) variants. DQ, DW and YD show improved FcRn characteristics, with enhanced binding at pH 6.0 and minimal binding at pH 7.4.

In one embodiment, DQ (T256D/T307Q), DW (T256D/ T307W) and YD (M252Y/T256D) variants were incorpo- rated into an additional IgG1 antibody and a recombinant Fc fragment: mAb2 recognizes a different antigen from mAb1, and mAb3 is an Fc fragment. In each case, the pH-dependent FcRn binding kinetics (FIG. 22) were highly similar in addition to the elution pH, thermal stability and FcγRIIIa binding affinities (Table 2B, and Table 6). Without being bound to any theory, these results indicate that the DQ, DW and YD variants conferred their improved FcRn binding properties to proteins consisting of an Fc domain.

TABLE 6

| Concentrations of the Saturation Library Variants in Conditioned Media | | | | | | | | | |
|---|---|---|---|---|---|---|---|---|---|
| | | FcRn | | Biacore ™ FcγRIIIa | Biacore ™ pH 6.0 | | | Biacore ™ pH 7.4 | | |
| | | Affinity | | V158 | | | | hFcRn | cFcRn | mFcRn |
| | | Column | DSF | Affinity | hFcRn | cFcRn | mFcRn | Steady | Steady | Steady |
| Ab | Variant | pH | $T_m$ | Fold Change | $*K_{D, app}$ | $*K_{D, app}$ | $*K_{D, app}$ | State RU | State RU | State RU |
| 2 | WT | 7.61 | 69.3 ± 0.1 | 1.0 | 678 ± 97 | 1440 ± 360 | 107 ± 9 | 1.3 ± 0.2 | 1.3 ± 0.3 | 92 ± 8 |
| 2 | LS | 8.32 | 69.0 ± 0.1 | 1.23 ± 0.02 | 113 ± 22 | 210 ± 43 | 20 ± 9 | 44 ± 4 | 38 ± 6 | 285 ± 8 |
| 2 | DQ | 8.06 | 69.3 ± 0.1 | 1.05 ± 0.01 | 97 ± 33 | 110 ± 42 | 24 ± 11 | 14 ± 1 | 11 ± 1 | 248 ± 5 |
| 2 | DW | 8.11 | 58.1 ± 0.1 | 1.15 ± 0.01 | 69 ± 25 | 99 ± 9 | 13 ± 5 | 18 ± 2 | 15 ± 1 | 257 ± 8 |
| 2 | YD | 8.25 | 60.5 ± 0.1 | 0.58 ± 0.01 | 99 ± 49 | 120 ± 6 | 10 ± 3 | 27 ± 2 | 22 ± 3 | 394 ± 11 |
| 3 | WT | 7.62 | 67.5 ± 0.2 | 1.0 | 717 ± 23 | | 61 ± 1 | 2.2 ± 0.3 | | 72 ± 2 |
| 3 | LS | 8.32 | 66.6 ± 0.2 | 1.11 ± 0.03 | 51 ± 2 | | 16 ± 2 | 32 ± 2 | | 103 ± 1 |
| 3 | DQ | 8.07 | 63.8 ± 0.2 | 0.87 ± 0.02 | 51 ± 1 | | 24 ± 1 | 19 ± 2 | | 89 ± 1 |
| 3 | DW | 8.12 | 57.1 ± 0.2 | 0.93 ± 0.02 | 39 ± 6 | | 23 ± 1 | 22 ± 2 | | 99 ± 1 |
| 3 | YD | 8.23 | 59.5 ± 0.1 | 0.73 ± 0.02 | 54 ± 1 | | 0.5 ± 0.2 | 28 ± 3 | | 125 ± 2 |

Figure 23A:
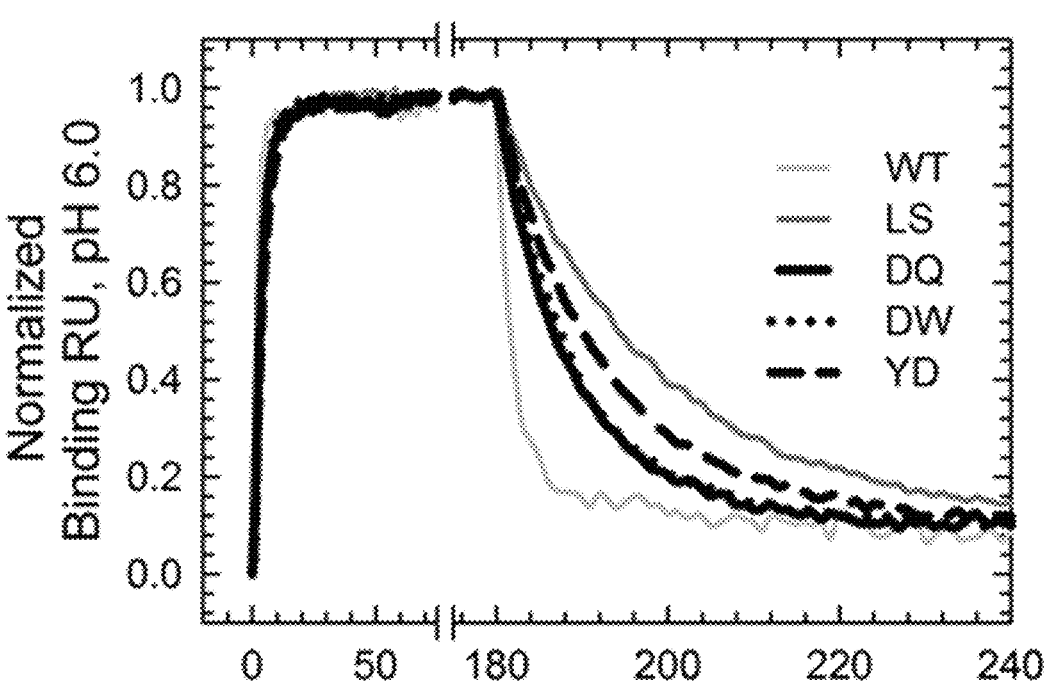
FIGS. 23A-C show that the three lead variants in the mAb2 backbone similarly improves the binding to cyno-molgus FcRn.
Figure 23B:
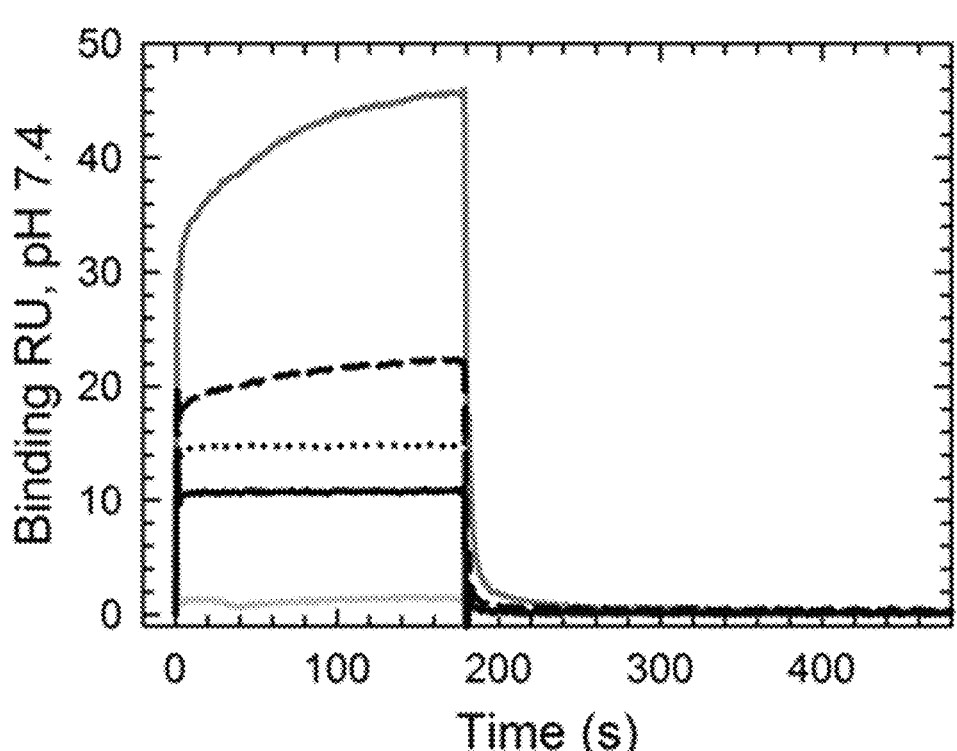
Figure 23C:
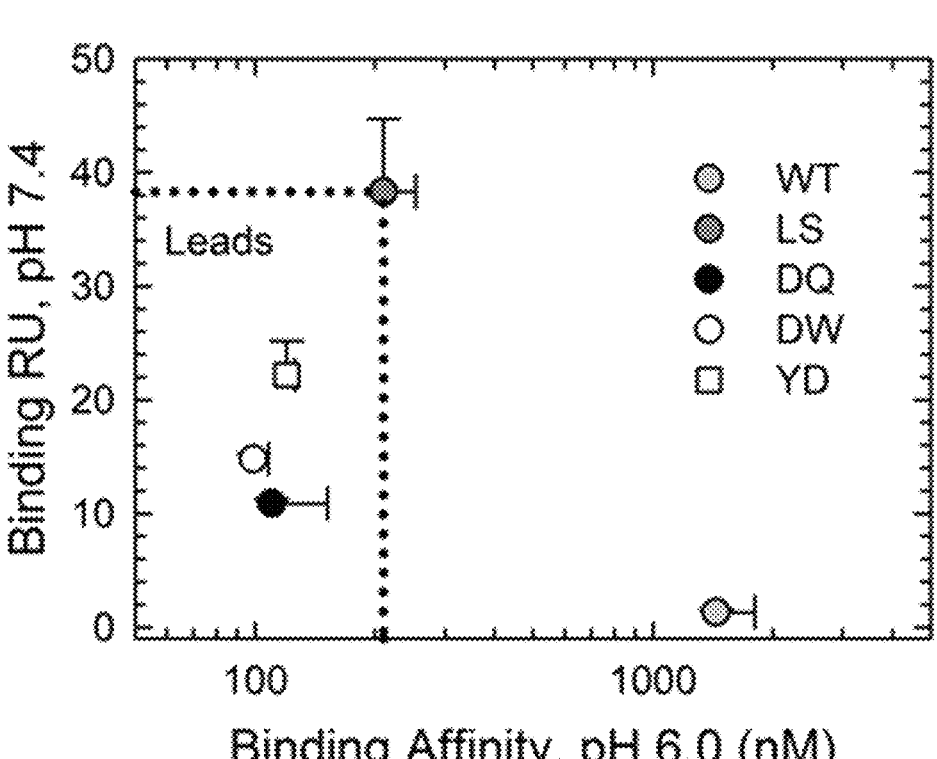
Figure 24A:
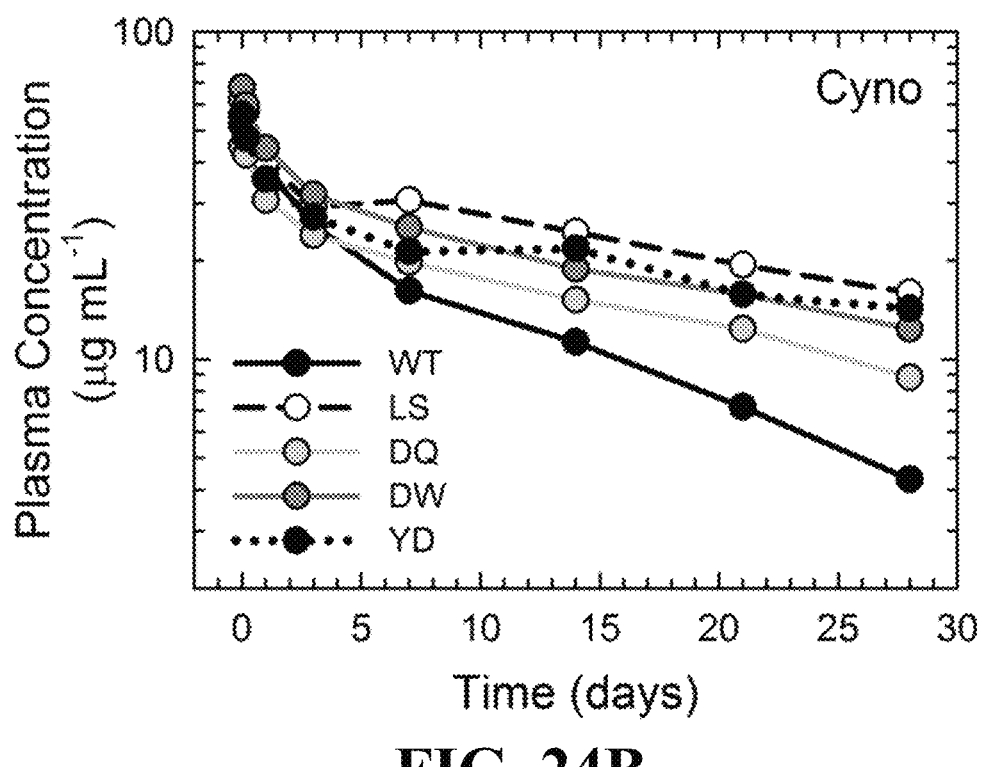
FIGS. 24A and 24B show that the lead variants prolonged the antibody serum half-life. Pharmacokinetic profiles of the plasma antibody concentration as a function of time in cynomolgus monkey (FIG. 24A) and hFcRn transgenic mouse (FIG. 24B) of the WT (black circles with solid black line), LS (white circles with dashed black line), DQ (light gray circles with solid light gray line), DW (dark gray circles with solid dark gray line) and YD (black circles with dotted black line) antibodies. All three lead variants prolong the antibody half-life compared to the WT.
Figure 24B:
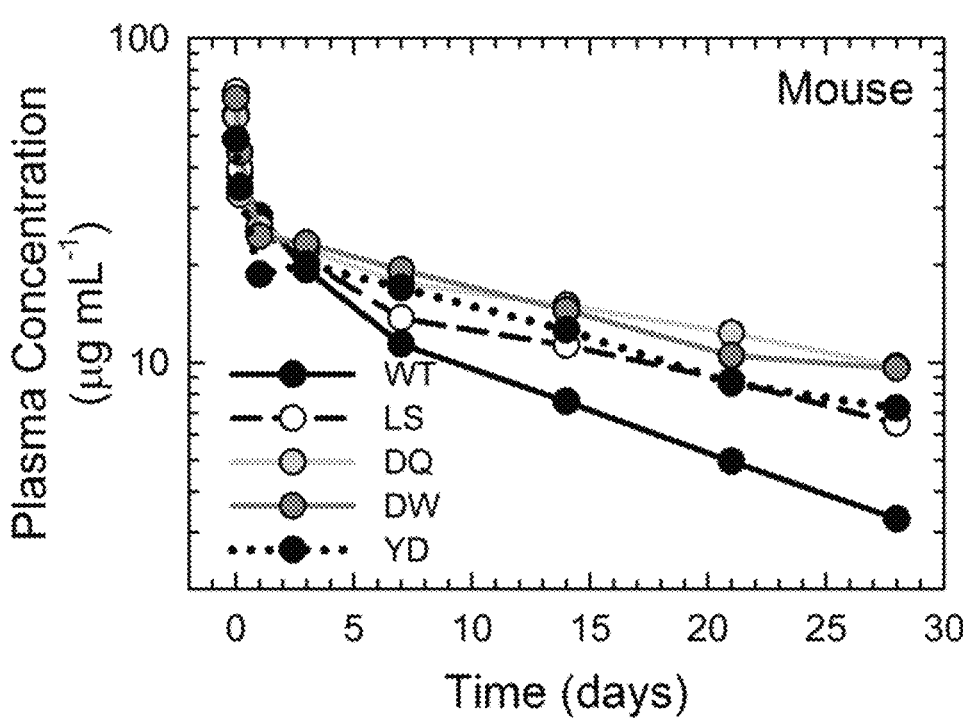

Example 12: Lead Variants Extended the In Vivo Plasma Antibody Elimination Half-Life The pharmacokinetics (PK) of the DQ, DW and YD variants were examined for their effect on antibody circulation half-life with cynomolgus monkeys and hFcRn transgenic mice (strain Tg32) (see, e.g., Avery et al. Mabs (2016) 8:1064-78) in comparison to WT and LS controls. FcRn binding studies with cynomolgus FcRn revealed similar binding affinities to hFcRn (FIGS. 23A-23B; Table 6). Each animal was intravenously injected with the WT, LS, DQ, DW or YD variants, and the antibody concentration was quantified through a mass spectrometry approach to determine the clearance rate and serum half-life in monkeys (FIG. 24A) and hFcRn transgenic mice (FIG. 24B). The clearance rates and serum half-lives were obtained from a non-compartmental model of the antibody concentration as a function of time. All three lead variants and LS showed a significantly reduced clearance rate compared to WT in both monkeys and mice ($p<0.001$). The plasma half-life of the WT antibody was $9.9\pm0.5$ and 11.7 days for monkeys and mice, respectively. Furthermore, the LS benchmark and variants identified exhibited a significant increase of elimination half-life compared to wild type in both species (2.5- and 1.7-fold increase in monkey and mouse, respectively) (Table 7). DQ, DW and YD showed a similar prolongation of half-life compared to the LS benchmark (Table 7). The DQ, DW and YD mutations identified herein through saturation mutagenesis demonstrated significantly prolonged plasma half-life than their WT counterparts in both mouse and non-human primate animal models.

TABLE 7

Clearance Rates and Serum Half-Lives of the Benchmark and Lead Variants

| mAb2 | Cynomolgus Monkey (n = 3) | | | | hFcRn Tg32 Mouse (n = 6) | | | |
| | Clearance (mL day$^{-1}$ kg$^{-1}$) | $t_{1/2}$ (days) | | | Clearance (mL day$^{-1}$ kg$^{-1}$) | $t_{1/2}$ (days) | | |
| Variant | Mean ± SD | Mean ± SD | Fold vs. WT | Fold vs. LS | Mean | Mean | Fold vs. WT | Fold vs. LS |
|---|---|---|---|---|---|---|---|---|
| WT | 5.6 ± 0.5 | 9.9 ± 0.5 | 1.0 | 0.4 | 7.4 | 11.7 | 1.0 | 0.6 |
| LS | 2.1** | 22.5 ± 2.4 | 2.3 | 1.0 | 4.6 | 19.5 | 1.7 | 1.0 |
| DQ | 3.4* | 20.8 | 2.1 | 0.9 | 3.2 | 24.5 | 2.1 | 1.3 |
| DW | 2.5 ± 0.2 | 20.4 ± 0.9 | 2.1 | 0.9 | 3.5 | 20.1 | 1.7 | 1.0 |
| YD | 2.4 ± 0.3 | 23.5 ± 2.1 | 2.4 | 1.0 | 4.5 | 17.5 | 1.5 | 0.9 |

In Table 7, the clearance rate and plasma-half-lives were determined using mAb2. Each clearance rate and half-life were the average of n=3 for the cynomolgus monkey and a single evaluation from a pool of n=6 hFcRn transgenic mice. Fold vs. WT and Fold vs. LS show the relative improvement in serum half-life compared to the WT and LS, respectively. *n=2 due to ADA formation, **n=2 due to partial subcutaneous route of administration Example 13: Combination Variants with Enhanced FcRn Binding at pH 6.0 and pH 7.4

Based on the Octet screening (BLI-based screen) as described in Example 2, various single, double, triple, and quadruple variants were generated and their binding to FcRn at pH 6.0 and pH 7.4 were assessed (Table 8; substituted residues are underlined).

TABLE 8

Binding Affinity (pH 6.0) and Steady State Binding (pH 7.4) of Variants

| Variant | Type | Binding Affinity (M$^{-1}$) | Binding Affinity Error (M$^{-1}$) | Steady State Binding, pH 7.4 (RU) | Steady State Binding Error, pH 7.4 (RU) | Ratio (pH 6.0/pH 7.4) | Ratio (pH 6.0/pH 7.4) |
|---|---|---|---|---|---|---|---|
| WT (MTTN) | Benchmark | 420000 | 83000 | 4.2 | 0.9 | 100000 | 1.00E−05 |
| AAA | Benchmark | 562000 | 120000 | 13.9 | 3.1 | 40432 | 2.47E−05 |
| LS | Benchmark | 3680000 | 541000 | 18.3 | 4.6 | 201093 | 4.97E−06 |
| YTE | Benchmark | 2920000 | 1000000 | 13.2 | 3.5 | 221212 | 4.52E−06 |
| MDQN | Double | 4310000 | 446000 | 10.7 | 1 | 402804 | 2.48E−06 |
| MDTF | Double | 33400000 | 2240000 | 29.2 | 4 | 1143836 | 8.74E−07 |
| MDTY | Double | 64100000 | 2050000 | 37.1 | 5 | 1727763 | 5.79E−07 |
| MDWN | Double | 5920000 | 280000 | 12.2 | 1.3 | 485246 | 2.06E−06 |
| MEQN | Double | 2000000 | 24100 | 5.8 | 0.6 | 344828 | 2.90E−06 |
| METF | Double | 12800000 | 3350000 | 23.3 | 3.2 | 549356 | 1.82E−06 |
| METY | Double | 16000000 | 4130000 | 26.8 | 3.7 | 597015 | 1.68E−06 |
| MEWN | Double | 3100000 | 259000 | 7.7 | 0.9 | 402597 | 2.48E−06 |
| MTQF | Double | 23300000 | 4290000 | 34.2 | 4.6 | 681287 | 1.47E−06 |

TABLE 8-continued

| | | Binding Affinity (M⁻¹) | Binding Affinity Error (M⁻¹) | Steady State Binding, pH 7.4 (RU) | Steady State Binding Error, pH 7.4 (RU) | Ratio (pH 6.0/pH 7.4) | Ratio (pH 6.0/pH 7.4) |
|---|---|---|---|---|---|---|---|
| Variant | Type | | | | | | |
| MTQY | Double | 30900000 | 6950000 | 38.4 | 5.2 | 804688 | 1.24E−06 |
| MTWF | Double | 26200000 | 1230000 | 30.5 | 4.2 | 859016 | 1.16E−06 |
| MTWY | Double | 46500000 | 2600000 | 37.2 | 4.9 | 1250000 | 8.00E−07 |
| YDTN | Double | 10700000 | 2100000 | 9.7 | 1.8 | 1103093 | 9.07E−07 |
| YETN | Double | 7810000 | 305000 | 9.8 | 1.2 | 796939 | 1.25E−06 |
| YTQN | Double | 3600000 | 298000 | 10.6 | 1.2 | 339623 | 2.94E−06 |
| YTTF | Double | 55600000 | 3090000 | 43.8 | 5.8 | 1269406 | 7.88E−07 |
| YTTY | Double | 120000000 | 2890000 | 54.1 | 7.1 | 2218115 | 4.51E−07 |
| YTWN | Double | 8470000 | 359000 | 15.9 | 1.7 | 532704 | 1.88E−06 |
| MDQF | Triple | 6620000 | 1840000 | 55.3 | 11.2 | 119711 | 8.35E−06 |
| MDQY | Triple | 36900000 | 4360000 | 49.4 | 6.7 | 746964 | 1.34E−06 |
| MDWF | Triple | 28100000 | 2840000 | 47.1 | 6.4 | 596603 | 1.68E−06 |
| MDWY | Triple | 84000000 | 9890000 | 59 | 7.9 | 1423729 | 7.02E−07 |
| MEQF | Triple | 142000 | 6490 | 8.6 | 0.8 | 16512 | 6.06E−05 |
| MEQY | Triple | 23800000 | 2660000 | 38.6 | 5.2 | 616580 | 1.62E−06 |
| MEWF | Triple | 56200000 | 8520000 | 41.9 | 5.6 | 1341289 | 7.46E−07 |
| MEWY | Triple | 70400000 | 7440000 | 46.6 | 6.3 | 1510730 | 6.62E−07 |
| YDQN | Triple | 8700000 | 560000 | 19.8 | 2.7 | 439394 | 2.28E−06 |
| YDTF | Triple | 29600000 | 2540000 | 57.7 | 7.7 | 512998 | 1.95E−06 |
| YDTY | Triple | 90100000 | 812000 | 65.4 | 8.9 | 1377676 | 7.26E−07 |
| YDWN | Triple | 10100000 | 1540000 | 25.9 | 3.6 | 389961 | 2.56E−06 |
| YEQN | Triple | 4590000 | 126000 | 15.2 | 2.1 | 301974 | 3.31E−06 |
| YETY | Triple | 33400000 | 3580000 | 22.6 | 2.9 | 1477876 | 6.77E−07 |
| YEWN | Triple | 6410000 | 904000 | 69.6 | 9.3 | 92098 | 1.09E−05 |
| YTQF | Triple | 56500000 | 1280000 | 59.9 | 8 | 943239 | 1.06E−06 |
| YTQY | Triple | 63300000 | 4010000 | 71.5 | 9.6 | 885315 | 1.13E−06 |
| YTWF | Triple | 65400000 | 2990000 | 62.6 | 8.2 | 1044728 | 9.57E−07 |
| YTWY | Triple | 106000000 | 10600000 | 75.1 | 9.8 | 1411451 | 7.08E−07 |
| YDQF | Quadruple | 111000000 | 4320000 | 68.6 | 10 | 1618076 | 6.18E−07 |
| YDQY | Quadruple | 235000000 | 6060000 | 80.2 | 12 | 2930175 | 3.41E−07 |
| YDWF | Quadruple | 166000000 | 3050000 | 71.8 | 9.9 | 2311978 | 4.33E−07 |
| YDWY | Quadruple | 266000000 | 19100000 | 88.5 | 11.7 | 3005650 | 3.33E−07 |

In Table 8, binding affinity to FcRn at pH 6.0 and steady state binding to FcRn at pH 7.4 for various single, double, triple, and quadruple mutants, as well as benchmark variants (AAA, LS, YTE) are shown.

Figure 25:
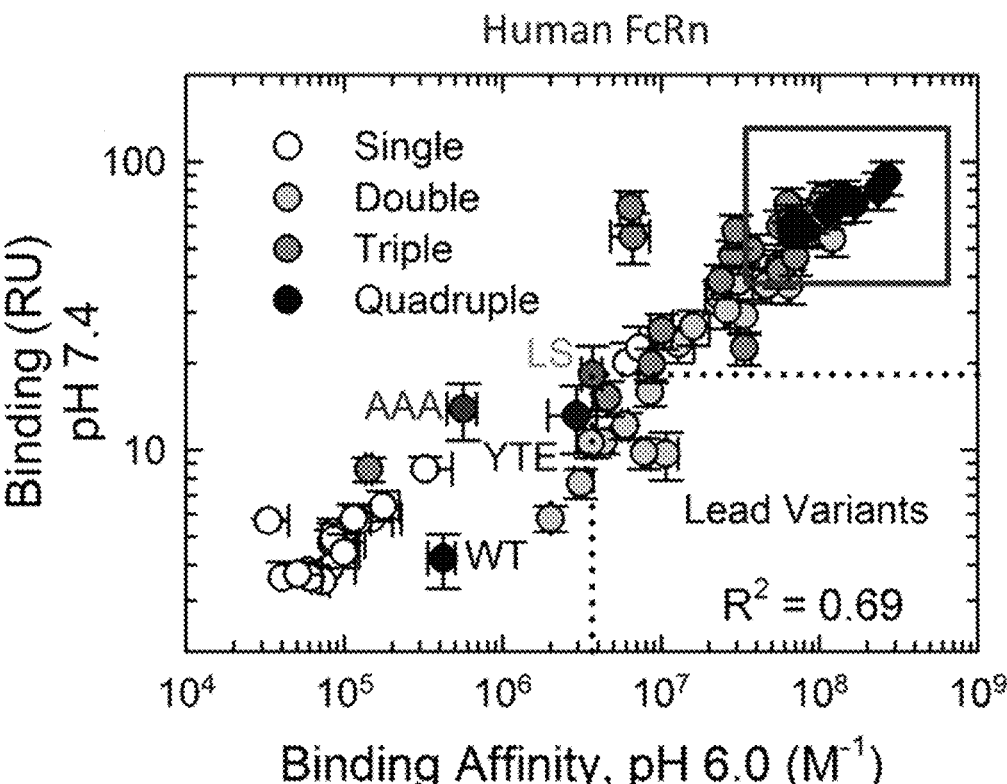
FIG. 25 depicts a plot of the steady state RU of all saturation variants to human FcRn at pH 7.4 as a function of the binding affinity at pH 6.0. Comparison of the residual FcRn binding at pH 7.4 with the FcRn binding affinity at pH 6.0 is shown. Quadruple combinations with improved FcRn binding properties at both pH 6.0 and pH 7.4 are shown boxed in upper right quadrant of plot. Single (white circles), double (light gray circles), triple (dark gray circles), and quadruple (black circles) variants as well as the benchmark AAA, LS, and YTE variants (as indicated) are shown.

These values are plotted in FIG. 25. FIG. 25 shows a comparison of the binding affinity at pH 6.0 and the RU at pH 7.4. As shown, the benchmark variant LS has the tightest binding affinity at pH 6.0 and largest residual binding at pH 7.4 of the benchmark variants tested (AAA, LS, YTE).

Figure 26:
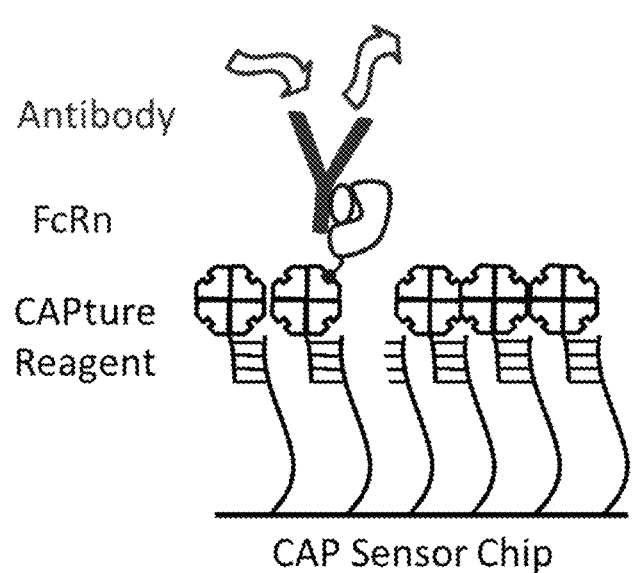
FIG. 26 depicts a schematic of the Biotin CAPture method used to capture biotinylated FcRn.

It was determined that several combination variants shown in FIG. 25 exhibited enhanced FcRn binding affinity at pH 6.0 and at pH 7.4. To investigate whether any of the combination variants showed a tighter binding than the MST-HN variant (referred to herein as "the YTEKF benchmark," containing mutations at Met252, Ser254, Thr256, His433 and Asn434 to Tyr252, Thr254, Glu256, Lys433 and Phe434) at both pH 6.0 and pH 7.4, the following methodology was performed. Capture of biotinylated human and cynomolgus FcRn was performed via the Biotin CAPture method (see FIG. 26 for schematic). For pH 6.0, a concentration series (5 pts) from 1000 nM was performed in duplicate. For pH 7.4 and 8.0, a single concentration (1000 nM) injection was performed in triplicate, in addition to a concentration series from 1000 nM performed in duplicate. The pH 7.4 and 8.0 experiments were performed at an FcRn capture level that was increased 10-fold compared to pH 6.0 to observe binding at this pH. For pH 9.0, a single concentration (1000 nM) injection was performed in triplicate. The pH 9.0 experiments were performed at an FcRn capture level that was increased 100-fold compared to pH 6.0 to observe binding at this pH. For pH 6.0, a concentration series (5 pts) from 1000 nM was performed in duplicate. For pH 7.4, a single concentration (1000 nM) injection was performed in triplicate (capture level of each FcRn was increased 10-fold to observe binding at this pH). Association: 180 sec; Dissociation: 300 sec.

Figure 27A:
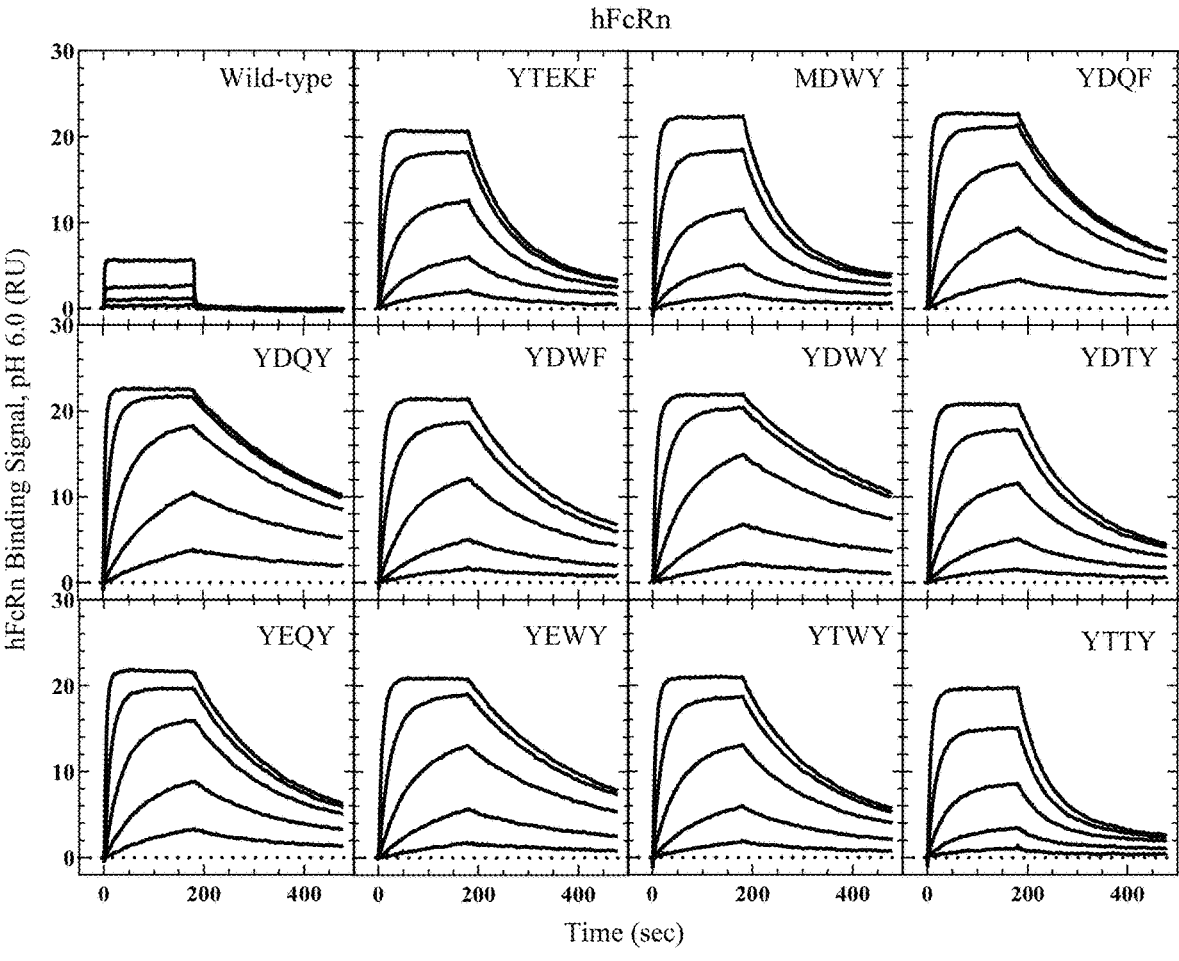
Figure 27B:
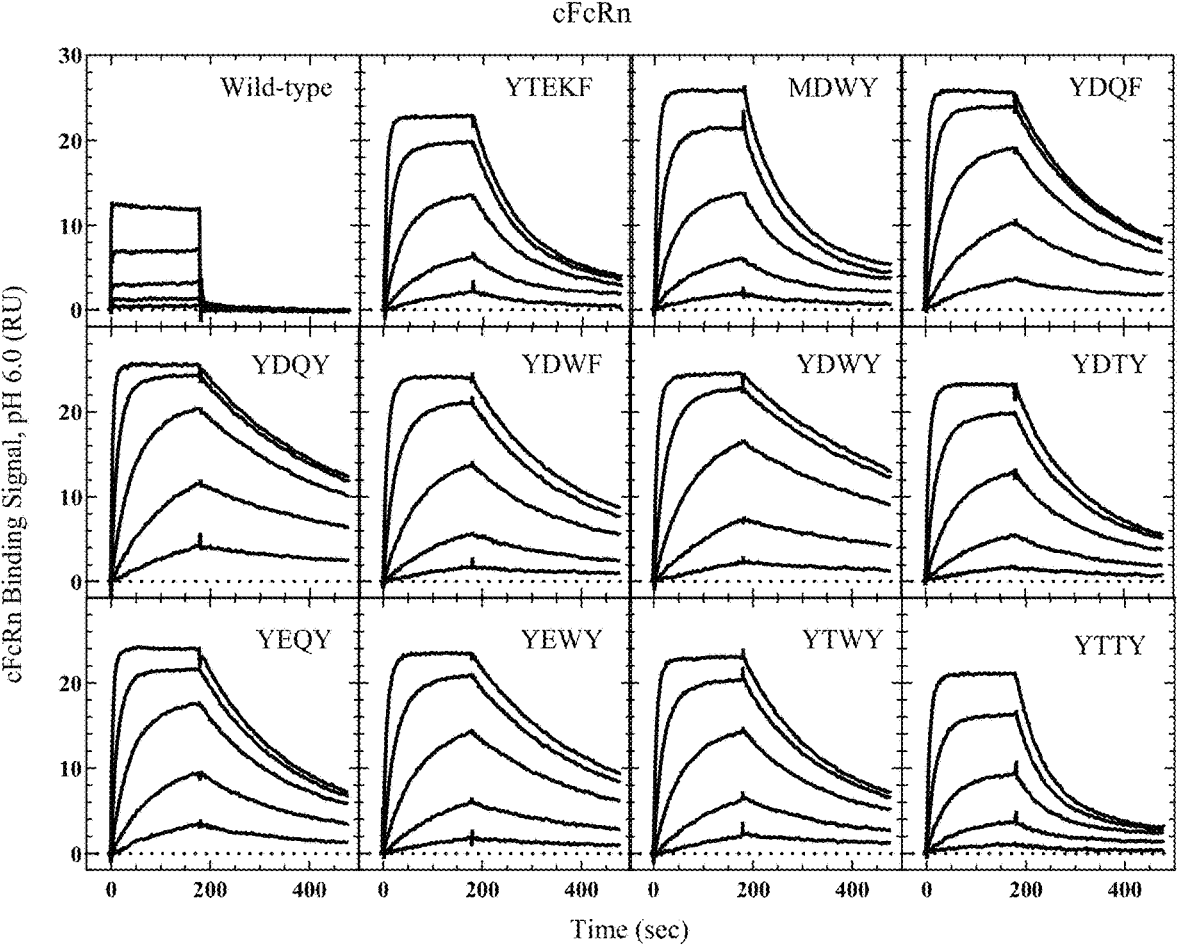
Figure 27C:
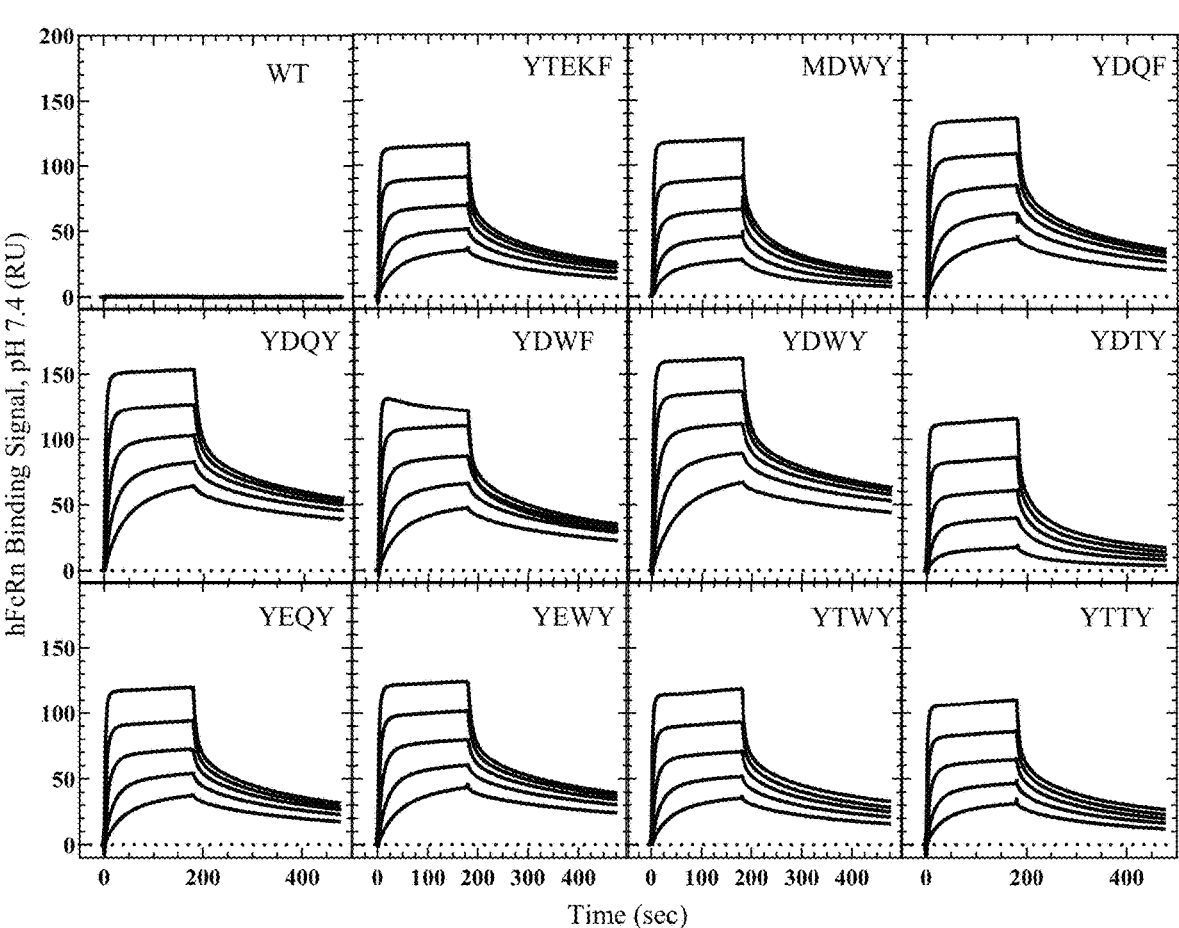
Figure 27D:
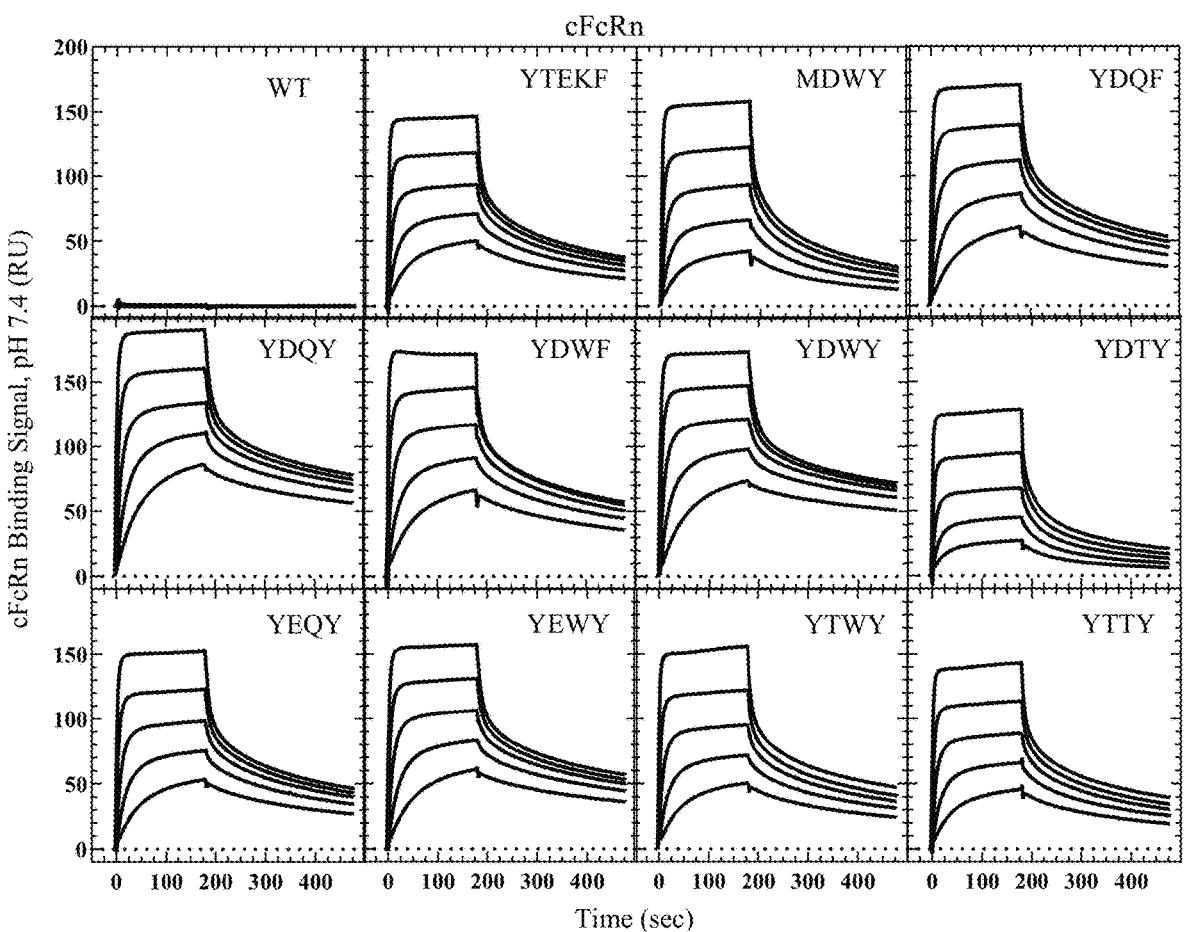
Figure 27F:
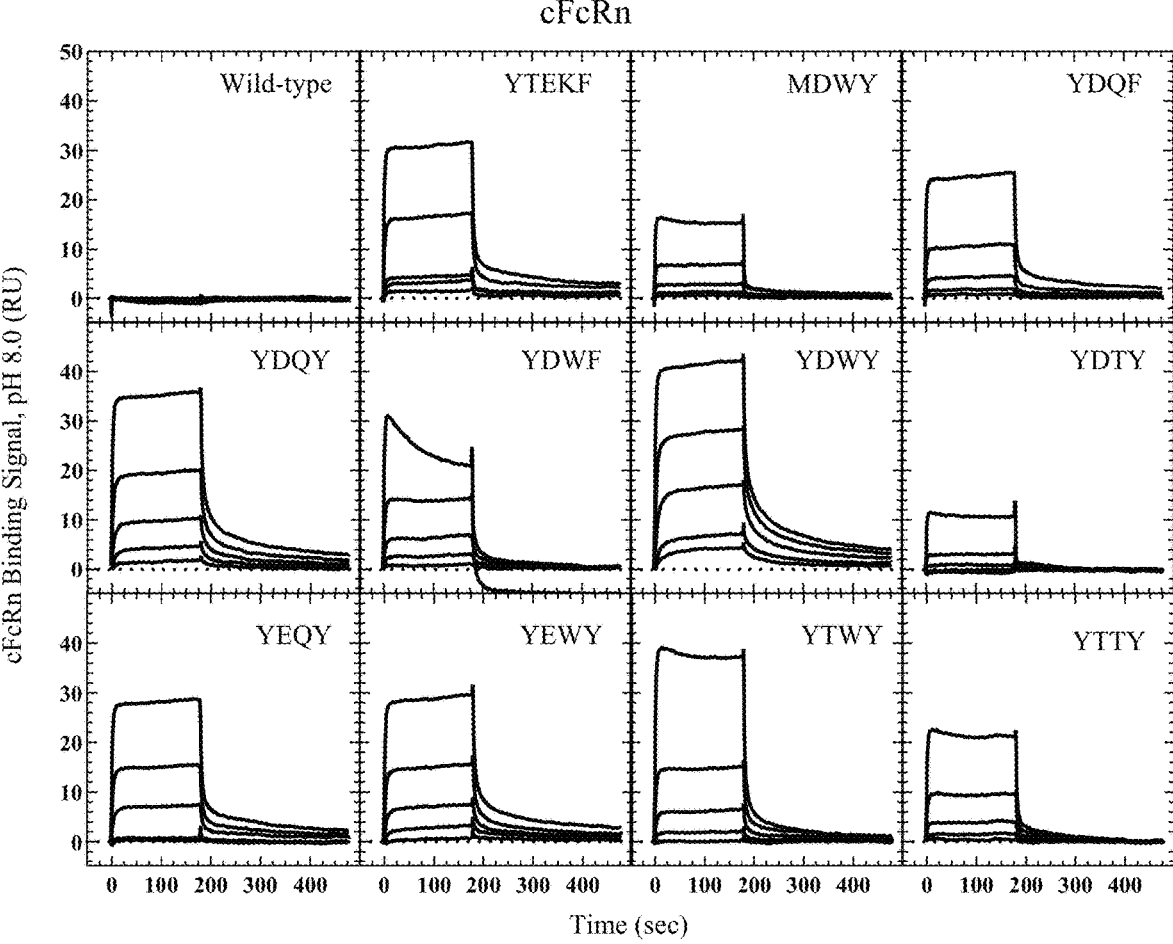
Figure 27G:
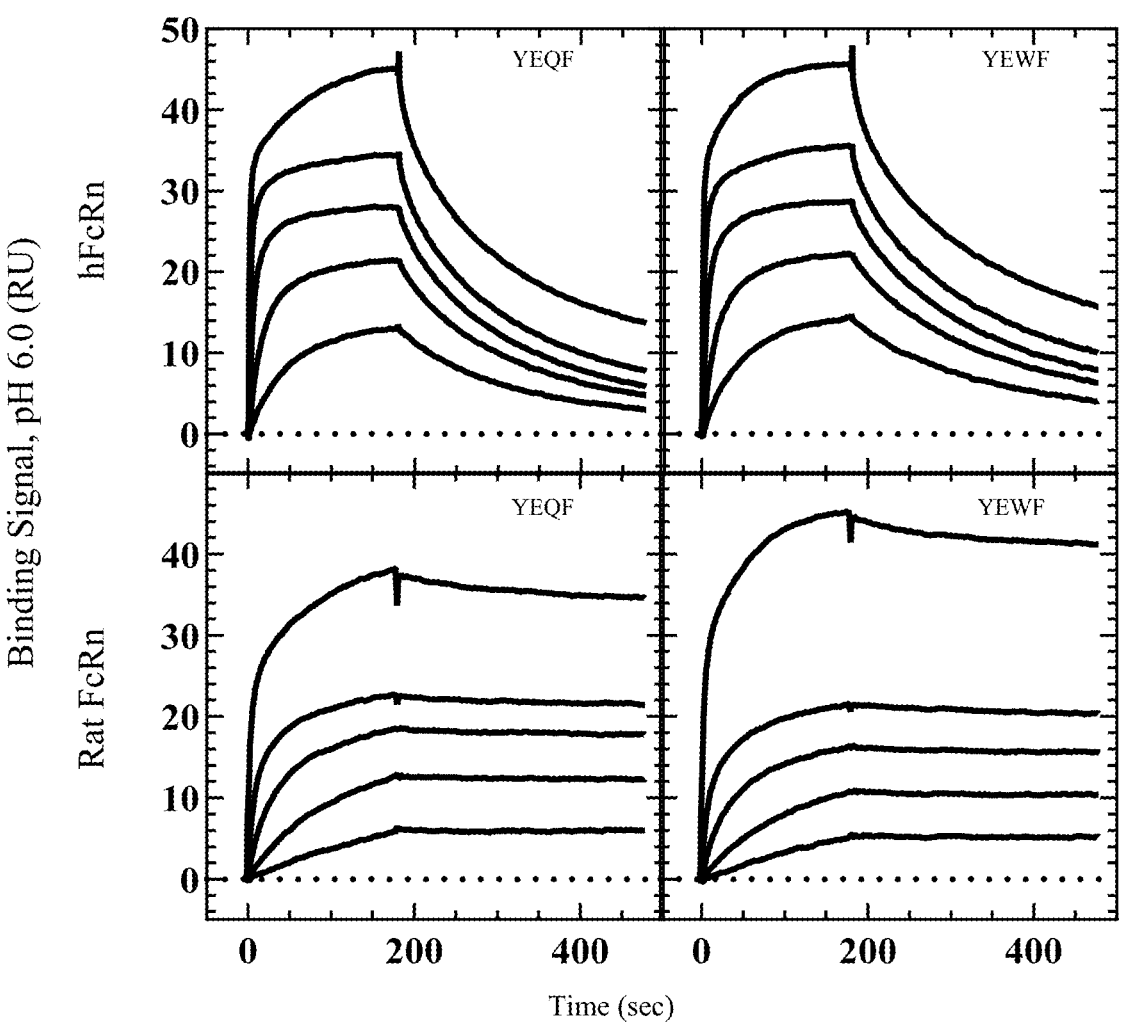

Human and cyno FcRn binding kinetic sensorgrams at pH 6.0 (Human: FIG. 27A, Cyno: FIG. 27B), pH 7.4 (Human: FIG. 27C, Cyno: FIG. 27D) and pH 8.0 (Human: FIG. 27E, Cyno: FIG. 27F) of the wildtype, YTEKF benchmark and 10 FcRn antagonist combination variants shown in FIGS. 27A-G. All examined variants showed a two order of magnitude tighter affinity to both human and cyno FcRn compared to the WT at pH 6.0 and observable kinetics at higher pH. Variants examined are 6 quadruple (YDQF, YDQY, YDWF, YDWY, YEQY and YEWY), three triple (MDWY, YDTY, YTWY) and one double (YY) combination due to their enhanced affinities to FcRn (Table 8). Two additional quadruple variants, YEQF and YEWF (FIG. 27G), were not selected as a result of the weaker affinities to human and rat FcRn.

Figure 28A:
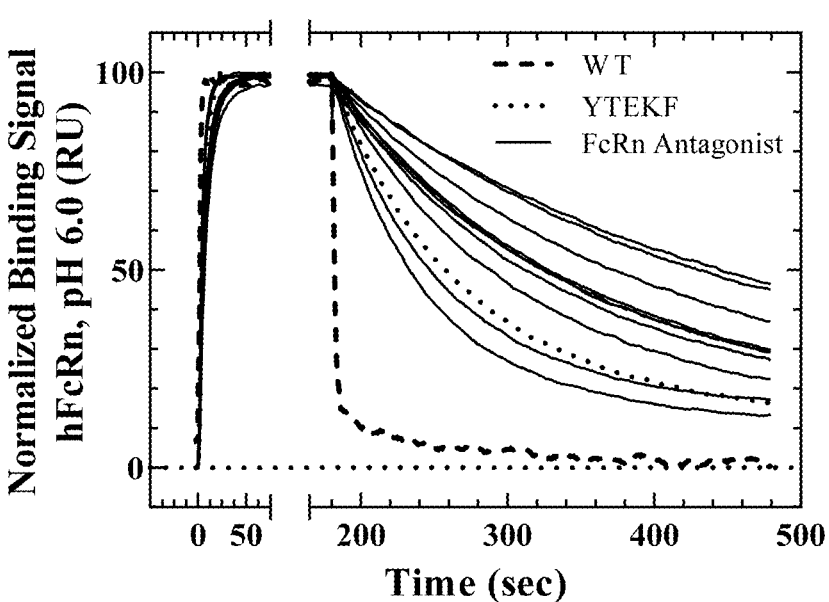
FIGS. 28A-H show the human FcRn binding kinetics of exemplary FcRn antagonists (YDQY, YEWY, YEQY, YDQF, YDWY, YTWY, YDWF, YDTY, MDWY, and YTTY) in comparison to the YTEKF benchmark at various pH levels.
Figure 28B:
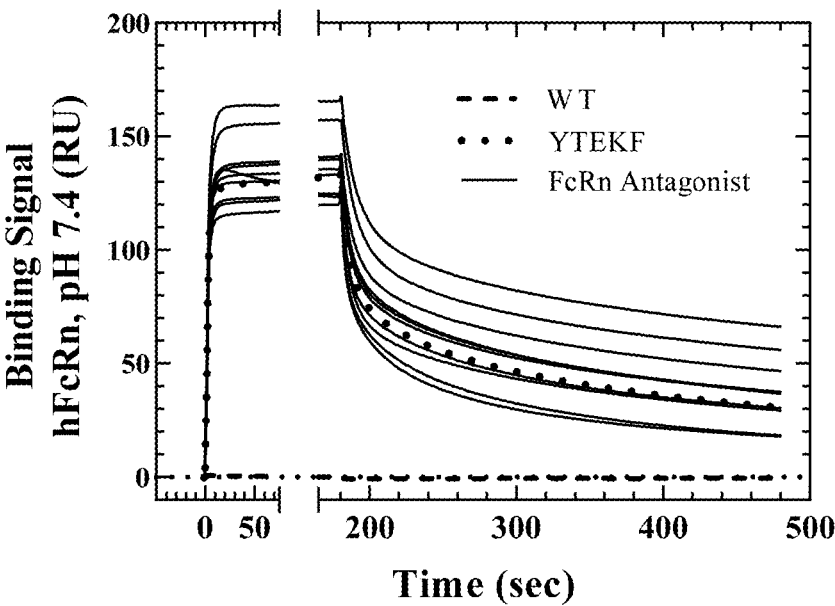
Figure 28C:
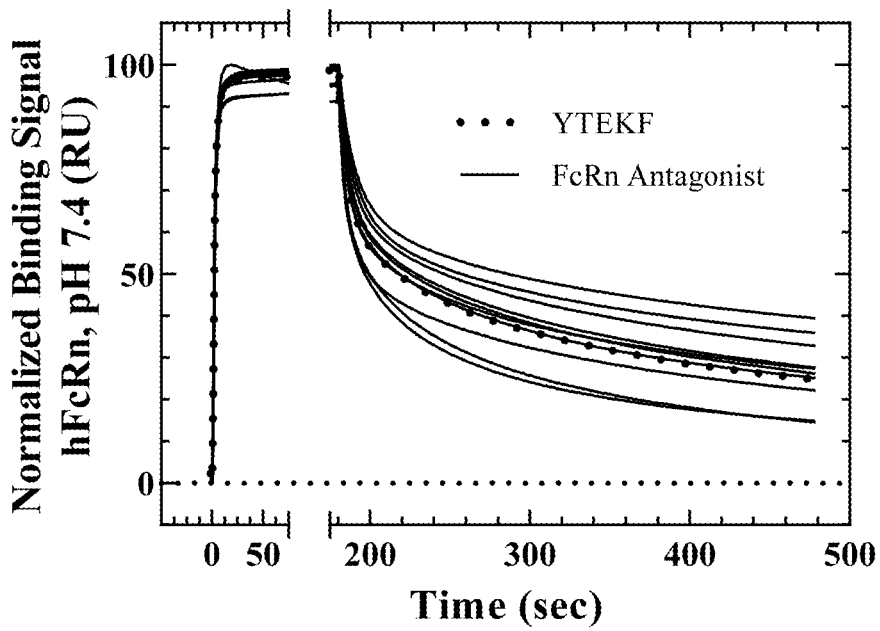
Figure 28D:
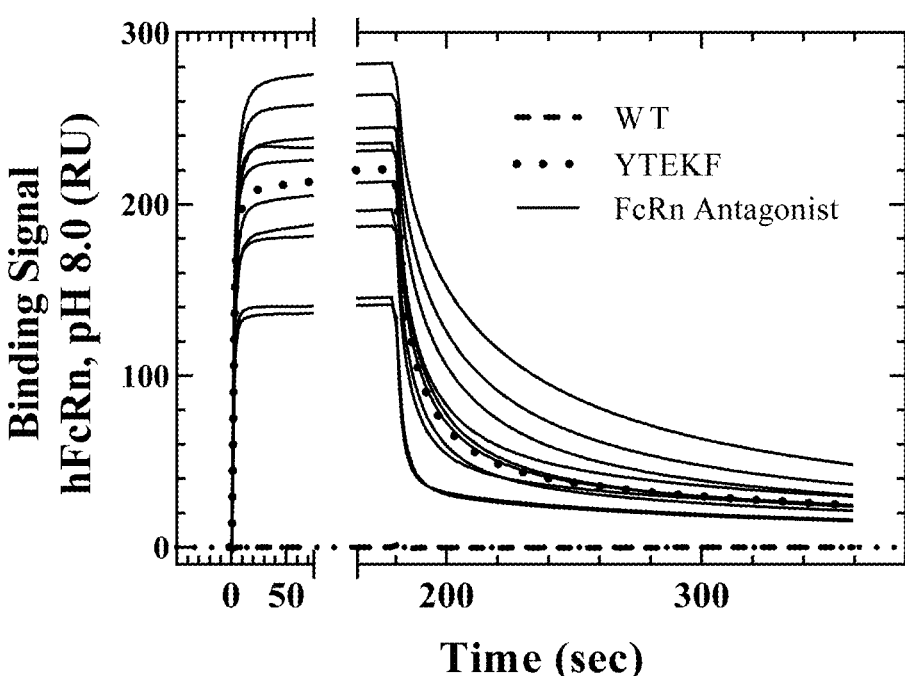
Figure 28E:
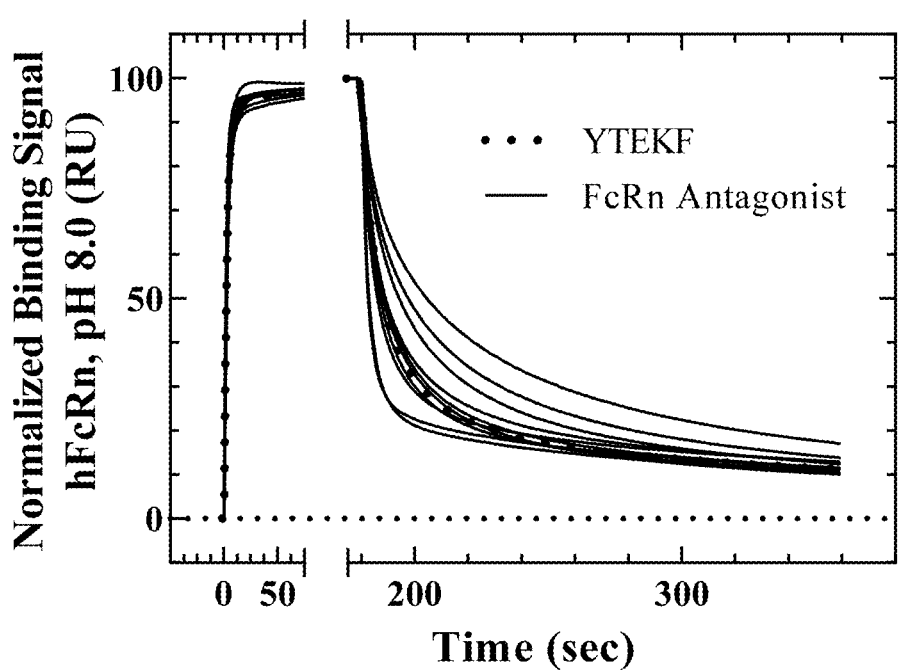
Figure 28F:
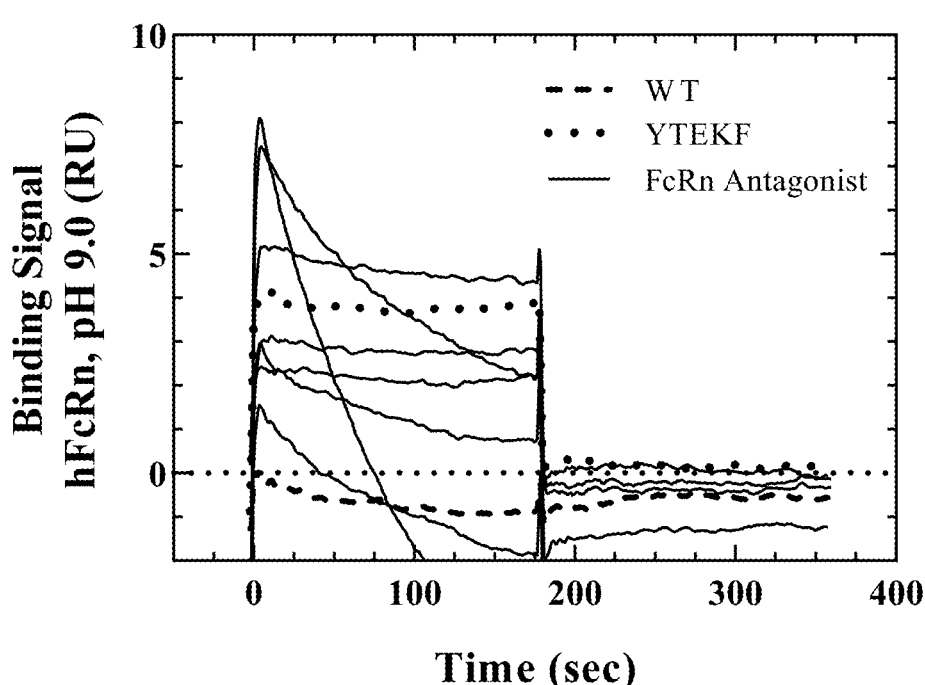
Figure 28G:
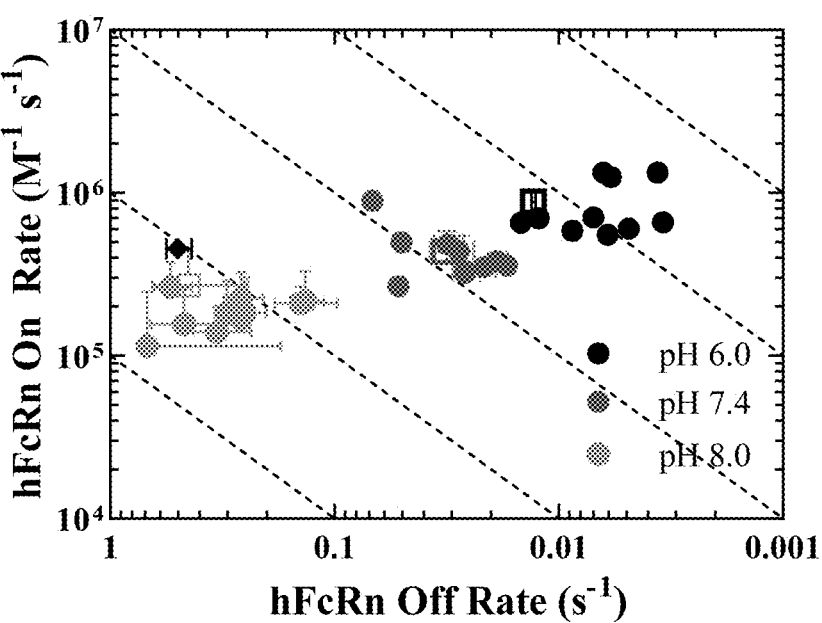
Figure 28H:
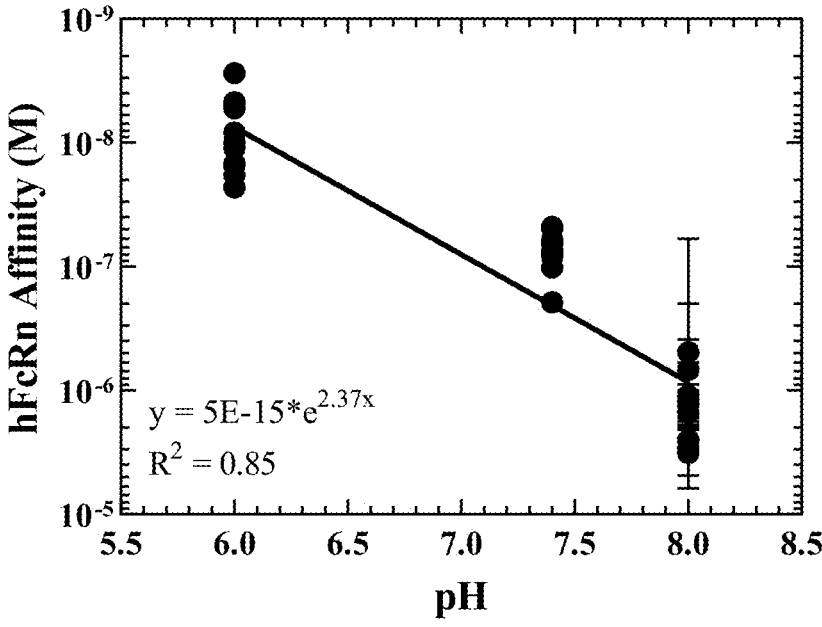
Figure 29A:
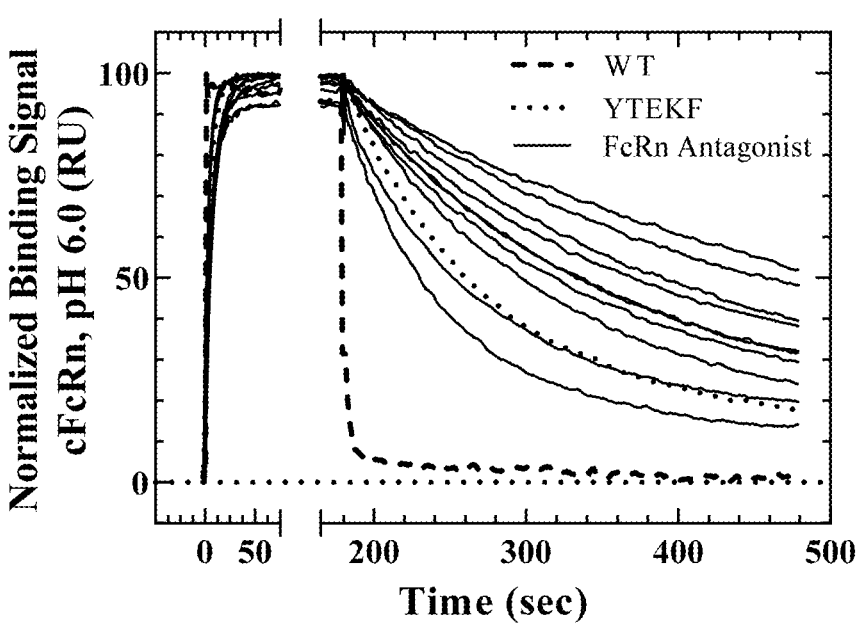
FIGS. 29A-H show the cyno FcRn (cFcRn) binding kinetics of the FcRn antagonists tested in FIGS. 28A-H in comparison to the YTEKF benchmark at various pH levels.
Figure 29B:
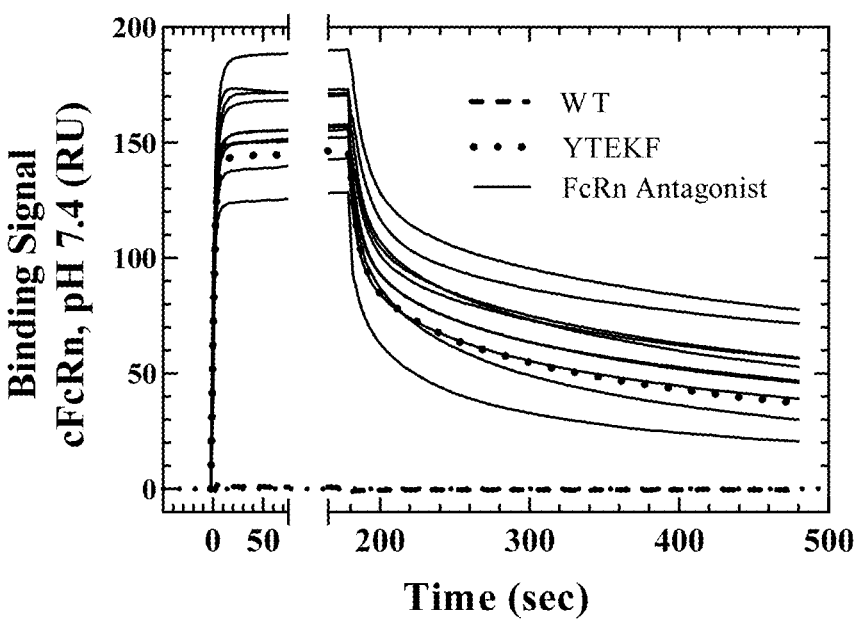
Figure 29C:
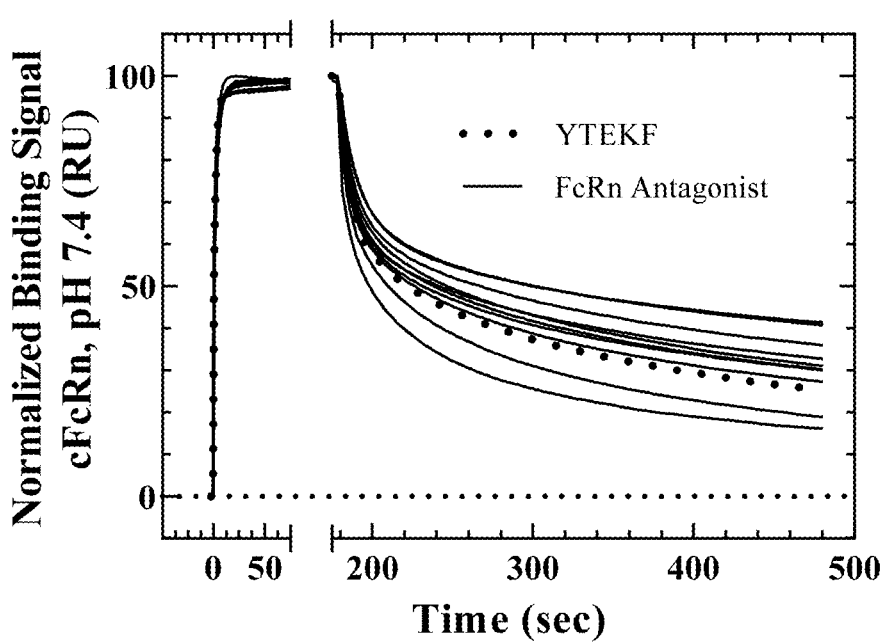
Figure 29D:
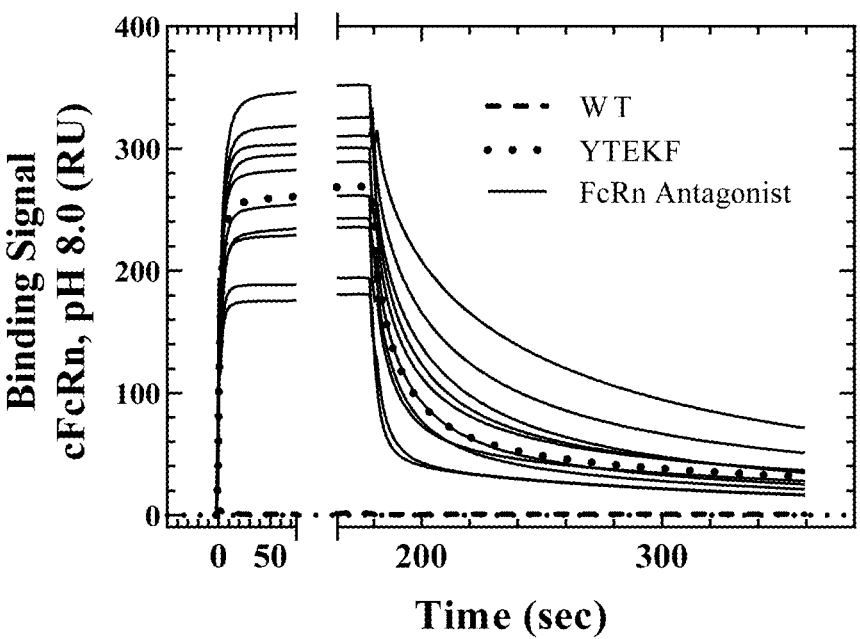
Figure 29E:
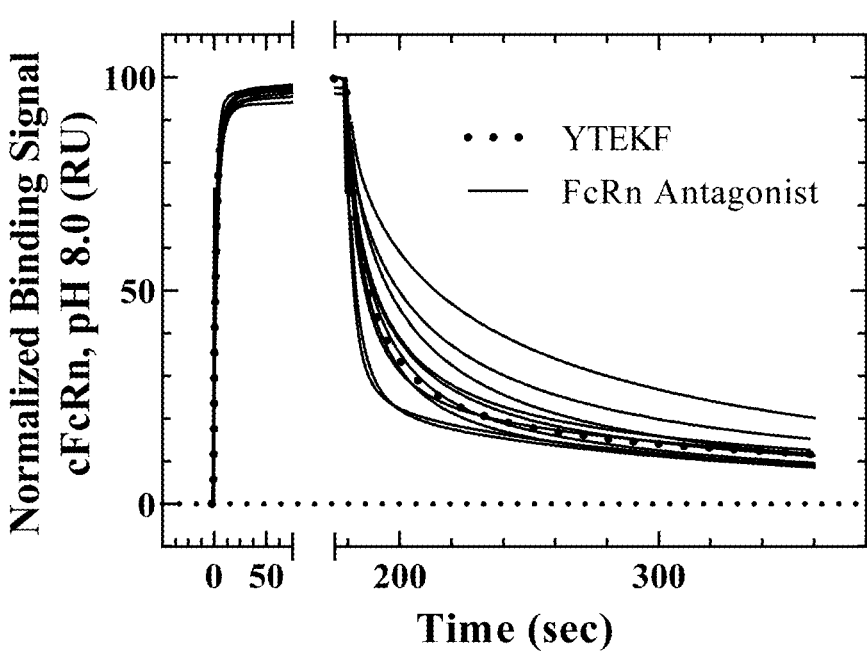

FIGS. 28A-H and 29A-H show the human and cyno FcRn binding kinetics of the 10 FcRn antagonist variants (solid black) in comparison to the YTEKF benchmark (dotted) and WT (dashed). In FIGS. 28A and 29A, eight of the 10 of the variants exhibited slower off rates than the YTEKF benchmark and had similar on rates at pH 6.0 to human and cyno FcRn (Tables 9 and 10). All variants exhibit significant FcRn binding to both human (FIGS. 28B and 28D) and cyno (FIGS. 29C and 29D) FcRn at pH 7.4 and pH 8.0 (Tables 9 and 10). Five quadruple variants, YDQF, YDQY, YDWY, YEQY and YEWY, showed higher binding signal than the YTEKF benchmark, an indication of enhanced affinity at this pH. Normalization of the sensorgrams at pH 7.4 (FIGS.

Figure 29F:
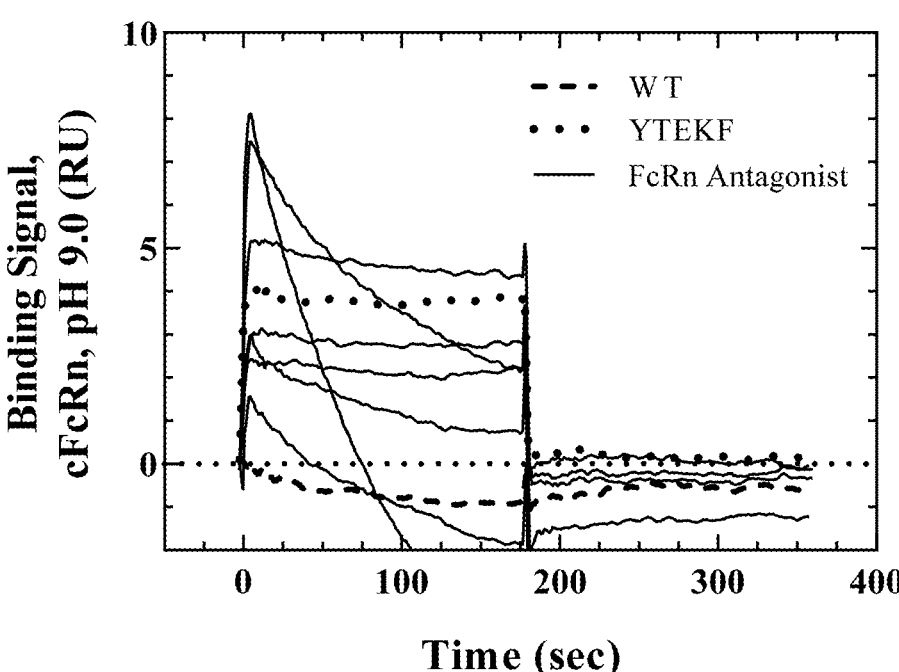
Figure 29G:
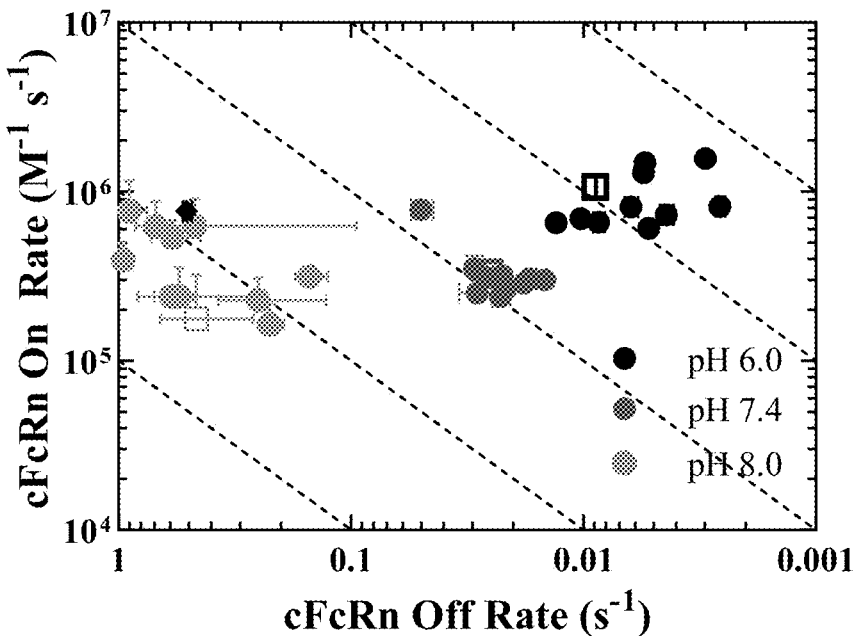
Figure 29H:
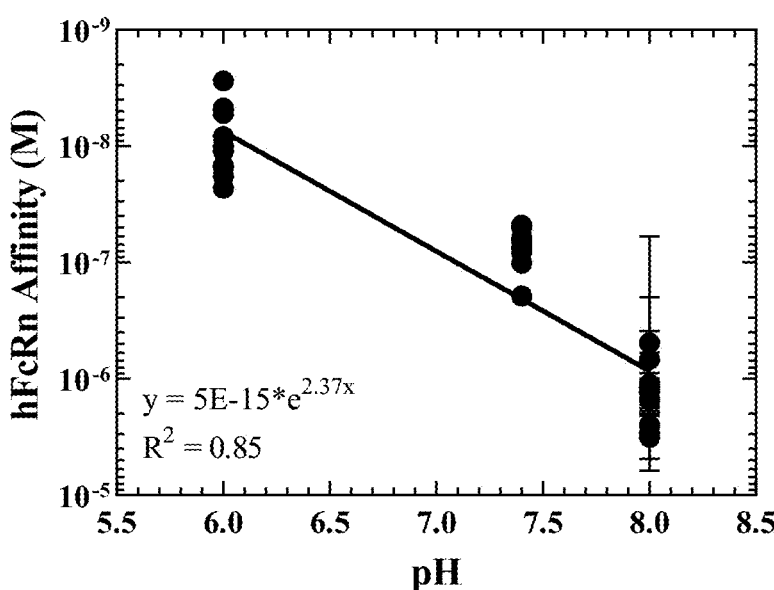

28C and 29C) and pH 8.0 (FIGS. 28E and 29E) for human and cyno FcRn, respectively, indicated that these five variants exhibit significant FcRn binding at these pHs with slower off rates than the YTEKF benchmark. In FIGS. 28F and 29F, pH 9.0 reduced the human and cyno FcRn binding to similar levels as the WT and YTEKF variant. FIGS. 28G an 29G show the isoaffinity plots at the three pH (pH 6.0, black; pH 7.4, dark gray; pH 8.0, gray) for human (FIG. 28G) and cyno (FIG. 29G) FcRn binding in comparison to the YTEKF benchmark (open square) and WT (black, pH 6.0 only). The YTEKF benchmark and lead combination variants have a 2-3 order of magnitude greater human and cyno FcRn binding affinity than WT at pH 6.0. The FcRn binding affinity decreased as the pH increased and the benchmark and combination variants displayed similar affinities at all pH examined. Three variants, YDQY, YDWY and YEWY, exhibited greater binding to human and cyno FcRn at all pH (Tables 9 and 10). Comparison the FcRn binding affinity to human (FIG. 28H) and cyno (FIG. 29H) FcRn as a function of pH indicated a 10-fold decrease in FcRn affinity per pH unit for all examined combination variants.

In FIG. 33 and FIG. 34, the on rate, off rate, binding affinity and steady state binding to human (FIG. 33) and cyno (FIG. 34) FcRn at pH 6.0, 7.4, 8.0 and 9.0 of selected combination variants, the YTEKF benchmark and WT are shown. No steady state binding levels are reported at pH 6.0 as all variants exhibited measurable binding kinetics (on rate, off rate and binding affinity) at this pH. Due to the significantly reduced FcRn binding affinity of all variants at pH 9.0, only the steady state binding level is shown as a measure of residual binding at this pH. The inserted mutations are bolded and underlined in the WT sequence (MTTN: M252/T256/T307/N434). For example: MDWY contained the T256D/T307W/N434Y mutation and the WT residue at position 252.

Other characterization parameters of the FcRn antagonist variants, YETK benchmark and WT, e.g., binding to FcγRIIIa, thermal stability and elution pH were determined and shown in Table 9. The inserted mutations are bolded and underlined in the WT sequence (MTTN: M252/T256/T307/N434). For example: MDWY contained the T256D/T307W/N434Y mutation and the WT residue at position 252.

TABLE 9

In Vitro Characterization Parameters of Fc Variants

| Fc Domain | FcγRIIIa Binding Steady State RU | DSF Tm (° C.) | FcRn Affinity Chromatography pH |
|---|---|---|---|
| WT | 195 ± 10 | 69.4 ± 0.2 | 7.37 ± 0.05 |
| YTEKF | 207 ± 15 | 59.8 ± 0.1 | N.P. |

TABLE 9-continued

In Vitro Characterization Parameters of Fc Variants

| Fc Domain | FcγRIIIa Binding Steady State RU | DSF Tm (° C.) | FcRn Affinity Chromatography pH |
|---|---|---|---|
| MDWY | 211 ± 4 | 55.4 ± 0.2 | 8.80 ± 0.03 |
| YDQF | 203 ± 18 | 59.7 ± 0.2 | 8.88 ± 0.07 |
| YDQY | 225 ± 21 | 59.4 ± 0.3 | 9.21 ± 0.03 |
| YDTY | 146 ± 12 | 52.1 ± 0.2 | 8.95 ± 0.01 |
| YDWF | 128 ± 6 | 52.0 ± 0.1 | 9.18 ± 0.02 |
| YDWY | 136 ± 2 | 58.7 ± 0.1 | 9.51 ± 0.01 |
| YEQF | 226 ± 26 | 59.8 ± 0.2 | 9.08 ± 0.01 |
| YEQY | 131 ± 9 | 52.3 ± 0.1 | 9.25 ± 0.03 |
| YEWF | 163 ± 22 | 56.3 ± 0.2 | 8.95 ± 0.02 |
| YEWY | 146 ± 19 | 62.3 ± 0.1 | 9.33 ± 0.08 |

As shown in Table 9, all FcRn antagonists were thermally destabilized at eluted at significantly higher pH from an FcRn column compared to the WT. The FcγRIIIa binding was highly variable with similar or reduced steady state binding compared to the WT. The inserted mutations are bolded and underlined in the WT sequence (MTTN: M252/T256/T307/N434). For example: MDWY contained the T256D/T307W/N434Y mutation and the WT residue at position 252.

Example 14: FcRn Antagonists Enhance IgG Degradation

FcRn antagonists are co-administered with human IgG to determine IgG depletion. The experiments are performed using human FcRn homozygous transgenic mice (Tg32; e.g., Jackson Laboratory stock #014565, M01 genotype), which allow for scaling to predict human kinetics.

The effect of an FcRn antagonist (e.g., any of the quadruple variants set forth in FIGS. 33 and 34; e.g., YDQY, YEWY, YEQY, YDQF, and YDWY) on serum IgG levels is determined in Tg32 mice. Tg32 mice are administered 5 mg/kg of a non-targeting human IgG1 by intravenous bolus injection. 6 hours later, the mice are administered either a human IgG1 comprising an FcRn antagonist (e.g., as set forth in FIGS. 33 and 34; e.g., YDQY, YEWY, YEQY, YDQF, and YDWY), or a targeting antibody comprising an FcRn antagonist (e.g., as set forth in FIGS. 33 and 34; e.g., YDQY, YEWY, YEQY, YDQF, and YDWY), or vehicle control. Animals are administered according to the dosing schedule set forth in Table 10.

TABLE 10

Dosing Schedule

| Group | Biomeasures[†] | Human IgG1 comprising an FcRn antagonist | Targeting antibody comprising an FcRn antagonist | Non-targeting human IgG1 |
|---|---|---|---|---|
| Group 1 (n = 3) | Antag + murAlb + murIgG | | 20 mg/kg @ t = 6 | Vehicle @ t = 0 |
| Group 2 (n = 3) | hIgG | | Vehicle @ t = 6 | 5 mg/kg @ t = 0 |
| Group 3 (n = 6) | Antag + hIgG + murAlb + murIgG | | 10 mg/kg @ t = 6 h | 5 mg/kg @ t = 0 |

TABLE 10-continued

| | | Dosing Schedule | | |
| Group | Biomeasures[†] | Human IgG1 comprising an FcRn antagonist | Targeting antibody comprising an FcRn antagonist | Non-targeting human IgG1 |
|---|---|---|---|---|
| Group 4 (n = 6) | Antag + hIgG + murAlb + murIgG | | 20 mg/kg @ t = 6 h | 5 mg/kg @ t = 0 |
| Group 5 (n = 6) | Antag + hIgG + murAlb + murIgG | | 40 mg/kg @ t = 6 h | 5 mg/kg @ t = 0 |
| Group 6 (n = 6) | Antag + hIgG + murAlb + murIgG | | 20mg/kg @ t = 6, 24, 48 h | 5 mg/kg @ t = 0 |
| Group 7 (n = 6) | Antag + hIgG + murAlb + murIgG | 20 mg/kg @ t = 6 h | | 5 mg/kg @ t = 0 |
| Protein estimates (mg)* | | 3.6 | 24.6 | 4.8 |

*total protein is estimated assuming 25 g body weight for a mouse

[†]biomeasures include each of the FcRn antagonist IgG1 (Antag; human IgG1 and targeting antibody comprising quadruple variant), non-targeting human IgG1 (hIgG), endogenous mouse IgG (murIgG), and mouse serum albumin (murAlb)

Blood samples are taken according to the bleed schedule set forth in Table 11. Levels of each of the FcRn antagonist IgG1 (FcRn-A; human IgG1 and targeting antibody comprising quadruple variant), non-targeting human IgG1 (hIgG), endogenous mouse IgG (murIgG), and mouse serum albumin (murAlb) are determined by quantitative LC-MS/MS and ELISA methodologies.

TABLE 11

| | | | | | Bleed Schedule | | | | | | |
| Group | ID* | Pre-dose | 5 min | 2 h | 6 h | 6.5 h | 10 h | 24 h | 48 h | 96 h | 168 h |
|---|---|---|---|---|---|---|---|---|---|---|---|
| 1 | 1-3 | | | | 15 µl | 15 µl | 15 µl | 15 µl | 15 µl | 15 µl | 15 µl |
| 2 | 4-6 | 40 µl | 40 µl | | | | | 40 µl | CP | | |
| | 7-9 | | | 40 µl | 40 µl | | | | | CP | |
| | 10-12 | | | | | 40 µl | 40 µl | | | | CP |
| 3 | 13-15 | 40 µl | 40 µl | | | | | 40 µl | CP | | |
| | 16-18 | | | 40 µl | 40 µl | | | | | CP | |
| | 19-21 | | | | | 40 µl | 40 µl | | | | CP |
| 4 | 22-24 | 40 µl | 40 µl | | | | | 40 µl | CP | | |
| | 25-27 | | | 40 µl | 40 µl | | | | | CP | |
| | 28-30 | | | | | 40 µl | 40 µl | | | | CP |
| 5 | 31-33 | 40 µl | 40 µl | | | | | 40 µl | CP | | |
| | 34-36 | | | 40 µl | 40 µl | | | | | CP | |
| | 37-39 | | | | | 40 µl | 40 µl | | | | CP |
| 6 | 40-42 | 40 µl | 40 µl | | | | | 40 µl | CP | | |
| | 43-45 | | | 40 µl | 40 µl | | | | | CP | |
| | 46-48 | | | | | 40 µl | 40 µl | | | | CP |
| 7 | 49-51 | 40 µl | 40 µl | | | | | 40 µl | CP | | |
| | 52-54 | | | 40 µl | 40 µl | | | | | CP | |
| | 55-57 | | | | | 40 µl | 40 µl | | | | CP |

*mouse identifier value;

µl bleeds are non-terminal; CP = terminal cardiac puncture

Example 15: FcRn Antagonist Enhances IgG
Degradation

This Example describes a study showing that an exemplary FcRn antagonist enhanced clearance of co-administered IgG. In this study, mAb1 YDQY (hIgG1 variant) was administered with wildtype mAb1 to hFcRn homozygous transgenic mice (Tg32; Jackson Laboratory stock #014565, M01 genotype), which allow scaling predictions to human for kinetics. As part of the study, PK measures were obtained for both YDQY hIgG1 and WT hIgG1. Measures of albumin would further confirm FcRn inhibition does not interfere with albumin binding site.

More specifically, 5 mg/kg of WT hIgG1 ("tracer IgG") was given to the Tg32 mice by intravenous bolus injection. Six hours later, either the YTEKF hIgG1 (ABDEG™) or the YDQY hIgG1 was administered to the mice according to the dosing schedule set forth in Table 12. All doses were administered at a dosing volume of 10 mL/kg.

TABLE 12

Dosing Schedule and PK Measures

| | Biomeasures | YTEKF hIgG1 Dosing Schedule | YDQY hIgG1 | WT IgG1 |
|---|---|---|---|---|
| Group 1 (n = 3) | murAlb + murIgG | — | 20 mg/kg @ t = 6 | Vehicle @ t = 0 |
| Group 2 (n = 3) | WT hIgG | — | Vehicle @ t = 6 | 5 mg/kg @ t = 0 |
| Group 3 (n = 9) | YDQY + WT hIgG + murAlb + murIgG | — | 10 mg/kg @ t = 6 h | 5 mg/kg @ t = 0 |
| Group 4 (n = 9) | YDQY + WT hIgG + murAlb + murIgG | — | 20 mg/kg @ t = 6 h | 5 mg/kg @ t = 0 |
| Group 5 (n = 9) | YDQY + WT hIgG + murAlb + murIgG | — | 40 mg/kg @ t = 6 h | 5 mg/kg @ t = 0 |
| Group 6 (n = 9) | YDQY + WT hIgG + murAlb + murIgG | — | 20 mg/kg @ t = 6, 24, 48 h | 5 mg/kg @ t = 0 |
| Group 7 (n = 9) | YTEKF + WT hIgG + murAlb + murIgG | 20 mg/kg @ t = 6 h | — | 5 mg/kg @ t = 0 |

Figure 30A:
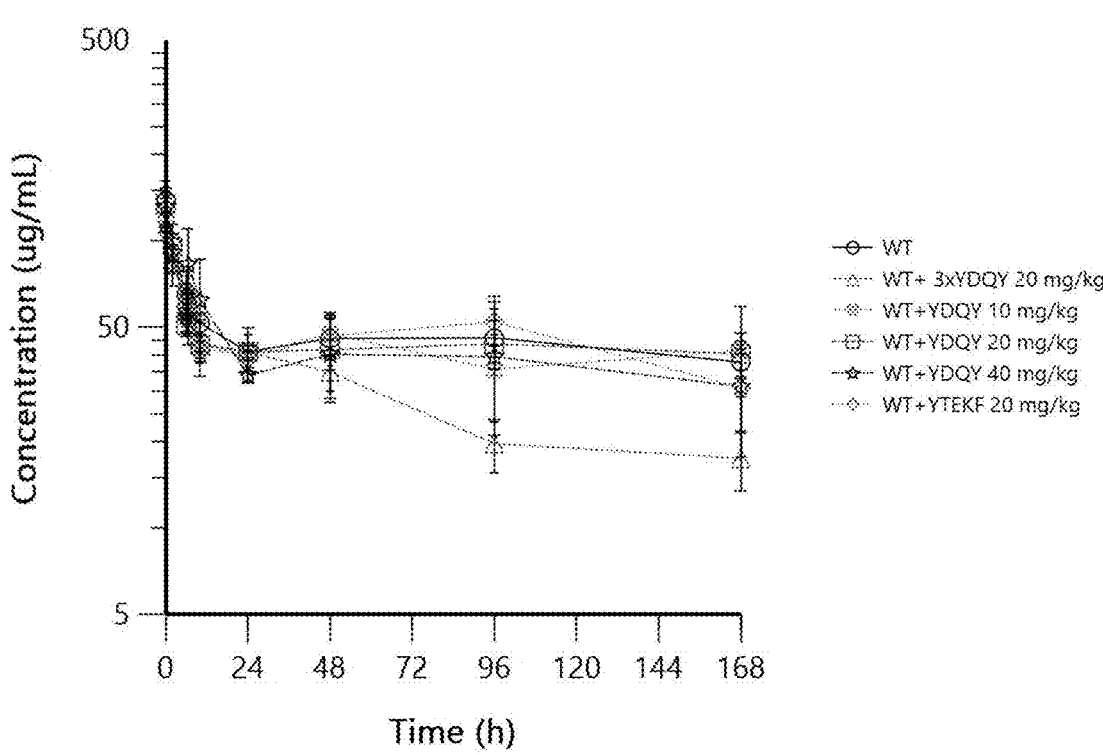
FIGS. 30A-C are graphs showing tracer (WT) hIgG concentrations over time following the indicated doses of the YDQY or YTEKF hIgG1 variant.
Figure 30B:
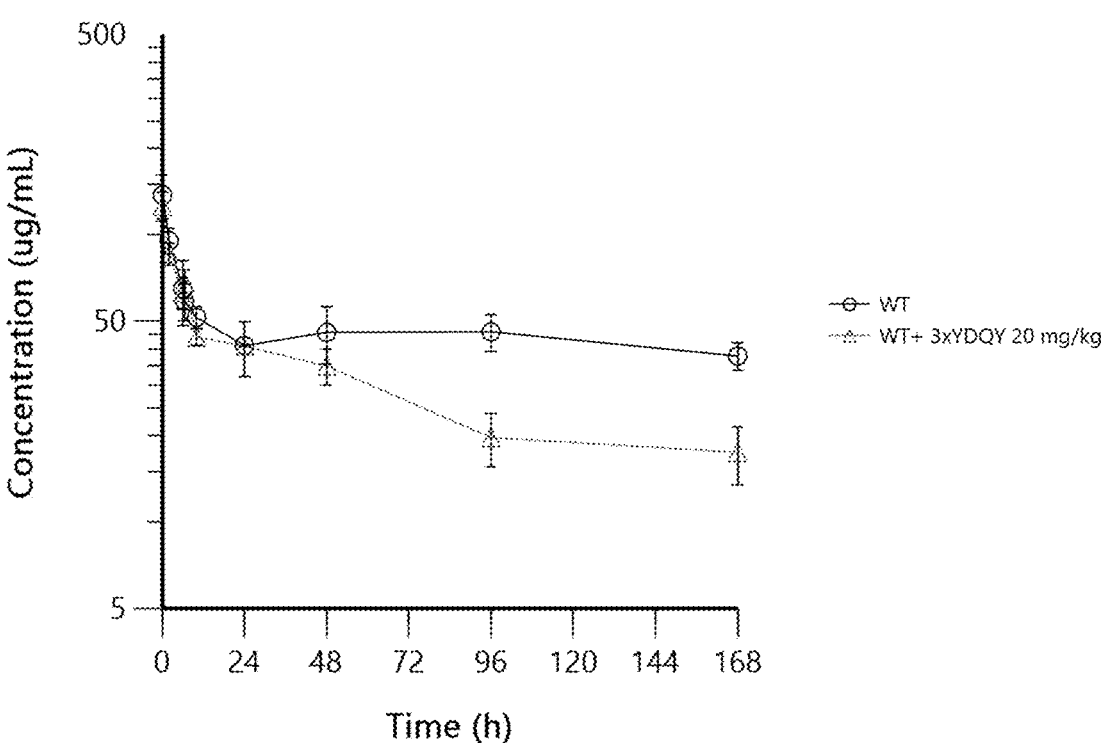
Figure 30C:
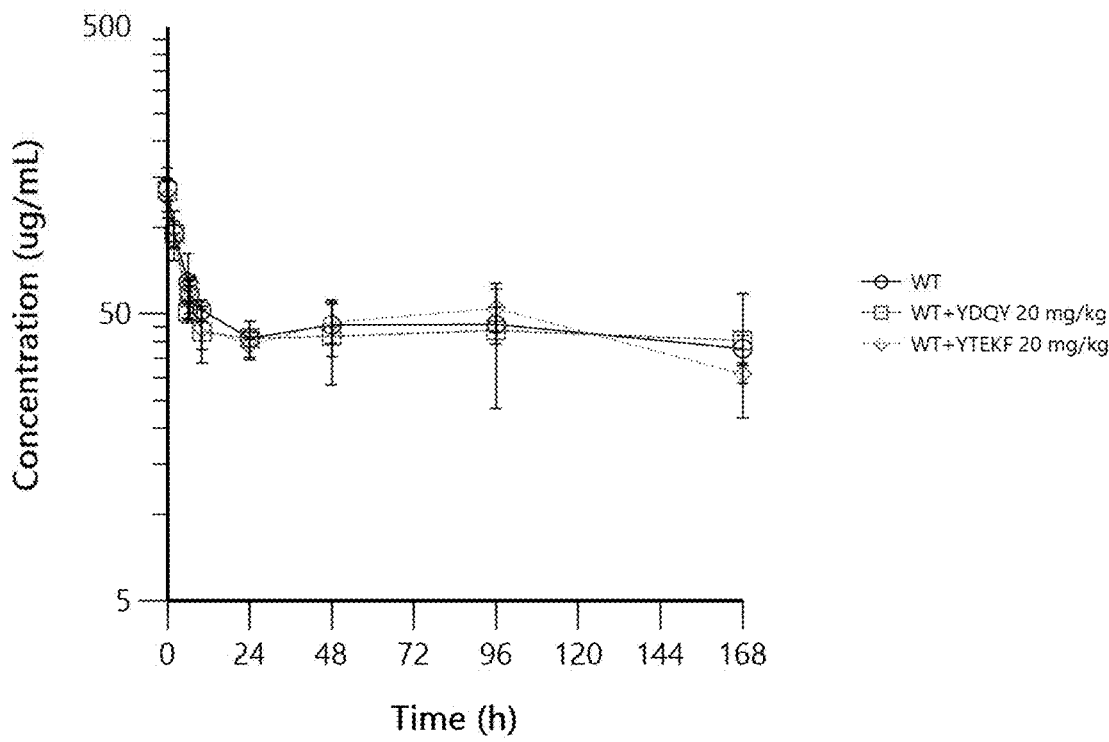

The data show that three 20 mg/kg doses of YDQY hIgG1 (at 6, 24 and 48 hrs) significantly reduced tracer WT hIgG1 concentration (Group 6; FIGS. 30A and 30B; Table 13) and yielded significantly improved results than YTEKF hIgG1. Single doses of YDQY hIgG1 or YTEKF hIgG1 did not appear to cause a robust decrease in tracer WT IgG (FIG. 30C; Table 13).

TABLE 13

WT hIgG Clearance

| Group | Treatment | WT IgG $AUC_{last\ (0-168\ hours)}$ (ug*h/mL) | WT Fold Decrease |
|---|---|---|---|
| 2 | WT | 7677 | — |
| 3 | WT + YDQY 10 mg/kg | 7101 | 0.93 |
| 4 | WT + YDQY 20 mg/kg | 7386 | 0.96 |

TABLE 13-continued

WT hIgG Clearance

| Group | Treatment | WT IgG $AUC_{last\ (0-168\ hours)}$ (ug*h/mL) | WT Fold Decrease |
|---|---|---|---|
| 5 | WT + YDQY 40 mg/kg | 6792 | 0.88 |
| 6 | WT + 3x YDQY 20 mg/kg | 4852 | 0.63 |
| 7 | WT + YTEKF 20 mg/kg | 7648 | 1.00 |

Figure 31A:
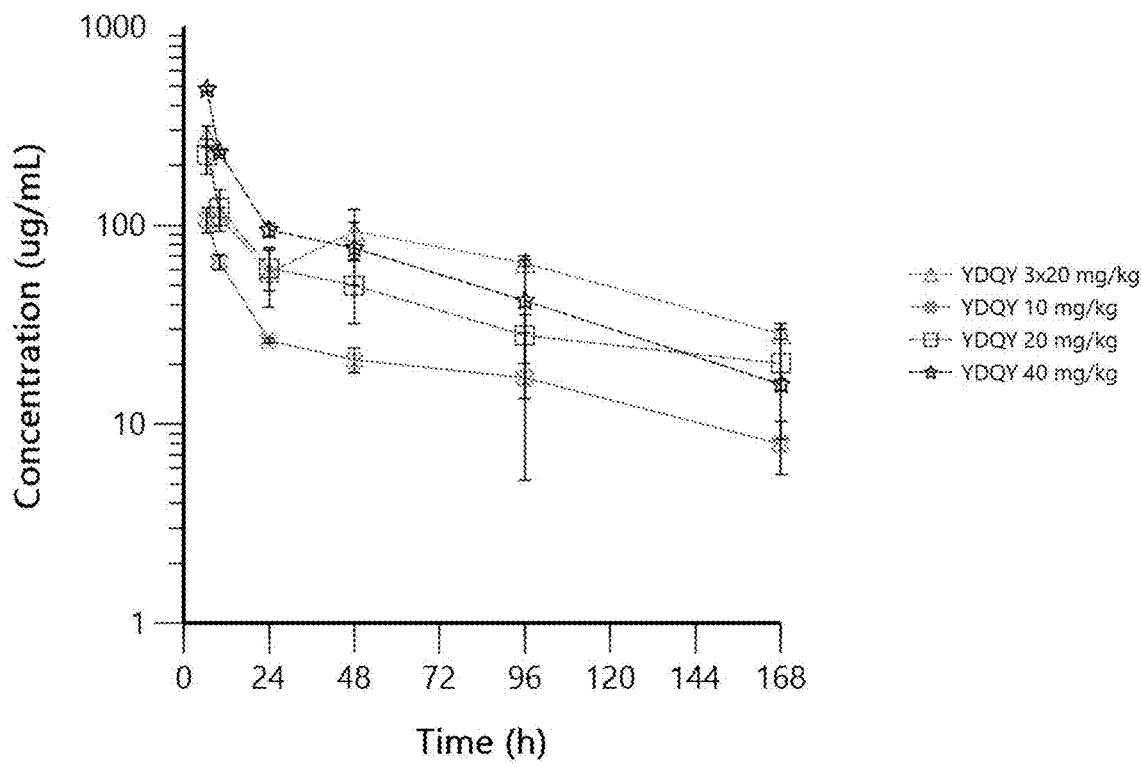
FIGS. 31A and 31B are graphs showing the protein concentrations of YDQY hIgG1 variant (A) or YTEKF hIgG1 variant (B) over time after being administered to mice at the indicated doses.
Figure 31B:
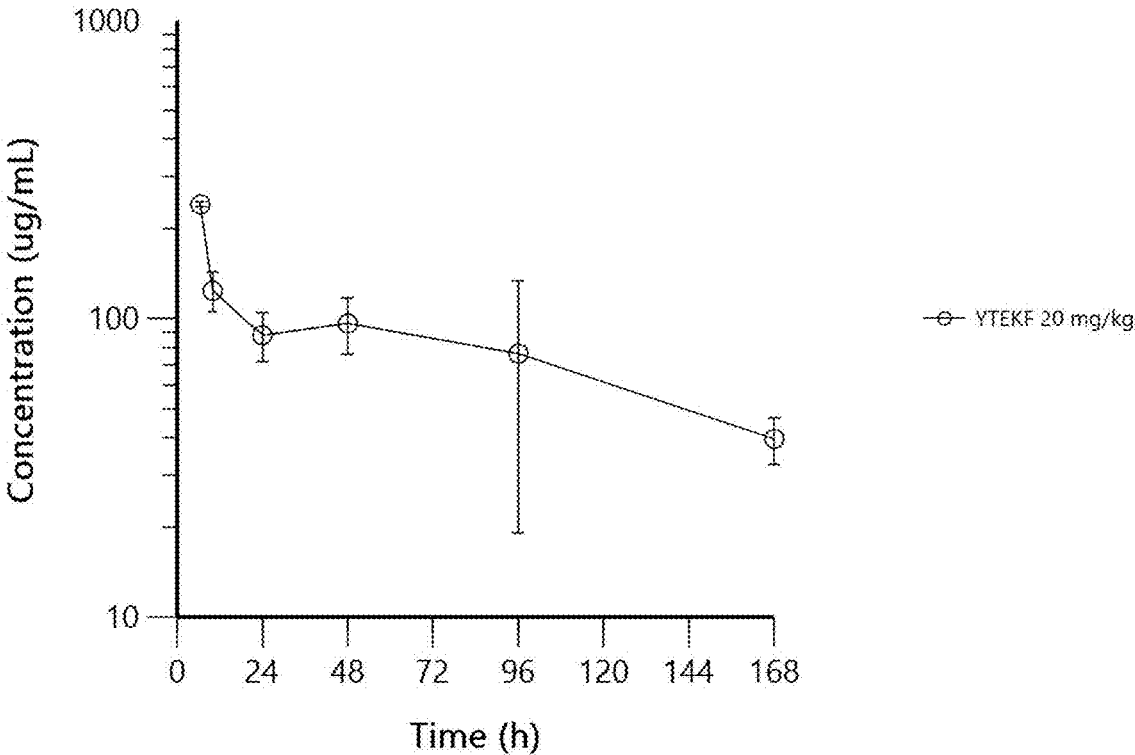

The clearance of YDQY hIgG1 (about 2.6 mL/h/kg) was faster than a typical IgG (~0.1-1.0 mL/h/kg) or YTEKF hIgG (~1.1 mL/h/kg) in Tg32 mice (FIGS. 31A and 31B) but sustained exposure throughout the study duration. The results show that this FcRn antagonist can remain in the host for a sufficient period of time to reduce FcRn-mediated recycling of WT IgG and promote WT IgG clearance.

The invention claimed is:

1. A method of treating an autoimmune disease in a subject in need thereof, comprising administering to the subject a therapeutically effective amount of an FcRn antagonist comprising a modified Fc domain comprising a combination of amino acid residues selected from the group consisting of:

a) a tyrosine (Y) at amino acid position 252, an aspartic acid (D) at amino acid position 256, a glutamine (Q) at amino acid position 307, and a tyrosine (Y) at amino acid position 434;

b) a tyrosine (Y) at amino acid position 252, a glutamic acid (E) at amino acid position 256, a tryptophan (W) at amino acid position 307, and a tyrosine (Y) at amino acid position 434;

c) a tyrosine (Y) at amino acid position 252, an aspartic acid (D) at amino acid position 256, a glutamine (Q) at amino acid position 307, and a phenylalanine (F) at amino acid position 434;

d) a tyrosine (Y) at amino acid position 252, an aspartic acid (D) at amino acid position 256, a tryptophan (W) at amino acid position 307, and a tyrosine (Y) at amino acid position 434;

e) a tyrosine (Y) at amino acid position 252, an aspartic acid (D) at amino acid position 256, a tryptophan (W) at amino acid position 307, and a phenylalanine (F) at amino acid position 434;

f) a tyrosine (Y) at amino acid position 252, a glutamic acid (E) at amino acid position 256, a tryptophan (W) at amino acid position 307, and a phenylalanine (F) at amino acid position 434; and g) a tyrosine (Y) at amino acid position 252, a glutamic acid (E) at amino acid position 256, a glutamine (Q) at amino acid position 307, and a phenylalanine (F) at amino acid position 434, according to Eu numbering, wherein the therapeutically effective amount of the FcRn antagonist increases the clearance of serum IgG in the subject.

2. The method of claim 1, wherein the autoimmune disease is selected from the group consisting of graft versus host disease (GVHD), systemic lupus erythematosus (SLE), myasthenia gravis, systemic sclerosis (SSc)/scleroderma, rheumatoid arthritis, psoriatic arthritis, osteoarthritis, diabetes, multiple sclerosis, pemphigus vulgaris, atopic dermatitis, psoriasis, asthma, allergy, idiopathic pulmonary fibrosis (IPF), idiopathic thrombocytopenia purpura (ITP), and hidradenitis suppurativa.

3. The method of claim 1, wherein the modified Fc domain is a modified human IgG Fc domain.

4. The method of claim 3, wherein the modified Fc domain is a modified human IgG1 Fc domain.

5. The method of claim 1, wherein the modified Fc domain has enhanced FcRn binding affinity at an acidic pH of 6.0 and at a non-acidic pH of 7.4 compared to a wildtype Fc domain.

6. The method of claim 1, wherein the modified Fc domain is a modified human IgG Fc domain and has enhanced FcRn binding affinity at an acidic pH of 6.0 and/or a non-acidic pH of 7.4 compared to a human IgG Fc domain of the same subtype comprising amino acid substitutions M252Y, S254T, T256E, H433K, and N434F.

7. The method of claim 1, wherein the modified Fc domain has reduced FcγRIIIa binding affinity compared to a wildtype Fc domain.

8. The method of claim 1, wherein the modified Fc domain comprises an amino acid sequence that is identical to SEQ ID NO:1, 2, 3, or 4, or an FcRn-binding portion thereof, except that said amino acid sequence comprises said combination of amino acid residues.

9. The method of claim 1, wherein the FcRn antagonist is a binding polypeptide that binds one or more targets that are not FcRn.

10. The method of claim 1, wherein the FcRn antagonist is an antibody or comprises an antigen-binding fragment thereof.

11. The method of claim 10, wherein the FcRn antagonist is a monoclonal antibody.

12. The method of claim 11, wherein the antibody is a chimeric, humanized, or human antibody.

13. The method of claim 1, wherein the FcRn antagonist is an Fc fusion protein.

14. The method of claim 13, wherein the Fc fusion protein is an immunoadhesin.

15. The method of claim 1, wherein the FcRn antagonist is an Fc fragment.

16. The method of claim 1, wherein the modified Fc domain comprises a combination of amino acid residues selected from the group consisting of:

a) a tyrosine (Y) at amino acid position 252, an aspartic acid (D) at amino acid position 256, a glutamine (Q) at amino acid position 307, and a tyrosine (Y) at amino acid position 434;

b) a tyrosine (Y) at amino acid position 252, a glutamic acid (E) at amino acid position 256, a tryptophan (W) at amino acid position 307, and a tyrosine (Y) at amino acid position 434;

c) a tyrosine (Y) at amino acid position 252, an aspartic acid (D) at amino acid position 256, a glutamine (Q) at amino acid position 307, and a phenylalanine (F) at amino acid position 434;

d) a tyrosine (Y) at amino acid position 252, an aspartic acid (D) at amino acid position 256, a tryptophan (W) at amino acid position 307, and a tyrosine (Y) at amino acid position 434; and e) a tyrosine (Y) at amino acid position 252, an aspartic acid (D) at amino acid position 256, a tryptophan (W) at amino acid position 307, and a phenylalanine (F) at amino acid position 434.

17. The method of claim 1, wherein the modified Fc domain is a modified human IgG Fc domain.

18. A method of treating an autoimmune disease in a subject in need thereof, comprising administering to the subject a therapeutically effective amount of an FcRn antagonist comprising a modified Fc domain comprising a tyrosine (Y) at amino acid position 252, an aspartic acid (D) at amino acid position 256, a glutamine (Q) at amino acid position 307, and a tyrosine (Y) at amino acid position 434, according to Eu numbering, wherein the therapeutically effective amount of the FcRn antagonist increases the clearance of serum IgG in the subject.

19. The method of claim 18, wherein the modified Fc domain is a modified human IgG Fc domain.

20. A method of treating an autoimmune disease in a subject in need thereof, comprising administering to the subject a therapeutically effective amount of an FcRn antagonist comprising a modified Fc domain comprising a tyrosine (Y) at amino acid position 252, a glutamic acid (E) at amino acid position 256, a tryptophan (W) at amino acid position 307, and a tyrosine (Y) at amino acid position 434, according to Eu numbering, wherein the therapeutically effective amount of the FcRn antagonist increases the clearance of serum IgG in the subject.

21. A method of treating an autoimmune disease in a subject in need thereof, comprising administering to the subject a therapeutically effective amount of an FcRn antagonist comprising a modified Fc domain comprising a tyrosine (Y) at amino acid position 252, an aspartic acid (D) at amino acid position 256, a glutamine (Q) at amino acid position 307, and a phenylalanine (F) at amino acid position 434, according to Eu numbering, wherein the therapeutically effective amount of the FcRn antagonist increases the clearance of serum IgG in the subject.

22. A method of treating an autoimmune disease in a subject in need thereof, comprising administering to the subject a therapeutically effective amount of an FcRn antagonist comprising a modified Fc domain comprising a tyrosine (Y) at amino acid position 252, an aspartic acid (D) at amino acid position 256, a tryptophan (W) at amino acid position 307, and a tyrosine (Y) at amino acid position 434, according to Eu numbering, wherein the therapeutically effective amount of the FcRn antagonist increases the clearance of serum IgG in the subject.

23. A method of treating an autoimmune disease in a subject in need thereof, comprising administering to the subject a therapeutically effective amount of an FcRn antagonist comprising a modified Fc domain comprising a combination of the following amino acid residues:

a) a tyrosine (Y) at amino acid position 252, an aspartic acid (D) at amino acid position 256, and a tyrosine (Y) at amino acid position 434, or b) an aspartic acid (D) at amino acid position 256, a tryptophan (W) at amino acid position 307, and a tyrosine (Y) at amino acid position 434, according to Eu numbering, wherein the therapeutically effective amount of the FcRn antagonist increases the clearance of serum IgG in the subject.

24. The method of claim 23, wherein the modified Fc domain is a modified human IgG Fc domain.

25. A method of treating an autoimmune disease in a subject in need thereof, comprising administering to the subject a therapeutically effective amount of an FcRn antagonist comprising a modified Fc domain, wherein all the modifications relative to a wildtype Fc domain that together increase the FcRn-binding affinity of the modified Fc domain consist of a tyrosine (Y) at amino acid position 252, a glutamic acid (E) at amino acid position 256, a glutamine (Q) at amino acid position 307, and a tyrosine (Y) at amino acid position 434, according to Eu numbering, wherein the therapeutically effective amount of the FcRn antagonist increases the clearance of serum IgG in the subject.

26. The method of claim 25, wherein the modified Fc domain is a modified human IgG Fc domain.

\* \* \* \* \*